(12) United States Patent
Pauls et al.

(10) Patent No.: US 8,410,150 B2
(45) Date of Patent: Apr. 2, 2013

(54) INHIBITORS OF CARNITINE PALMITOYLTRANSFERASE AND TREATING CANCER

(75) Inventors: Heinz W. Pauls, Oakville (CA); Peter Brent Sampson, Oakville (CA); Bryan T. Forrest, Toronto (CA); Radoslaw Laufer, Oakville (CA); Yong Liu, North York (CA); Miklos Feher, Toronto (CA); Yi Yao, Mississauga (CA); Guohua Pan, Oakville (CA)

(73) Assignee: University Health Network, Toronto (CA)

( * ) Notice: Subject to any disclaimer, the term of this patent is extended or adjusted under 35 U.S.C. 154(b) by 515 days.

(21) Appl. No.: 12/530,429

(22) PCT Filed: Mar. 6, 2008

(86) PCT No.: PCT/CA2008/000440
§ 371 (c)(1),
(2), (4) Date: Dec. 7, 2009

(87) PCT Pub. No.: WO2008/109991
PCT Pub. Date: Sep. 18, 2008

(65) Prior Publication Data
US 2010/0105900 A1   Apr. 29, 2010

Related U.S. Application Data

(60) Provisional application No. 60/893,999, filed on Mar. 9, 2007, provisional application No. 60/962,865, filed on Aug. 1, 2007.

(51) Int. Cl.
| | |
|---|---|
| *C07D 307/66* | (2006.01) |
| *C07D 333/32* | (2006.01) |
| *C07D 213/18* | (2006.01) |
| *C07D 233/70* | (2006.01) |
| *C07D 417/04* | (2006.01) |
| *C07D 263/36* | (2006.01) |
| *C07D 249/12* | (2006.01) |
| *C07D 261/10* | (2006.01) |
| *C07D 207/36* | (2006.01) |
| *C07D 275/03* | (2006.01) |
| *C07D 271/06* | (2006.01) |
| *C07D 285/08* | (2006.01) |
| *C07C 335/16* | (2006.01) |
| *C07C 327/40* | (2006.01) |
| *C07C 327/08* | (2006.01) |
| *C07C 311/10* | (2006.01) |
| *C07C 237/14* | (2006.01) |
| *A61K 31/34* | (2006.01) |
| *A61K 31/381* | (2006.01) |
| *A61K 31/4025* | (2006.01) |
| *A61K 31/40* | (2006.01) |
| *A61K 31/415* | (2006.01) |
| *A61K 31/4164* | (2006.01) |
| *A61K 31/4196* | (2006.01) |
| *A61K 31/42* | (2006.01) |
| *A61K 31/4245* | (2006.01) |
| *A61K 31/425* | (2006.01) |
| *A61K 31/433* | (2006.01) |
| *A61K 31/435* | (2006.01) |
| *A61K 31/64* | (2006.01) |
| *A61K 31/155* | (2006.01) |

(52) U.S. Cl. ........ 514/362; 514/639; 514/631; 514/580; 514/588; 514/601; 514/602; 514/607; 514/471; 514/472; 514/447; 514/448; 514/378; 514/371; 514/372; 514/377; 514/380; 514/383; 514/365; 514/364; 514/396; 514/398; 514/426; 514/423; 562/450; 562/426; 560/35; 560/317; 564/26; 564/30; 564/97; 564/98; 564/161; 564/192; 564/32; 548/530; 548/557; 548/537; 548/128; 548/131; 548/133; 548/262.2; 548/264.8; 548/146; 548/190; 548/214; 548/206; 548/233; 548/235; 548/240

(58) Field of Classification Search ........................ None
See application file for complete search history.

(56) References Cited

U.S. PATENT DOCUMENTS

| 4,673,763 A | 6/1987 | Buckler | |
|---|---|---|---|
| 4,767,781 A * | 8/1988 | Shinagawa et al. | 514/513 |

(Continued)

FOREIGN PATENT DOCUMENTS

| CA | 2192088 | 2/1996 |
|---|---|---|
| CA | 2373360 | 11/2000 |

(Continued)

OTHER PUBLICATIONS

Nelson, et al., Angew. Chem. Int. Ed. 39:1323 (2000).*

(Continued)

*Primary Examiner* — Michael Barker
(74) *Attorney, Agent, or Firm* — McCarter & English, LLP; Steven G. Davis; Wei Song

(57) ABSTRACT

A CPT inhibitor compound is represented by Structural Formula (I) or a pharmaceutically acceptable salt thereof: or a pharmaceutically acceptable salt thereof. A pharmaceutical composition comprises a compound represented by Structural Formula (I) or a pharmaceutically acceptable salt thereof. A method of treating a subject having cancer comprises administering to the subject a therapeutically effective amount of a compound represented by Structural Formula (I) or a pharmaceutically acceptable salt thereof.

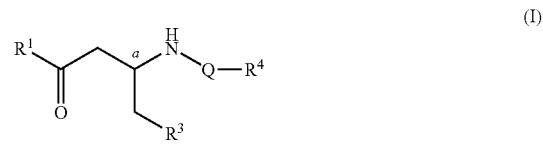

(I)

20 Claims, 2 Drawing Sheets

U.S. PATENT DOCUMENTS

| | | | |
|---|---|---|---|
| 5,593,967 | A | 1/1997 | Horwell et al. |
| 5,847,125 | A | 12/1998 | McDonald et al. |
| 6,369,073 | B1 | 4/2002 | Giannessi |
| 6,495,565 | B2 | 12/2002 | Duan |
| 6,528,684 | B1 | 3/2003 | Giannessi |
| 6,656,936 | B1 | 12/2003 | Savle et al. |
| 6,822,115 | B2 | 11/2004 | Giannessi |
| 2002/0187534 | A1 | 12/2002 | Pizer |
| 2003/0125315 | A1 | 7/2003 | Mjalli |
| 2004/0072802 | A1 | 4/2004 | Duan |
| 2005/0059705 | A1 | 3/2005 | Mjalli |
| 2006/0058287 | A1 | 3/2006 | Axten |
| 2011/0015174 | A1 | 1/2011 | Pauls |

FOREIGN PATENT DOCUMENTS

| | | |
|---|---|---|
| CA | 2366800 | 4/2003 |
| CA | 2572208 | 5/2006 |
| CN | 1919865 | 2/2007 |
| DE | 2217169 | 10/1973 |
| DE | 2217169 | 5/2006 |
| EP | 127098 | 12/1984 |
| EP | 1203766 | 5/2002 |
| EP | 1484313 | 12/2004 |
| EP | 1806342 | 7/2007 |
| WO | WO 99/65881 | 6/1999 |
| WO | WO 99/42435 | 8/1999 |
| WO | WO 99/59957 | 11/1999 |
| WO | WO 01/96310 | 12/2001 |
| WO | WO 03/010129 | 2/2003 |
| WO | WO 2004/063143 | 7/2004 |
| WO | WO 2005/077354 | 8/2005 |
| WO | WO 2005/105802 | 11/2005 |
| WO | WO 2006/002474 | 1/2006 |
| WO | WO 2006/092204 | 9/2006 |
| WO | WO 2008/015081 | 2/2008 |

OTHER PUBLICATIONS

International Search Report and Written Opinion—(PCT/CA2008/000440) Date of Mailing Jun. 23, 2008.

Chemical Abstracts Registry No. 886148-32-9 (AKos Consulting and Solutions GMBH) Feb. 7, 2006.

Giannessi, et al., "Reversible Carnitine Palmitoyltransferase Inhibitors with Broad Chemical Diversity as Potential Antidiabetic Agents", J. Med. Chem., 2001, vol. 44, pp. 2383-2386.

Giannessi, et al., "Discovery of a Long-Chain Carbamoyl Aminocarnitine Derivative, a Reversible Carnitine Palmitoyltransferase Inhibitor with Antiketotic and Antidiabetic Activity", J. Med. Chem., 2003, vol. 46, pp. 303-309.

Zhang, et al., "Total synthesis and reassignment of stereochemistry of obyanamide", Tetrahedron, 2006, vol. 62, pp. 9966-9972.

Zhang, et al., "Synthesis of Obyanamide, a Marine Cytotoxic Cyclic Depsipeptide", Chinese Chemical Letters, 2006, vol. 17, pp. 285-288.

International Search Report and Written Opinion for Application No. PCT/CA2008/001415, dated Nov. 18, 2008.

International Preliminary Report on Patentability for Application No. PCT/CA2008/000440, dated Sep. 15, 2009.

International Preliminary Report on Patentability for Application No. PCT/CA2008/001415, dated Feb. 2, 2010.

Gilmore, et al., "Synthesis and structure-activity relationship of a novel, achiral series of TNF-alpha converting enzyme inhibitors", Bioorganic & Medicinal Chemistry Letters, 2006, vol. 16, pp. 2699-2704.

STN International, File CAPLUS, CAPLUS accession No. 2004:310829, Document No. 140:303552, Duan, et al., "Preparation of beta-amino acid derivatives as inhibitors of matrix metalloproteases and TNF-alpha", English abstract, (2004).

STN International, File CAPLUS, CAPLUS accession No. 1989:22986, Document No. 110:22986, Dobrev, et al., "The influence of steric factors on the dehydration of 3-benzoylaminoproprionic acids by acetic anhydride"; Comptes Rendus de l'Academie des Sciences, 1988, English Abstract.

STN International, File CAPLUS, CAPLUS accession No. 1974:94833, Document No. 80:94833, Arnaudov, et al., "Infrared-spectroscopic study of hydrogen bodning in 3-(acylamino)propanoic acids", Godishnik na Sofiiskiya Universitet Sv. Kliment Okhridski, Khimicheski Fakultet, 1973, English Abstract.

Synthesis of novel, achiral, and reversible inhibitors of carnitine palmitoyltransferase I. Brinkman, John A. et al., Sandoz Research Institute, Sandoz Pharmaceutical Corporation, East Hanover, NJ, ESA. Book of Abstracts, 213th ACS National Meeting, San Francisco, Apr. 13-17, 1997, ORGN-565. Publisher: American Chemical Society, Washington DC CODEN: 64AOAA Conference; Meeting Abstract written in English. AN 1997:162827 CAPLUS (Copyright © 2008 ACS on SciFinder®).

* cited by examiner

INHIBITORS OF CARNITINE PALMITOYLTRANSFERASE AND TREATING CANCER

RELATED APPLICATIONS

This application is the U.S. National Stage of International Application No. PCT/CA2008/000440, filed Mar. 6, 2008, published in English, and claims priority under 35 U.S.C. §119 or 365 to U.S. Provisional Application No. 60/893,999, filed on Mar. 9, 2007 and U.S. Provisional Application No. 60/962,865, filed on Aug. 1, 2007. The entire teachings of the above applications are incorporated herein by reference.

BACKGROUND OF THE INVENTION

Fatty acids are catabolized, mostly, in the mitochondria through the β-oxidation pathway, where the carnitine palmitoyltransferase (CPT) system plays a key role in transporting long chain fatty acids (FAs) from the cytoplasm to the mitochondrial matrix. The CPT enzymatic system includes the members CPT1A and CPT1B, which are localized in the outer mitochondrial membrane, and CPT2, localized to the inner mitochondrial membrane. While CPT2 seems to be found in the mitochondrial membranes, regardless of the location of the organelle, the CPT1 isoforms have been found to vary with tissue. CPT1A occurs in the liver and CPT has been found in muscle. A new protein having sequence homology with CPT1 has been recently identified and given then name CPT1C.

Applicants described in a co-pending U.S. Provisional Application No. 60/893,649, filed on Mar. 8, 2007 (the entire teachings of which are incorporated herein by reference), that CPT1C is a determinant of cell growth and survival, in particular under hypoxic conditions, such as in a tumor in which the cells are rapidly dividing to the point where hypoxic conditions develop locally in the patient tissue: (a) CPT1C has been found to be up-regulated transcriptionally by p53 in vitro and in vivo; (b) depletion of CPT1C in mouse embryonic (ES) stem cells using a gene-trap was found to result in a decrease of cell proliferation, a smaller cell size and a spontaneous activation of the intrinsic mitochondrial apoptosis pathway evidenced by reduced mitochondrial membrane potential and increased caspase activation; (c) CPT1C-deficient mouse ES cells were more sensitive to glucose deprivation or hypoxia, a condition widely observed in tumors; (d) examination by electron microscopy showed swelling of the mitochondria of the CPT1C-depleted ES cells and lipid droplets in the cell, neither being present in the ES cells heterozygous for CPT1C; (e) CPT expression was shown to increase in human breast, lung and colon cancer cells lines subjected to hypoxic conditions; (f) CPT1C mRNA levels were measured in paired tumor and matched normal tissues and found to be increased in 15 out of 19 of the lung tumor tissues examined; and (g) growth of human cancer cells in which CPT1C expression was knocked down by small interference RNA was inhibited and further reduced under hypoxic conditions.

In addition, Applicants described in a co-pending U.S. Provisional Application No. 60/893,999, filed on Mar. 9, 2007 (the entire teachings of which are incorporated herein by reference), that CPT expression is increased in a large portion of lung tumor tissues compared to normal lung tissues, and that molecular depletion or pharmacological inhibition of CPT1A leads to cell death and growth inhibition of cancer cells.

Therefore, agents which inhibit CPT1, in particular, CPT1A and/or CPT1C, have the potential to treat conditions associated with altered fatty acid metabolism. There is a need for additional agents which can act as glucosylceramide synthase inhibitors.

SUMMARY OF THE INVENTION

It has now been discovered that compounds represented by Structural Formula (I) and pharmaceutically acceptable salts thereof can effectively inhibit CPT1, in particular CPT1A. As such, these compounds can be used for treating cancer. In addition, these compounds can be used for treating diabetes. Based upon this discovery, novel CPT inhibitors, pharmaceutical compositions comprising CPT inhibitors, and methods of treatment using CPT inhibitors are disclosed herein.

In one embodiment, the present invention is directed to a compound represented by Structural Formula (I) or a pharmaceutically acceptable salt thereof:

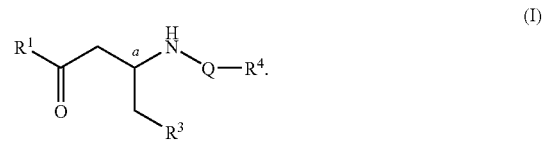

(I)

$R^1$ is —OH or —OC$_{1-6}$ alkyl.
$R^3$ is —N($R^7R^8$), —N$^+$($R^7R^8R^9$)X$^-$, or —C($R^7R^8R^9$).
Each of $R^7$, $R^8$, $R^9$ independently is —H or C$_{1-6}$ alkyl.
X$^-$ is a pharmaceutically acceptable counter ion.
Q is —C(=O)—, —C(=S)—, —C(O)NH— or —C(S)NH—; and $R^4$ is a substituted or unsubstituted aryl group, or a substituted or unsubstituted heteroaryl group, provided that when $R^4$ is a substituted or unsubstituted phenyl group, then $R^3$ is —N$^+$($R^7R^8R^9$)X$^-$.

Alternatively, Q is —C(=NH)—, —S(O)—, —S(O)$_2$—, —S(O)—NH—, or —S(O)$_2$—NH—; and $R^4$ is a substituted or unsubstituted aryl group, or substituted or unsubstituted heteroaryl group, provided that when Q is —S(O)$_2$—, then $R^4$ is not a tolyl group.

Alternatively, Q is —C(=O)—N($R^5$)—, —C(=S)—N($R^5$)—, —C(=NH)—N($R^5$)—, —S(O)—N($R^5$)— or —S(O)$_2$—N($R^5$)—; and $R^4$ and $R^5$ are each independently a substituted or unsubstituted aliphatic group, a substituted or unsubstituted aryl group, or a substituted or unsubstituted heteroaryl group, or $R^4$ and $R^5$ taken together with the nitrogen atom of N($R^4R^5$) form a substituted or unsubstituted non-aromatic heterocyclic ring.

In another embodiment, the present invention is directed to a pharmaceutical composition comprising a pharmaceutically acceptable carrier and a compound represented by Structural Formula (I) or a pharmaceutically acceptable salt thereof.

$R^1$ is —OH or —OC$_{1-6}$alkyl.
$R^3$ is —N($R^7R^8$), —N$^+$($R^7R^8R^9$)X$^-$, or —C($R^7R^8R^9$).
Each of $R^7$, $R^8$ and $R^9$ independently is —H or C$_{1-6}$alkyl.
X$^-$ is a pharmaceutically acceptable counter ion.
Q is —C(=O)—, —C(=S)—, —C(O)NH—, —C(S)NH—, —C(=NH)—, —S(O)—, —S(O)$_2$—, —S(O)—NH—, or —S(O)$_2$—NH—; and $R^4$ is a substituted or unsubstituted aryl group, or a substituted or unsubstituted heteroaryl group, provided that when $R^4$ is a substituted or unsubstituted phenyl group, then $R^3$ is —N$^+$($R^7R^8R^9$)X$^-$.

Alternatively, Q is —C(=O)—N($R^5$)—, —C(=S)—N($R^5$)—, —C(=NH)—N($R^5$)—, —S(O)—N($R^5$)— or —S(O)$_2$—N($R^5$)—; and $R^4$ and $R^5$ are each independently a substituted or unsubstituted aliphatic group, a substituted or unsubstituted aryl group, or a substituted or unsubstituted heteroaryl group, or R⁴ and R⁵ taken together with the nitrogen atom of N(R⁴R⁵) form a substituted or unsubstituted non-aromatic heterocyclic ring.

In yet another embodiment, the present invention is directed to a method of treating a subject having cancer, comprising administering to the subject a therapeutically effective amount of a compound represented by Structural Formula (I) or a pharmaceutically acceptable salt thereof. Values for the variables of Structural Formula (I) are as described above for the pharmaceutical composition of the invention.

The present invention also includes a method of treating a subject with a condition or disease selected from the group consisting of diabetes; a condition or disease mediated by metalloproteases, tumor necrosis factor, aggrecanase or a combination thereof; and a condition or disease mediated by Cholecystokinins. The method comprises administering to the subject a therapeutically effective amount of a compound represented by Structural Formula (I) or a pharmaceutically acceptable salt thereof. Values for the variables of Structural Formula (I) are as described above for the pharmaceutical composition of the invention.

Also, included in the present invention is the use of a compound represented by Structural Formula (I) or a pharmaceutically acceptable salt thereof for the manufacture of a medicament, wherein values for the variables of Structural Formula (I) are as described above for the pharmaceutical composition of the invention. The medicament is for treating a subject having cancer. Alternatively, the medicament is for treating a condition or disease of a subject in need thereof, wherein the condition or disease is diabetes; a condition or disease mediated by metalloproteases, tumor necrosis factor, aggrecanase or a combination thereof; or a condition or disease mediated by Cholecystokinins.

Also, included in the present invention is the use of a compound represented by Structural Formula (I) or a pharmaceutically acceptable salt thereof for therapy, such as treating cancer, diabetes, a condition or disease mediated by metalloproteases, tumor necrosis factor, aggrecanase or a combination thereof, or a condition or disease mediated by Cholecystokinins. Values for the variables of Structural Formula (I) are as described above for the pharmaceutical composition of the invention.

Also, included in the present invention is the use of a compound represented by Structural Formula (I) or a pharmaceutically acceptable salt thereof for treating cancer, diabetes, a condition or disease mediated by metalloproteases, tumor necrosis factor, aggrecanase or a combination thereof, or a condition or disease mediated by Cholecystokinins. Values for the variables of Structural Formula (I) are as described above for the pharmaceutical composition of the invention.

The present invention also includes a method of treating cancer comprising administering an effective amount of a compound represented by Structural Formula (XVIII):

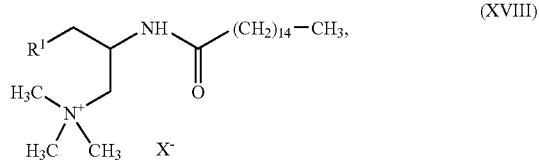

(XVIII)

wherein R¹ is —OH or —OC₁₋₆ alkyl, and X⁻ is a pharmaceutically acceptable counter ion. The cancer is selected from the group consisting of lung cancer, breast cancer, colon cancer, brain cancer, neuroblastoma, prostate cancer, melanoma, glioblastoma mutiform, ovarian cancer, lymphoma, leukemia, melanoma, sarcoma, paraneoplasia, osteosarcoma, germinoma, glioma and mesothelioma.

Also, included in the present invention is the use of a compound represented by Structural Formula (XVIII) or a pharmaceutically acceptable salt thereof for the manufacture of a medicament, wherein values for the variables of Structural Formula (XVIII) are as described above. The medicament is for treating a subject having cancer.

The use of a compound represented by Structural Formula (XVIII) or a pharmaceutically acceptable salt thereof for therapy, such as treating cancer, is also included in the present invention. Values for the variables of Structural Formula (XVIII) are as described above.

The present invention also includes the use of a compound represented by Structural Formula (XVIII) or a pharmaceutically acceptable salt thereof for treating cancer. Values for the variables of Structural Formula (XVIII) are as described above.

The compounds of the invention are inhibitors of CPT1, in particular CPT1A. As such, they can be used for treating various disorders associated with fatty acid metabolism, including cancer and diabetes.

DETAILED DESCRIPTION OF THE INVENTION

Figure 1:
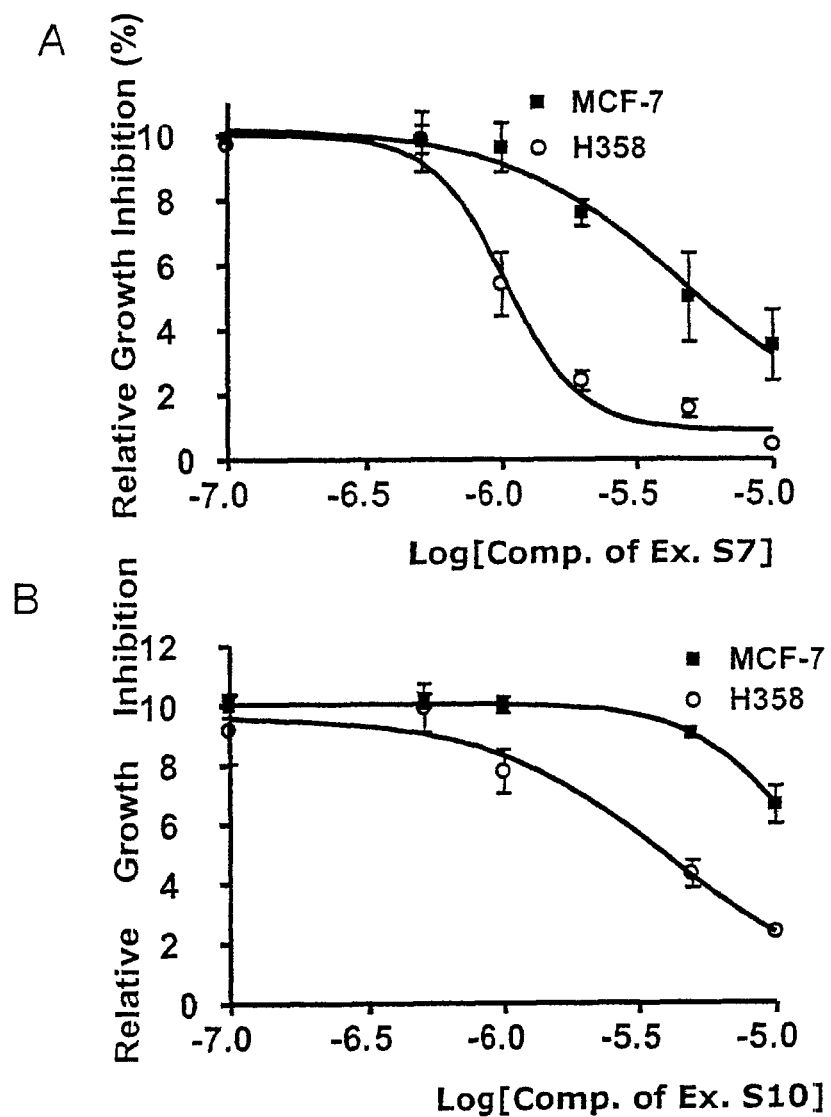
FIG. 1 shows that the compounds of Example S7 and S10 inhibit the growth of human cancer cells. Breast (MCF-7) and lung cancer cell line (H358) were cultured in 96-well plates for 24 h, and then treated with different concentrations of the compound of Example S7 (A)(GI$_{50}$ for MCF-7=5±1.3 µM, GI$_{50}$ for H358=1.0±0.3 µM) or S10 (B) (GI$_{50}$ for MCF-7=1±0.1 µM, GI$_{50}$ for H358=4.1±1.3 µM) for 6 days. Cell growth was measured by SRB assay. The percentage (%) of relative growth inhibition was calculated by comparing to DMSO treatment only (100%). The compound concentration axes were presented in log-space. The values were mean±SD from 2 independent experiments with triplicated data per experiment. GI$_{50}$ (growth inhibition) is the compound concentration that causes 50% inhibition of cell growth. IC$_{50}$ is the compound concentration that causes 50% inhibition of CPT1A activity measured in a biochemical assay.

In one aspect, the invention is directed to a compound represented by Structural Formula (I), or a pharmaceutically acceptable salt thereof. A first set of values and preferred values for the variables in Structural Formula (I) are provided in the following paragraphs.

$R^1$ is —OH or —OC$_{1-6}$ alkyl. Preferably, $R^1$ is —OH, —OCH$_3$ or —OC$_2$H$_5$.

$R^3$ is —N(R$^7$R$^8$), —N$^+$(R$^7$R$^8$R$^9$)X$^-$, or —C(R$^7$R$^8$R$^9$). Preferably, $R^3$ is —N(R$^7$R$^8$) or —N$^+$(R$^7$R$^8$R$^9$)X$^-$. More preferably, $R^3$ is —N$^+$(R$^7$R$^8$R$^9$)X$^-$.

X$^-$ is a pharmaceutically acceptable counter ion. Suitable pharmaceutically acceptable counter ions include acetate, trifluoroacetate, benzenesulfonate, benzoate, citrate, ethanesulfonate, fumarate, gluconate, glycolate, lactate, methanesulfonate, p-toluenesulfonate, tartrate, chloride, bromide, iodide, perchlorate and the like.

Q is —C(═O)—, —C(═S)—, —C(O)NH— or —C(S)NH—; and $R^4$ is a substituted or unsubstituted aryl group, or a substituted or unsubstituted heteroaryl group, provided that when $R^4$ is a substituted or unsubstituted phenyl group, then $R^3$ is —N$^+$(R$^7$R$^8$R$^9$)X$^-$.

Alternatively, Q is —C(═NH)—, —S(O)—, —S(O)$_2$—, —S(O)—NH—, or —S(O)$_2$—NH—; and $R^4$ is a substituted or unsubstituted aryl group, or substituted or unsubstituted heteroaryl group, provided that when Q is —S(O)$_2$—, then $R^4$ is not a tolyl group.

In another alternative, Q is —C(═O)—N(R$^5$)—, —C(═S)—N(R$^5$)—, —C(═NH)—N(R$^5$)—, —S(O)—N(R$^5$)— or —S(O)$_2$—N(R$^5$)—; and $R^4$ and $R^5$ are each independently a substituted or unsubstituted aliphatic group, a substituted or unsubstituted aryl group, or a substituted or unsubstituted heteroaryl group, or $R^4$ and $R^5$ taken together with the nitrogen atom of N(R$^4$R$^5$) form a substituted or unsubstituted non-aromatic heterocyclic ring.

Preferably, $R^4$ is a substituted or unsubstituted C$_{6-14}$ aryl group, or a substituted or unsubstituted 5-14 membered heterocyclic group. More preferably, $R^4$ is an optionally substituted monocyclic aryl or optionally substituted monocyclic heteroaryl group, such as an optionally substituted phenyl group, or an optionally substituted 5- or 6-membered heteroaryl group, optionally not a substituted or unsubstituted six-membered N-containing heteroaryl group. Specifically preferred values for $R^4$ include:

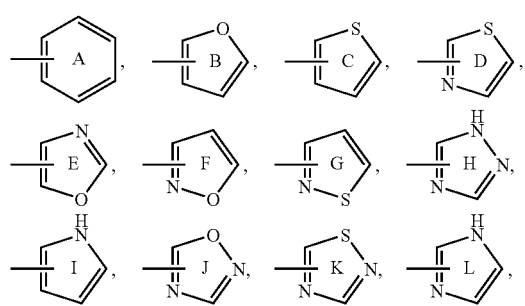

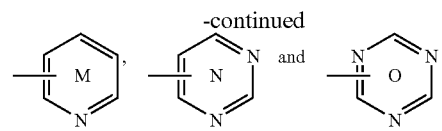

wherein each of rings A-O is optionally and independently substituted with one or more substituents. Alternatively, specifically preferred values for $R^4$ include:

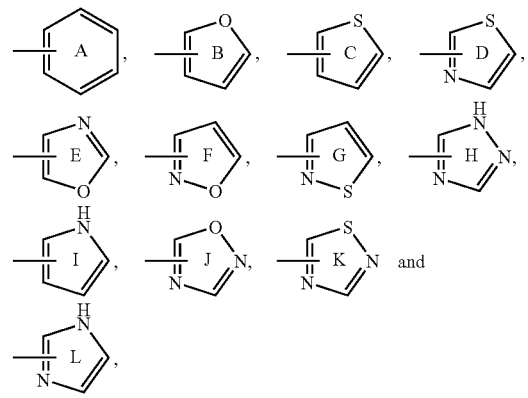

wherein each of rings A-L is optionally and independently substituted with one or more substituents. More specifically preferred values for $R^4$ include:

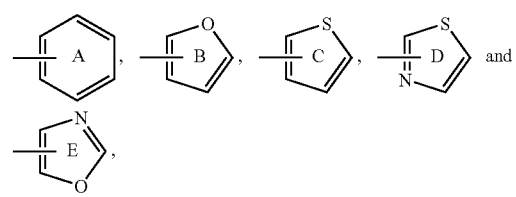

wherein each rings A-E is optionally and independently substituted with one or more substituents. Even more specifically preferred values for $R^4$ include:

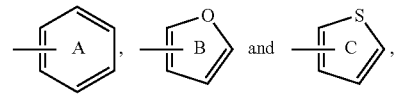

wherein each rings A-C is optionally and independently substituted with one or more substituents. A common value for $R^4$ is

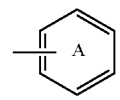

wherein ring A is optionally substituted.

Suitable substituents for the aryl or the heteroaryl group represented by $R^4$, including rings A-O, include halogen, Ak$^1$, Ar$^1$, —NO$_2$, —CN, —NCS, —C(O)OR$^{10}$, —C(O)R$^{10}$, —C(S)R$^{10}$, —OC(O)R$^{10}$, —C(O)N(R$^{11}$)$_2$, —C(S)N(R$^{11}$)$_2$, —S(O)R$^{12}$, —S(O)$_2$R$^{12}$, —SO$_3$R$^{12}$, —SO$_2$N(R$^{11}$)$_2$, —$SO_2N(R^{11})$—$NR^{11}$, —$OR^{10}$, —$SR^{10}$, —$N(R^{11})_2$, —$NR^{11}C(O)R^{10}$, —$NR^{11}S(O)R^{12}$, —$NR^{11}C(O)OR^{12}$, —$N(R^{11})C(O)N(R^{11})_2$, —$NR^{11}SO_2N(R^{11})_2$, —$NR^{11}SO_2R^{12}$, —$O$—$[CH_2]_p$—$O$—, —$S$—$[CH_2]_p$—$S$— and —$[CH_2]_q$—. Preferably, substituents for the aryl or the heteroaryl group represented by $R^4$, including rings A-O, include $Ak^1$, —$NO_2$, —$CN$, —$OR^{10}$, —$SR^{10}$, —$C(O)OR^{10}$, —$C(O)R^{10}$, —$C(S)R^{10}$, —$OC(O)R^{10}$, —$C(O)N(R^{11})_2$, —$C(S)N(R^{11})_2$, —$N(R^{11})_2$, —$NR^{11}C(O)R^{10}$, —$NR^{11}C(O)OR^{12}$, —$N(R^{11})C(O)N(R^{11})_2$ and —$NR^{11}SO_2R^{12}$. More preferably, substituents for the aryl or the heteroaryl group represented by $R^4$, including rings A-O, include halogen, $Ak^1$, —$OR^{10}$ and —$SR^{10}$. Even more preferably, substituents for the aryl or the heteroaryl group represented by $R^4$, including rings A-O, include halogen, $C_{1-15}$ alkyl, $C_{1-15}$ haloalkyl, —$C_{2-6}$ alkynylene-$(C_{1-10}$ alkyl), —$C_{2-6}$ alkynylene-$Ar^2$, —$C_{1-6}$ alkylene-$Ar^2$, —$C_{1-6}$ alkylene-$N(R^{21})_2$, —$C_{1-6}$ alkylene-$O$—$Ar^2$, —$C_{1-6}$ alkylene-$O$-$Ak^2$-$Ar^2$, —$C_{1-6}$ alkylene-$S$—$Ar^2$, —$C_{1-6}$ alkylene-$S$-$Ak^2$-$Ar^2$, —$OC_{1-10}$ alkyl, —$O$—$C_{1-6}$ alkylene-$Ar^0$, —$SC_{1-10}$ alkyl and —$S$—$C_{1-6}$ alkylene-$Ar^0$. Specific examples of substituents for the aryl or the heteroaryl group represented by $R^4$, including rings A-O, include halogen; C1-C10 alkyl (e.g., methyl, ethyl, propyl, butyl and pentyl); C1-C3 haloalkyl; —O(C1-C10 alkyl); —$O$—$CH_2$—$CF_3$; phenyl; —O-Ph; —O-naphthyl; —O—$(CH_2)$-Ph; —$(CH_2)_2$-Ph;

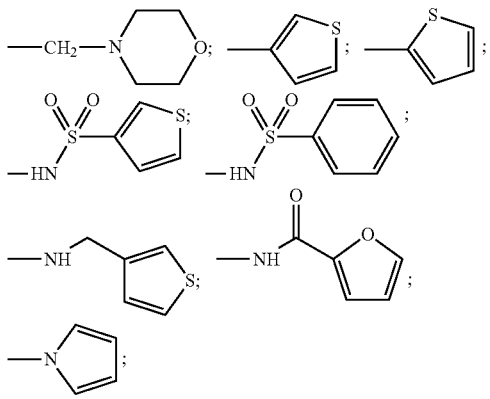

—$(C\equiv C)$-Ph; —$(C\equiv C)$—C1-C5 alkyl, —$CH_2$—O-Ph; —$CH_2$—S-Ph; —$CH_2$—O—$CH_2$-Ph; —$CH_2$—S—$CH_2$-Ph; and —$NH(C=O)$—$CH_3$, wherein each of the Ph (i.e., phenyl), naphthyl, thionyl, pyrrolyl and furanyl group is optionally substituted with one or more substituents selected from the group consisting of halogen, C1-C5 alkyl, methoxy, ethoxy and —$CF_3$.

Alternatively, when Q is —$C(=O)$—$N(R^5)$—, —$C(=S)$—$N(R^5)$—, —$C(=NH)$—$N(R^5)$—, —$S(O)$—$N(R^5)$— or —$S(O)_2$—$N(R^5)$—, $R^4$ is a substituted or unsubstituted aliphatic group. Specifically, $R^4$ is a substituted or unsubstituted $C_{1-15}$ aliphatic group, such as $C_{1-15}$ alkyl, $C_{1-15}$ haloalkyl, —$C_{2-6}$ alkynylene-$(C_{1-10}$alkyl), —$C_{2-6}$ alkynylene-$Ar^2$, —$C_{1-6}$ alkylene-$Ar^2$, —$C_{1-6}$ alkylene-$N(R^{21})_2$, —$C_{1-6}$alkylene-$O$—$Ar^2$, alkylene-$O$-$Ak^2$-$Ar^2$, —$C_{1-6}$alkylene-$S$—$Ar^2$ or —$C_{1-6}$alkylene-$S$-$Ak^2$-$Ar^2$. More specific examples of $R^4$ include —$(C_{1-10}$ aliphatic group)-O-Ph-O—$(C_{1-10}$ aliphatic group) and —$(C_{1-10}$ aliphatic group)-S-Ph-S—$(C_{1-10}$ aliphatic group), wherein Ph is phenyl.

Suitable substituents for the aliphatic group represented by $R^4$ include halogen, $Ar^1$, —$NO_2$, —$CN$, —$NCS$, —$C(O)$$OR^{10}$, —$C(O)R^{10}$, —$C(S)R^{10}$, —$OC(O)R^{10}$, —$C(O)N(R^{11})_2$, —$C(S)N(R^{11})_2$, —$S(O)R^{12}$, —$S(O)_2R^{12}$, —$SO_3R^{12}$, —$SO_2N(R^{11})_2$, —$SO_2N(R^{11})$—$NR^{11}$, —$OR^{10}$, —$SR^{10}$, —$N(R^{11})_2$, —$NR^{11}C(O)R^{10}$, —$NR^{11}S(O)R^{12}$, —$NR^{11}C(O)$$OR^{12}$, —$N(R^{11})C(O)N(R^{11})_2$, —$NR^{11}SO_2N(R^{11})_2$, —$NR^{11}SO_2R^{12}$, —$O$—$[CH_2]_p$—$O$—, —$S$—$[CH_2]_p$—$S$— and —$[CH_2]_q$—. Preferably, substituents for the aliphatic group represented by $R^4$ include $Ar^1$, —$NO_2$, —$CN$, —$OR^{10}$, —$SR^{10}$, —$C(O)OR^{10}$, —$C(O)R^{10}$, —$C(S)R^{10}$, —$OC(O)R^{10}$, —$C(O)N(R^{11})_2$, —$C(S)N(R^{11})_2$, —$N(R^{11})_2$, —$NR^{11}C(O)R^{10}$, —$NR^{11}C(O)OR^{12}$, —$N(R^{11})C(O)N(R^{11})_2$ and —$NR^{11}SO^2R^{12}$. More preferably, substituents for the aliphatic group represented by $R^4$ include halogen, $Ar^1$, —$OR^{10}$ and —$SR^{10}$. Even more preferably, substituents for the aliphatic group represented by $R^4$ include halogen, —$O$—$Ar^2$, —$O$-$Ak^2$-$Ar^2$, —$S$—$Ar^2$, —$S$-$Ak^2$-$Ar^2$, —$OC_{1-10}$ alkyl, —$O$—$C_{1-6}$ alkylene-$Ar^0$, —$SC_{1-10}$ alkyl and —$S$—$C_{1-6}$ alkylene-$Ar^0$.

Each $R^5$ is independently an optionally substituted aliphatic group, optionally substituted aryl, or optionally substituted heteroaryl group. Preferred values of the aryl and heteroaryl group represented by $R^5$ are as described above for the aryl and heteroaryl group represented by $R^4$. Preferably, $R^5$ is an optionally substituted aliphatic group. More preferably, $R^5$ is an optionally substituted C1-C20 aliphatic group. More preferably, $R^5$ is an optionally substituted C1-C20 alkyl group. Even more preferably, $R^5$ is an unsubstituted C1-C10 alkyl group, such as methyl, ethyl, propyl, butyl and pentyl.

Suitable substituents for the aliphatic group represented by $R^5$ include halogen, $Ar^3$, —$NO_2$, —$CN$, —$NCS$, —$C(O)$$OR^{30}$, —$C(O)R^{30}$, —$C(S)R^{30}$, —$OC(O)R^{30}$, —$C(O)N(R^{31})_2$, —$C(S)N(R^{31})_2$, —$S(O)R^{32}$, —$S(O)_2R^{32}$, —$SO_3R^{32}$, —$SO_2N(R^{31})_2$, —$SO_2N(R^{31})$—$NR^{31}$, —$OR^{30}$, —$SR^{30}$, —$N(R^{31})_2$, —$NR^{31}C(O)R^{30}$, —$NR^{31}S(O)R^{32}$, —$NR^{31}C(O)$$OR^{32}$, —$N(R^{31})C(O)N(R^3)_2$, —$NR^{31}SO_2N(R^{31})_2$, and —$NR^{31}SO_2R^{32}$. Preferably, substituents for the aliphatic group represented by $R^5$ include $Ar^3$, —$NO_2$, —$CN$, —$OR^{30}$, —$SR^{30}$, —$C(O)OR^{30}$, —$C(O)R^{30}$, —$C(S)R^{30}$, —$OC(O)R^{30}$, —$C(O)N(R^{31})_2$, —$C(S)N(R^{31})_2$, —$N(R^{31})_2$, —$NR^{31}C(O)R^{30}$, —$NR^{31}C(O)OR^{32}$, —$N(R^{31})C(O)N(R^{31})_2$ and —$NR^{31}SO_2R^{32}$. Specific examples of substituents for the aliphatic group represented by $R^5$ include halogen, C1-C3 haloalkyl, —$O$—$CH_2$—$(C_{1-3}$ haloalkyl), Ph; —O-Ph, —$S$—$CH_2$—$(C_{1-3}$ haloalkyl), and —S-Ph, wherein each of the Ph (i.e., phenyl) group is optionally substituted with one or more substituents selected from the group consisting of halogen, C1-C7 alkyl (e.g., C3-C7 alkyl), C1-C7 alkoxy (e.g., —$OC_5H_{11}$ or —$OC_6H_{13}$), C1-3 haloalkyl (e.g., —$CF_3$).

Suitable substituents for the aryl or the heteroaryl group represented by $R^5$ include halogen, $Ak^3$, $Ar^3$, —$NO_2$, —$CN$, —$NCS$, —$C(O)OR^{30}$, —$C(O)R^{30}$, —$C(S)R^{30}$, —$OC(O)$$R^{30}$, —$C(O)N(R^{31})_2$, —$C(S)N(R^{31})_2$, —$S(O)R^{32}$, —$S(O)_2$$R^{32}$, —$SO_3R^{32}$, —$SO_2N(R^{31})_2$, —$SO_2N(R^{31})$—$NR^{31}$, —$OR^{30}$, —$SR^{30}$, —$N(R^{31})_2$, —$NR^{31}C(O)R^{30}$, —$NR^{31}S(O)$$R^{32}$, —$NR^{31}C(O)OR^{32}$, —$N(R^{31})C(O)N(R^{31})_2$, —$NR^-$$SO_2N(R^{31})_2$, —$NR^{31}SO_2R^{32}$, —$O$—$[CH_2]_p$—$O$—, —$S$—$[CH_2]_p$—$S$— and —$[CH_2]_q$—. Preferably, substituents for the aryl or the heteroaryl group represented by $R^5$ include $Ak^3$, —$NO_2$, —$CN$, —$OR^{30}$, —$SR^{30}$, —$C(O)OR^{30}$, —$C(O)$$R^{30}$, —$C(S)R^{30}$, —$OC(O)R^{30}$, —$C(O)N(R^{31})_2$, —$C(S)N$$(R^{31})_2$, —$N(R^{31})_2$, —$NR^{31}C(O)R^{30}$, —$NR^{31}C(O)OR^{32}$, —$N(R^{31})C(O)N(R^{31})_2$ and —$NR^{31}SO_2R^{32}$. More preferably, substituents for the aryl or the heteroaryl group represented by $R^5$ include halogen, $Ak^3$, —$OR^{30}$ and —$SR^{30}$. Even more preferably, substituents for the aryl or the heteroaryl group represented by $R^5$ halogen, $C_{1-15}$ alkyl, $C_{1-15}$ haloalkyl, —$C_{2-6}$ alkynylene-$(C_{1-10}$alkyl), —$C_{2-6}$ alkynylene-$Ar^4$, —$C_{1-6}$ alkylene-$Ar^4$, —$C_{1-6}$ alkylene-$N(R^{31})_2$, —$C_{1-6}$ alkylene-O—$Ar^4$, —$C_{1-6}$ alkylene-O-$Ak^4$-$Ar^4$, —$C_{1-6}$ alkylene-S—$Ar^4$, —$C_{1-6}$ alkylene-S-$Ak^4$-$Ar^4$, —$OC_{1-10}$alkyl, —O—$C_{1-6}$ alkylene-$Ar^{00}$, —$SC_{1-10}$alkyl and —S—$C_{1-6}$ alkylene-$Ar^{00}$. Specific examples of substituents for the aryl or the heteroaryl group represented by $R^5$, including rings A-O, include halogen; C1-C10 alkyl (e.g., methyl, ethyl, propyl, butyl and pentyl); C1-C3 haloalkyl; —O(C1-C10 alkyl); —O—$CH_2$—$CF_3$; phenyl; —O-Ph; —O-naphthyl; —O—$(CH_2)$-Ph; —$(CH_2)_2$-Ph;

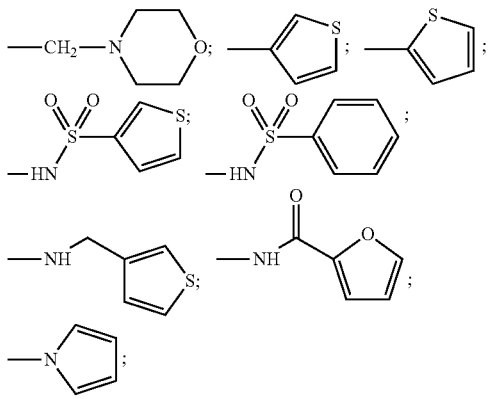

—(CC)-Ph; —(CC)—C1-C5 alkyl, —$CH_2$—O-Ph; —$CH_2$—S-Ph; —$CH_2$—O—$CH_2$-Ph; —$CH_2$—S—$CH_2$-Ph; and —NH(C═O)—$CH_3$, wherein each of the Ph (i.e., phenyl), naphthyl, thionyl, pyrrolyl and furanyl group is optionally substituted with one or more substituents selected from the group consisting of halogen, C1-C5 alkyl, methoxy, ethoxy and —$CF_3$.

Alternatively, $R^4$ and $R^5$ taken together with the nitrogen atom of $N(R^4R^5)$ form a substituted or unsubstituted non-aromatic heterocyclic ring. Preferably, the non-aromatic heterocyclic ring is 5-14 membered. More preferably, the non-aromatic heterocyclic ring is an unsubstituted five- or six-membered ring.

Suitable substituents for the non-aromatic heterocyclic ring represented by $N(R^4R^5)$ include halogen, $C_{1-10}$ alkyl, $C_{2-10}$ alkenyl, $C_{2-10}$ alkynyl, amino, $C_{1-10}$ alkylamino, $C_{1-10}$ dialkylamino, $C_{1-10}$alkoxy, nitro, cyano, hydroxy, $C_{1-10}$ alkoxycarbonyl, $C_{1-10}$ alkylcarbonyl, $C_{1-10}$haloalkoxy, $(C_{1-10}$ haloalkoxy)$C_{1-10}$ alkyl, $C_{1-10}$ haloalkyl, $C_{6-14}$ aryl and $C_{5-14}$ heteroaryl. Preferably, suitable substituents for the non-aromatic heterocyclic ring represented by $N(R^4R^5)$ include halogen, $C_{1-6}$ alkyl, $C_{2-6}$ alkenyl, $C_{2-6}$ alkynyl, amino, $C_{1-6}$ alkylamino, $C_{1-6}$ dialkylamino, $C_{1-6}$ alkoxy, nitro, cyano, hydroxy, $C_{1-6}$ alkoxycarbonyl, $C_{1-6}$ alkylcarbonyl, $C_{1-6}$ haloalkoxy, $(C_{1-6}$ haloalkoxy)$C_{1-6}$ alkyl, $C_{1-6}$ haloalkyl, $C_{6-14}$ aryl and $C_{5-14}$ heteroaryl.

Each of $R^7$, $R^8$ and $R^9$ independently is —H or $C_{1-6}$ alkyl. Preferably, each of $R^7$, $R^8$ and $R^9$ independently is $C_{1-6}$ alkyl. More preferably, each of $R^7$, $R^8$ and $R^9$ independently is methyl or ethyl. Even more preferably, each of $R^7$, $R^8$ and $R^9$ independently is methyl.

Each $R^{10}$ independently is i) hydrogen; ii) a $C_{1-20}$ aliphatic group optionally substituted with one or more substituents selected from the group consisting of halogen, —$NO_2$, —CN, —$Ar^0$, —$OR^{25}$, —O-$Ak^0$-$Ar^0$, —$SR^{25}$, —S-$Ak^0$-$Ar^0$, —$N(R^{26})_2$, —$NR^{26}C(O)R^{25}$, —$NR^{26}C(O)$-$Ak^0$-$Ar^0$, —$N(R^{26})C(O)N(R^{26})_2$, —$C(O)R^{25}$, —C(O)-$Ak^0$-$Ar^0$, —$C(S)R^{25}$, —C(S)-$Ak^0$-$Ar^0$, —$CO_2R^{25}$, —$CO_2$-$Ak^0$-$Ar^0$, —OC(O)—$R^{25}$, —OC(O)-$Ak^0$-$Ar^0$, —$C(O)N(R^{26})_2$—, —$C(S)N(R^{26})_2$, —$S(O)_2R^{27}$, —$S(O)_2$-$Ak^0$-$Ar^0$, —$SO_2N(R^{26})_2$, —$NR^{26}SO_2N(R^{26})_2$, —$NR^{26}SO_2R^{27}$ and —$NR^{26}SO_2$-$Ak^0$-$Ar^0$; or iii) a $C_{6-14}$ aryl or a 5-14 membered heteroaryl group each optionally and independently substituted with one or more substituents selected from the group consisting of halogen, nitro, cyano, hydroxy, $C_{1-20}$ alkyl, $C_{2-20}$ alkenyl, $C_{2-20}$ alkynyl, amino, $C_{1-20}$ alkylamino, $C_{1-20}$ dialkylamino, $C_{1-20}$ alkoxy, $(C_{1-10}$ alkoxy)$C_{1-20}$ alkyl, $C_{1-20}$ haloalkoxy, $(C_{1-10}$ haloalkoxy)$C_{1-20}$ alkyl and $C_{1-20}$ haloalkyl.

Each $R^{11}$ independently is $R^{10}$, —$CO_2R^{10}$, —$SO_2R^{10}$, or —$C(O)R^{10}$, or —$N(R^{11})_2$ taken together is an optionally substituted, 5-14 membered non-aromatic heterocyclic group. Preferably, the non-aromatic heterocyclic ring is a substituted or unsubstituted five-membered ring, or a substituted or unsubstituted six-membered ring. More preferably, the non-aromatic heterocyclic ring is an unsubstituted five- or six-membered ring. Suitable substituents, including preferred values, for the non-aromatic heterocyclic group represented by —$N(R^{11})_2$ are as described above for the non-aromatic heterocyclic group represented by —$N(R^4R^5)$.

Each $R^{12}$ independently is i) a $C_{1-20}$ aliphatic group optionally and independently substituted with one or more substituents selected from the group consisting of halogen, —$NO_2$, —CN, —$Ar^0$, —$OR^{25}$, —O-$Ak^0$-$Ar^0$, —$SR^{25}$, —S-$Ak^0$-$Ar^0$, —$N(R^{26})_2$, —$NR^{26}C(O)R^{25}$, —$NR^{26}C(O)$-$Ak^0$-$Ar^0$, —$N(R^{26})C(O)N(R^{26})_2$  $N(R^{26})C(O)N(R^{26})_2$—$C(O)R^{25}$, —C(O)-$Ak^0$-$Ar^0$, —$C(S)R^{25}$, —C(S)-$Ak^0$-$Ar^0$, —$CO_2R^{25}$, —$CO_2$-$Ak^0$-$Ar^0$, —OC(O)—$R^{25}$, —OC(O)-$Ak^0$-$Ar^0$, —$C(O)N(R^{26})_2$—, —$C(S)N(R^{26})_2$, —$S(O)_2R^{27}$, —$S(O)_2$-$Ak^0$-$Ar^0$, —$SO_2N(R^{26})_2$, —$NR^{26}SO_2N(R^{26})_2$, —$NR^{26}SO_2R^{27}$ and —$NR^2SO_2$-$Ak^0$-$Ar^0$; or ii) a $C_{6-14}$ aryl or a 5-14 membered heteroaryl group each optionally and independently substituted with one or more substituents selected from the group consisting of halogen, nitro, cyano, hydroxy, $C_{1-20}$ alkyl, $C_{2-20}$ alkenyl, $C_{2-20}$ alkynyl, amino, $C_{1-20}$ alkylamino, $C_{1-20}$ dialkylamino, $C_{1-20}$ alkoxy, $(C_{1-10}$ alkoxy)$C_{1-20}$ alkyl, $C_{1-20}$ haloalkoxy, $(C_{1-10}$ haloalkoxy)$C_{1-20}$ alkyl and $C_{1-20}$ haloalkyl.

Preferably, each of $R^{10}$ and $R^{12}$ independently is i) a $C_{1-10}$ aliphatic group optionally substituted with one or more substituents selected from the group consisting of halogen, —$NO_2$, —CN, —$Ar^0$, —$OR^{25}$, —O-$Ak^0$-$Ar^0$, —$SR^{25}$, —S-$Ak^0$-$Ar^0$—$N(R^{26})_2$, —$NR^{26}C(O)R^{25}$, —$NR^{26}C(O)$-$Ak^0$-$Ar^0$, —$C(O)R^{25}$, —C(O)-$Ak^0$-$Ar^0$, —$CO_2R^{25}$, —$CO_2$-$Ak^0$-$Ar^0$ and —$C(O)N(R^{26})_2$—; or a $C_{6-14}$ aryl or a 5-14 membered heteroaryl group each optionally and independently substituted with one or more substituents selected from the group consisting of halogen, nitro, cyano, hydroxy, $C_{1-10}$ alkyl, $C_{2-10}$ alkenyl, $C_{2-10}$ alkynyl, amino, $C_{1-10}$ alkylamino, $C_{1-10}$ dialkylamino, $C_{1-10}$ alkoxy, $(C_{1-6}$ alkoxy)$C_{1-10}$ alkyl, $C_{1-10}$ haloalkoxy, $(C_{1-6}$ haloalkoxy)$C_{1-10}$ alkyl and $C_{1-10}$ haloalkyl. More preferably, each of $R^{10}$ and $R^{12}$ independently is i) a $C_{1-10}$ aliphatic group optionally substituted with one or more substituents selected from the group consisting of halogen, —$Ar^0$, —$OR^{25}$, —O-$Ak^0$-$Ar^0$, —$SR^{25}$, —S-Ale-$Ar^0$ and —$N(R^{26})_2$; or ii) an $C_{6-14}$ aryl or a 5-14 membered heteroaryl group each optionally and independently substituted with one or more substituents selected from the group consisting of halogen, nitro, cyano, hydroxy, $C_{1-6}$ alkyl, $C_{2-6}$ alkenyl, $C_{2-6}$ alkynyl, amino, $C_{1-6}$ alkylamino, $C_{1-6}$ dialkylamino, $C_{1-6}$ alkoxy, $(C_{1-6}$ alkoxy)$C_{1-6}$ alkyl, $C_{1-6}$ haloalkoxy, $(C_{1-6}$ haloalkoxy)$C_{1-6}$ alkyl and $C_{1-6}$ haloalkyl.

Each of $R^{20}$ and $R^{25}$ independently is i) hydrogen; ii) a $C_{6-14}$ aryl or a 5-14 membered heteroaryl group each optionally and independently substituted with one or more substituents selected from the group consisting of halogen, nitro, cyano, hydroxy, $C_{1-15}$ alkyl, $C_{2-15}$ alkenyl, $C_{2-15}$ alkynyl, amino, $C_{1-15}$ alkylamino, $C_{1-15}$ dialkylamino, $C_{1-15}$ alkoxy, $(C_{1-10}$alkoxy$)C_{1-15}$alkyl, $C_{1-15}$ haloalkoxy, $C_{1-15}$ haloalkyl and $(C_{1-10}$haloalkoxy$)C_{1-15}$ alkyl; or iii) a $C_{1-15}$ alkyl group optionally substituted with one or more substituents selected from the group consisting of halogen, hydroxyl, amino, $C_{1-15}$ alkylamino, $C_{1-15}$ dialkylamino, $C_{1-15}$alkoxy, nitro, cyano, $C_{1-15}$ alkoxycarbonyl, $C_{1-15}$ alkylcarbonyl and $C_{1-15}$ haloalkoxy. Preferably, each of $R^{20}$ and $R^{25}$ independently is i) hydrogen, ii) a $C_{6-14}$ aryl or a 5-14 membered heteroaryl group optionally and independently substituted with one or more substituents selected from the group consisting of halogen, nitro, cyano, hydroxy, $C_{1-10}$ alkyl, $C_{2-10}$ alkenyl, $C_{2-10}$ alkynyl, amino, $C_{1-10}$ alkylamino, $C_{1-10}$ dialkylamino, $C_{1-10}$ alkoxy, $(C_{1-6}$ alkoxyl$)C_{1-10}$alkyl, $C_{1-10}$haloalkoxy, $C_{1-10}$haloalkyl and $(C_{1-6}$ haloalkoxy$)C_{1-10}$ alkyl; or iii) a $C_{1-10}$ alkyl group optionally and independently substituted with one or more substituents selected from the group consisting of halogen, hydroxyl, amino, $C_{1-10}$ alkylamino, $C_{1-10}$ dialkylamino, $C_{1-10}$ alkoxy, nitro, cyano, $C_{1-10}$ alkoxycarbonyl, $C_{1-10}$ alkylcarbonyl and $C_{1-10}$ haloalkoxy. More preferably, each of $R^{20}$ and $R^{25}$ independently is i) hydrogen; ii) a $C_{6-14}$ aryl or a 5-14 membered heteroaryl group each optionally and independently substituted with one or more substituents selected from the group consisting of halogen, nitro, cyano, hydroxy, $C_{1-6}$ alkyl, $C_{2-6}$ alkenyl, $C_{2-6}$ alkynyl, amino, $C_{1-6}$alkylamino, $C_{1-6}$ dialkylamino, $C_{1-6}$ alkoxy, $(C_{1-6}$alkoxy$)C_{1-6}$ alkyl, $C_{1-6}$ haloalkoxy, $C_{1-6}$ haloalkyl and $(C_{1-6}$ haloalkoxy$)C_{1-6}$ alkyl; or iii) a $C_{1-10}$ alkyl group optionally substituted with one or more substituents selected from the group consisting of halogen, hydroxyl, amino, $C_{1-6}$ alkylamino, $C_{1-6}$ dialkylamino, $C_{1-6}$ alkoxy, nitro, cyano, $C_{1-6}$ alkoxycarbonyl, $C_{1-6}$ alkylcarbonyl and $C_{1-6}$ haloalkoxy.

Each $R^{21}$ independently is $R^{20}$, —$CO_2R^{20}$, —$SO_2R^{20}$ or —$C(O)R^{20}$, or —$N(R^{21})_2$ taken together is an optionally substituted non-aromatic heterocyclic group. Preferably, the non-aromatic heterocyclic ring is a substituted or unsubstituted five-membered ring, or a substituted or unsubstituted six-membered ring. More preferably, the non-aromatic heterocyclic ring is an unsubstituted five- or six-membered ring. Suitable substituents, including preferred values, for the non-aromatic heterocyclic group represented by —$N(R^{21})_2$ are as described above for the non-aromatic heterocyclic group represented by —$N(R^4R^5)$.

Each $R^{26}$ independently is $R^{25}$, —$CO_2R^{25}$, —$SO_2R^{25}$ or —$C(O)R^{25}$, or —$N(R^{26})_2$ taken together is an optionally substituted non-aromatic heterocyclic group. Preferably, the non-aromatic heterocyclic ring is a substituted or unsubstituted five-membered ring, or a substituted or unsubstituted six-membered ring. More preferably, the non-aromatic heterocyclic ring is an unsubstituted five- or six-membered ring. Suitable substituents, including preferred values, for the non-aromatic heterocyclic group represented by —$N(R^{26})_2$ are as described above for the non-aromatic heterocyclic group represented by —$N(R^4R^5)$.

Each of $R^{22}$ and $R^{27}$ independently is i) a $C_{6-14}$ aryl or a 5-14 membered heteroaryl group each optionally and independently substituted with one or more substituents selected from the group consisting of halogen, nitro, cyano, hydroxy, $C_{1-15}$ alkyl, $C_{2-15}$ alkenyl, $C_{2-15}$ alkynyl, amino, $C_{1-15}$ alkylamino, $C_{1-15}$ dialkylamino, $C_{1-15}$ alkoxy, $(C_{1-10}$ alkoxy$)C_{1-15}$ alkyl, $C_{1-15}$ haloalkoxy, $C_{1-15}$ haloalkyl and $(C_{1-10}$ haloalkoxy$)C_{1-15}$ alkyl; or ii) a $C_{1-15}$ alkyl group optionally substituted with one or more substituents selected from the group consisting of halogen, hydroxyl, amino, $C_{1-15}$ alkylamino, $C_{1-15}$ dialkylamino, $C_{1-15}$ alkoxy, nitro, cyano, $C_{1-15}$ alkoxycarbonyl, $C_{1-15}$ alkylcarbonyl, $(C_{1-10}$ haloalkoxy$)C_{1-15}$ alkyl and $C_{1-15}$ haloalkoxy. Preferably, each $R^{22}$ and $R^{27}$ independently is i) a $C_{6-14}$ aryl or a 5-14 membered heteroaryl group optionally and independently substituted with one or more substituents selected from the group consisting of halogen, nitro, cyano, hydroxy, $C_{1-10}$ alkyl, $C_{2-10}$ alkenyl, $C_{2-10}$ alkynyl, amino, $C_{1-10}$ alkylamino, $C_{1-10}$ dialkylamino, $C_{1-10}$ alkoxy, $(C_{1-6}$ alkoxy$)C_{1-10}$ alkyl, $C_{1-10}$ haloalkoxy, $C_{1-10}$ haloalkyl and $(C_{1-6}$ haloalkoxy$)C_{1-10}$ alkyl; or ii) a $C_{1-10}$ alkyl group optionally substituted with one or more substituents selected from the group consisting of halogen, hydroxyl, amino, $C_{1-10}$ alkylamino, $C_{1-10}$ dialkylamino, $C_{1-10}$ alkoxy, nitro, cyano, $C_{1-10}$ alkoxycarbonyl, $C_{1-10}$ alkylcarbonyl and $C_{1-10}$ haloalkoxy. More preferably, each $R^{22}$ and $R^{27}$ independently is i) a $C_{6-14}$ aryl or a 5-14 membered heteroaryl group optionally and independently substituted with one or more substituents selected from the group consisting of halogen, nitro, cyano, hydroxy, $C_{1-6}$ alkyl, $C_{2-6}$ alkenyl, $C_{2-6}$ alkynyl, amino, $C_{1-6}$ alkylamino, $C_{1-6}$ dialkylamino, $C_{1-6}$ alkoxy, $(C_{1-6}$ alkoxy$)C_{1-6}$ alkyl, $C_{1-6}$ haloalkoxy, $C_{1-6}$ haloalkyl and $(C_{1-6}$ haloalkoxy$)C_{1-6}$ alkyl; or ii) a $C_{1-6}$ alkyl group optionally substituted with one or more substituents selected from the group consisting of halogen, hydroxyl, amino, $C_{1-6}$ alkylamino, $C_{1-6}$ dialkylamino, $C_{1-6}$ alkoxy, nitro, cyano, $C_{1-6}$ alkoxycarbonyl, $C_{1-6}$ alkylcarbonyl and $C_{1-6}$ haloalkoxy.

Each $R^{30}$ independently is i) hydrogen; ii) a $C_{1-20}$ aliphatic group optionally substituted with one or more substituents selected from the group consisting of halogen, —$NO_2$, —$CN$, —$Ar^{00}$, —$OR^{45}$, —$O$-$Ak^{00}$-$Ar^{00}$, —$SR^{45}$, —$S$-$Ak^{00}$-$Ar^{00}$, —$N(R^{46})_2$, —$NR^{46}C(O)R^{45}$, —$NR^{46}C(O)$-$Ak^{00}$-$Ar^{00}$, —$N(R^{46})C(O)N(R^{46})_2$, —$C(O)R^{45}$, —$C(O)$-$Ak^{00}$-$Ar^{00}$, —$C(S)R^{45}$, —$C(S)Ak^{00}$-$Ar^{00}$, —$CO_2R^{45}$, $CO_2R^{45}$, —$CO_2$-$Ak^{00}$-$Ar^{00}$, —$OC(O)$—$R^{45}$, —$OC(O)$-$Ak^{00}$-$Ar^{00}$, —$C(O)N(R^{46})_2$—, —$C(S)N(R^{46})_2$, —$S(O)_2R^{47}$, —$S(O)_2$-$Ak^{00}$-$Ar^{00}$, —$SO_2N(R^{46})_2$, —$NR^{46}SO_2N(R^{46})_2$, —$NR^{46}SO_2R^{47}$ and —$NR^{46}SO_2$-$Ak^{00}$-$Ar^{00}$; or iii) a $C_{6-14}$ aryl or a 5-14 membered heteroaryl group each optionally and independently substituted with one or more substituents selected from the group consisting of halogen, nitro, cyano, hydroxy, $C_{1-20}$ alkyl, $C_{2-20}$ alkenyl, $C_{2-20}$ alkynyl, amino, $C_{1-20}$ alkylamino, $C_{1-20}$ dialkylamino, $C_{1-20}$ alkoxy, $(C_{1-10}$ alkoxy$)C_{1-20}$ alkyl, $C_{1-20}$ haloalkoxy, $(C_{1-10}$ haloalkoxy$)C_{1-20}$ alkyl and $C_{1-20}$ haloalkyl.

Each $R^{31}$ independently is $R^{30}$, —$CO_2R^{30}$, —$SO_2R^{30}$ or —$C(O)R^{30}$, or —$N(R^{31})_2$ taken together is an optionally substituted, 5-14 membered non-aromatic heterocyclic group. Preferably, the non-aromatic heterocyclic ring is a substituted or unsubstituted five-membered ring, or a substituted or unsubstituted six-membered ring. More preferably, the non-aromatic heterocyclic ring is an unsubstituted five- or six-membered ring. Suitable substituents, including preferred values, for the non-aromatic heterocyclic group represented by —$N(R^{31})_2$ are as described above for the non-aromatic heterocyclic group represented by —$N(R^4R^5)$.

Each $R^{32}$ independently is i) a $C_{1-20}$ aliphatic group optionally substituted with one or more substituents selected from the group consisting of halogen, —$NO_2$, —$CN$, —$Ar^{00}$, —$OR^{45}$, —$O$-$Ak^{00}$-$Ar^{00}$, —$SR^{45}$, —$S$-$Ak^{00}$-$Ar^{00}$, —$N(R^{46})_2$, —$NR^{46}C(O)R^{45}$, —$NR^{46}C(O)$-$Ak^{00}$-$Ar^{00}$, —$N(R^{46})C(O)N(R^{46})_2$, —$C(O)R^{45}$, —$C(O)$-$Ak^{00}$-$Ar^{00}$, —$C(S)R^{45}$, —$C(S)$-$Ak^{00}$-$Ar^{00}$, —$CO_2R^{45}$, —$CO_2$-$Ak^{00}$-$Ar^{00}$, —$OC(O)$—$R^{45}$, —$OC(O)$-$Ak^{00}$-$Ar^{00}$, —$C(O)N(R^{46})_2$—, —$C(S)N(R^{46})_2$, —$S(O)_2R^{47}$, —$S(O)_2$-$Ak^{00}$-$Ar^{00}$, —$SO_2N(R^{46})_2$, —$NR^{46}SO_2N(R^{46})_2$, —$NR^{46}SO_2R^{47}$ and —$NR^{46}SO_2$-$Ak^{00}$-$Ar^{00}$; or ii) a $C_{6-14}$ aryl or a 5-14 membered heteroaryl group each optionally and independently substituted with one or more substituents selected from the group consisting of halogen, nitro, cyano, hydroxy, $C_{1-20}$ alkyl, $C_{2-20}$ alkenyl, $C_{2-20}$ alkynyl, amino, $C_{1-20}$ alkylamino, $C_{1-20}$ dialkylamino, $C_{1-20}$ alkoxy, ($C_{1-10}$ alkoxy)$C_{1-20}$ alkyl, $C_{1-20}$ haloalkoxy, ($C_{1-10}$ haloalkoxy)$C_{1-20}$ alkyl and $C_{1-20}$ haloalkyl.

Preferably, each of $R^{30}$ and $R^{32}$ independently is i) a $C_{1-10}$ aliphatic group optionally substituted with one or more substituents selected from the group consisting of halogen, $-NO_2$, $-CN$, $-Ar^{00}$, $-OR^{45}$, $-O-Ak^{00}-Ar^{00}$, $-SR^{45}$, $-S-Ak^{00}-Ar^{00}$, $-N(R^{46})_2$, $-NR_{46}C(O)R^{45}$, $-NR^{46}C(O)-Ak^{00}-Ar^{00}$, $-C(O)R^{45}$, $-C(O)-Ak^{00}-Ar^{00}$, $-CO_2R^{45}$, $-CO_2-Ak^{00}-Ar^{00}$ and $-C(O)N(R^{46})_2-$; or ii) a $C_{6-14}$ aryl or a 5-14 membered heteroaryl group each optionally and independently substituted with one or more substituents selected from the group consisting of halogen, nitro, cyano, hydroxy, $C_{1-10}$ alkyl, $C_{2-10}$ alkenyl, $C_{2-10}$ alkynyl, amino, $C_{1-10}$ alkylamino, $C_{1-10}$ dialkylamino, $C_{1-10}$ alkoxy, ($C_{1-6}$ alkoxy)$C_{1-10}$ alkyl, $C_{1-10}$ haloalkoxy, ($C_{1-6}$ haloalkoxy)$C_{1-10}$ alkyl and $C_{1-10}$ haloalkyl. More preferably, each of $R^{30}$ and $R^{32}$ independently is i) a $C_{1-10}$ aliphatic group optionally substituted with one or more substituents selected from the group consisting of halogen, $-Ar^{00}$, $-OR^{45}$, $-O-Ak^{00}-Ar^{00}$, $-SR^{45}$, $-S-Ak^{00}-Ar^{00}$ and $-N(R^{46})_2$; or ii) an $C_{6-14}$ aryl or a 5-14 membered heteroaryl group each optionally and independently substituted with one or more substituents selected from the group consisting of halogen, nitro, cyano, hydroxy, $C_{1-6}$ alkyl, $C_{2-6}$ alkenyl, $C_{2-6}$ alkynyl, amino, $C_{1-6}$ alkylamino, $C_{1-6}$ dialkylamino, $C_{1-6}$ alkoxy, ($C_{1-6}$ alkoxy)$C_{1-6}$ alkyl, $C_{1-6}$ haloalkoxy, ($C_{1-6}$ haloalkoxy)$C_{1-6}$ alkyl and $C_{1-6}$ haloalkyl.

Each of $R^{40}$ and $R^{45}$ independently is i) hydrogen; ii) a $C_{6-14}$ aryl or a 5-14 membered heteroaryl group each optionally and independently substituted with one or more substituents selected from the group consisting of halogen, nitro, cyano, hydroxy, $C_{1-15}$ alkyl, $C_{2-15}$ alkenyl, $C_{2-15}$ alkynyl, amino, $C_{1-15}$ alkylamino, $C_{1-15}$ dialkylamino, $C_{1-15}$ alkoxy, ($C_{1-10}$ alkoxy)$C_{1-15}$ alkyl, $C_{1-15}$ haloalkoxy, $C_{1-15}$ haloalkyl and ($C_{1-10}$ haloalkoxy)$C_{1-15}$ alkyl; or iii) a $C_{1-15}$ alkyl group optionally substituted with one or more substituents selected from the group consisting of halogen, hydroxyl, amino, $C_{1-15}$ alkylamino, $C_{1-15}$ dialkylamino, $C_{1-15}$ alkoxy, nitro, cyano, $C_{1-15}$ alkoxycarbonyl, $C_{1-15}$ alkylcarbonyl and $C_{1-15}$ haloalkoxy. Preferably, each of $R^{40}$ and $R^{45}$ independently is i) hydrogen, ii) a $C_{6-14}$ aryl or a 5-14 membered heteroaryl group optionally and independently substituted with one or more substituents selected from the group consisting of halogen, nitro, cyano, hydroxy, $C_{1-10}$ alkyl, $C_{2-10}$ alkenyl, $C_{2-10}$ alkynyl, amino, $C_{1-10}$ alkylamino, $C_{1-10}$ dialkylamino, $C_{1-10}$ alkoxy, ($C_{1-6}$ alkoxy)$C_{1-10}$ alkyl, $C_{1-10}$ haloalkoxy, $C_{1-10}$ haloalkyl and ($C_{1-6}$ haloalkoxy)$C_{1-10}$ alkyl; or iii) a $C_{1-19}$ alkyl group optionally and independently substituted with one or more substituents selected from the group consisting of halogen, hydroxyl, amino, $C_{1-10}$ alkylamino, $C_{1-10}$ dialkylamino, $C_{1-10}$ alkoxy, nitro, cyano, $C_{1-10}$ alkoxycarbonyl, $C_{1-10}$ alkylcarbonyl and $C_{1-10}$ haloalkoxy. More preferably, each of $R^{40}$ and $R^{45}$ independently is i) hydrogen; ii) a $C_{6-14}$ aryl or a 5-14 membered heteroaryl group each optionally and independently substituted with one or more substituents selected from the group consisting of halogen, nitro, cyano, hydroxy, $C_{1-6}$ alkyl, $C_{2-6}$ alkenyl, $C_{2-6}$ alkynyl, amino, $C_{1-6}$ alkylamino, $C_{1-6}$ dialkylamino, $C_{1-6}$ alkoxy, ($C_{1-6}$ alkoxy)$C_{1-6}$ alkyl, $C_{1-6}$ haloalkoxy, $C_{1-6}$ haloalkyl and ($C_{1-6}$ haloalkoxy)$C_{1-6}$ alkyl; or iii) a $C_{1-10}$ alkyl group optionally substituted with one or more substituents selected from the group consisting of halogen, hydroxyl, amino, $C_{1-6}$ alkylamino, $C_{1-6}$ dialkylamino, $C_{1-6}$ alkoxy, nitro, cyano, $C_{1-6}$ alkoxycarbonyl, $C_{1-6}$ alkylcarbonyl and $C_{1-6}$ haloalkoxy.

Each $R^{41}$ independently is $R^{40}$, $-CO_2R^{40}$, $SO_2R^{40}$ or $-C(O)R^{40}$, or $-N(R^{41})_2$ taken together is an optionally substituted, 5-14 membered non-aromatic heterocyclic group. Preferably, the non-aromatic heterocyclic ring is a substituted or unsubstituted five-membered ring, or a substituted or unsubstituted six-membered ring. More preferably, the non-aromatic heterocyclic ring is an unsubstituted five- or six-membered ring. Suitable substituents, including preferred values, for the non-aromatic heterocyclic group represented by $-N(R^{41})_2$ are as described above for the non-aromatic heterocyclic group represented by $-N(R^4R^5)$.

Each $R^{46}$ independently is $R^{45}$, $-CO_2R^{45}$, $-SO_2R^{45}$ or $-C(O)R^{45}$, or $-N(R^{46})_2$ taken together is an optionally substituted, 5-14 membered non-aromatic heterocyclic group. Preferably, the non-aromatic heterocyclic ring is a substituted or unsubstituted five-membered ring, or a substituted or unsubstituted six-membered ring. More preferably, the non-aromatic heterocyclic ring is an unsubstituted five- or six-membered ring. Suitable substituents, including preferred values, for the non-aromatic heterocyclic group represented by $-N(R^{46})_2$ are as described above for the non-aromatic heterocyclic group represented by $-N(R^4R^5)$.

Each of $R^{42}$ and $R^{47}$ independently is i) a $C_{6-14}$ aryl or a 5-14 membered heteroaryl group each optionally and independently substituted with one or more substituents selected from the group consisting of halogen, nitro, cyano, hydroxy, $C_{1-15}$ alkyl, $C_{2-15}$ alkenyl, $C_{2-15}$ alkynyl, amino, $C_{1-15}$ alkylamino, $C_{1-15}$ dialkylamino, $C_{1-15}$ alkoxy, ($C_{1-10}$ alkoxy)$C_{1-15}$ alkyl, $C_{1-15}$ haloalkoxy, $C_{1-15}$ haloalkyl and ($C_{1-10}$ haloalkoxy)$C_{1-15}$ alkyl; or ii) a $C_{1-15}$ alkyl group optionally substituted with one or more substituents selected from the group consisting halogen, hydroxyl, amino, $C_{1-15}$ alkylamino, $C_{1-15}$ dialkylamino, $C_{1-15}$ alkoxy, nitro, cyano, $C_{1-15}$ alkoxycarbonyl, $C_{1-15}$ alkylcarbonyl and $C_{1-15}$ haloalkoxy. Preferably, each $R^{42}$ and $R^{47}$ independently is i) a $C_{6-14}$ aryl or a 5-14 membered heteroaryl group optionally and independently substituted with one or more substituents selected from the group consisting of halogen, nitro, cyano, hydroxy, $C_{1-10}$ alkyl, $C_{2-10}$ alkenyl, $C_{2-10}$ alkynyl, amino, $C_{1-10}$ alkylamino, $C_{1-10}$ dialkylamino, $C_{1-10}$ alkoxy, ($C_{1-6}$ alkoxy)$C_{1-10}$ alkyl, $C_{1-10}$ haloalkoxy, $C_{1-10}$ haloalkyl and ($C_{1-6}$ haloalkoxy)$C_{1-10}$ alkyl; or ii) a $C_{1-10}$ alkyl group optionally substituted with one or more substituents selected from the group consisting of halogen, hydroxyl, amino, $C_{1-10}$ alkylamino, $Cl_{1-10}$ dialkylamino, $C_{1-10}$ alkoxy, nitro, cyano, $C_{1-10}$ alkoxycarbonyl, $C_{1-10}$ alkylcarbonyl and $C_{1-10}$ haloalkoxy. More preferably, each $R^{42}$ and $R^{47}$ independently is i) a $C_{6-14}$ aryl or a 5-14 membered heteroaryl group optionally and independently substituted with one or more substituents selected from the group consisting of halogen, nitro, cyano, hydroxy, $C_{1-6}$ alkyl, $C_{2-6}$ alkenyl, $C_{2-6}$ alkynyl, amino, $C_{1-6}$ alkylamino, $C_{1-6}$ dialkylamino, $C_{1-6}$ alkoxy, ($C_{1-6}$ alkoxy) $C_{1-6}$ alkyl, $C_{1-6}$ haloalkoxy, $C_{1-6}$ haloalkyl and ($C_{1-6}$ haloalkoxy)$C_{1-6}$ alkyl; or ii) a $C_{1-6}$ alkyl group optionally substituted with one or more substituents selected from the group consisting of halogen, hydroxyl, amino, $C_{1-6}$ alkylamino, $C_{1-6}$ dialkylamino, $C_{1-6}$ alkoxy, nitro, cyano, $C_{1-6}$ alkoxycarbonyl, $C_{1-6}$ alkylcarbonyl and $C_{1-6}$ haloalkoxy.

Each of $Ak^0$ and $Ak^2$ independently is a $C_{1-20}$ alkylene, $C_{2-20}$ alkenylene or $C_{2-20}$ alkynylene group. Preferably, each of $Ak^0$ and $Ak^2$ independently is a $C_{1-10}$ alkylene, $C_{2-10}$ alkenylene or $C_{2-10}$ alkynylene group. More preferably, each of $Ak^0$ and $Ak^2$ independently is a $C_{1-10}$ alkylene group. Even more preferably, each of $Ak^0$ and $Ak^2$ independently is a $C_{1-6}$ alkylene group, such as $-CH_2-$ or $-(CH_2)_2-$.

Each $Ak^1$ independently is an optionally substituted C1-C20 aliphatic group, preferably an optionally substituted C1-C15 aliphatic group. Suitable substituents for $Ak^1$ include halogen, $-NO_2$, $-CN$, $-Ar^2$, $-OR^{20}$, $-O-Ak^2-Ar^2$, $-SR^{20}$, $-S-Ak^2-Ar^2$, $-N(R^{21})_2$, $-NR^{21}C(O)R^{20}$, $-NR^{21}C(O)-Ak^2-Ar^2$, $-N(R^{21})C(O)N(R^{21})_2$, $-C(O)R^{20}$, $-C(O)-Ak^2-Ar^2$, $-C(S)R^{20}$, $-C(S)-Ak^2-Ar^2$, $-CO_2R^{20}$, $-CO_2-Ak^2-Ar^2$, $-OC(O)-R^{20}$, $-OC(O)-Ak^2-Ar^2$, $-C(O)N(R^{21})_2-$, $-C(S)N(R^{21})_2$, $-S(O)_2R^{22}$, $-S(O)_2-Ak^2-Ar^2$, $-SO_2N(R^{21})_2$, $-SO_2N(R^{21})-NR^{21}$, $-S(O)R^{22}$, $-S(O)-Ak^2-Ar^2$, $-SO_3R^{22}$, $-SO_3-Ak^2-Ar^2$, $-NR^{21}SO_2N(R^{21})_2$, $-NR$ and $-NR-Ak^2-Ar^2$. Preferred substituents for $Ak^1$ include $-Ar^2$, $-OR^{20}$, $-O-Ak^2-Ar^2$, $-SR^N$, $-S-Ak^2-Ar^2$, $-N(R^{21})_2$, $-NR^{21}C(O)R^{20}$, $-NR^{21}C(O)-Ak^2-Ar^2$, $-C(O)R^{20}$, $-C(O)-Ak^2-Ar^2$, $-C(S)R^{20}$, $-C(S)-Ak^2-Ar^2$, $-CO_2R^{20}$, $-CO_2-Ak^2-Ar^2$, $-OC(O)-R^{20}$, $-OC(O)-Ak^2-Ar^2$, $-C(O)N(R^{21})_2-$, $-S(O)_2-R^{22}$, $-S(O)_2-Ak^2-Ar^2$, $-SO_2N(R^{21})_2$, $-SO_2N(R^{21})-NR^{21}$, $-S(O)R^{22}$, $-S(O)-Ak^2-Ar^2$, $-NR^{21}SO_2R^{22}$ and $-NR^{21}SO_2-Ak^2-Ar^2$. More preferred substituents for $Ak^1$ include $-Ar^2$, $-OR^{20}$, $-O-Ak^2-Ar^2$, $-SR^{20}$, $-S-Ak^2-Ar^2$, $-N(R^{21})_2$ and $-S(O)_2-Ak^2-Ar^2$.

Each $Ak^3$ independently is an optionally substituted $C_1-C_{20}$ aliphatic group, preferably an optionally substituted C1-C15 aliphatic group, more preferably an optionally substituted C1-C10 aliphatic group. Suitable substituents for $Ak^3$ include halogen, $-NO_2$, $-CN$, $-Ar^4$, $-OR^{40}$, $-O-Ak^4-Ar^4$, $-SR^{40}$, $-S-Ak^4-Ar^4$, $-N(R^{41})_2$, $-NR^{41}C(O)R^{40}$, $-NR^{41}C(O)-Ak^4-Ar^4$, $-N(R^{41})C(O)N(R^{41})_2$, $-C(O)R^{40}$, $-C(O)-Ak^4-Ar^4$, $-C(S)R^{40}$, $-C(S)-Ale-Ar^4$, $-CO_2R^{40}$, $-CO_2-Ak^4-Ar^4$, $-OC(O)-R^{40}$, $-OC(O)-Ak^4-Ar^4$, $-C(O)N(R^{41})_2-$, $-C(S)N(R^{41})_2$, $-S(O)_2R^{42}$, $-S(O)_2-Ak^4-Ar^4$, $-SO_2N(R^{41})_2$, $-SO_2N(R^{41})-NR^{41}$, $-S(O)R^{42}$, $-S(O)-Ale-Ar^4$, $-SO_3R^{42}$, $SO_3-Ak^4-Ar^4$, $-NR^{41}SO_2N(R^{41})_2$, $-NR^{41}SO_2R^{42}$ and $-NR^{41}SO_2-Ak^4-Ar^4$. Preferred substituents for $Ak^3$ include $-Ar^4$, $-OR^{40}$, $-O-Ak^4-Ar^4$, $-SR^{40}$, $-S-Ak^4-Ar^4$, $-N(R^{41})_2$, $-NR^{41}C(O)R^{40}$, $-NR^{41}C(O)-Ak^4-Ar^4$, $-C(O)R^{40}$, $-C(O)-Ak^4-Ar^4$, $-C(S)R^{40}$, $-C(S)-Ak^4-Ar^4$, $-CO_2R^{40}$, $-CO_2-Ak^4-Ar^4$, $-OC(O)-R^{40}$, $-OC(O)-Ak^4-Ar^4$, $-C(O)N(R^{41})_2-$, $-S(O)_2-R^{42}$, $-S(O)_2-Ak^4-Ar^4$, $-SO_2N(R^{41})_2$, $-SO_2N(R^{41})-NR^{41}$, $-S(O)R^{42}$, $-S(O)-Ak^4-Ar^4$, $-NR^{41}SO_2R^{42}$ and $-NR^{41}SO_2-Ak^4-Ar^4$. More preferred substituents for $Ak^3$ include $-Ar^4$, $-OR^{40}$, $-O-Ak^4-Ar^4$, $-SR^{40}$, $-S-Ak^4-Ar^4$, $-N(R^{41})_2$ and $-S(O)_2-Ak^4-Ar^4$.

Each of $Ak^{00}$ and $Ak^4$ independently is a $C_{1-20}$ alkylene, $C_{2-20}$ alkenylene or $C_{2-20}$ alkynylene group. Preferably, each of $Ak^{00}$ and $Ak^4$ independently is a $C_{1-10}$ alkylene, $C_{2-10}$ alkenylene or $C_{2-10}$ alkynylene group. More preferably, each of $Ak^{00}$ and $Ak^4$ independently is a $C_{1-10}$ alkylene group. Even more preferably, each of $Ak^{00}$ and $Ak^4$ independently is a $C_{1-6}$ alkylene group, such as $-CH_2-$ or $-(CH_2)_2-$.

Each of $Ar^0$, $Ar^{00}$, $Ar^1$, $Ar^2$, $Ar^3$ and $Ar^4$ independently is an optionally substituted $C_{6-14}$ aryl or an optionally substituted 5-14 membered heteroaryl group. Preferably, each of $Ar^0$, $Ar^{00}$, $Ar^1$, $Ar^2$, $Ar^3$ and $Ar^4$ independently is an optionally substituted monocyclic aryl group or an optionally substituted monocyclic heteroaryl group, such as an optionally substituted phenyl group, or an optionally substituted 5- or 6-membered heteroaryl group.

Suitable substituents for each of the aryl and heteroaryl groups represented by $Ar^0$, $Ar^{00}$, $Ar^1$, $Ar^2$, $Ar^3$ and $Ar^4$ include halogen, nitro, cyano, hydroxy, $C_{1-20}$ alkyl, $C_{2-20}$ alkenyl, $C_{2-20}$ alkynyl, amino, $C_{1-20}$ alkylamino, $C_{1-20}$ dialkylamino, $C_{1-20}$ alkoxy, $(C_{1-10}$ alkoxy$)C_{1-20}$ alkyl, $C_{1-20}$ haloalkoxy, $(C_{1-10}$haloalkoxy$)C_{1-20}$ alkyl and $C_{1-20}$ haloalkyl. Preferred substituents for each of the aryl and heteroaryl groups represented by $Ak^0$, $Ar^{00}$, $Ar^1$, $Ar^2$, $Ar^3$ and $Ar^4$ include halogen, nitro, cyano, hydroxy, $C_{1-10}$ alkyl, $C_{2-10}$ alkenyl, $C_{2-10}$ alkynyl, amino, $C_{1-10}$ alkylamino, $C_{1-10}$ dialkylamino, $C_{1-10}$ alkoxy, $(C_{1-6}$ alkoxy$)C_{1-10}$ alkyl, $C_{1-10}$haloalkoxy, $(C_{1-6}$ haloalkoxy$)C_{1-10}$alkyl and $C_{1-10}$haloalkyl. More preferred substituents for each of the aryl and heteroaryl groups represented by $Ar^0$, $Ar^{00}$, $Ar^1$, $Ar^2$, $Ar^3$ and $Ar^4$ include, halogen, nitro, cyano, hydroxy, $C_{1-10}$alkyl, $C_{2-10}$ alkenyl, $C_{2-10}$ alkynyl, amino, $C_{1-10}$ alkylamino, $C_{1-10}$ dialkylamino, $C_{1-10}$ alkoxy, $(C_{1-6}$ alkoxy$)C_{1-10}$alkyl, $C_{1-10}$ haloalkoxy, $(C_{1-6}$ haloalkoxy$)C_{1-10}$alkyl and $C_{1-10}$ haloalkyl.

Each p independently is 1, 2, 3 or 4.

Each q independently is 3, 4, 5 or 6.

A second set of values for the variables in Structural Formula (I) is provided in the following paragraphs:

Q is $-C(=O)-$, $-C(=S)-$, $-C(O)NH-$ $-C(S)NH-$, $-C(=NH)-$, $-S(O)-$, $-S(O)_2-$ or $-S(O)_2-NH-$.

Each $R^4$ independently is an optionally substituted monocyclic aryl or optionally substituted monocyclic heteroaryl group, such as an optionally substituted phenyl group, or an optionally substituted 5- or 6-membered heteroaryl group.

Values and preferred values for the remainder of the variables of Structural Formula (I) are as described above for the first set of values.

A third set of values for the variables in Structural Formula (I) is provided in the following paragraphs:

Q is $-C(=O)-$, $-C(=S)-$, $-C(O)NH-$ $-C(S)NH-$, $-C(=NH)-$, $-S(O)-$, $-S(O)_2-$ or $-S(O)_2-NH-$.

$R^3$ is $-N(R^7R^8)$ or $-N^+(R^7R^8R^9)X^-$.

Each $R^4$ independently is an optionally substituted monocyclic aryl or optionally substituted monocyclic heteroaryl group, such as an optionally substituted phenyl group, or an optionally substituted 5- or 6-membered heteroaryl group.

Each of $R^7$, $R^8$ and $R^9$ independently is $C_{1-6}$ alkyl. More preferably, each of $R^7$, $R^8$ and $R^9$ independently is methyl or ethyl. Even more preferably, each of $R^7$, $R^8$ and $R^9$ independently is methyl.

Values and preferred values for the remainder of the variables of Structural Formula (I) are as described above for the first set of values.

A fourth set of values for the variables in Structural Formula (I) is provided in the following paragraphs:

Q is $-S(O)_2-$, $-S(O)_2-NH-$ or $-S(O)-NH-$.

Each $R^4$ independently is an optionally substituted monocyclic aryl or optionally substituted monocyclic heteroaryl group, such as an optionally substituted phenyl group, or an optionally substituted 5- or 6-membered heteroaryl group.

Values and preferred values for the remainder of the variables of Structural Formula (I) are as described above for the first set of values.

A fifth set of values for the variables in Structural Formula (I) are provided in the following paragraphs.

Q is $-S(O)_2-$, $-S(O)_2-NH-$ or $-S(O)-NH-$.

Each $R^3$ independently is $-N(R^7R^8)$ or $N^+(R^7R^8R^9)_{X^-}$.

Each $R^4$ independently is an optionally substituted monocyclic aryl or optionally substituted monocyclic heteroaryl group, such as an optionally substituted phenyl group, or an optionally substituted 5- or 6-membered heteroaryl group.

Each of $R^7$, $R^8$ and $R^9$ independently is $C_{1-6}$ alkyl. More preferably, each of $R^7$, $R^8$ and $R^9$ independently is methyl or ethyl. Even more preferably, each of $R^7$, $R^8$ and $R^9$ independently is methyl.

Values and preferred values for the remainder of the variables of Structural Formula (I) are as described above for the first set of values.

A six set of values for the variables in Structural Formula (I) is provided in the following paragraphs:

Q is —C(=O)—N($R^5$)—, —C(=S)—N($R^5$)—, —C(=NH)—N($R^5$)—, —S(O)—N($R^5$)— or —S(O)$_2$—N($R^5$)—.

Each $R^4$ independently is an optionally substituted monocyclic aryl or optionally substituted monocyclic heteroaryl group, such as an optionally substituted phenyl group, or an optionally substituted 5- or 6-membered heteroaryl group.

Each $R^5$ independently is an optionally substituted aliphatic group.

Values and preferred values for the remainder of the variables of Structural Formula (I) are as described above for the first set of values.

A seventh set of values for the variables in Structural Formula (I) is provided in the following paragraphs:

Q is —C(=O)—N($R^5$)—, —C(=S)—N($R^5$)—, —C(=NH)—N($R^5$)—, —S(O)—N($R^5$)— or —S(O)$_2$—N($R^5$)—;

Each $R^3$ independently is —N($R^7R^8$) or —N$^+$($R^7R^8R^9$)X$^-$.

Each $R^4$ independently is an optionally substituted monocyclic aryl or optionally substituted monocyclic heteroaryl group, such as an optionally substituted phenyl group, or an optionally substituted 5- or 6-membered heteroaryl group.

Each $R^5$ independently is an optionally substituted aliphatic group.

Each of $R^7$, $R^8$ and $R^9$ independently is $C_{1-6}$ alkyl. More preferably, each of $R^7$, $R^8$ and $R^9$ independently is methyl or ethyl. Even more preferably, each of $R^7$, $R^8$ and $R^9$ independently is methyl.

Values and preferred values for the remainder of the variables of Structural Formula (I) are as described above for the first set of values.

In a second embodiment, the compound of the invention is represented by Structural Formula (II)-(IX):

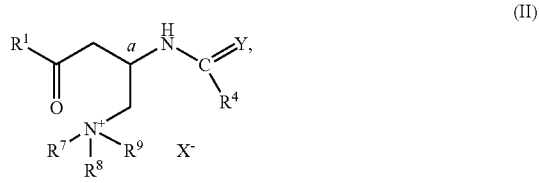

(II)

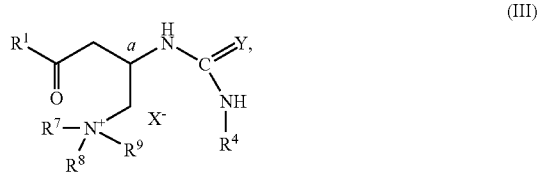

(III)

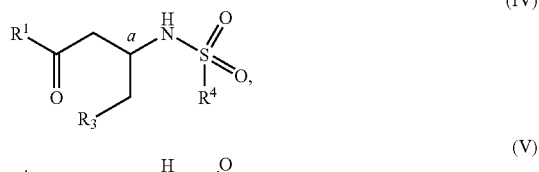

(IV)

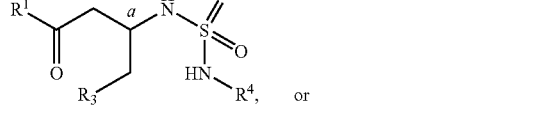

(V)

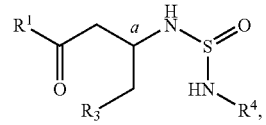

(VI)

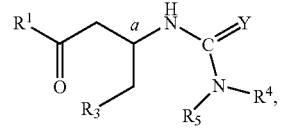

(VII)

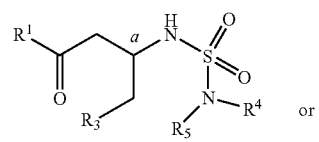

(VIII)

or

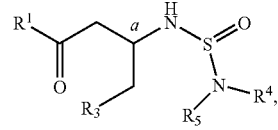

(IX)

or a pharmaceutically acceptable salt thereof. A first set of values for the variables of Structural Formulas (II)-(IX) is provided in the following paragraphs:

Each X$^-$ independently is a pharmaceutically acceptable counter ion.

Each Y for Structural Formulas (II), (III) and (VII) independently is O, S or NH, and preferably O or S.

Each $R^3$ for Structural Formulas (IV)-(IX) independently is —N($R^7R^8$) or —N$^{30}$($R^7R^8R^9$)X$^-$, and preferably —N$^+$($R^7R^8R^9$)X$^-$.

Each $R^4$ independently is a monocyclic aryl or heteroaryl group optionally substituted with one or more substituents selected from the group consisting of Ak$^1$, —NO$_2$, —CN, —OR$^{10}$, —SR$^{10}$, —C(O)OR$^{10}$, —C(O)R$^{10}$, —C(S)R$^{10}$, —OC(O)R$^{10}$, —C(O)N($R^{11}$)$_2$, —C(S)N($R^{11}$)$_2$, —N($R^{11}$)$_2$, —NR$^{11}$C(O)R$^{10}$, —NR$^{11}$C(O)R$^{12}$, —N($R^{11}$)C(O)N($R^{11}$)$_2$ and —NR$^{11}$SO$^2$R$^{12}$.

Each $R^5$ for structural Formula (VII), (VIII) and (IX) independently is an optionally substituted aliphatic group.

Each of $R^7$, $R^8$ and $R^9$ independently is $C_{1-6}$ alkyl. More preferably, each of $R^7$, $R^8$ and $R^9$ independently is methyl or ethyl. Even more preferably, each of $R^7$, $R^8$ and $R^9$ independently is methyl.

Values and preferred values of the remainder of the variables of Structural Formulas (II)-(IX) are each independently as described above in the first set of values for Structural Formula (I).

A second set of values for the variables of Structural Formulas (II)-(IX) is provided in the following paragraphs:

Each $R^5$ for Structural Formulas (VII), (VIII) and (IX) independently is a C1-C20 aliphatic group optionally substituted with one or more substituents selected from the group consisting of Ar$^3$, —NO$_2$, —CN, —OR$^{30}$, —SR$^{30}$, —C(O)OR$^{30}$, —C(O)R$^{30}$, —C(S)R$^{30}$, —OC(O)R$^{30}$, —C(O)N($R^{31}$)$_2$, —C(S)N($R^{31}$)$_2$, —N($R^{31}$)$_2$, —NR$^{31}$C(O)R$^{30}$, —NR$^{31}$C(O)OR$^{32}$, —N($R^{31}$)C(O)N($R^{31}$)$_2$ and —NR$^{31}$SO$^2$R$^{32}$.

Each of $R^{10}$ and $R^{12}$ independently is i) a $C_{1-10}$ aliphatic group optionally substituted with one or more substituents selected from the group consisting of halogen, —NO$_2$, —CN, —Ar$^0$, —OR$^{25}$, —O-Ak$^0$-Ar$^0$, —SR$^{25}$, —S-Ak$^0$-Ar$^0$, —N(R$^{26}$)$_2$, —NR$^{26}$C(O)R$^{25}$, —NR$^{26}$C(O)-Ak$^0$-Ar$^0$, —C(O)R$^{25}$, —C(O)-Ak$^0$-Ar$^0$, —CO$_2$R$^{25}$, —CO$_2$-Ak$^0$-Ar$^0$ and —C(O)N(R$^{26}$)$_2$—; or ii) a C$_{6-14}$ aryl or a 5-14 membered heteroaryl group each optionally and independently substituted with one or more substituents selected from the group consisting of halogen, nitro, cyano, hydroxy, C$_{1-10}$ alkyl, C$_{2-10}$ alkenyl, C$_{2-10}$ alkynyl, amino, C$_{1-10}$ alkylamino, C$_{1-10}$ dialkylamino, C$_{1-10}$ alkoxy, (C$_{1-6}$ alkoxy)C$_{1-10}$ alkyl, C$_{1-10}$ haloalkoxy, (C$_{1-6}$ haloalkoxy)C$_{1-10}$ alkyl and C$_{1-10}$ haloalkyl.

Each Ak$^1$ independently is optionally substituted with one or more substituents selected from the group consisting of —Ar$^2$, —OR$^{20}$, —O-Ak$^2$-Ar$^2$, —SR$^{20}$, —S-Ak$^2$-Ar$^2$, —N(R$^{21}$)$_2$, —NR$^{21}$C(O)R$^{20}$, —NR$^{21}$C(O)-Ak$^2$-Ar$^2$, —C(O)R$^{20}$, —C(O)-Ak$^2$-Ar$^2$, —C(S)R$^{20}$, —C(S)-Ak$^2$-Ar$^2$, —CO$_2$R$^{20}$, —CO$_2$-Ak$^2$-Ar$^2$, —OC(O)—R$^{20}$ —OC(O)-Ak$^2$-Ar$^2$, —C(O)N(R$^{21}$)$_2$—, —S(O)$_2$—R$^{22}$, —-Ak$^2$-Ar$^2$, —SO$_2$N(R$^{21}$)$_2$, —SO$_2$N(R$^{21}$)—R$^{21}$, —S(O)R$^{22}$, —S(O)-Ak$^2$-Ar$^2$, —NR$^{21}$SO$_2$R$^{22}$ and —NR$^{21}$SO$_2$-Ak$^2$-Ar$^2$.

Each of X$^-$, Y, R$^3$, R$^4$, R$^7$, R$^8$ and R$^9$ independently is as described above in the first set of values for the variables of Structural Formulas (II)-(IX).

Values and preferred values of the remainder of the variables of Structural Formulas (II)-(IX) are each independently as described above in the first set of values for Structural Formula (I).

A third set of values for the variables of Structural Formulas (II)-(IX) is provided in the following paragraphs:

Each of R$^{20}$ and R$^{25}$ independently is i) hydrogen, ii) a C$_{6-14}$ aryl or a 5-14 membered heteroaryl group each optionally and independently substituted with one or more substituents selected from the group consisting of halogen, nitro, cyano, hydroxy, C$_{1-10}$ alkyl, C$_{2-10}$ alkenyl, C$_{2-10}$ alkynyl, amino, C$_{1-10}$ alkylamino, C$_{1-10}$ dialkylamino, C$_{1-10}$ alkoxy, (C$_{1-6}$ alkoxy)C$_{1-10}$ alkyl, C$_{1-10}$ haloalkoxy, C$_{1-10}$ haloalkyl and (C$_{1-6}$ haloalkoxy)C$_{1-10}$ alkyl; or iii) a C$_{1-10}$ alkyl group optionally substituted with one or more substituents selected from the group consisting of halogen, hydroxyl, amino, C$_{1-10}$ alkylamino, C$_{1-10}$ dialkylamino, C$_{1-10}$ alkoxy, nitro, cyano, C$_{1-10}$ alkoxycarbonyl, C$_{1-10}$ alkylcarbonyl and C$_{1-10}$ haloalkoxy.

Each of the non-aromatic heterocyclic groups represented by —N(R$^{21}$)$_2$ and —N(R$^{26}$)$_2$ is optionally and independently substituted with one or more substituents selected from the group consisting of halogen, C$_{1-6}$ alkyl, C$_{2-6}$ alkenyl, C$_{2-6}$ alkynyl, amino, C$_{1-6}$ alkylamino, C$_{1-6}$ dialkylamino, C$_{1-6}$ alkoxy, nitro, cyano, hydroxy, C$_{1-6}$ alkoxycarbonyl, C$_{1-6}$ alkylcarbonyl, C$_{1-6}$ haloalkoxy, (C$_{1-6}$ haloalkoxy)C$_{1-6}$ alkyl, C$_{1-6}$ haloalkyl, C$_{6-14}$ aryl and 5-14 membered heteroaryl.

Each R$^{22}$ independently is i) a C$_{6-14}$ aryl or a 5-14 membered heteroaryl group each optionally and independently substituted with one or more substituents selected from the group consisting of halogen, nitro, cyano, hydroxy, C$_{1-10}$ alkyl, C$_{2-10}$ alkenyl, C$_{2-10}$ alkynyl, amino, C$_{1-10}$ alkylamino, C$_{1-10}$ dialkylamino, C$_{1-10}$ alkoxy, (C$_{1-6}$ alkoxy)C$_{1-10}$ alkyl, C$_{1-10}$ haloalkoxy, C$_{1-10}$ haloalkyl and (C$_{1-6}$ haloalkoxy)C$_{1-10}$ alkyl; or ii) a C$_{1-10}$ alkyl group optionally substituted with one or more substituents selected from the group consisting of halogen, hydroxyl, amino, C$_{1-10}$ alkylamino, C$_{1-10}$ dialkylamino, C$_{1-10}$ alkoxy, nitro, cyano, C$_{1-10}$ alkoxycarbonyl, C$_{1-10}$ alkylcarbonyl and C$_{1-10}$ haloalkoxy.

For Structural Formulas (VI)-(IX), each of R$^{30}$ and R$^{32}$ independently is a C$_{1-10}$ aliphatic group optionally substituted with one or more substituents selected from the group consisting of halogen, —NO$_2$, —CN, —Ar$^{00}$, —OR$^{45}$, —O-Ak$^{00}$-Ar$^{00}$, —SR$^{45}$, —S-Ak$^{00}$-Ar$^{00}$, —N(R$^{46}$)$_2$, NR$^{46}$C(O)R$^{45}$, —NR$^{46}$C(O)-Ak$^{00}$-Ar$^{00}$, —C(O)R$^{45}$, —C(O)-Ak$^{00}$-Ar$^{00}$, —CO$_2$R$^{45}$, —CO$_2$-Ak$^{00}$-Ar$^{00}$ and —C(O)N(R$^{46}$)$_2$—; or ii) a C$_{6-14}$ aryl or a 5-14 membered heteroaryl group each optionally and independently substituted with one or more substituents selected from the group consisting of halogen, nitro, cyano, hydroxy, C$_{1-10}$ alkyl, C$_{2-10}$ alkenyl, C$_{2-10}$ alkynyl, amino, C$_{1-10}$ alkylamino, C$_{1-10}$ dialkylamino, C$_{1-10}$ alkoxy, (C$_{1-6}$ alkoxy)C$_{1-10}$ alkyl, C$_{1-10}$ haloalkoxy, (C$_{1-6}$ haloalkoxy)C$_{1-10}$ alkyl and C$_{1-10}$ haloalkyl.

For Structural Formulas (VI)-(IX), each R$^{45}$ independently is i) hydrogen, ii) a C$_{6-14}$ aryl or a 5-14 membered heteroaryl group each optionally and independently substituted with one or more substituents selected from the group consisting of halogen, nitro, cyano, hydroxy, C$_{1-10}$ alkyl, C$_{2-10}$ alkenyl, C$_{2-10}$ alkynyl, amino, C$_{1-10}$ alkylamino, C$_{1-10}$ dialkylamino, C$_{1-10}$ alkoxy, (C$_{1-6}$ alkoxy)C$_{1-10}$ alkyl, C$_{1-10}$ haloalkoxy, C$_{1-10}$ haloalkyl and (C$_{1-6}$ haloalkoxy)C$_{1-10}$ alkyl; or iii) a C$_{1-10}$ alkyl group optionally substituted with one or more substituents selected from the group consisting of halogen, hydroxyl, amino, C$_{1-10}$ alkylamino, C$_{1-10}$ dialkylamino, C$_{1-10}$ alkoxy, nitro, cyano, C$_{1-10}$ alkoxycarbonyl, C$_{1-10}$ alkylcarbonyl and C$_{1-10}$ haloalkoxy.

For Structural Formulas (VI)-(IX), each R$^{46}$ independently is R$^{45}$, —CO$_2$R$^{45}$, —SO$_2$R$^{45}$ or —C(O)R$^{45}$, or —N(R$^{46}$)$_2$ taken together is a 5-14 membered non-aromatic heterocyclic group optionally substituted with one or more substituents selected from the group consisting of halogen, C$_{1-6}$ alkyl, C$_{2-6}$ alkenyl, C$_{2-6}$ alkynyl, amino, C$_{1-6}$ alkylamino, C$_{1-6}$ dialkylamino, C$_{1-6}$ alkoxy, nitro, cyano, hydroxy, C$_{1-6}$ alkoxycarbonyl, C$_{1-6}$ alkylcarbonyl, C$_{1-6}$ haloalkoxy, (C$_{1-6}$ haloalkoxy) C$_{1-6}$ alkyl, C$_{1-6}$ haloalkyl, C$_{6-14}$ aryl and 5-14 membered heteroaryl.

For Structural Formulas (VI)-(IX), each Ak$^{00}$ independently is a C$_1$-C$_{10}$ alkylene group.

Each Ak$^0$ and Ak$^2$ independently is a C1-C10 alkylene group.

Each of X$^-$, Y, R$^3$, R$^4$, R$^5$, R$^7$, R$^8$, R$^9$, R$^{10}$, R$^{12}$ and Ak$^1$ independently is as described above in the second set of values for the variables of Structural Formulas (II)-(IX).

Values and preferred values of the remainder of the variables of Structural Formulas (II)-(IX) are each independently as described above in the first set of values for Structural Formula (I).

A fourth set of values for the variables of Structural Formulas (II)-(IX) is provided in the following paragraphs:

For Structural Formulas (II), (III) and (VII), each R$^4$ independently is selected from the group consisting of:

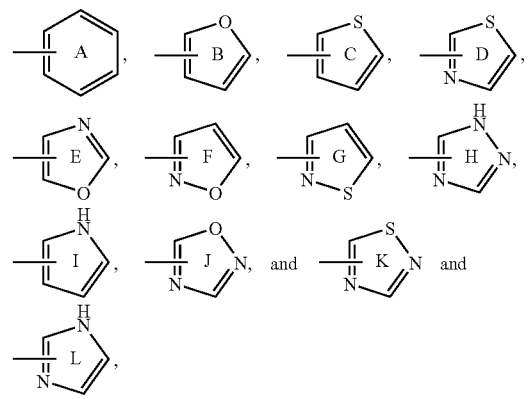

wherein each of rings A-L is optionally substituted. For Structural Formulas (IV), (V), (VI), (VIII) and (IX), each R$^4$ independently is selected from the group consisting of:

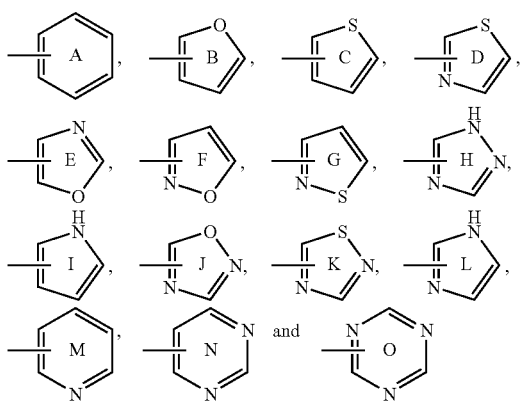

wherein each of rings A-O is optionally substituted. Preferably, for Structural Formulas (IV), (V), (VI), (VIII) and (IX), each $R^4$ independently is selected from rings A-N.

Each $R^5$ for Structural Formulas (VII), (VIII) and (IX) independently is an unsubstituted C1-C10 alkyl group.

Each of $X^-$, $Y$, $R^3$, $R^7$, $R^8$, $R^9$, $R^{10}$, $R^{11}$, $R^{12}$, $R^{20}$, $R^{21}$, $R^{22}$, $R^{25}$, $R^{26}$, $Ak^0$, $Ak^1$ and $Ak^2$ independently is as described above in the third set of values for the variables of Structural Formulas (II)-(IX).

Values and preferred values of the remainder of the variables of Structural Formulas (II)-(IX) are each independently as described above in the first set of values for Structural Formula (I).

A fifth set of values for the variables of Structural Formulas (II)-(IX) is provided in the following paragraphs:

Each of $R^4$ independently is as described above in the fourth set of values for the variables of Structural formulas (II)-(IX), wherein each ring A-O independently and optionally substituted with one or more substituents selected from the group consisting of halogen, $Ak^1$, —$OR^{10}$ and —$SR^{10}$.

Each $Ak^1$ independently is a C1-C15 aliphatic group optionally substituted with one or more substituents selected from the group consisting of halogen, —$Ar^2$, —$OR^{20}$, —O-$Ak^2$-$Ar^2$, —$SR^{20}$, —S-$Ak^2$-$Ar^2$, —$N(R^{21})_2$ and —$S(O)_2$-$Ak^2$-$Ar^2$.

Each of $X^-$, $Y$, $R^3$, $R^5$, $R^7$, $R^8$, $R^9$, $R^{10}$, $R^{20}$, $R^{21}$, $R^{25}$, $R^{26}$, $Ak^0$, $Ak^1$ and $Ak^2$ independently is as described above in the fourth set of values for the variables of Structural Formulas (II)-(IX).

Values and preferred values of the remainder of the variables of Structural Formulas (II)-(IX) are each independently as described above in the first set of values for Structural Formula (I).

A sixth set of values for the variables of Structural Formulas (II)-(IX) is provided in the following paragraphs:

Each $R^{10}$ independently is i) a $C_{1-10}$ aliphatic group optionally substituted with one or more substituents selected from the group consisting of halogen, —$Ar^0$, —$OR^{25}$, —O-$Ak^0$-$Ar^0$, —$SR^{25}$, —S-$Ak^0$-$Ar^0$ and —$N(R^{26})_2$; or ii) an $C_{6-14}$ aryl or a 5-14 membered heteroaryl group each optionally and independently substituted with one or more substituents selected from the group consisting of halogen, nitro, cyano, hydroxy, $C_{1-6}$ alkyl, $C_{2-6}$ alkenyl, $C_{2-6}$ alkynyl, amino, $C_{1-6}$ alkylamino, $C_{1-6}$ dialkylamino, $C_{1-6}$ alkoxy, ($C_{1-6}$alkoxy)$C_{1-6}$ alkyl, $C_{1-6}$ haloalkoxy, ($C_{1-6}$ haloalkoxy)$C_{1-6}$ alkyl and $C_{1-6}$haloalkyl.

Each of $X^-$, $Y$, $R^3$, $R^4$, $R^5$, $R^7$, $R^8$, $R^9$, $R^{20}$, $R^{21}$, $R^{25}$, $R^{26}$, $Ak^0$, $Ak^1$ and $Ak^2$ independently is as described above in the fifth set of values for the variables of Structural Formulas (II)-(IX).

Values and preferred values of the remainder of the variables of Structural Formulas (II)-(IX) are each independently as described above in the first set of values for Structural Formula (I).

A seventh set of values for the variables of Structural Formulas (II)-(IX) is provided in the following paragraphs:

Each $R^4$ independently is selected from the group consisting of:

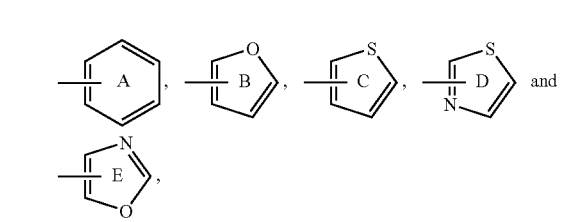

wherein each of rings A-L is optionally substituted with one or more substituents selected from the group consisting of halogen, $Ak^1$, —$OR^{10}$ and —$SR^{10}$. Preferably, each $R^4$ independently is selected from the group consisting of:

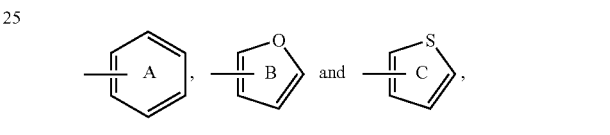

wherein each of rings A-C is optionally substituted with one or more substituents selected from the group consisting of halogen, $Ak^1$, —$OR^{10}$ and —$SR^{10}$. More preferably, each $R^4$ independently is selected from the group consisting of:

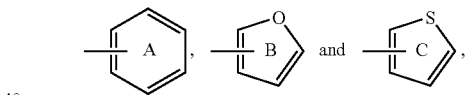

wherein each of rings A-C is optionally substituted with one or more substituents selected from the group consisting of: $C_{1-15}$ alkyl, $C_{1-15}$ haloalkyl, —$C_{2-6}$ alkynylene-($C_{1-10}$ alkyl), —$C_{2-6}$ alkynylene-$Ar^2$, —$C_{1-6}$ alkylene-$Ar^2$, —$C_{1-6}$ alkylene-N($R^{21}$)$_2$, —$C_{1-6}$ alkylene-O-$Ar^2$, —$C_{1-6}$ alkylene-O-$Ak^2$-$Ar^2$, —$C_{1-6}$ alkylene-S-$Ar^2$, —$C_{1-6}$ alkylene-S-$Ak^2$-$Ar^2$, —$OC_{1-10}$ alkyl, —O—$C_{1-6}$ alkylene-$Ar^0$, —$SC_{1-10}$ alkyl and —S—$C_{1-6}$ alkylene-$Ar^0$.

Each of $R^{20}$ and $R^{25}$ independently is i) hydrogen; ii) a $C_{6-14}$ aryl or a 5-14 membered heteroaryl group each optionally and independently substituted with one or more substituents selected from the group consisting of halogen, nitro, cyano, hydroxy, $C_{1-6}$ alkyl, $C_{2-6}$ alkenyl, $C_{2-6}$ alkynyl, amino, $C_{1-6}$ alkylamino, $C_{1-6}$ dialkylamino, $C_{1-6}$ alkoxy, ($C_{1-6}$ alkoxy)$C_{1-6}$ alkyl, $C_{1-6}$ haloalkoxy, $C_{1-6}$haloalkyl and ($C_{1-6}$ haloalkoxy)$C_{1-6}$ alkyl; or iii) a $C_{1-10}$ alkyl group optionally substituted with one or more substituents selected from the group consisting of halogen, hydroxyl, amino, $C_{1-6}$ alkylamino, $C_{1-6}$ dialkylamino, $C_{1-6}$ alkoxy, nitro, cyano, $C_{1-6}$ alkoxycarbonyl, $C_{1-6}$ alkylcarbonyl, ($C_{1-6}$ haloalkoxy)$C_{1-6}$ alkyl, and $C_{1-6}$ haloalkoxy.

Each of the non-aromatic heterocyclic groups represented by —$N(R^{21})_2$ and —$N(R^{26})_2$ is optionally and independently substituted with one or more substituents selected from the group consisting of halogen, $C_{1-6}$ alkyl, $C_{2-6}$ alkenyl, $C_{2-6}$ alkynyl, amino, $C_{1-6}$ alkylamino, $C_{1-6}$ dialkylamino, $C_{1-6}$ alkoxy, nitro, cyano, hydroxy, $C_{1-6}$ alkoxycarbonyl, $C_{1-6}$ alkylcarbonyl, $C_{1-6}$haloalkoxy, $(C_{1-6}$ haloalkoxy)$C_{1-6}$ alkyl, $C_{1-6}$ haloalkyl, $C_{6-14}$ aryl and 5-14 membered heteroaryl.

Each $Ak^0$ and $Ak^2$ independently is a $C_1$-$C_6$ alkylene group.

Each of $X^-$, $Y$, $R^3$, $R^4$, $R^5$, $R^7$, $R^8$, $R^9$, $R^{10}$ and $Ak^1$ independently is as described above in the sixth set of values for the variables of Structural Formulas (II)-(IX).

Values and preferred values of the remainder of the variables of Structural Formulas (II)-(IX) are each independently as described above in the first set of values for Structural Formula (I).

An eighth set of values for the variables of Structural Formulas (II)-(IX) is provided in the following paragraphs:

Each $R^3$ for Structural Formulas (IV)-(IX) independently is $-N(R^7R^8R^9)^+$.

Each of $X^-$, $Y$, $R^4$, $R^5$, $R^7$, $R^8$, $R^9$, $R^{10}$, $R^{20}$, $R^{21}$, $R^{25}$, $R^{26}$, $Ak^0$, $Ak^1$ and $Ak^2$ independently is as described above in the seventh set of values for the variables of Structural Formulas (II)-(IX).

Values and preferred values of the remainder of the variables of Structural Formulas (II)-(IX) are each independently as described above in the first set of values for Structural Formula (I).

A ninth set of values for the variables in Structural Formulas (II)-(IX) independently is as defined in the first set, second set, third set, fourth set, fifth set, sixth set or seventh set of values for the variables for Structural Formula (I).

In a third embodiment, the compound of the invention is represented by Structural Formula (X)-(XVI):

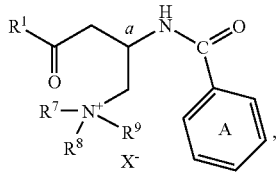
(X)

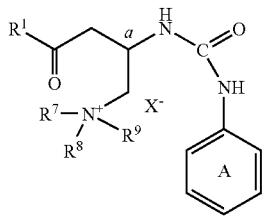
(XI)

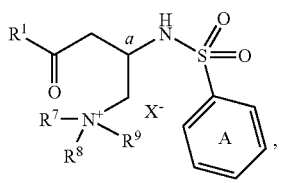
(XII)

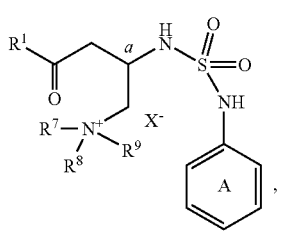
(XIII)

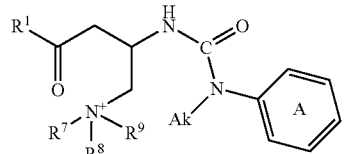
(XIV)

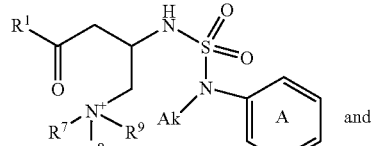
(XV)
and

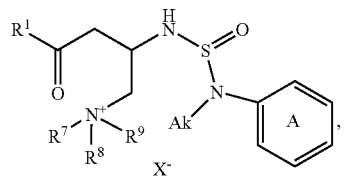
(XVI)

or a pharmaceutically acceptable salt thereof. A first set of values for the variables in Structural Formulas (X) and (XVI) is provided in the following paragraphs:

Each of $R^7$, $R^8$ and $R^9$ independently is $C_{1-6}$ alkyl. More preferably, each of $R^7$, $R^8$ and $R^9$ independently is methyl or ethyl. Even more preferably, each of $R^7$, $R^8$ and $R^9$ independently is methyl.

Each ring A is optionally substituted with one or more substituents. Suitable substitutents are selected from the group consisting of: halogen, $C_{1-15}$ alkyl, $C_{1-15}$ haloalkyl, $-C_{2-6}$ alkynylene-$(C_{1-10}$alkyl), $-C_{2-6}$ alkynylene-$Ar^2$, $-C_{1-6}$ alkylene-$Ar^2$, $-C_{1-6}$ alkylene-$N(R^{21})_2$, $-C_{1-6}$ alkylene-O-$Ar^2$, $-C_{1-6}$ alkylene-O-$Ak^2$-$Ar^2$, $-C_{1-6}$ alkylene-S-$Ar^2$, $-C_{1-6}$ alkylene-S-$Ak^2$-$Ar^2$, $-OC_{1-10}$ alkyl, $-O-C_{1-6}$ alkylene-$Ar^0$, $-SC_{1-10}$ alkyl and $-S-C_{1-6}$ alkylene-$Ar^0$.

For Structural Formulas Ak is an unsubstituted C1-C5 alkyl group.

Values and preferred values of the remainder of the variables of Structural Formulas (II)-(IX) are each independently as described above in the first set of values for Structural Formula (I).

A second set of for the variables in Structural Formulas (X) and (XVI) is provided in the following paragraphs:

Each of $R^7$, $R^8$, $R^9$ and Ak independently is as described above in the first set of values for the variables in Structural Formulas (X)-(XVI).

Each ring A is optionally substituted with one or more substituents as described above in the first set of values for the variables in Structural Formulas (X)-(XVI).

Each of $Ar^0$ and $Ar^2$ is an optionally substituted phenyl group.

A third set of values for the variables in Structural Formulas (X)-(XVI) independently is as defined in the first set, second set, third set, fourth set, fifth set, sixth set or seventh set of values for the variables for Structural Formula (I).

A fourth set of values for the variables in Structural Formulas (X)-(XVI) independently is as defined in the first set, second set, third set, fourth set, fifth set, sixth set, seventh set, eighth set and ninth set of values for the variables for Structural Formulas (II)-(IX).

In a fourth embodiment, the compound of the invention is represented by Structural Formula (XVII):

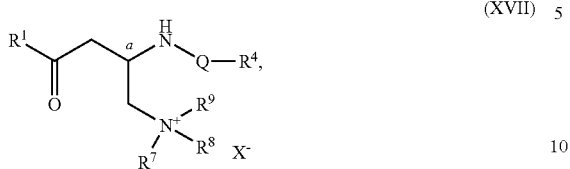

(XVII)

or a pharmaceutically acceptable salt thereof. Values for the variables for Structural Formula (VII) are each independently defined in the following paragraphs:

$R^1$ is —OH or —$OC_{1-6}$ alkyl.

Each of $R^7$, $R^8$ and $R^9$ independently is —H or $C_{1-6}$ alkyl.

$X^-$ is a pharmaceutically acceptable counter ion.

Q is —C(=O)—, —C(=S)—, —C(O)NH—, —C(S)NH—, —C(=NH)—, —S(O)—, —S(O)$_2$—, —S(O)—NH—, —S(O)$_2$—NH—, —C(=O)—N($R^5$)—, —C(=S)—N($R^5$)—, —C(=NH)—N($R^5$)—, —S(O)—N($R^5$)— or —S(O)$_2$—N($R^5$)—.

$R^4$ is selected from:

(a) $C_{6-14}$aryl which is unsubstituted or substituted with one to three substituents independently selected from:

halo, nitro, cyano, C(O)OH, C(O)$OC_{1-6}$alkyl, C(O)$NH_2$, C(O)NH$NC_{1-6}$alkyl, S(O)$C_{1-6}$alkyl, $SO_2C_{1-6}$alkyl, $SO_2NH_2$, $SO_2NHNC_{1-6}$alkyl, C(O)$C_{1-6}$alkyl OH, $OC_{1-6}$ alkyl, $OCF_3$, $CF_3$, $NH_2$, NH($C_{1-6}$alkyl) and N($C_{1-6}$alkyl)($C_{1-6}$alkyl), $C_{1-20}$alkyl, $C_{2-20}$alkene, $C_{2-20}$alkyne, $C_{5-14}$heteroaryl, $C_{6-14}$aryl, O—$C_{1-20}$alkyl, O—$C_{2-20}$alkene, O—$C_{2-20}$alkyne, O—$C_{6-14}$aryl, O—$C_{5-14}$heteroaryl, NH—SO—$C_{6-14}$aryl, $NHSO_2$—$C_{6-14}$aryl, NH—SO—$O_{5-14}$heteroaryl, $NHSO_2$—$O_{5-14}$heteroaryl, NH—C(X)—$C_{6-14}$aryl, C(X)NH—$C_{6-14}$ aryl, NH—C(X)—$O_{5-14}$heteroaryl, C(X)NH—$C_{5-14}$ heteroaryl, C(X)—$C_{6-14}$aryl and C(X)—$C_{5-14}$ heteroaryl, and all alkyl, alkenyl, alkynyl, aryl and heteroaryl groups, either alone or part of another function grouping, in the one to three substituents on $C_{6-14}$aryl are either unsubstituted or further substituted with one to three substituents independently selected from:

$C_{1-20}$alkyl, $OC_{1-20}$alkyl, halo substituted $C_{1-20}$alkyl, halo substituted O—$C_{1-20}$alkyl, $C_{2-20}$alkene, $C_{2-20}$alkyne, halo, OH, $NH_2$, NH($C_{1-6}$alkyl), N($C_{1-6}$alkyl)($C_{1-6}$alkyl), $C_{6-14}$aryl and $C_5$-$C_{14}$-heteroaryl, and all alkyl, alkene and alkyne groups, either alone or part of another function grouping, in the one to three substituents on $C_{6-14}$aryl optionally contain a heteroatom selected from:

O, S, N, NH and $NC_{1-6}$alkyl, in place of 1-5 carbon atoms; and (b) $C_5$-$C_{14}$-heteroaryl which is unsubstituted or substituted with one to three substituents independently selected from:

halo, nitro, cyano, C(O)OH, C(O)$OC_{1-6}$alkyl, C(O)$NH_2$, C(O)NH$NC_{1-6}$alkyl, S(O)$C_{1-6}$alkyl, $SO_2C_{1-6}$alkyl, $SO_2NH_2$, $SO_2NHNC_{1-6}$alkyl, C(O)$C_{1-6}$alkyl OH, $OC_{1-6}$ alkyl, $OCF_3$, $CF_3$, $NH_2$, NH($C_{1-6}$alkyl) and N($C_{1-6}$alkyl)($C_{1-6}$alkyl), $C_{1-20}$alkyl, $C_{2-20}$alkene, $C_{2-20}$alkyne, $C_{5-14}$heteroaryl, $C_{6-14}$aryl, O—$C_{1-20}$alkyl, O—$C_{2-20}$alkene, O—$C_{2-20}$alkyne O—$C_{6-14}$aryl, O—$C_{5-14}$heteroaryl, NH—SO—$C_{6-14}$aryl, $NHSO_2$—$C_{6-14}$aryl, NH—SO—$C_{5-14}$heteroaryl, $NHSO_2$—$C_{5-14}$ heteroaryl, NH—C(X)—$C_{6-14}$aryl, C(X)NH—$C_{6-14}$ aryl, NH—C(X)—$C_{5-14}$heteroaryl, C(X)NH—$C_{5-14}$ heteroaryl, C(X)—$C_{6-14}$aryl and C(X)—$C_{5-14}$ heteroaryl, and all alkyl, alkenyl, alkynyl, aryl and heteroaryl groups, either alone or part of another function grouping, in the one to three substituents on $C_5$-$C_{14}$-heteroaryl, are either unsubstituted or further substituted with one to three substituents independently selected from:

$C_{1-20}$alkyl, $OC_{1-20}$alkyl, halo substituted $C_{1-20}$alkyl, halo substituted O—$C_{1-20}$alkyl, $C_{2-20}$alkene, $C_{2-20}$alkyne, halo, OH, $NH_2$, NH($C_{1-6}$alkyl), N($C_{1-6}$alkyl)($C_{1-6}$alkyl), $C_{6-14}$aryl and $C_5$-$C_{14}$-heteroaryl, and all alkyl, alkene and alkyne groups, either alone or part of another function grouping, in the one to three substituents on $C_5$-$C_{14}$-heteroaryl optionally contain a heteroatom selected from:

O, S, N, NH and $NC_{1-6}$alkyl, in place of 1-5 carbon atoms.

$R^5$ and $R^6$ are independently selected from;

(a) $C_{1-20}$alkyl, $C_{1-20}$alkene and $C_{1-20}$alkyne where the $C_{1-20}$alkyl, $C_{1-20}$alkene and $C_{1-20}$alkyne are unsubstituted or substituted with one to three substituents independently selected from:

halo, nitro, cyano, C(O)OH, C(O)$OC_{1-6}$alkyl, C(O)$NH_2$, C(O)NH$NC_{1-6}$alkyl, S(O)$C_{1-6}$alkyl, $SO_2C_{1-6}$ alkyl, $SO_2NH_2$, $SO_2NHNC_{1-6}$alkyl, C(O)$C_{1-6}$alkyl OH, $OC_{1-6}$alkyl, $OCF_3$, $CF_3$, $NH_2$, NH($C_{1-6}$alkyl) and N($C_{1-6}$alkyl)($C_{1-6}$alkyl), $C_{1-20}$alkyl, $C_{2-20}$alkene, $C_{2-20}$alkyne, $C_{5-14}$heteroaryl, $C_{6-14}$aryl, O—$C_{1-20}$ alkyl, O—$C_{2-20}$alkene, O—$C_{2-20}$alkyne, O—$C_{6-14}$ aryl, O—$C_{5-14}$heteroaryl, NH—SO—$C_{6-14}$aryl, $NHSO_2$—$C_{6-14}$aryl, NH—SO—$C_{5-14}$heteroaryl, $NHSO_2$—$C_{5-14}$heteroaryl, NH—C(X)—$C_{6-14}$aryl, C(X)NH—$C_{6-14}$aryl, NH—C(X)—$C_{5-14}$heteroaryl, C(X)NH—$C_{5-14}$heteroaryl, C(X)—$C_{6-14}$aryl and C(X)—$C_{5-14}$heteroaryl, and all alkyl, alkenyl, alkynyl, aryl and heteroaryl groups, either alone or part of another function grouping, in the one to three substituents on $C_{6-14}$aryl are either unsubstituted or further substituted with one to three substituents independently selected from:

$C_{1-20}$alkyl, $OC_{1-20}$alkyl, halo substituted $C_{1-20}$alkyl, halo substituted O—$C_{1-20}$alkyl, $C_{2-20}$alkene, $C_{2-20}$alkyne, halo, OH, $NH_2$, NH($C_{1-6}$alkyl), N($C_{1-6}$ alkyl)($C_{1-6}$alkyl), $C_{6-14}$aryl and $C_5$-$C_{14}$-heteroaryl, and all alkyl, alkene and alkyne groups, either alone or part of another function grouping, in the one to three substituents on $C_{6-14}$aryl optionally contain a heteroatom selected from:

O, S, N, NH and $NC_{1-6}$alkyl, in place of 1-5 carbon atoms;

(b) $C_{6-14}$aryl which is unsubstituted or substituted with one to three substituents independently selected from:

halo, nitro, cyano, C(O)OH, C(O)$OC_{1-6}$alkyl, C(O)$NH_2$, C(O)NH$NC_{1-6}$alkyl, S(O)$C_{1-6}$alkyl, $SO_2C_{1-6}$ alkyl, $SO_2NH_2$, $SO_2NHNC_{1-6}$alkyl, C(O)$C_{1-6}$alkyl OH, $OC_{1-6}$alkyl, $OCF_3$, $CF_3$, $NH_2$, NH($C_{1-6}$alkyl) and N($C_{1-6}$alkyl)($C_{1-6}$alkyl), $C_{1-20}$alkyl, $C_{2-20}$alkene, $C_{2-20}$alkyne, $C_{5-14}$heteroaryl, $C_{6-14}$aryl-$C_{2-20}$alkene, O—$C_{2-20}$alkyne, O—$C_{6-14}$aryl, O—$C_{5-14}$heteroaryl, NH—SO—$C_{6-14}$aryl, $NHSO_2$—$C_{6-14}$aryl, NH—SO—$C_{5-14}$heteroaryl, $NHSO_2$—$C_{5-14}$heteroaryl, NH—C(X)—$C_{6-14}$aryl, C(X)NH—$C_{6-14}$ aryl, NH—C(X)—$C_{5-14}$heteroaryl, C(X)NH—$C_{5-14}$ heteroaryl, C(X)—$C_{6-14}$aryl and C(X)—$C_{5-14}$ heteroaryl, and all alkyl, alkenyl, alkynyl, aryl and heteroaryl groups, either alone or part of another function grouping, in the one to three substituents on $C_{6-14}$aryl are either unsubstituted or further substituted with one to three substituents independently selected from:

$C_{1-20}$alkyl, $OC_{1-20}$alkyl, halo substituted $C_{1-20}$alkyl, halo substituted $O-C_{1-20}$alkyl, $C_{2-20}$alkene, $C_{2-20}$alkyne, halo, OH, $NH_2$, $NH(C_{1-6}$alkyl), $N(C_{1-6}$ alkyl)($C_{1-6}$alkyl), $C_{6-14}$aryl and $C_5$-$C_{14}$-heteroaryl, and all alkyl, alkene and alkyne groups, either alone or part of another function grouping, in the one to three substituents on $C_{6-14}$aryl optionally contain a heteroatom selected from:

O, S, N, NH and $NC_{1-6}$alkyl, in place of 1-5 carbon atoms; and (c) $C_5$-$C_{14}$-heteroaryl which is unsubstituted or substituted with one to three substituents independently selected from:

halo, nitro, cyano, C(O)OH, C(O)O$C_{1-6}$alkyl, C(O)$NH_2$, C(O)NHN$C_{1-6}$alkyl, S(O)$C_{1-6}$alkyl, $SO_2C_{1-6}$alkyl, $SO_2NH_2$, $SO_2$NHN$C_{1-6}$alkyl, C(O)$C_{1-6}$alkyl OH, O$C_{1-6}$alkyl, $OCF_3$, $CF_3$, $NH_2$, $NH(C_{1-6}$alkyl) and $N(C_{1-6}$alkyl)($C_{1-6}$alkyl), O—$C_{2-20}$alkene, $C_{2-20}$-alkyne, $C_{5-14}$heteroaryl, $C_{6-14}$aryl, O—$C_{1-20}$alkyl, O—$C_{2-20}$alkene, O—$C_{2-20}$-alkyne, O—$C_{6-14}$aryl, O—$C_{5-14}$heteroaryl, NH—SO—$C_{6-14}$aryl, NHSO$_2$—$C_{6-14}$aryl, NH—SO—$C_{5-14}$heteroaryl, NHSO$_2$—$C_{5-14}$heteroaryl, NH—C(X)—$C_{6-14}$aryl, C(X)NH—$C_{6-14}$aryl, NH—C(X)—$C_{5-14}$heteroaryl, C(X)NH—$C_{5-14}$heteroaryl, C(X)—$C_{6-14}$aryl and C(X)—$C_{5-14}$heteroaryl, and all alkyl, alkenyl, alkynyl, aryl and heteroaryl groups, either alone or part of another function grouping, in the one to three substituents on $C_5$-$C_{14}$-heteroaryl, are either unsubstituted or further substituted with one to three substituents independently selected from:

$C_{1-20}$alkyl, $OC_{1-20}$alkyl, halo substituted $C_{1-20}$alkyl, halo substituted $O-C_{1-20}$alkyl, $C_{2-20}$alkene, $C_{2-20}$alkyne, halo, OH, $NH_2$, $NH(C_{1-6}$alkyl), $N(C_{1-6}$ alkyl)($C_{1-6}$alkyl), $C_{6-14}$aryl and $C_5$-$C_{14}$-heteroaryl, and all alkyl, alkene and alkyne groups, either alone or part of another function grouping, in the one to three substituents on $C_5$-$C_{14}$-heteroaryl optionally contain a heteroatom selected from:

O, S, N, NH and $NC_{1-6}$alkyl, in place of 1-5 carbon atoms; or (d) $R^5$ and $R^6$ together with the nitrogen atom to which they are attached, form a mono- or polycyclic, saturated or unsaturated, ring system containing from 4 to 14 atoms of which 1 to 5 atoms are a heteroatom selected from O, S, N, NH and $NC_{1-6}$alkyl and the remaining atoms are carbon, said ring system being unsubstituted or substituted with one to three substituents independently selected from:

halo, nitro, cyano, C(O)OH, C(O)O$C_{1-6}$alkyl, C(O)$NH_2$, C(O)NHN$C_{1-6}$alkyl, S(O)$C_{1-6}$alkyl, $SO_2C_{1-6}$alkyl, $SO_2NH_2$, $SO_2$NHN$C_{1-6}$alkyl, C(O)$C_{1-6}$alkyl OH, O$C_{1-6}$alkyl, $OCF_3$, $CF_3$, $NH_2$, $NH(C_{1-6}$alkyl) and $N(C_{1-6}$alkyl)($C_{1-6}$alkyl), $C_{1-21}$alkyl, $C_{2-20}$alkene, $C_{2-20}$alkyne, $C_{5-14}$heteroaryl, $C_{6-14}$aryl, O—$C_{1-20}$alkyl, O—$C_{2-20}$alkene, O—$C_{2-20}$-alkyne, O—$C_{6-14}$aryl, O—$C_{5-14}$heteroaryl, NH—SO—$C_{6-14}$aryl, NHSO$_2$—$C_{6-14}$aryl, NH—SO—$C_{5-14}$heteroaryl, NHSO$_2$—$C_{5-14}$heteroaryl, NH—C(X)—$C_{6-14}$aryl, C(X)NH—$C_{6-14}$aryl, NH—C(X)—$C_{5-14}$heteroaryl, C(X)NH—$C_{5-14}$heteroaryl, C(X)—$C_{6-14}$aryl and C(X)—$C_{5-14}$heteroaryl, and all alkyl, alkenyl, alkynyl, aryl and heteroaryl groups, either alone or part of another function grouping, in the one to three substituents on the ring system, are either unsubstituted or further substituted with one to three substituents independently selected from:

$C_{1-20}$alkyl, $OC_{1-20}$alkyl, halo substituted $C_{1-20}$alkyl, halo substituted $O-C_{1-20}$alkyl, $C_{2-20}$alkene, $C_{2-20}$alkyne, halo, OH, $NH_2$, $NH(C_{1-6}$alkyl), $N(C_{1-6}$ alkyl)($C_{1-6}$alkyl), $C_{6-14}$aryl and $C_5$-$C_{14}$-heteroaryl, and all alkyl, alkene and alkyne groups, either alone or part of another function grouping, in the one to three substituents on the ring system optionally contain a heteroatom selected from:

O, S, N, NH and $NC_{1-6}$alkyl, in place of 1-5 carbon atoms;

$R^7$, $R^8$ and $R^9$ are independently selected from H and $C_{1-6}$alkyl; and heteroaryl is a mono- or polycyclic heteroaromatic ring system containing a heteroatom independently selected from N, NH, $NC_{1-6}$alkyl, S and O in place of at least 1 carbon atom. In this embodiment, the terms "amine" and "amino" are used interchangeably and mean —$NH_2$, —NHR or —$NR_2$, wherein R is alkyl.

Specific examples of the compound of the invention include:

(R)-3-(4-propoxybenzamido)-4-(trimethylammonio)butanoate;

(R)-3-(4-(thiophene-2-sulfonamido)benzamido)-4-(trimethylammonio)-butanoate;

(R)-3-(5-(phenylethynyl)furan-2-carboxamido)-4-(trimethylammonio)-butanoate;

(R)-3-(5-(hex-1-ynyl)furan-2-carboxamido)-4-(trimethylammonio)butanoate;

(R)-3-(4-(3-methylfuran-2-carboxamido)benzamido)-4-(trimethylammonio)-butanoate;

(R)-3-(3-(2-chloro-4-(trifluoromethyl)phenyl)ureido)-4-(trimethylammonio)-butanoate;

(R)-3-(3-(4-octylphenyl)ureido)-4-(trimethylammonio) butanoate;

(R)-3-(3-(4-phenoxyphenyl)ureido)-4-(trimethylammonio)butanoate;

(R)-3-(3-(4-methyl-2-phenylthiazol-5-yl)ureido)-4-(trimethylammonio)-butanoate;

(R)-3-(3-(4-(heptyloxy)phenypureido)-4-(trimethylammonio)butanoate;

(R)-3-(3-(4-(thiophen-2-yl)phenyl)ureido)-4-(trimethylammonio)butanoate;

(R)-3-(3-(4-(Benzyloxy)phenyl)ureido)-4-(trimethylammonio)butanoate acetate;

(R)-2-(3-(4-Butyl-2-methylphenyl)ureido)-3-carboxy-N,N,N-trimethylpropan-1-aminium;

(R)-3-Carboxy-N,N,N-trimethyl-2-(3-(2,3,4-trifluorophenyl)ureido)-propan-1-aminium acetate;

(R)-3-Carboxy-N,N,N-trimethyl-2-(3-(4-pentylphenypureido)propan-1-aminium;

(R)-2-(3-(4-Benzoylphenyl)ureido)-3-carboxy-N,N,N-trimethylpropan-1-aminium acetate;

(R)-2-(3-Biphenyl-4-ylureido)-3-carboxy-N,N,N-trimethylpropan-1-aminium acetate;

(R)-3-(4-(trifluoromethyl)phenylsulfonamido)-4-(trimethylammonio)-butanoate;

(R)-3-(6-phenoxypyridine-3-sulfonamido)-4-(trimethylammonio)-butanoate 2,2,2-trifluoroacetate;

(R)-3-(4'-fluorobiphenyl-4-ylsulfonamido)-4-(trimethylammonio)butanoate;

(R)-3-(5-(pyridin-2-yl)thiophene-2-sulfonamido)-4-(trimethylammonio)-butanoate 2,2,2-trifluoroacetate;

(R)-3-carboxy-2-(5-(isoxazol-5-yl)thiophene-2-sulfonamido)-N,N,N-trimethylpropan-1-aminium 2,2,2-trifluoroacetate;
(R)-3-(4-pentylphenylsulfonamido)-4-(trimethylammonio)butanoate 2,2,2-trifluoroacetate;
(R)-3-(benzofuran-2-sulfonamido)-4-(trimethylammonio)butanoate;
(R)-3-(3-(benzyloxy)phenylsulfonamido)-4-(trimethylammonio)butanoate;
(R)-3-(3-phenoxyphenylsulfonamido)-4-(trimethylammonio)butanoate;
(R)-3-(N-dodecyl-N-methylsulfamoylamino)-4-(trimethylammonio)-butanoate;
(R)-3-(N-methyl-N-(4-phenylbutyl)sulfamoylamino)-4-(trimethylammonio)-butanoate;
(R)-3-(N-methyl-N-(4-phenoxyphenyl)sulfamoylamino)-4-(trimethyl-ammonio)butanoate;
(R)-3-(N-(4-octylphenyl)sulfamoylamino)-4-(trimethylammonio)butanoate;
(R)-3-carboxy-N,N,N-trimethyl-2-(N-(3-phenoxyphenyl)sulfamoyl-amino)propan-1-aminium 2,2,2-trifluoroacetate;
(R)-3-(N-dodecyl-N-phenylsulfamoylamino)-4-(trimethylammonio)-butanoate;
(R)-4-(dimethylammonio)-3-(3-methyl-3-(4-phenoxyphenyl)-ureido)butanoate;
(R)-3-(3-methyl-3-(4-phenoxyphenyl)ureido)-4-(trimethyl-ammonio)butanoate;
(R)-3-(3-(3-(4-Fluorophenyl)-3-oxopropyl)-3-(4-phenoxyphenyl)ureido)-4-(trimethylammonio)butanoate;
(R)-3-(3-methyl-3-(4-octylphenyl)ureido)-4-(trimethylammonio)butanoate;
(R)-3-(3-(Biphenyl-4-yl)-3-(2-methoxyethyl)ureido)-4-(trimethylammonio)-butanoate;
(R)-3-(3-(3-Phenoxyphenyl)ureido)-4-(trimethylammonio)butanoate;
(R)-3-(3-(3-(phenylsulfonamido)phenyl)ureido)-4-(trimethylammonio)-butanoate;
(R)-3-(3-methyl-3-tetradecylureido)-4-(trimethylammonio)-butanoate;
(R)-3-(3-Dodecyl-3-phenylureido)-4-(trimethylammonio)butanoate;
(R)-3-(5-phenethylfuran-2-carboxamido)-4-(trimethylammonio)-butanoate;
(R)-3-(5-(phenylethynyl)thiophene-2-carboxamido)-4-(trimethylammonio)-butanoate;
(R)-3-(2,2'-bithiophene-5-carboxamido)-4-(trimethylammonio)butanoate;
(R)-3-(5-phenethylthiophene-2-carboxamido)-4-(trimethylammonio)-butanoate;
(R)-3-(3-phenethylbenzamido)-4-(trimethylammonio)butanoate;
(R)-3-(5-(benzyloxymethyl)furan-2-carboxamido)-4-(trimethylammonio)-butanoate;
(R)-3-(3-(phenylethynyl)benzamido)-4-(trimethylammonio)butanoate;
(R)-3-(2,2'-bithiophene-5-carboxamido)-4-(trimethylammonio)butanoate;
(R)-3-(6-phenoxynicotinamido)-4-(trimethylammonio)butanoate;
(R)-3-(4-methyl-2-(pyrazin-2-yl)thiazole-5-carboxamido)-4-(trimethyl-ammonio)butanoate;
(R)-3-(6-(2,2,2-trifluoroethoxy)nicotinamido)-4-(trimethylammonio)butanoate;
(R)-3-(4-acetamidobenzamido)-4-(trimethylammonio)butanoate;
(R)-3-(3-methyl-1-propyl-1H-pyrazole-4-carboxamido)-4-(trimethyl-ammonio)butanoate;
(R)-3-(5-((2-methoxy-4-propylphenoxy)methyl)furan-2-carboxamido)-4-(trimethylammonio)butanoate;
(R)-3-(5-(benzylthiomethyl)furan-2-carboxamido)-4-(trimethylammonio)-butanoate;
(R)-3-(3-(1H-pyrazol-3-yl)benzamido)-4-(trimethylammonio)butanoate trifluoroacetate;
(R)-3-(5-((naphthalen-1-yloxy)methylfuran-2-carboxamido)-4-(trimethyl-ammonio)butanoate;
(R)-3-(5-(morpholinomethyl)furan-2-carboxamido)-4-(trimethylammonio)-butanoate;
(R)-3-(5-((4-tert-butylphenoxy)methyl)furan-2-carboxamido)-4-(trimethyl-ammonio)butanoate;
(R)-3-(5-(benzylsulfonylmethyl)furan-2-carboxamido)-4-(trimethyl-ammonio)butanoate 2,2,2-trifluoroacetate;
(R)-3-(4-(phenylethynyl)benzamido)-4-(trimethylammonio)butanoate 2,2,2-trifluoroacetate;
(R)-3-(4-(decyloxy)benzamido)-4-(trimethylammonio) butanoate 2,2,2-trifluoroacetate;
(R)-3-(4-phenethylbenzamido)-4-(trimethylammonio)butanoate;
(R)-3-(3-methyl-5-(phenoxymethyl)furan-2-carboxamido)-4-(trimethyl-ammonio)butanoate;
(R)-3-(4-decylbenzamido)-4-(trimethylammonio)butanoate;
(R)-3-(3-(decyloxy)benzamido)-4-(trimethylammonio) butanoate;
(R)-3-(5-((4-ethoxyphenoxy)methyl)furan-2-carboxamido)-4-(trimethyl-ammonio)butanoate;
(R)-3-(2,2-difluoro-2-phenylacetamido)-4-(trimethylammonio)butanoate;
(R)-3-(5-(m-tolyloxymethyl)furan-2-carboxamido)-4-(trimethylammonio)-butanoate;
(R)-3-(5-((4-chlorophenylthio)methyl)furan-2-carboxamido)-4-(trimethyl-ammonio)butanoate;
(R)-3-carboxy-N,N,N-trimethyl-2-(5-(1-methyl-3-(trifluoromethyl)-1H-pyrazol-5-yl)thiophene-2-sulfonamido)propan-1-aminium 2,2,2-trifluoroacetate;
(R)-3-carboxy-N,N,N-trimethyl-2-(4-(octyloxycarbonylamino)phenyl-sulfonamido)propan-1-aminium 2,2,2-trifluoroacetate;
(R)-3-carboxy-2-(4-ethoxy-3-(morpholine-4-carboxamido)phenyl-sulfonamido)-N,N,N-trimethylpropan-1-aminium 2,2,2-trifluoroacetate;
(R)-3-carboxy-2-(4-decylphenylsulfonamido)-N,N,N-trimethylpropan-1-aminium 2,2,2-trifluoroacetate;
(R)-3-carboxy-N,N,N-trimethyl-2-(5-(m-tolylethynyl)thiophene-2-sulfonamido)propan-1-aminium 2,2,2-trifluoroacetate;
(R)-3-carboxy-N,N,N-trimethyl-2-(5-(3-methylphenethyl)thiophene-2-sulfonamido)propan-1-aminium 2,2,2-trifluoroacetate;
(R)-3-carboxy-N,N,N-trimethyl-2-(5-(phenylethynyl)thiophene-2-sulfonamido)propan-1-aminium 2,2,2-trifluoroacetate;
(R)-3-carboxy-N,N,N-trimethyl-2-(5-phenethylthiophene-2-sulfonamido)-propan-1-aminium 2,2,2-trifluoroacetate;
(R)-3-carboxy-N,N,N-trimethyl-2-(5-(p-tolylethynyl)thiophene-2-(R)-3-carboxy-N,N,N-trimethyl-2-(5-(4-methylphenethyl)thiophene-2-sulfonamido)propan-1-aminium 2,2,2-trifluoroacetate;
(R)-3-carboxy-N,N,N-trimethyl-2-(5-((4-pentylphenypethynyl)thiophene-2-sulfonamido)propan-1-aminium 2,2,2-trifluoroacetate;

(R)-3-carboxy-N,N,N-trimethyl-2-(5-(4-pentylphenethyl)thiophene-2-sulfonamido)propan-1-aminium 2,2,2-trifluoroacetate;
(R)-3-(3-(3-(1H-pyrrol-1-yl)phenyl)ureido)-4-(trimethylammonio)butanoate;
(R)-3-(3-(2-chloro-5-(trifluoromethyl)phenyl)ureido)-4-(trimethyl-ammonio)butanoate;
(R)-3-(3-(3-benzylphenyl)ureido)-4-(trimethylammonio)butanoate;
(R)-3-(3-(4-Octylphenyl)-3-phenylureido)-4-(trimethylammonio)butanoate;
(R)-3-(N-(4-heptylphenyl)sulfamoylamino)-4-(trimethylammonio)butanoate;
(R)-3-(N-(4-dodecylphenyl)sulfamoylamino)-4-(trimethylammonio)-butanoate;
(R)-3-(N-(4-tetradecylphenyl)sulfamoylamino)-4-(trimethylammonio)-butanoate;
(R)-3-(N-(4-pentylphenyl)sulfamoylamino)-4-(trimethylammonio)butanoate;
(R)-3-(N-(4-decylphenyl)sulfamoylamino)-4-(trimethylammonio)butanoate;
(R)-3-(N-methyl-N-(4-octylphenyl)sulfamoylamino)-4-(trimethylammonio)-butanoate;
(R)-3-(3-(5-(3-(hexyloxy)phenoxy)pentyl)-3-methylureido)-4-(trimethyl-ammonio)butanoate;
(R)-2-(5-bromothiophene-2-carboxamido)-3-carboxy-N,N,N-trimethyl-propan-1-aminium;
(R)-2-(5-bromothiophene-2-carboxamido)-3-carboxy-N,N,N-trimethyl-propan-1-aminium 2,2,2-trifluoroacetate;
(R)-3-carboxy-N,N,N-trimethyl-2-(5-(thiophen-3-ylethynyl)thiophene-2-carboxamido)propan-1-aminium 2,2,2-trifluoroacetate;
(R)-3-carboxy-N,N,N-trimethyl-2-(5-(2-(thiophen-3-yl)ethyl)thiophene-2-carboxamido)propan-1-aminium 2,2,2-trifluoroacetate;
(R)-3-carboxy-2-(3-(2-iodophenyl)ureido)-N,N,N-trimethylpropan-1-aminium;
(R)-3-carboxy-N,N,N-trimethyl-2-(3-(2-phenoxyphenyl)ureido)propan-1-aminium;
(R)-2-(3-biphenyl-2-ylureido)-3-carboxy-N,N,N-trimethylpropan-1-aminium;
and
(R)-3-carboxy-N,N,N-trimethyl-2-(5-(4-pentylphenethyl)thiophene-2-carboxamido)propan-1-aminium 2,2,2-trifluoroacetate;
and pharmaceutically acceptable salts thereof.

Additional specific examples of the compound of the invention include:
(R)-3-(N-(4-(octyloxy)phenyl)sulfamoylamino)-4-(trimethylammonio) butanoate;
(R)-3-(N-(4-(non-1-ynyl)phenyl)sulfamoylamino)-4-(trimethylammonio) butanoate;
(R)-3-(N-(4-nonylphenyl)sulfamoylamino)-4-(trimethylammonio)-butanoate;
(R)-3-(N-(4-(oct-1-ynyl)phenyl)sulfamoylamino)-4-(trimethylammonio) butanoate;
(R)-3-(N-(4-((4-pentylphenyl)ethynyl)phenyl)sulfamoylamino)-4-(trimethylammonio)butanoate;
(R)-3-(N-(4-(4-pentylphenethyl)phenyl)sulfamoylamino)-4-(trimethyl-ammonio)butanoate;
(R)-3-(N-(5-(3-(hexyloxy)phenoxy)pentyl)-N-methylsulfamoylamino)-4-(trimethylammonio)butanoate;
(R)-3-(N-(3-(oct-1-ynyl)phenyl)sulfamoylamino)-4-(trimethylammonio) butanoate;
(R)-3-(N-(3-octylphenyl)sulfamoylamino)-4-(trimethylammonio)-butanoate;
(R)-3-(N-methyl-N-(3-(oct-1-ynyl)phenyl)sulfamoylamino)-4-(trimethyl-ammonio)butanoate;
(R)-3-carboxy-N,N,N-trimethyl-2-(methyl(N-methyl-N-(3-octylphenyl)-sulfamoyl)amino)propan-1-aminium 2,2,2-trifluoroacetate;
(R)-3-(5-bromofuran-2-carboxamido)-4-(trimethylammonio)butanoate;
(R)-3-carboxy-N,N,N-trimethyl-2-(5-((4-pentylphenyl)ethynyl)furan-2-carboxamido)propan-1-aminium 2,2,2-trifluoroacetate;
(R)-3-carboxy-N,N,N-trimethyl-2-(5-(thiophen-3-ylethynyl)furan-2-carboxamido)propan-1-aminium 2,2,2-trifluoroacetate;
(R)-3-carboxy-2-(5-((2-methoxypyrimidin-5-yl)ethynyl)furan-2-carboxamido)-N,N,N-trimethylpropan-1-aminium 2,2,2-trifluoroacetate;
(R)-3-carboxy-2-(5-((5-hexylthiophen-2-yl)ethynyl)furan-2-carboxamido)-N,N,N-trimethylpropan-1-aminium 2,2,2-trifluoroacetate;
(R)-3-(5-(2-(5-hexylthiophen-2-yl)ethyl)furan-2-carboxamido)-4-(trimethylammonio)butanoate;
(R)-3-carboxy-N,N,N-trimethyl-2-(2-oxooctanamido)propan-1-aminium 2,2,2-trifluoroacetate;
(R)-3-(5-(4-pentylphenethyl)tetrahydrofuran-2-carboxamido)-4-(trimethylammonio)butanoate;
(R)-3-(5-((3-(hexyloxy)phenyl)ethynyl)furan-2-carboxamido)-4-(trimethylammonio)butanoate;
(R)-3-carboxy-N,N,N-trimethyl-2-(5-(4-pentylphenethyl)furan-2-carboxamido)propan-1-aminium 2,2,2-trifluoroacetate;
(R)-3-carboxy-N,N,N-trimethyl-2-(5-(2-(thiophen-3-yl)ethyl)furan-2-carboxamido)propan-1-aminium 2,2,2-trifluoroacetate;
(R)-3-carboxy-2-(5-(3-(hexyloxy)phenethyl)furan-2-carboxamido)-N,N,N-trimethylpropan-1-aminium 2,2,2-trifluoroacetate; and
pharmaceutically acceptable salts thereof.

Other specific examples of the compounds of the invention include compounds exemplified in the examples below, stereoisomers thereof, and pharmaceutically acceptable salts thereof.

It is to be understood that when any compound is referred to herein by name or structure, solvates, hydrates and polymorphs thereof are included.

The compounds of the invention may contain one or more chiral center and/or double bond and, therefore, exist as stereoisomers, such as double-bond isomers (i.e., geometric isomers), enantiomers, or diastereomers. When compounds of the invention are depicted or named without indicating the stereochemistry, it is to be understood that both stereomerically pure forms (e.g., geometrically pure, enantiomerically pure, or diastereomerically pure) and stereoisomeric mixtures are encompassed. For example, the compound represented by Structural Formula (I) below has chiral center a. Accordingly, the compounds of the invention depicted by Structural Formula (I) include the pure R stereoisomers, the pure S stereoisomers and mixtures thereof.

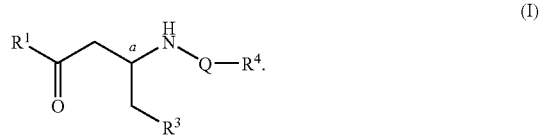

As used herein, a racemic mixture means about 50% of one enantiomer and about 50% of is corresponding enantiomer relative to all chiral centers in the molecule. The invention encompasses all enantiomerically-pure, enantiomerically-enriched, diastereomerically pure, diastereomerically enriched, and racemic mixtures of the compounds of the invention.

In some preferred embodiments, the compounds of the invention are R stereoisomers.

Enantiomeric and diastereomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

When the stereochemistry of the disclosed compounds is named or depicted by structure or name, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% optically pure. Percent optical purity by weight is the ratio of the weight of the enantiomer over the weight of the enantiomer plus the weight of its optical isomer.

Included in the invention are pharmaceutically acceptable salts of the compounds disclosed herein. The disclosed compounds have basic amine groups and therefore can form pharmaceutically acceptable salts with pharmaceutically acceptable acid(s). Suitable pharmaceutically acceptable acid addition salts of the compounds of the invention include salts of inorganic acids (such as hydrochloric acid, hydrobromic, phosphoric, metaphosphoric, nitric, and sulfuric acids) and of organic acids (such as, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, and tartaric acids). Compounds of the invention with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts). Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, maleates, acetates, citrates, fumarates, tartrates [e.g. (+)-tartrates, (−)-tartrates or mixtures thereof including racemic mixtures], succinates, benzoates and salts with amino acids such as glutamic acid.

The term "halo" as used herein means halogen and includes chloro, fluoro, bromo and iodo.

An "aliphatic group" is non-aromatic, consists solely of carbon and hydrogen and may optionally contain one or more units of unsaturation, e.g., double and/or triple bonds. An aliphatic group may be straight chained or branched. When straight chained or branched, an aliphatic group typically contains between about one and about twenty carbon atoms, typically between about one and about ten carbon atoms, more typically between about one and about six carbon atoms. A "substituted aliphatic group" is substituted at any one or more "substitutable carbon atom". A "substitutable carbon atom" in an aliphatic group is a carbon in an aliphatic group that is bonded to one or more hydrogen atoms. One or more hydrogen atoms can be optionally replaced with a suitable substituent group. A "haloaliphatic group" is an aliphatic group, as defined above, substituted with one or more halogen atoms. Suitable substituents on a substitutable carbon atom of an aliphatic group are the same as those for an alkyl group.

The term "alkyl" used alone or as part of a larger moiety, such as "alkoxy", "haloalkyl", "arylalkyl", "alkylamine", "cycloalkyl", "dialkyamine", "alkylamino", "dialkyamino" "alkylcarbonyl", "alkoxycarbonyl" and the like, includes as used herein means saturated straight-chain, cyclic or branched aliphatic group. As used herein, a C1-C6 alkyl group is referred to "lower alkyl." Similarly, the terms "lower alkoxy", "lower haloalkyl", "lower arylalkyl", "lower alkylamine", "lower cycloalkylalkyl", "lower dialkyamine", "lower alkylamino", "lower dialkyamino" "lower alkylcarbonyl", "lower alkoxycarbonyl" include straight and branched saturated chains containing one to six carbon atoms.

The term "$C_{1-n}$alkyl" as used herein means straight and/or branched chain, saturated alkyl radicals containing from one to "n" carbon atoms and includes (depending on the identity of n) methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like, where the variable n is an integer representing the largest number of carbon atoms in the alkyl radical. Typically, n is an integer between 1 and 20, more typically between 1 and 15, even more typically between 1 and 10, and yet even more typically between 1 and 6.

The term "fluoro-substituted $C_{1-n}$alkyl" as used herein means straight and/or branched chain, saturated alkyl radicals containing from one to n carbon atoms in which one or all of the hydrogen atoms have been replaced with a fluorine, and includes (depending on the identity of "n") trifluoromethyl, pentafluoroethyl, fluoromethyl and the like, where the variable n is an integer representing the largest number of carbon atoms in the alkyl radical. Typically, n is an integer between 1 and 20, more typically between 1 and 15, even more typically between 1 and 10, and yet even more typically between 1 and 6.

The term "alkoxy" means —O-alkyl; "hydroxyalkyl" means alkyl substituted with hydroxy; "aralkyl" means alkyl substituted with an aryl group; "alkoxyalkyl" mean alkyl substituted with an alkoxy group; "alkylamine" means amine substituted with an alkyl group; "cycloalkylalkyl" means alkyl substituted with cycloalkyl; "dialkylamine" means amine substituted with two alkyl groups; "alkylcarbonyl" means —C(O)—R, wherein R is alkyl; "alkoxycarbonyl" means —C(O)—OR, wherein R is alkyl; and where alkyl is as defined above.

The terms "haloalkyl" and "haloalkoxy" means alkyl or alkoxy, as the case may be, substituted with one or more halogen atoms. The term "halogen" means F, Cl, Br or I. Preferably the halogen in a haloalkyl or haloalkoxy is F.

The term "acyl group" mean —C(O)R, wherein R is an optionally substituted alkyl group or aryl group (e.g., optionally substituted phenyl). R is preferably an unsubstituted alkyl group or phenyl.

As used herein, the term "alkenyl" refers to a straight or branched hydrocarbon group that contains one or more double bonds between carbon atoms. An alkenyl group may be substituted. The term "$C_{1-n}$alkenyl" as used herein means straight and/or branched chain, unsaturated alkyl radicals containing from one to n carbon atoms and one to three double bonds, and includes (depending on the identity of n) vinyl, allyl, 2-methylprop-1-enyl, but-1-enyl, but-2-enyl, but-3-enyl, 2-methylbut-1-enyl, 2-methylpent-1-enyl, 4-methylpent-1-enyl, 4-methylpent-2-enyl, 2-methylpent-2-enyl, 4-methylpenta-1,3-dienyl, hexen-1-yl and the like, where the variable n is an integer representing the largest number of carbon atoms in the alkenyl radical. Typically, n is an integer between 2 and 20, more typically between 2 and 15, even more typically between 2 and 10, and yet even more typically between 2 and 6.

As used herein, the term "alkynyl" refers to a straight or branched hydrocarbon group that contains one or more triple bonds between carbon atoms. An alkynyl group may be substituted. The term "$C_{1-n}$alkynyl" as used herein means straight and/or branched chain, unsaturated alkyl radicals containing from one to n carbon atoms and one to three triple bonds, and includes (depending on the identity of n) propargyl, but-1-ynyl, but-2-ynyl, but-3-ynyl, 4-methylpent-1-ynyl, 4-methylpent-2-ynyl, hex-1-ynyl and the like, where the variable n is an integer representing the largest number of carbon atoms in the alkynyl radical. Typically, n is an integer between 2 and 20, more typically between 2 and 15, even more typically between 2 and 10, and yet even more typically between 2 and 6.

An "alkylene group" is represented by $-[CH_2]_z-$, wherein z is a positive integer, preferably from one to eight, more preferably from one to four.

An "alkenylene group" is an alkylene in which at least a pair of adjacent methylenes are replaced with $-CH=CH-$.

An "alkynylene group" is an alkylene in which at least a pair of adjacent methylenes are replaced with $-C\equiv C-$.

The term "aryl group" used alone or as part of a larger moiety as in "aralkyl", "aralkoxy", or "aryloxyalkyl", means carbocyclic aromatic rings. The term "carbocyclic aromatic group" may be used interchangeably with the terms "aryl", "aryl ring" "carbocyclic aromatic ring", "aryl group" and "carbocyclic aromatic group". An aryl group typically has six-fourteen ring atoms. A "substituted aryl group" is substituted at any one or more substitutable ring atom. The term "$C_{6-14}$aryl" as used herein means a monocyclic, bicyclic or tricyclic carbocyclic ring system containing from 6 to 14 carbon atoms and includes phenyl, naphthyl, anthracenyl, 1,2-dihydronaphthyl, 1,2,3,4-tetrahydronaphthyl, fluorenyl, indanyl, indenyl and the like.

The term "heteroaryl", "heteroaromatic", "heteroaryl ring", "heteroaryl group" and "heteroaromatic group", used alone or as part of a larger moiety as in "heteroaralkyl" or "heteroarylalkoxy", refers to aromatic ring groups having five to fourteen ring atoms selected from carbon and at least one (typically 1-4, more typically 1 or 2) heteroatom (e.g., oxygen, nitrogen or sulfur). They include monocyclic rings and polycyclic rings in which a monocyclic heteroaromatic ring is fused to one or more other carbocyclic aromatic or heteroaromatic rings. The term "$C_{5-14}$heteroaryl" as used herein means a monocyclic, bicyclic or tricyclic ring system containing one or two aromatic rings and from 5 to 14 atoms of which, unless otherwise specified, one, two, three, four or five are heteroatoms independently selected from N, NH, N($C_{1-6}$alkyl), O and S and includes thienyl, furyl, pyrrolyl, pyrididyl, indolyl, quinolyl, isoquinolyl, tetrahydroquinolyl, benzofuryl, benzothienyl and the like.

Examples of monocyclic heteroaryl groups include furanyl (e.g., 2-furanyl, 3-furanyl), imidazolyl (e.g., N-imidazolyl, 2-imidazolyl, 4-imidazolyl, 5-imidazolyl), isoxazolyl(e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiaz-olyl, 5-thiazolyl), triazolyl (e.g., 2-triazolyl, 5-triazolyl), tetrazolyl (e.g., tetrazolyl) and thienyl (e.g., 2-thienyl, 3-thienyl. Examples of monocyclic six-membered nitrogen-containing heteraryl groups include pyrimidinyl, pyridinyl and pyridazinyl. Examples of polycyclic aromatic heteroaryl groups include carbazolyl, benzimidazolyl, benzothienyl, benzofuranyl, indolyl, quinolinyl, benzotriazolyl, benzothiazolyl, benzoxazolyl, benzimidazolyl, isoquinolinyl, indolyl, isoindolyl, acridinyl, or benzisoxazolyl.

Other examples for the aryl and heteroaryl groups, including the $C_{6-14}$ aryl and the 5-14 membered heteroaryl groups represented by each of $R^{10}$, $R^{12}$, $R^{20}$, $R^{25}$, $R^{30}$, $R^{32}$, $R^{40}$, $R^{45}$, $Ar^0$, $Ar^{00}$, $Ar^1$, $Ar^2$, $Ar^3$, and $Ar^4$, include:

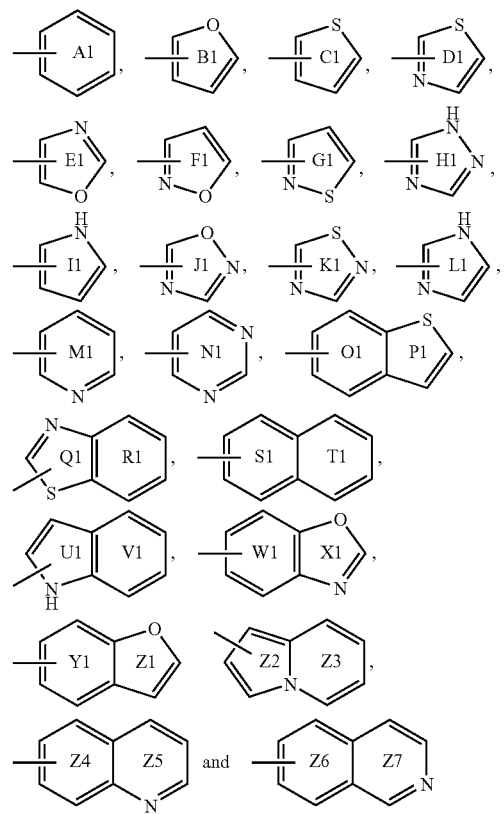

wherein each of rings A1-Z7 is optionally substituted. It is noted that, as shown above, rings O1-Z7 can be attached to their designated atom through any ring carbon of the rings which is not at a position bridging two aryl groups. For example,

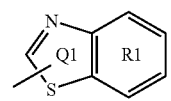

means that the group is attached to its designated atom through either ring Q1 or ring R1. Yet other examples for the aryl and heteroaryl groups, including the $C_{6-14}$ aryl and the 5-14 membered heteroaryl groups represented by each of $R^{10}$, $R^{12}$, $R^{20}$, $R^{25}$, $R^{30}$, $R^{32}$, $R^{40}$, $R^{45}$, $Ar^0$, $Ar^{00}$, $Ar^1$, $Ar^2$, $Ar^3$ and $Ar^4$, include:

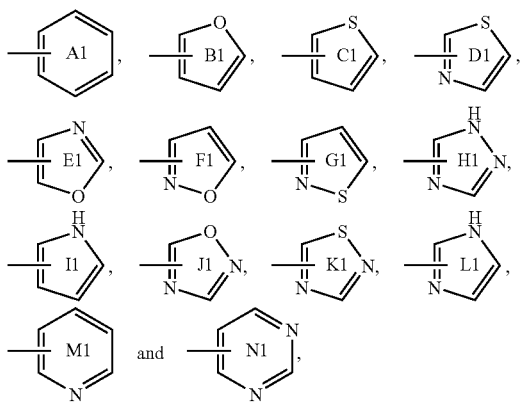

wherein each of rings A1-N1 is optionally substituted. More specific values for the aryl and heteroaryl groups, including the $C_{6-14}$ aryl and the 5-14 membered heteroaryl groups represented by each of $R^{10}$, $R^{12}$, $R^{20}$, $R^{25}$, $R^{30}$, $R^{32}$, $R^{40}$, $R^{45}$, $Ar^0$, $Ar^{00}$, $Ar^1$, $Ar^2$, $Ar^3$ and $Ar^4$, include:

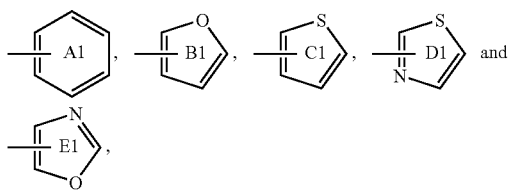

wherein each of rings A1-E1 is optionally substituted. Even more specific values for the aryl and heteroaryl groups, including the $C_{6-14}$ aryl and the 5-14 membered heteroaryl groups represented by each of $R^{10}$, $R^{12}$, $R^{20}$, $R^{25}$, $R^{30}$, $R^{32}$, $R^{40}$, $R^{45}$, $Ar^0$, $Ar^{00}$, $Ar^1$, $Ar^2$, $Ar^3$ and $Ar^4$, include:

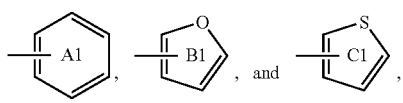

wherein each of rings A1-C1 is optionally substituted. An optionally substituted ring A is the most common specific value for each of the aryl group, including the $C_{6-14}$ aryl group represented by $R^{10}$, $R^{12}$, $R^{20}$, $R^{25}$, $R^{30}$, $R^{32}$, $R^{40}$, $R^{45}$, $Ar^0$, $Ar^{00}$, $Ar^1$, $Ar^2$, $Ar^3$ and $Ar^4$.

The aryl and heteroaryl groups, including the $C_{6-14}$ aryl and the 5-14 membered heteroaryl groups represented by each of $R^{10}$, $R^{12}$, $R^{20}$, $R^{25}$, $R^{30}$, $R^{32}$, $R^{40}$, $R^{45}$, $Ar^0$, $Ar^{00}$, $Ar^1$, $Ar^2$, $Ar^3$ and $Ar^4$, can be optionally substituted with one or more substituents selected from the group consisting of halogen, nitro, cyano, hydroxy, $C_{1-20}$ alkyl, $C_{2-20}$ alkenyl, $C_{2-20}$ alkynyl, amino, $C_{1-20}$ alkylamino, $C_{1-20}$ dialkylamino, $C_{1-20}$ alkoxy, $(C_{1-10}$ alkoxy$)C_{1-20}$ alkyl, $C_{1-20}$ haloalkoxy, $(C_{1-10}$ haloalkoxy$)C_{1-20}$ alkyl and $C_{1-20}$ haloalkyl. Specific substituents for the aryl and heteroaryl groups, including the $C_{6-14}$ aryl and the 5-14 membered heteroaryl groups represented by each of $R^{10}$, $R^{12}$, $R^{20}$, $R^{25}$, $R^{30}$, $R^{32}$, $R^{40}$, $R^{45}$, $Ar^0$, $Ar^{00}$, $Ar^1$, $Ar^2$, $Ar^3$ and $Ar^4$ include halogen, nitro, cyano, hydroxy, $C_{1-10}$ alkyl, $C_{2-10}$ alkenyl, $C_{2-10}$ alkynyl, amino, $C_{1-10}$ alkylamino, $C_{1-10}$ dialkylamino, $C_{1-10}$ alkoxy, $(C_{1-6}$ alkoxy$)C_{1-10}$ alkyl, $C_{1-10}$ haloalkoxy, $(C_{1-6}$haloalkoxy$)C_{1-10}$ alkyl and $C_{1-10}$ haloalkyl. More specific substituents include $C_{1-10}$ alkyl, —OH, $C_{1-10}$alkoxy, $C_{1-10}$ haloalkyl, halogen, $C_{1-10}$ haloalkoxy, amino, nitro and cyano.

In accordance with another aspect of the present invention, the compounds of the invention can be prepared by processes analogous to those established in the art. By way of illustration, compounds of Formula (I), wherein $Q-R^4$ is —C(X)—$R^4$, wherein X is O, S or NH, and $R^4$ is as defined in Formula (I), may be prepared by the methods outlined in Scheme 1. Reaction of aminocarnitine or derivatives thereof (collectively, reagents of Formula 2A, wherein $R^1$ and $R^3$ are as defined in Formula (I)) with a suitable acylating agent of Formula 3A (wherein X is O, S or NH, and $R^4$ are as defined in Formula (I) and LG is a suitable leaving group), such as an activated ester, an acyl chloride, an acyl imidazole or a mixed anhydride, is carried out in an organic solvent in the presence of an organic base such as a tertiary amine. In another aspect of the invention the acylating agent 3A may be generated in situ prior to reaction with aminocarnitine or a salt of an aminocarnitine ester. In the case where the reacting substrate is aminocarnitine, then acid compounds of Formula (IA), wherein $R^1$ is $O^-$ or OH, are obtained directly, whereas if the substrate is an aminocarnitine ester then compounds of Formula (IA), wherein $R^1$ is $C_{1-6}$ alkyl are obtained directly and a subsequent hydrolysis step generates the acid, wherein $R^1$ is $O^-$ or OH.

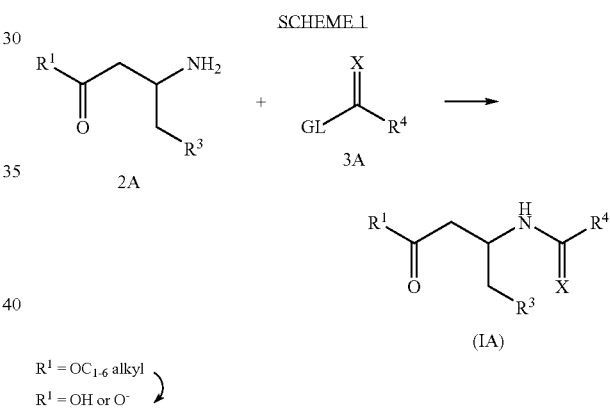

Compounds of Formula I, wherein $Q-R^4$ is —$SO_2$—$R^4$ or —SO—$R^4$, wherein $R^4$ is as defined in Formula I, may be prepared, for example, by the methods outlined in Scheme 2. Reaction of aminocarnitine or derivatives thereof (collectively, reagents of Formula 2A, wherein $R^1$ and $R^3$ are as defined in Formula (I)) with a suitable sulfonylating agent 4A, wherein $R^4$ is as defined in Formula I, such as a sulfonyl halide (LG=Br, Cl, F) or an aryl sulfonate (LG=$OC_6F_5$, $OC_6H_4$-p$NO_2$), or a suitable thionylating agent 5A, wherein $R^4$ is as defined in Formula I, such as a thionyl halide (LG=Br, Cl, F) or an aryl thioate (LG=$OC_6F_5$, $OC_6H_4$-p$NO_2$), affords the compounds of Formula (IB) wherein $Q-R^4$ is —$SO_2$—$R^4$, or the compound of Formula (IC) wherein $Q-R^4$ is —SO—$R^4$. In the case where the reacting substrate is aminocarnitine, then acid compounds of Formula (IB), wherein $R^1$ is $O^-$ or OH, are obtained directly, whereas if the substrate is an aminocarnitine ester then compounds of Formula IB, wherein $R^1$ is $C_{1-6}$ alkyl are obtained directly and a subsequent hydrolysis step generates the acid, wherein $R^1$ is $O^-$ or OH.

SCHEME 2

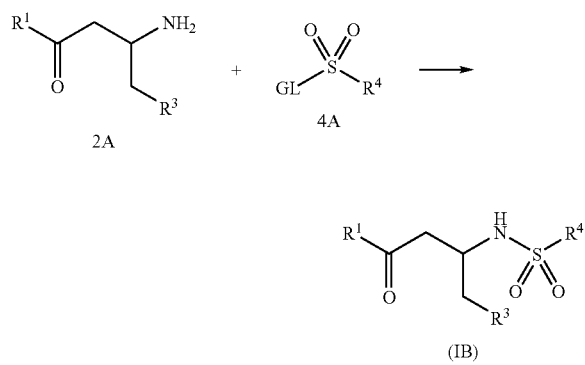

Compounds of Formula I, wherein Q-R⁴ is —C(O)—NH—R⁴ or —C(S)—NH—R⁴, wherein R⁴ is as defined in Formula I, may be prepared, for example, by the methods outlined in Scheme 3. Reaction of aminocarnitine or derivatives thereof (collectively, reagents of Formula 2A, wherein $R^1$ and $R^3$ are as defined in Formula (I) with an isocyanate (6A, X=O) or thioisocyanate (6A, X=S) yields the urea or thiourea. Conversion of the thiourea to the urea is possible through an additional oxidation step. In the case where the reacting substrate is aminocarnitine, then acid compounds of Formulas (ID) or (IE), wherein $R^1$ is O⁻ or OH, are obtained directly, whereas if the substrate is an aminocarnitine ester then compounds of Formulas (ID) or (IE), wherein $R^1$ is $C_{1-6}$ alkyl are obtained directly and a subsequent hydrolysis step generates the acid, wherein $R^1$ is O⁻ or OH.

SCHEME 3

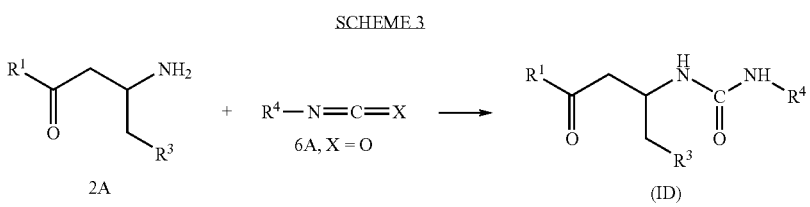

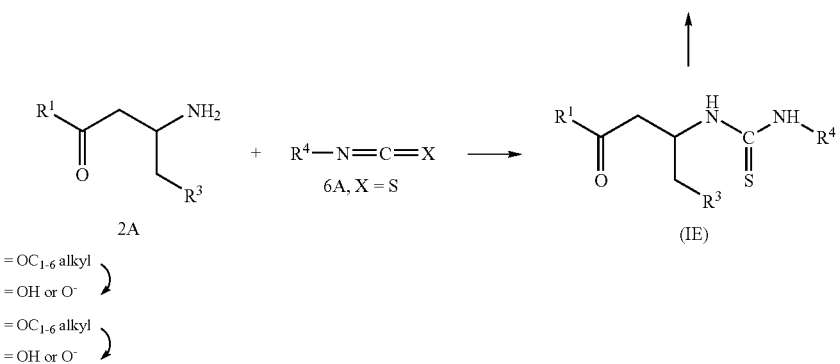

-continued

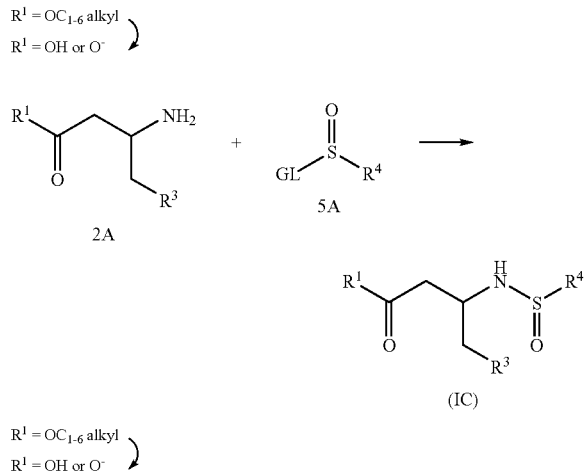

Compounds of Formula (I), wherein Q-R⁴ is —C(X)NR⁵R⁴, wherein X is O or S, and R⁴ and R⁵ are as defined in Formula (I), may be prepared, for example, by the methods outlined in Scheme 4. Reaction of an alkyl ester of aminocarnitine or derivatives thereof (collectively, reagents of Formula 2A, wherein $R^1$ and $R^3$ are as defined in Formula (I)) with phosgene (7A, X=O and LG=Cl), triphosgene (7A, X=O and LG=OCCl₃), (thiophosgene (7A, X=S and LG=Cl) or an equivalent thereof provides a compound of Formula 8A, wherein $R^1$ and $R^3$ are as defined in Formula (I), X is O or S and LG is Cl or OCCl₃ which may subsequently be reacted with an amine or aniline (9A, wherein R⁵ and R⁶ are as defined in Formula (I)) to yield the desired urea or thiourea. Alternatively, as shown in Scheme 4, the amine or aniline (9A) may first be reacted with phosgene, triphosgene, thiophosgene or an equivalent thereof to provide compounds of Formula 10A, wherein X, R⁴ and R⁵ are as defined in Formula (I) and LG is, for example, Cl or OCCl₃, and then reacted with an alkyl ester of aminocarnitine or derivative thereof to yield the desired compounds of Formula (IF). In this case, compounds of Formula (IF), wherein $R^1$ is $C_{1-6}$ alkyl are obtained directly and a subsequent hydrolysis step generates the acid compounds of Formula (IF), wherein $R^1$ is O⁻ or OH.

SCHEME 4

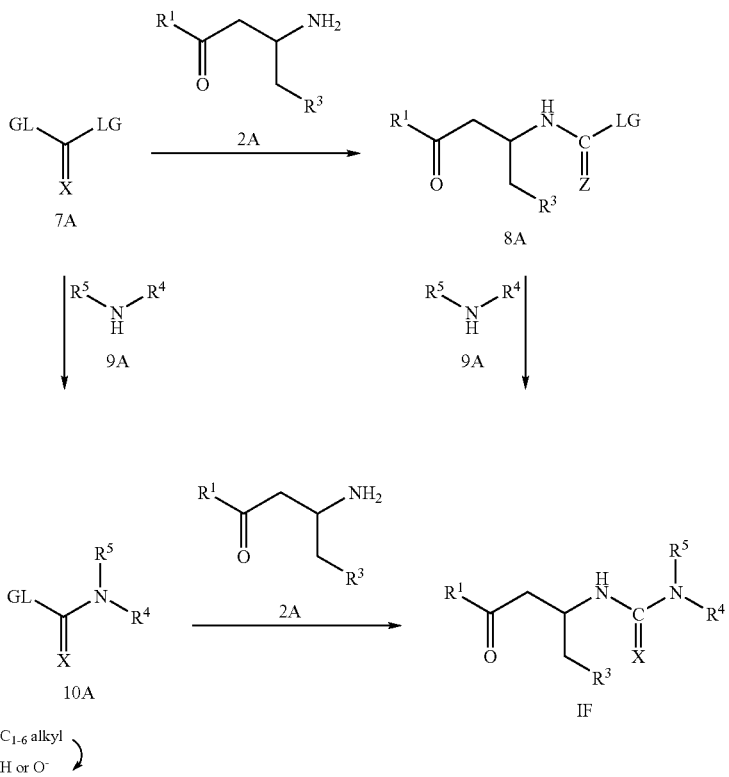

Compounds of Formula (I), wherein Q-$R^4$ is —$SO_2NR^4R^5$ or —$SONR^4R^5$, where $R^4$ and $R^5$ are as defined in Formula (I) may be prepared, for example, by the methods outlined in Scheme 5. Compounds of Formula 8A or 9A, wherein $R^1$ and $R^3$ are as defined in Formula (I) and LG is a suitable leaving group, for example Cl or imidazolium, may be prepared by reaction of an alkyl ester of aminocarnitine or derivatives thereof (collectively, reagents of Formula 2A, wherein $R^1$ and $R^3$ are as defined in Formula (I)) with a compound of Formula 11A or 12A, wherein LG is a suitable leaving group, for example Cl or imidazolium, which may subsequently be reacted with an amine or aniline of Formula 9A, wherein $R^4$ and $R^5$ are as defined in Formula (I), to yield the desired compounds of Formula (IG). Alternatively the amine or aniline (9A) may first be reacted with the compounds of Formula 11A or 12A and then reacted with an alkyl ester of aminocarnitine or a derivative thereof, to yield the desired products. In this case, compounds of Formula (IG), wherein $R^1$ is $C_{1-6}$ alkyl are obtained directly and a subsequent hydrolysis step generates the acid compounds of Formula (IG), wherein $R^1$ is $O^-$ or OH.

SCHEME 5

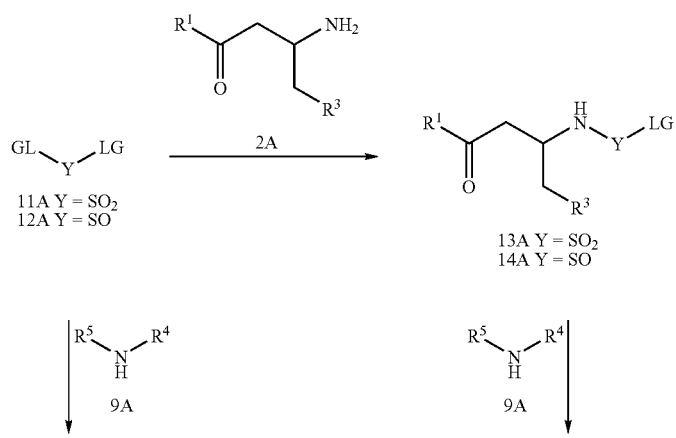

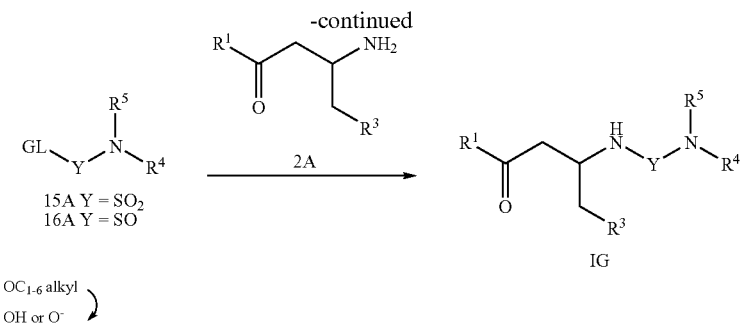

Reagents of Formula 2A include aminocarnitine, alkyl esters thereof and derivatives of aminocarnitine, which include, for example, 3-amino-4-(dialkylamino)butanoate alkyl esters or 3-amino-4-(dialkylamino)butanoate and various salts thereof. Such compounds are commercially available or may be prepared using methods known in the art.

The methods described above can result in the formation of the corresponding free acid and/or free amine or one or both of the corresponding salts thereof. This will depend on the reaction conditions and final isolation procedures as would be known to a person skilled in the art. The formation of, or transformation to, a desired compound salt is achieved using standard techniques. For example, the neutral compound is treated with an acid or base in a suitable solvent and the formed salt is isolated by filtration, extraction or any other suitable method. In a particular example, quaternization of the compounds of Formula (I), wherein $R^3$ is $NR^7R^8$, wherein $R^7$ and $R^8$ are $C_{1-6}$ alkyl, may be performed by reacting a compound of Formula (I), wherein $R^1$ is as defined in Formula (I), suitably $C_{1-6}$ alkyl, and Q-$R^4$ is as defined in Formula (I), with a $C_{1-6}$ alkyl halide, yields compounds of Formula (I), wherein $R^3$ is a trialkylamminimium. If $R^1$ is a ester, subsequent ester hydrolysis yields the acid compounds of Formula (I), where $R^1$ is O⁻ or OH.

The formation of solvates of the compounds of the invention will vary depending on the compound and the solvate. In general, solvates are formed by dissolving the compound in the appropriate solvent and isolating the solvate by cooling or using an antisolvent. The solvate is typically dried or azeotroped under ambient conditions.

Prodrugs of the compounds of Formula (I) may be, for example, conventional esters formed with available hydroxy, thiol, amino or carboxyl groups. For example, available hydroxy or amino groups may be acylated using an activated acid in the presence of a base, and optionally, in inert solvent (e.g. an acid chloride in pyridine). Some common esters which have been utilized as prodrugs are phenyl esters, aliphatic ($C_1$-$C_{24}$) esters, acyloxymethyl esters, carbamates and amino acid esters.

The present invention includes radiolabeled forms of the compounds of the invention, for example, compounds of the invention labeled by incorporation within the structure of $^3$H, $^{11}$C or $^{14}$C or a radioactive halogen such as $^{125}$I and $^{18}$F. A radiolabeled compound of the invention may be prepared using standard methods known in the art. For example, tritium may be incorporated into a compound of the invention using standard techniques, for example by hydrogenation of a suitable precursor to a compound of the invention using tritium gas and a catalyst. Alternatively, a compound of the invention containing radioactive iodine may be prepared from the corresponding trialkyltin (suitably trimethyltin) derivative using standard iodination conditions, such as [$^{125}$I] sodium iodide in the presence of chloramine-T in a suitable solvent, such as dimethylformamide. The trialkyltin compound may be prepared from the corresponding non-radioactive halo-, suitably iodo-, compound using standard palladium-catalyzed stannylation conditions, for example hexamethylditin in the presence of tetrakis(triphenylphosphine) palladium (0) in an inert solvent, such as dioxane, and at elevated temperatures, suitably 50-100° C. Further, a compound of the invention containing a radioactive fluorine may be prepared, for example, by reaction of K[$^{18}$F]/K222 with a suitable precursor compound, such as a compound of Formula I comprising a suitable leaving group, for example a tosyl group, that may be displaced with the $^{18}$F anion.

In some cases the chemistries outlined above may have to be modified, for instance by use of protective groups, to prevent side reactions due to reactive groups, such as reactive groups attached as substituents. This may be achieved by means of conventional protecting groups, for example as described in "Protective Groups in Organic Chemistry" McOmie, J. F. W. Ed., Plenum Press, 1973 and in Greene, T. W. and Wuts, P. G. M., "Protective Groups in Organic Synthesis", John Wiley & Sons, 3$^{rd}$ Edition, 1999.

In some embodiments, the compound of the invention is represented by Structural Formula (I) or (XVII), or a pharmaceutically acceptable salt thereof, wherein: i) when Q is —C(=O)—, —C(O)NH— or —C(=O)—N($R^5$)—, then each of $R^4$ and $R^5$ independently is not a substituted or unsubstituted, six-membered N-containing heteroaryl group, ii) when Q is —C(=O)— or —C(O)NH—, then $R^4$ is not a phenyl group substituted with —OCH$_2$—(optionally substituted quinolyl), and not a phenyl group substituted with one or more substituents selected from the group consisting of benzoyloxy, formyloxy, acetyloxy, trifluoroacetyloxy, glycosyloxy and silyloxy, and/or iii) when Q is —S(O)$_2$—, then $R^4$ is not a substituted or unsubstituted naphthyl or a substituted or unsubstituted indanyl group. In other embodiments, the compound of the invention is represented by Structural Formula (I) or (XVII), or a pharmaceutically acceptable salt thereof, wherein: i) when Q is —C(=O)—, —C(O)NH—or —C(=O)—N($R^5$)—, then each of $R^4$ and $R^5$ independently is not a substituted or unsubstituted, six-membered N-containing heteroaryl group, and ii) when Q is —C(=O)— or —C(O)NH—, then $R^4$ is not a phenyl group substituted with —OCH$_2$-(optionally substituted quinolyl), and not a phenyl group substituted with one or more substituents selected from the group consisting of benzoyloxy, formyloxy, acetyloxy, trifluoroacetyloxy, glycosyloxy and silyloxy; or i) when Q is —C(=O)— or —C(O)NH—, then $R^4$ is not a phenyl group substituted with —OCH$_2$— (optionally substituted quinolyl), and not a phenyl group substituted with one or more substituents selected from the group consisting of benzoyloxy, formyloxy, acetyloxy, trifluoroacetyloxy, glycosyloxy and silyloxy, and ii) when Q is —S(O)$_2$—, then R$^4$ is not a substituted or unsubstituted naphthyl or a substituted or unsubstituted indanyl group; or i) when Q is —C(=O)—, —C(O)NH— or —C(=O)—N(R$^5$)—, then each of R$^4$ and R$^5$ independently is not a substituted or unsubstituted, six-membered N-containing heteroaryl group, and ii) when Q is —S(O)$_2$—, then R$^4$ is not a substituted or unsubstituted naphthyl or a substituted or unsubstituted indanyl group.

In yet some other embodiments, the compound of the invention is represented by Structural Formula (I), (II), (III), (IV), (V), (VI), (VII), (VIII), (IX) or (XVII), or a pharmaceutically acceptable salt thereof, wherein: i) each R$^4$ independently is not a substituted or unsubstituted, six-membered N-containing heteroaryl group, and each R$^5$, for Structural Formulas (I), (VII), (VIII), (IX) and (XVII), independently is not a substituted or unsubstituted, six-membered N-containing heteroaryl group, ii) R$^4$ is not a phenyl group substituted with —OCH$_2$-(optionally substituted quinolyl), and not a phenyl group substituted with one or more substituents selected from the group consisting of benzoyloxy, formyloxy, acetyloxy, trifluoroacetyloxy, glycosyloxy and silyloxy, and/or iii) R$^4$ is not a substituted or unsubstituted naphthyl or a substituted or unsubstituted indanyl group. In still some other embodiments, the compound of the invention is represented by Structural Formula (I), (II), (III), (IV), (V), (VI), (VII), (VIII), (IX) or (XVII), or a pharmaceutically acceptable salt thereof, wherein: i) each R$^4$ independently is not a substituted or unsubstituted, six-membered N-containing heteroaryl group, and each R$^5$, for Structural Formulas (I), (VII), (VIII), (IX) and (XVII), independently is not a substituted or unsubstituted, six-membered N-containing heteroaryl group, ii) each R$^4$ independently is not a phenyl group substituted with —OCH$_2$— (optionally substituted quinolyl), and not a phenyl group substituted with one or more substituents selected from the group consisting of benzoyloxy, formyloxy, acetyloxy, trifluoroacetyloxy, glycosyloxy and silyloxy; or i) each R$^4$ independently is not a phenyl group substituted with —OCH$_2$— (optionally substituted quinolyl), and not a phenyl group substituted with one or more substituents selected from the group consisting of benzoyloxy, formyloxy, acetyloxy, trifluoroacetyloxy, glycosyloxy and silyloxy, and ii) each R$^4$ independently is not a substituted or unsubstituted naphthyl or a substituted or unsubstituted indanyl group; or i) when Q is —C(=O)—, —C(O)NH—or —C(=O)—N(R$^5$)—, then each of R$^4$ and R$^5$ independently is not a substituted or unsubstituted, six-membered N-containing heteroaryl group, and ii) when Q is —S(O)$_2$—, then R$^4$ is not a substituted or unsubstituted naphthyl or a substituted or unsubstituted indanyl group.

Figure 2:
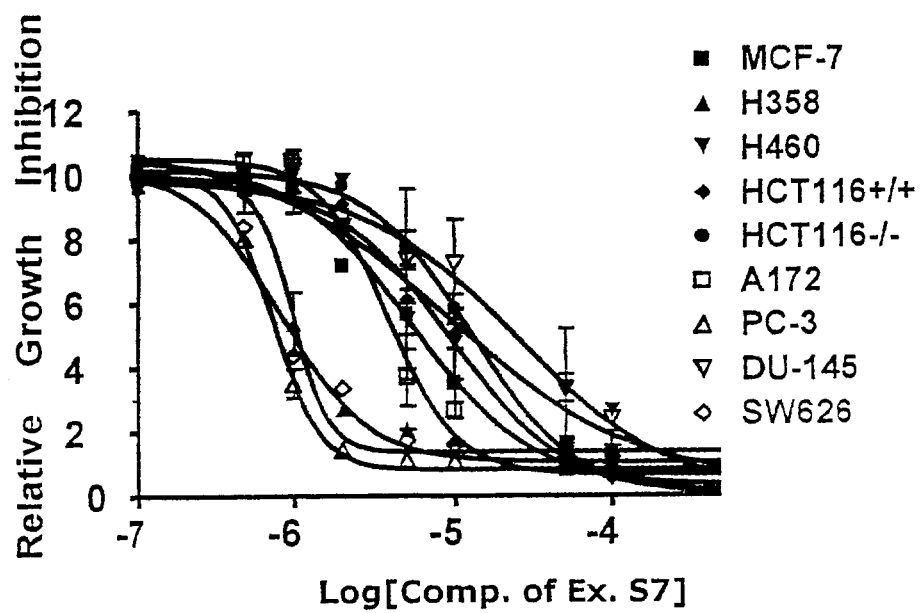
FIG. 2 shows that the compound of Example S7 inhibits growth of cancer cells but not normal cells. Cell culture and compound treatment were conducted as described in Examples. Cell growth was measured by SRB assay. The percentage (%) of relative growth inhibition was calculated by comparing to DMSO treatment only (100%). The compound concentration axes were presented in log-space. The values were mean±SD from 2 independent experiments with triplicated data per experiment. GI$_{50}$ (growth inhibition) is the compound concentration that causes 50% inhibition of cell growth. A. The effect of the compound of Example S7 on breast cancer cell (MCF-7), lung cancer cells (H358, H460), colon cancer cells (HCT116 p53$^{+/+}$, HCT116 p53$^{-/-}$), brain cancer cell (A172), prostate cancer cells (PC-3, DU-145) and ovarian cancer cell (SW626): GI$_{50}$ for MCF-7=5±1.3 µM; GI$_{50}$ for H358=1.0±0.3 µM; GI$_{50}$ for H460=8.8±2 µM; GI$_{50}$ for HCT116+/+=9.3±1.7 µM; HCT116-/-=13±0.8 µM; GI$_{50}$ for A172=3.8±0.5 µM; GI$_{50}$ for PC-3=0.8±0.3 µM; GI$_{50}$ for DU-145=24±2.8 µM; GI$_{50}$ for SW626=0.8±0.7 µM; B. The effect of the compound of Example S7 on normal cells, including human mammary epithelial cell line 184A1 and human primary epithelial cells HMEC (mammary); NHBE (lung) and PrEC (prostate).
Figure 2:
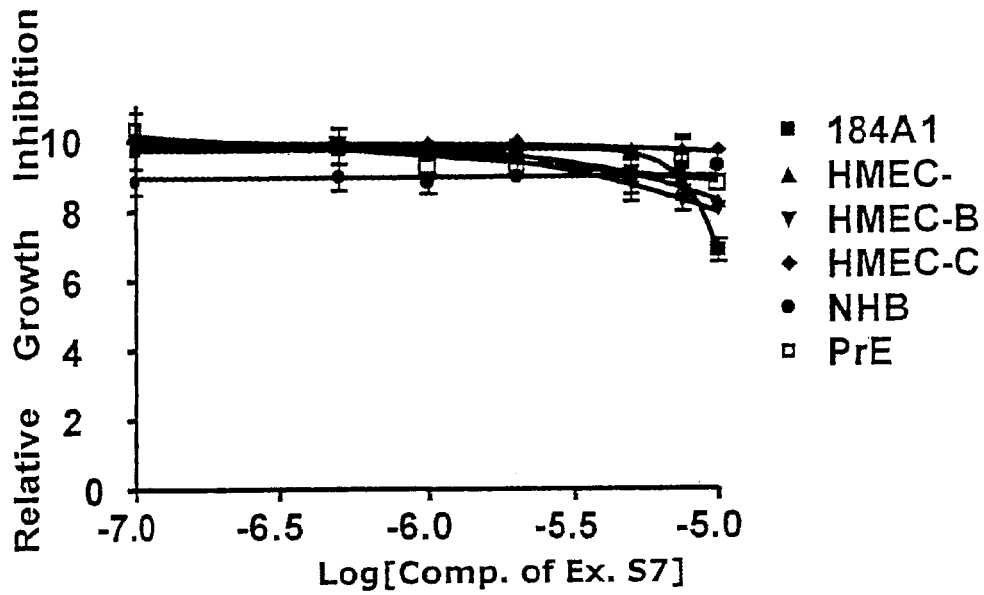

Carnitine palmitoyl transferase 1 (CPT1A and CPT1C) has been implicated in growth and survival of cancer cells. Thus, small molecule inhibitors of these enzymes are potential anti-tumor agents. Several compounds disclosed herein have been synthesized that have IC$_{50}$ values against CPT1 in the low μM range in a biochemical assay. It has also been shown that these compounds inhibit growth of cancer cell lines originated from multiple human cancers, including MCF7 (breast), H358 and H460 (lung), HCT116 (colon), A172 (brain), PC3 and DU145 (prostate) and SW626 (ovary) with GI$_{50}$ (growth inhibition) in the low μM or nM range (see FIGS. 1 and 2, for Example). When these compounds were tested on normal human epithelial cells of mammary gland, lung and prostate, little inhibitory activity was seen (see FIG. 2B, for Example). Furthermore, the inhibitory activity on cancer cells was found to be increased by hypoxia, a condition widely observed in tumors (see Table 2, for Example). This data indicates that these compounds will have tumor cell-selective inhibitory activity and therefore be anti-tumor or anti-cancer agents.

The compounds of Formula (I) are CPT1 inhibitors and are useful in inhibiting CPT1 activity for the treatment of various conditions such as cancers. Accordingly, the present invention includes a method of treating a disease which benefits from an inhibition of CPT1 activity comprising administering an effective amount of a compound of the invention to a subject in need thereof. The present invention also includes the use of a compound of the invention to treat a disease which benefits from an inhibition of CPT1 activity and a use of a compound of the invention to prepare a medicament to treat a disease which benefits from an inhibition of CPT1 activity. In an embodiment, CPT1 is CPT1A and/or CPT1C. In yet another embodiment of the invention the disease which benefits from an inhibition of CPT1, suitably CPT1A and/or CPT1C, activity is cancer.

The present invention therefore includes a method of treating cancer comprising administering an effective amount of one or more compounds selected from a compound of Formula (I), and pharmaceutically acceptable salts thereof, to a subject in need thereof. In an embodiment, the cancer is one that depends on CPT1A and/or CPT1C for tumor cell survival. In a further embodiment, the cancer is one that depends on CPT and/or CPT for tumor cell survival under hypoxic conditions. In another embodiment, the cancer is selected from the group consisting of lung cancer, breast cancer, colon cancer, brain cancer, neuroblastoma, prostate cancer, melanoma, glioblastoma multiform, ovarian cancer, lymphoma, leukemia, melanoma, sarcoma, paraneoplasia, osteosarcoma, germinoma, glioma and mesothelioma. In a preferred embodiment, the cancer is selected from the group consisting of lung cancer, colon cancer, brain cancer, neuroblastoma, prostate cancer, melanoma, glioblastoma mutiform and ovarian cancer. In another preferred embodiment, the cancer is selected from one or more of lung cancer, breast cancer, colon cancer, brain cancer, neuroblastoma, prostate cancer, melanoma, glioblastoma multiform and ovarian cancer.

The present invention also includes a method of treating cancer comprising administering to a subject with cancer an effective amount of a compound represented by Structural Formula (XVIII):

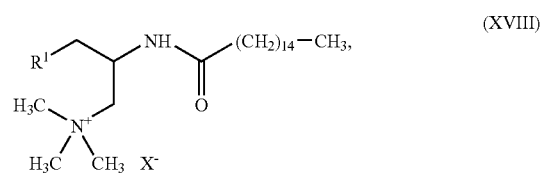

(XVIII)

wherein R$^1$ is —OH or —OC$_{1-6}$ alkyl, and X$^-$ is a pharmaceutically acceptable counter ion. The cancer is selected from the group consisting of lung cancer, breast cancer, colon cancer, brain cancer, neuroblastoma, prostate cancer, melanoma, glioblastoma mutiform, ovarian cancer, lymphoma, leukemia, melanoma, sarcoma, paraneoplasia, osteosarcoma, germinoma, glioma and mesothelioma. In a preferred embodiment, the cancer is selected from the group consisting of lung cancer, colon cancer, brain cancer, neuroblastoma, prostate cancer, melanoma, glioblastoma mutiform and ovarian cancer. In another preferred embodiment, the cancer is selected from one or more of lung cancer, breast cancer, colon cancer, brain cancer, neuroblastoma, prostate cancer, melanoma, glioblastoma multiform and ovarian cancer.

The invention further relates to a method of treating tumor cells in a subject in need thereof, comprising administering to the subject, an amount of a compound disclosed herein that is effective to reduce the effective amount of CPT1A and/or CPT in the subject.

The invention further includes a method for treating tumor cells in a subject suffering from a cancer that expresses CPT1A and/or CPT1C in amounts higher that in normal tissue of the same type, comprising administering to the subject a compound disclosed herein in an amount that is effective to inhibit expression of CPT1A and/or CPT1C in the tumor cells and/or to increase apoptosis in the tumor cells.

The invention still further includes a method for treating tumor cells in a subject suffering from a cancer that depends on CPT and/or CPT for survival under hypoxic conditions, comprising administering to the subject an amount of a compound disclosed herein that is effect to inhibit expression of CPT1A and/or CPT1C by the tumor cells, increase apoptosis and/or reduce proliferation in the tumor cells.

The present invention also includes a method of treating diabetes of a subject in need thereof, by administering to the subject a therapeutically effective amount of a compound of the invention disclosed herein.

The compounds of the invention can also be used for treating a condition or disease of a subject in need thereof, wherein the condition or disease is a condition or disease mediated by metalloproteases, tumor necrosis factor, aggrecanase or a combination thereof. (see U.S. Pat. No. 6,495,565, and U.S. 2004/0072802, the teachings all of which are incorporated herein by reference). The condition or disease mediated by metalloproteases, tumor necrosis factor, aggrecanase is selected from the group consisting of: inflammatory diseases, fever, acute infection and acute shock, and wherein the condition or disease mediated by Cholecystokinins is selected from the group consisting of: appetite disorders, pancreatic inflammation, pancreatic cancer, biliary tract diseases and Zollinger-Ellison syndrome. Specific examples include: septic shock, haemodynamic shock, sepsis syndrome, post ischemic reperfusion injury, malaria, Crohn's disease, inflammatory bowel diseases, mycobacterial infection, meningitis, psoriasis, congestive heart failure, fibrotic diseases, cachexia, graft rejection, cancer, diseases involving angiogenesis, autoimmune diseases, skin inflammatory diseases, osteoarthritis, rheumatoid arthritis, multiple sclerosis, radiation damage, hyperoxic alveolar injury, periodontal disease, HIV and non-insulin dependent diabetes mellitus The compounds of the invention can also be used for treating a condition or disease of a subject in need thereof, wherein the condition or disease is a condition or disease mediated by Cholecystokinins (See U.S. Pat. No. 5,847,125, the teachings of which are incorporated herein by reference). Specific examples of such diseases or conditions include appetite disorders, such as anorexia nervosa, pancreatic inflammation, pancreatic cancer, binary tract diseases, Zollinger-Ellison syndrome, analgesia, opiate and various psychiatric disorders.

The compounds of the invention are suitably formulated into pharmaceutical compositions for administration to human subjects in a biologically compatible form suitable for administration in vivo. The pharmaceutical compositions of the invention optionally include one or more pharmaceutically acceptable carriers and/or diluents therefore, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients (5$^{th}$ Ed., Pharmaceutical Press (2005)).

The carriers, diluents and/or excipients are "acceptable" in the sense of being compatible with the other ingredients of the pharmaceutical composition and not deleterious to the recipient thereof.

In accordance with the methods of the invention, the described compounds of the invention, may be administered to a patient in a variety of forms depending on the selected route of administration, as will be understood by those skilled in the art. The compounds of the invention may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

A compound of the invention may be orally administered, for example, with an inert diluent or with an assailable edible carrier, or it may be enclosed in hard or soft shell gelatin capsules, or it may be compressed into tablets, or it may be incorporated directly with the food of the diet. For oral therapeutic administration, the compound of the invention may be incorporated with excipient and used in the form of ingestible tablets, buccal tablets, troches, capsules, elixirs, suspensions, syrups, wafers, and the like.

A compound of the invention may also be administered parenterally. Solutions of a compound of the invention can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999.

The pharmaceutical forms suitable for injectable use include sterile aqueous solutions or dispersion and sterile powders for the extemporaneous preparation of sterile injectable solutions or dispersions. In all cases the form must be sterile and must be fluid to the extent that easy syringability exists.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

The compounds of the invention, may be administered to an animal, suitably a human patient, alone or in combination with pharmaceutically acceptable carriers, as noted above, the proportion of which is determined by the solubility and chemical nature of the compound, chosen route of administration and standard pharmaceutical practice.

The compounds of the invention, can be formulated alone or for contemporaneous administration with other agents that inhibit CPT1 activity, or inhibit CPT1 activity and other targets, or in combination with other types of treatment (which may or may not modulate CPT1) for treating cancer. Therefore, according to yet another aspect of the present invention, there is included a pharmaceutical composition comprising one or more compounds selected from a compound of Formula I, and pharmaceutically acceptable salts thereof, and a pharmaceutically acceptable carrier, for the preparation of a medicament for the treatment of cancer to be used contemporaneously with another anti-cancer agent, for example, but not limited to a glucose metabolism inhibitor.

Typically, the pharmaceutical compositions of the invention can be administered before or after a meal, or with a meal. As used herein, "before" or "after" a meal is typically within two hours, preferably within one hour, more preferably within thirty minutes, most preferably within ten minutes of commencing or finishing a meal, respectively.

In one embodiment, the method of the present invention is a mono-therapy where the pharmaceutical compositions of the invention are administered alone. Accordingly, in this embodiment, the compound of the invention is the only pharmaceutically active ingredient in the pharmaceutical compositions.

In another embodiment, the method of the invention is a co-therapy with other therapeutically active drugs known in the art for treating the desired diseases or indications. In a specific embodiment, the compounds disclosed herein can be co-administered with one or more of other anticancer drugs known in the art. In another specific embodiment, the compounds disclosed herein can be co-administered with one or more of other agents that inhibit CPT1A and/or CPT1C activity. For example, but not limited to, the compounds of the invention are administered contemporaneously with glucose metabolism inhibitors (such as glycolysis inhibitors).

The term a "therapeutically effective amount", "effective amount" or a "sufficient amount" of a compound of the present invention is a quantity sufficient to, when administered to the subject, including a mammal, for example a human, effect beneficial or desired results, including clinical results, and, as such, an "effective amount" or synonym thereto depends upon the context in which it is being applied. For example, in the context of inhibiting CPT and/or CPT1A, for example, it is an amount of the compound sufficient to achieve such an inhibition in CPT1C and/or CPT1A activity as compared to the response obtained without administration of the compound. In the context of disease, therapeutically effective amounts of the compounds of the present invention are used to treat, modulate, attenuate, reverse, or affect cancer in a subject. An "effective amount" is intended to mean that amount of a compound that is sufficient to treat, prevent or inhibit cancer disease associated with cancer. The amount of a given compound of the present invention that will correspond to such an amount will vary depending upon various factors, such as the given drug or compound, the pharmaceutical formulation, the route of administration, the type of disease or disorder, the identity of the subject or host being treated, and the like, but can nevertheless be routinely determined by one skilled in the art. Also, as used herein, a "therapeutically effective amount" of a compound of the present invention is an amount which prevents, inhibits, suppresses or reduces cancer (e.g., as determined by clinical symptoms or the amount of cancer cells) in a subject as compared to a control. As defined herein, a therapeutically effective amount of a compound of the present invention may be readily determined by one of ordinary skill by routine methods known in the art.

In an embodiment, a therapeutically effective amount of a compound of the present invention ranges from about 0.1 to about 15 mg/kg body weight, suitably about 1 to about 5 mg/kg body weight, and more suitably, from about 2 to about 3 mg/kg body weight. The skilled artisan will appreciate that certain factors may influence the dosage required to effectively treat a subject, or prevent a subject, suffering from cancer and these factors include, but are not limited to, the severity of the disease or disorder, previous treatments, the general health and/or age of the subject and other diseases present.

Moreover, a "treatment" or "prevention" regime of a subject with a therapeutically effective amount of the compound of the present invention may consist of a single administration, or alternatively comprise a series of applications. For example, the compound of the present invention may be administered at least once a week. However, in another embodiment, the compound may be administered to the subject from about one time per week to about once daily for a given treatment. The length of the treatment period depends on a variety of factors, such as the severity of the disease, the age of the patient, the concentration and the activity of the compounds of the present invention, or a combination thereof. It will also be appreciated that the effective dosage of the compound used for the treatment or prophylaxis may increase or decrease over the course of a particular treatment or prophylaxis regime. Changes in dosage may result and become apparent by standard diagnostic assays known in the art. In some instances, chronic administration may be required.

As used herein, "administered contemporaneously" means that two substances are administered to a subject such that they are both biologically active in the subject at the same time. The exact details of the administration will depend on the pharmacokinetics of the two substances in the presence of each other, and can include administering one substance within 24 hours of administration of the other, if the pharmacokinetics are suitable. Designs of suitable dosing regimens are routine for one skilled in the art. In particular embodiments, two substances will be administered substantially simultaneously, i.e. within minutes of each other, or in a single composition that comprises both substances.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder.

The term "prevention" or "prophylaxis", or synonym thereto, as used herein refers to a reduction in the risk or probability of a patient becoming afflicted with cancer or manifesting a symptom associated with cancer.

To "inhibit" or "suppress" or "reduce" a function or activity, such as ODCase activity, is to reduce the function or activity when compared to otherwise same conditions except for a condition or parameter of interest, or alternatively, as compared to another conditions.

The term "subject" or "patient" or synonym thereto, as used herein includes all members of the animal kingdom, especially mammals, including human. The subject or patient is suitably a human.

The term "CPT1" as used herein refers to CPT1A and/or CPT1C (see U.S. Provisional Application No. 60/893,649, filed Mar. 8, 2007, and U.S. Provisional Application No. 60/893,999, filed on Mar. 9, 2007).

The term "a cell" as used herein includes a plurality of cells. Administering a compound to a cell includes in vivo, ex vivo and in vitro treatment.

The invention is illustrated by the following examples which are not intended to be limiting in any way.

EXEMPLIFICATION

1: Synthesis of Compounds of the Invention

Preparation 1

(R)-2-amino-4-(benzyloxy)-N,N,N-trimethyl-4-oxobutan-1-aminium methanesulfonate (AKA (R)-aminocarnitine benzyl ester mesylate)

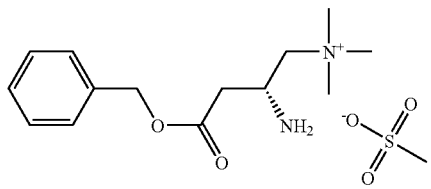

a) (R)-benzyl 3-(tert-butoxycarbonylamino)-4-(methylsulfonyloxy)butanoate (R)-benzyl 3-(tent-butoxycarbonylamino)-4-hydroxybutanoate, prepared according to known methods (Sagi, K. et al. J. Med. Chem. 2003, 46, 1845) (497 mg, 1.60 mmol) was dissolved in DCM (20 mL) and treated with anhydrous pyridine (0.25 mL) under $N_2$ at 0-5° C. Subsequently, $Ms_2O$ (409 mg, 1.4 equiv) was added dropwise as a solution in anh DCM (2 mL). The stirred reaction was allowed to slowly warm to rt overnight. Later it was diluted with EtOAc, washed (0.1 M aq HCl, 2×, satd aq $NaHCO_3$ 1×, brine 1×), dried ($Na_2SO_4$) and concentrated under reduced pressure to provide a white solid (0.65 g). A portion of this crude material (520 mg) was filtered through a plug of silica gel using 2:1 hexanes:EtOAc as the eluent to afford the title compound as a white solid (0.42 g, 84%). $^1$H NMR (300 MHz, DMSO-$d_6$): δ=7.39-7.25 (m, 5H), 7.09 (d, J=7.2 Hz, 1H), 5.08 (s, 2H), 4.15-4.00 (m, 3H), 3.15 (s, 3H), 2.66-2.52 (m, 2H), 1.36 (s, 9H).

b) (R)-4-(benzyloxy)-2-(tert-butoxycarbonylamino)-N,N,N-trimethyl-4-oxobutan-1-aminium methanesulfonate To a suspension of (R)-benzyl 3-(tert-butoxycarbonylamino)-4-(methylsulfonyloxy)-butanoate (149 mg, 0.38 mmol) in EtOH (2 mL) at 0° C. was added xs $Me_3N$ in EtOH (4.2 M, 2 mL, 8.4 mmol). The reaction was sealed and stirred at the temperature for 15 min and then at rt for 3 d. Later, the reaction was concentrated to dryness and purified by preparative TLC (silica gel, 5% MeOH/DCM) to afford the title compound as a colorless gum (43 mg, 37%). $^1$H NMR (300 MHz, CDCl$_3$): δ=7.35-7.20 (m, 5H), 5.14-5.00 (AB quartet, J=12 Hz, 2H), 4.46 (br, 1H), 3.50-3.25 (m, 2H), 3.24 (s, 9H), 2.85-2.65 (m 2H), 2.70 (s, 3H), 1.38 (s, 9H); MS ESI [M]$^+$, calcd for [$C_{19}H_{31}N_2O_4$]$^+$ 351.5 found 351.2 m/z (100).

c) (R)-2-amino-4-(benzyloxy)-N,N,N-trimethyl-4-oxobutan-1-aminium methanesulfonate (R)-4-(benzyloxy)-2-(tert-butoxycarbonylamino)-N,N,N-trimethyl-4-oxobutan-1-aminium methanesulfonate was treated with a solution of 10% trifluoroacetic acid at 0° C. The reaction mixture was warmed to ambient temperature. After the starting material is consumed (HPLC) the volatiles are removed in vacuo to yield the title compound. The material may be used without further purification or subjected to chromatographic purification prior to subsequent reaction.

Preparation 2

(R)-benzyl 3-(tert-butoxycarbonylamino)-4-(dimethylamino)butanoate

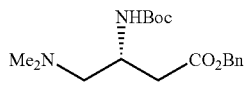

In a sealed vial, (R)-benzyl 3-(tert-butoxycarbonylamino)-4-(methylsulfonyloxy)-butanoate (130.8 mg, 0.34 mmol) was stirred at rt in a THF solution of $Me_2NH$ (2.0 M, 10 mL, 20 mmol) for 3 d. Then the reaction was concentrated under reduced pressure and purified by preparative TLC (0.5% MeOH in DCM, and then 5% MeOH/DCM) to afford the title compound as a colorless gum (28 mg, 25%). $^1$H NMR (300 MHz, CDCl$_3$): δ=7.85-7.25 (m, 5H), 5.25-5.00 (m, 2H), 4.15 (br s, 1H), 2.58-2.50 (m, 4H), 2.41 (br s, 6H), 1.39 (s, 9H); MS ESI [M]$^+$, calcd for [$C_{18}H_{28}N_2O_4$+H]$^+$ 336.4 found m/z 337.2 (100).

Preparation 3

(R)-3-amino-4-(trimethylammonio)butanoate (AKA R-aminocarnitine)

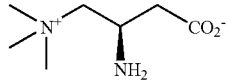

a) (R)-4-tert-butyl 1-(2,5-dioxopyrrolidin-1-yl)2-(tert-butoxycarbonylamino)succinate (R)-4-tert-butoxy-2-(tert-butoxycarbonylamino)-4-oxobutanoic acid (5 g, 17.3 mmol) and N-hydroxysuccinimide (2.18 g, 19.0 mmol) were dissolved into ethyl acetate (20 mL). N,N'-Dicyclohexylcarbodiimide (3.91 g, 19.0 mmol) was dissolved into ethyl acetate (10 mL) and added dropwise to the solution. The mixture was stirred overnight, filtered and concentrated to dryness. The residue was taken up into methylene chloride (200 mL) and washed with saturated sodium bicarbonate (2×25 mL) and brine (25 mL), dried over $MgSO_4$, and concentrated to dryness to give the title compound (4.6 g, 69%) as a clear oil.

b) (R)-tert-butyl 3-(tert-butoxycarbonylamino)-4-hydroxybutanoate

Sodium borohydride (0.63 g, 16.3 mmol) was dissolved into THF (30 mL) and water (4 mL) and cooled to 0° C. (R)-4-tert-butyl 1-(2,5-dioxopyrrolidin-1-yl) 2-(tert-butoxycarbonylamino)succinate (4.6 g, 11.9 mmol) was dissolved into THF (5 mL) and added dropwise to the solution. After 1 h, saturated ammonium chloride (10 mL) was added and the mixture was extracted with ethyl acetate (4×50 mL), dried over $MgSO_4$ and concentrated. The residue was filtered through silica gel with ethyl acetate/hexanes 1:1. The solvent was removed in vacuo to give the title compound (1.91 g, 59%) as a white foam. $^1$H NMR (300 MHz, DMSO-$d_6$) δ 6.55-6.52 (m, 1H), 4.74-4.69 (m, 1H), 3.81-3.72 (m, 1H), 3.21-3.14 (m, 1H), 2.50-2.39 (m, 1H), 2.19-2.06 (m, 1H), 1.39 (s, 9H), 1.36 (s, 9H).

c) (R)-tert-butyl 3-(tert-butoxycarbonylamino)-4-iodobutanoate

Triphenylphosphine (1.07 g, 4 mmol), imidazole (277 mg, 4 mmol) and iodine (1.02 g, 4 mmol) were dissolved into methylene chloride (12 mL) under nitrogen atmosphere. (R)-tert-butyl 3-(tert-butoxycarbonylamino)-4-hydroxybutanoate (275 mg, 1 mmol) was dissolved into methylene chloride (4 mL) and added dropwise to the solution. After 1 h, methylene chloride (100 mL) was added and the solution was filtered through celite. The filtrate was washed with 1% sodium bisulfite solution (2×10 mL), brine (20 mL), dried over $MgSO_4$ and concentrated to dryness. The residue was purified by silica gel chromatography (ethyl acetate/hexanes 1:1) to give the title compound (225 mg, 58%) as a white solid. $^1$H NMR (300 MHz, DMSO-$d_6$) δ 7.05-6.95 (m, 1H), 4.04-3.97 (m, 1H), 3.77-3.65 (m, 2H), 2.55-2.50 (m, 1H), 2.38-2.27 (m, 1H), 1.39 (s, 9H), 1.36 (s, 9H).

d) R-aminocarnitine (R)-tert-butyl 3-(tert-butoxycarbonylamino)-4-iodobutanoate (210 mg, 0.55 mmol) was dissolved into DMF (5 mL). Trimethylamine (0.26 mL of 4.2M solution in ethanol) was added and the mixture was stirred at room temperature overnight. The solution was concentrated in vacuo and the residue was dissolved into methylene chloride and the product precipitated upon addition of hexane. The crude residue was dissolved into TFA (2 mL) and stirred overnight. The mixture was concentrated, dissolved into water (1 mL) and transferred onto Amberlite IRA-402 (OH-form) and eluted with deionized water. The aqueous layer was lyophilized to give the title compound (34 mg, 39%) as the inner salt. Analytical data was consistent with published results (J. Org. Chem. 1995, 60, 8318-8319). Note that in some preparations of R-aminocarintine (J. Org. Chem. 1995, 60, 8318-8319) are obtained as partial HBr salts and equivalents of reagents are adjusted accordingly.

Preparation 4

General Method for N-hydroxysuccinimide esters

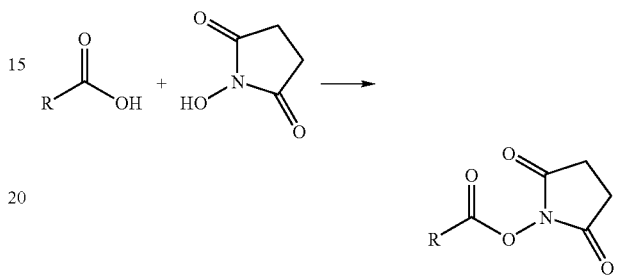

To a solution of carboxylic acid (1 mmol) in $CH_2Cl_2$ (5 mL) was added N-hydroxysuccinimide (138 mg, 1.2 mmol), EDC (230 mg, 1.2 mmol) and diisopropylethyl amine (0.7 mL, 4 mmol). The solution was stirred for 16 h at room temperature. Methylene chloride (75 mL) was added and the solution was washed with saturated sodium bicarbonate (2×10 mL), water (20 mL), dried over $MgSO_4$ and concentrated to give the desired ester which was used without further purification. Proton NMRs and MS were consistent with the desired products.

Preparation 5

(R)-benzyl 3-(5-bromothiophene-2-sulfonamido)-4-(dimethylamino)-butanoate

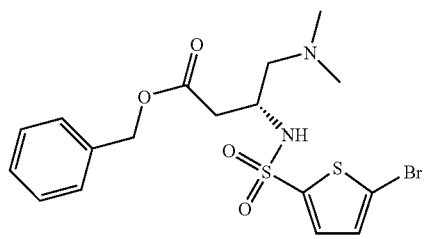 [SMILES: CN(C)C[C@@H](CC(=O)OCc1ccccc1)NS(=O)(=O)c1ccc(Br)s1]

To a solution of (R)-benzyl 3-amino-4-(dimethylamino) butanoate dihydrochloride (1 g, 3.2 mmol), triethylamine (1.3 mL, 9.6 mmol) and DMAP (20 mg, 0.16 mmol) in anhydrous $CH_2Cl_2$ (25 mL) was added 5-bromothiophene-2-sulfonyl chloride (2.5 g, 9.6 mmol). Methylene chloride (200 mL) was added and the solution was washed with dilute NaOH (10 mL), water (10 mL), dried over $MgSO_4$ and concentrated to dryness. The residue was purified by silica gel chromatography (95:5 $CH_2Cl_2$/MeOH) to give the title compound as a yellow solid (650 mg, 44%). $^1$H NMR (400 MHz, CDCl$_3$) δ 7.44 (d, 1H, J=3.8 Hz), 7.41-7.27 (m, 5H), 7.04 (d, 1H, J=3.8 Hz), 5.14-5.07 (m, 2H), 3.87-8.83 (m, 1H), 2.92-2.89 (m, 1H), 2.83-2.78 (m, 1H), 2.69-2.64 (m, 1H), 2.60-2.54 (m, 1H), 2.43 (s, 6H); MS ESI 461.3 [M+H]$^+$, calcd for [$C_{17}H_{21}BrN_2O_4S_2$]$^+$ 461.00.

Preparation 6

(R)-4-methoxy-N1,N1,N1-trimethyl-4-oxobutane-1,2-diaminium dichloride (AKA (R)-aminocarnitine methyl ester dichloride)

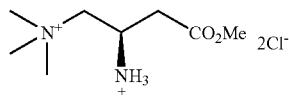

To a solution of (R)-aminocarnitine (3.0 g, 11.4 mmol) in methanol (120 mL) at 0° C. was added thionyl chloride (12 mL) dropwise. After addition, the resulting mixture was refluxed (oil temp 80° C.) for overnight (18 h) and cooled to rt. After removal of solvent, (R)-aminocarnitine methyl ester was obtained as a light green gum (4.8 g) which was used without further purification. $^1$H NMR (400 MHz, $CD_3OD$) δ 4.40-4.30 (m, 1H), 3.93 (d, 2H, J=4.0 Hz), 3.31 (s, 9H), 3.13-2.95 (m, 2H); MS. ESI 175.1 [M]$^+$, calcd for [$C_8H_{19}N_2O_2$]$^+$ 175.14.

Preparation 7

General method for 2-chloroethyl N-(alkylphenyl)sulfamoylcarbamates

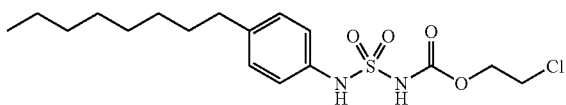 [SMILES: CCCCCCCCc1ccc(NS(=O)(=O)NC(=O)OCCCl)cc1]

To a solution of chlorosulfonyl isocyanate (1.41 g, 10 mmol) in dichloromethane (5 mL) was added 2-chloroethanol (810 mg, 10 mmol). After addition, the solution was stirred for 10 min at rt. The resulting solution can be stored at 4° C. or reacted with corresponding amines. A solution of alkylaniline (10 mmol) and triethylamine (1.54 mL, 11 mmol) in dichloromethane (20 mL) at 0° C. was treated dropwise with a the solution of sulfamoyl chloride prepared as described above. The resulting mixture was stirred for 60 min at 0° C. and diluted with dichloromethane (40 mL). After washing with 0.1 N HCl (20 mL), the dichloromethane layer was dried ($Na_2SO_4$) and concentrated. The precipitate which formed was collected by suction filtration to give the title compound as a white solid. The filtrate was concentrated to give additional amounts of the title compound as a white solid.

For 2-chloroethyl N-(4-octylphenyl)sulfamoylcarbamate the total yield was 2.62 g (67%) from 4-n-octylaniline (2.05 g, 10 mmol). $^1$H NMR (400 MHz, $CDCl_3$) δ 7.21 (s, 1H), 7.20-7.10 (m, 4H), 7.11 (s, 1H), 4.46 (s, 2H), 3.71 (s, 2H), 2.60 (t, 2H, J=6.8 Hz), 1.58 (s, 2H), 1.37-1.20 (m, 10H), 0.88 (t, 3H, J=6.4 Hz).

For 2-chloroethyl N-(4-tetradecylphenyl)sulfamoylcarbamate: (789 mg, 84%) was obtained as white solid starting from 4-n-tetradecylaniline (578 mg, 2 mmol).

For 2-chloroethyl N-(4-dodecylphenyl)sulfamoylcarbamate: (387 mg, 87%) was obtained as white solid starting from 4-n-dodecylaniline (261 mg, 1 mmol).

For 2-chloroethyl N-(4-decylphenyl)sulfamoylcarbamate: (1.35 g, 80%)was obtained as white solid starting from 4-decylaniline (933 mg, 4 mmol).

For 2-chloroethyl N-(4-pentylphenyl)sulfamoylcarbamate: (4.40 g, 85%)was obtained as white solid starting from 4-pentylaniline (2.45 g, 15 mmol).

For 2-chloroethyl N-(4-(octyloxy)phenyl)sulfamoylcarbamate: (1.635 g, 80%) was obtained as white solid starting from 4-(octyloxy)aniline (1.105 g, 5 mmol).

Example S1

(R)-3-(4-propoxybenzamido)-4-(trimethylammonio)butanoate

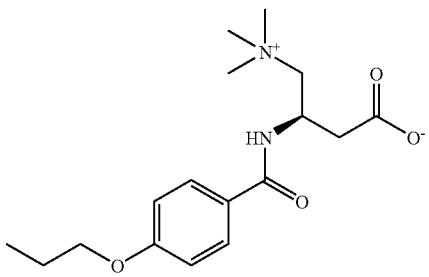 [SMILES: CCCOc1ccc(C(=O)N[C@H](CC(=O)[O-])C[N+](C)(C)C)cc1]

(R)-aminocarnitine (20 mg, 0.12 mmol) and 2,5-dioxopyrrolidin-1-yl 4-propoxybenzoate (42 mg, 0.15 mmol) were dissolved into DMF (0.5 mL). Diisopropylethylamine (63 µL, 0.36 mmol) was added and the solution was stirred at room temperature for 18 h. Diethyl ether (20 mL) was added and a white precipitate was collected. The white solid was triturated with 1:1 acetone/ether and dried to give the title compound as a white powder (8.1 mg, 21%). $^1$H NMR (300 MHz, $CD_3OD$) δ 7.89-7.78 (m, 2H), 7.01 (d, 2H, J=7.8 Hz), 4.75-4.63 (m, 1H), 4.02 (t, 2H, J=7.2 Hz), 3.75-3.51 (m, 2H), 3.21 (s, 9H), 2.82-2.71 (m, 2H), 1.85-1.75 (m, 2H), 1.05 (t, 3H, J=7.0 Hz); MS ESI 323.1 [M+H]$^+$, calcd for [$C_{17}H_{26}N_2O_4$+H]$^+$ 323.19.

Example S2

(R)-3-(4-(thiophene-2-sulfonamido)benzamido)-4-(trimethylammonio)-butanoate

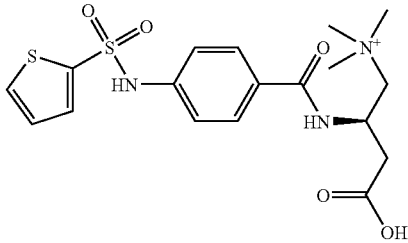 [SMILES: C[N+](C)(C)C[C@@H](CC(=O)O)NC(=O)c1ccc(NS(=O)(=O)c2cccs2)cc1]

R)-aminocarnitine (16 mg, 0.1 mmol) and 2,5-dioxopyrrolidin-1-yl 4-(thiophene-2-sulfonamido)benzoate (57 mg, 0.15 mmol) were dissolved into DMF (1 mL). triethylamine (50 µL, 0.36 mmol) was added and the solution was stirred at room temperature for 18 h. Diethyl ether (20 mL) was added and a white precipitate was collected. The powder was purified by silica gel chromatography (elution 10% MeOH/CH$_2$Cl$_2$ to 80% MeOH/CH$_2$Cl$_2$) to give the title compound as a white powder (20 mg, 47%). $^1$H NMR (400 MHz, D$_2$O) δ 7.63-7.61 (m, 1H), 7.56-7.53 (m, 2H), 7.48-7.45 (m, 1H), 7.12-7.09 (m, 2H), 6.96-6.90 (m, 1H), 4.90-4.80 (m, 1H), 3.61-3.41 (m, 2H), 3.08 (s, 9H), 2.43-2.41 (m, 2H); MS ESI 426.1 [M+H]$^+$, calcd for [C$_{18}$H$_{23}$N$_3$O$_5$S$_2$+H]$^+$ 426.11.

Example S3

(R)-3-(5-(phenylethynyl)furan-2-carboxamido)-4-(trimethylammonio)-butanoate

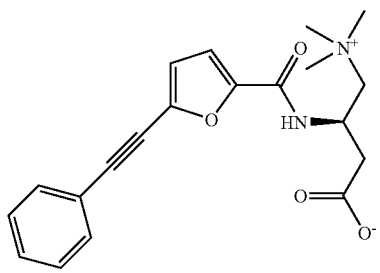 [SMILES: C[N+](C)(C)C[C@@H](CC(=O)[O-])NC(=O)c1ccc(C#Cc2ccccc2)o1]

(R)-aminocarnitine (16 mg, 0.1 mmol) and 2,5-dioxopyrrolidin-1-yl 5-(phenylethynyl)furan-2-carboxylate (60 mg, 0.19 mmol) were dissolved into DMF (1 mL). Triethylamine (50 μL, 0.36 mmol) was added and the solution was stirred at room temperature for 18 h. Diethyl ether (20 mL) was added and a white precipitate was collected. The powder was purified by silica gel chromatography (elution 10% MeOH/CH$_2$Cl$_2$ to 100% MeOH) to give the title compound as a white powder (10 mg, 24%). $^1$H NMR (400 MHz, D$_2$O) δ 7.35-7.33 (m, 2H), 7.25-7.16 (m, 3H), 7.02 (d, 1H, J=3.7 Hz), 6.58 (d, 1H, J=3.6 Hz), 4.90-4.80 (m, 1H), 3.63-3.55 (m, 1H), 3.47-3.42 (m, 1H), 3.04 (s, 9H), 2.51-2.41 (m, 2H); MS ESI 355.1 [M+H]$^+$, calcd for [C$_{20}$H$_{22}$N$_2$O$_4$+H]$^+$ 355.16.

Example S4

(R)-3-(5-(hex-1-ynyl)furan-2-carboxamido)-4-(trimethylammonio)butanoate

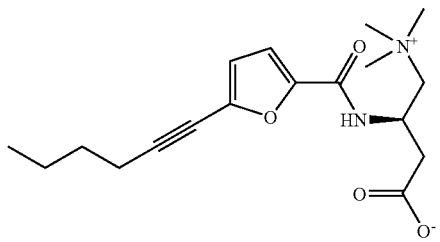 [SMILES: CCCCC#Cc1ccc(C(=O)N[C@H](CC(=O)[O-])C[N+](C)(C)C)o1]

(R)-aminocarnitine (20 mg, 0.12 mmol) and 2,5-dioxopyrrolidin-1-yl 5-(hex-1-ynyl)furan-2-carboxylate (68 mg, 0.23 mmol) were dissolved into DMF (1 mL). Triethylamine (50 μL, 0.36 mmol) was added and the solution was stirred at room temperature for 18 h. Diethyl ether (20 mL) was added and a white precipitate was collected. The powder was purified by silica gel chromatography (elution 10% MeOH/CH$_2$Cl$_2$ to 80% MeOH/CH$_2$Cl$_2$) to give the title compound as a white powder (16 mg, 40%). $^1$H NMR (400 MHz, D$_2$O) δ 7.02 (d, 1H, J=3.7 Hz), 6.53 (d, 1H, J=3.6 Hz), 4.90-4.80 (m, 1H), 3.63-3.58 (m, 1H), 3.47-3.42 (m, 1H), 3.06 (s, 9H), 2.45-2.42 (m, 2H), 2.35 (t, 2H, J=6.9 Hz), 1.47-1.41 (m, 2H), 1.35-1.29 (m, 2H), 0.78 (t, 3H, J=7.3 Hz); MS ESI 335.2 [M+H]$^+$, calcd for [C$_{18}$H$_{26}$N$_2$O$_4$+H]$^+$ 335.19.

Example S5

(R)-3-(4-(3-methylfuran-2-carboxamido)benzamido)-4-(trimethylammonio)-butanoate

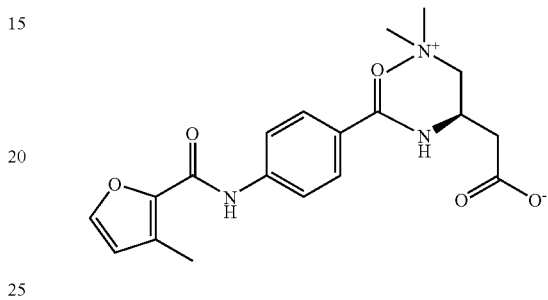

(R)-aminocarnitine (20 mg, 0.12 mmol) and 2,5-dioxopyrrolidin-1-yl 4-(3-methylfuran-2-carboxamido)benzoate (82 mg, 0.24 mmol) were dissolved into DMF (1 mL). Triethylamine (50 μL, 0.36 mmol) was added and the solution was stirred at room temperature for 48 h. Diethyl ether (20 mL) was added and a white precipitate was collected. The powder was purified by silica gel chromatography (elution 10% MeOH/CH$_2$Cl$_2$ to 80% MeOH/CH$_2$Cl$_2$) to give the title compound as a white solid (20 mg, 43%). $^1$H NMR (400 MHz, D$_2$O) δ 7.62 (d, 1H, J=1.4 Hz), 7.32-7.30 (m, 1H), 7.27-7.16 (m, 3H), 6.55 (d, 1H, J=1.8 Hz), 4.90-4.80 (m, 1H), 3.63-3.42 (m, 2H), 3.13 (s, 9H), 2.48-2.45 (m, 2H), 2.10 (s, 3H); MS ESI 388.2 [M+H]$^+$, calcd for [C$_{20}$H$_{25}$N$_3$O$_5$+H]$^+$ 388.18.

Example S6

(R)-3-(3-(2-chloro-4-(trifluoromethyl)phenyl)ureido)-4-(trimethylammonio)-butanoate

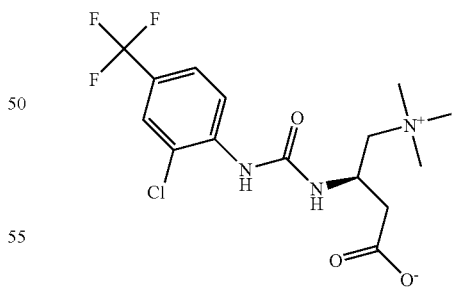

To a solution of (R)-aminocarnitine (35 mg, 0.22 mmol) and diisopropylethylamine (0.11 mL, 0.65 mmol) in MeOH (2 mL) was added 2-chloro-1-isocyanato-4-(trifluoromethyl)benzene (67 uL, 0.44 mmol) and the reaction stirred at room temperature overnight. The MeOH was removed in vacuo and the residue titurated several times with 1:1 ether/EtOAc, the resulting solid was filtered and dried to give the title compound as a white powder (15 mg, 18%). NMR (300 MHz, CD$_3$OD) δ 8.37 (m, 1H), 7.68 (m, 1H), 7.53 (m, 1H), 4.29 (m, 1H), 3.78-3.48 (m, 2H), 3.25 (s, 9H), 2.70-2.49 (m, 2H); MS ESI 382.1 [M+H]+, calcd for [C$_{15}$H$_{19}$ClF$_3$N$_3$O$_3$+H]+ 382.78.

Example S7

(R)-3-(3-(4-octylphenyl)ureido)-4-(trimethylammonio)butanoate

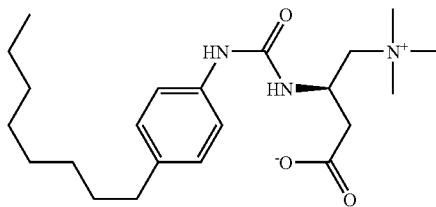

To a solution of (R)-aminocarnitine (22 mg, 0.14 mmol) and diisopropylethylamine (71 uL, 0.41 mmol) in MeOH (2 mL) was added 1-isocyanato-4-octylbenzene (63 uL, 0.27 mmol) and the reaction stirred for 18 h. The MeOH was removed in vacuo and the residue stirred with 1:1 ether/EtOAc. Impurities dissolved into the ether/EtOAc which were discarded and the remaining material taken up into 90:10 CH$_2$Cl$_2$/MeOH and then loaded onto a short SiOH plug. The title compound was eluted by increasing MeOH content in 10% steps to 60%. The compound was then taken up into 90:10 CH$_2$Cl$_2$/MeOH and filtered through a plug of celite which gave after drying the title compound as a white powder (9 mg, 17%). $^1$H NMR (400 MHz, CD$_3$OD) δ 7.27 (d, 2H, J=8.4 Hz), 7.09 (d, 2H, J=8.4 Hz), 4.73-4.71 (m, 1H), 3.78-3.53 (m, 2H), 3.25 (s, 9H), 2.75-2.72 (m, 2H), 2.55 (t, 2H, J=8.0 Hz), 1.60-1.29 (m, 12H), 0.90 (t, 3H, J=6.8 Hz); MS ESI 392.3 [M+H]+, calcd for [C$_{22}$H$_{37}$N$_3$O$_3$+H]+ 392.55.

Example S8

(R)-3-(3-(4-phenoxyphenyl)ureido)-4-(trimethylammonio)butanoate

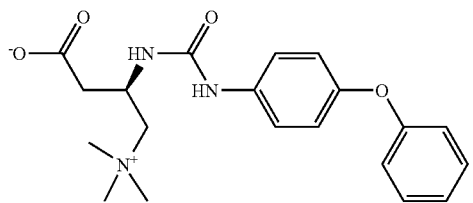

To a solution of (R)-aminocarnitine (27 mg, 0.17 mmol) and diisopropylethylamine (88 uL, 0.51 mmol) in MeOH (2 mL) was added 1-isocyanato-4-phenoxybenzene (71 mg, 0.34 mmol) and the reaction stirred for 18 h. The MeOH was removed in vacuo and the residue stirred with 1:1 ether/EtOAc. Impurities were dissolved in the ether/EtOAc and discarded and the remaining material was taken up into 90:10 CH$_2$Cl$_2$/MeOH and then loaded onto a short SiOH plug. The title compound was eluted by increasing MeOH content in 10% steps to 60%. The compound was then taken up into 90:10 CH$_2$Cl$_2$/MeOH and filtered through a plug of celite which gave after drying the title compound as a white powder (10 mg, 16%). $^1$H NMR (400 MHz, CD$_3$OD) δ 7.37-7.30 (m, 4H), 7.07 (t, 1H, J=7.2 Hz), 6.95-6.92 (m, 4H), 4.73-4.71 (m, 1H), 3.80-3.54 (m, 2H), 3.26 (s, 9H), 2.81-2.68 (m, 2H); MS ESI 372.2 [M+H]+, calcd for [C$_{20}$H$_{25}$N$_3$O$_4$+H]+ 372.43.

Example S9

(R)-3-(3-(4-methyl-2-phenylthiazol-5-yl)ureido)-4-(trimethylammonio)-butanoate

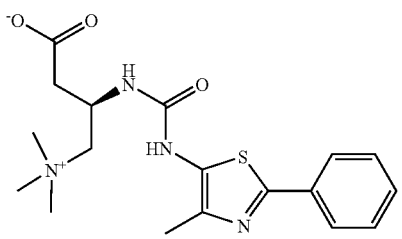

To a solution of (R)-aminocarnitine (21 mg, 0.13 mmol) and diisopropylethylamine (68 uL, 0.39 mmol) in MeOH (2 mL) was added 5-isocyanato-4-methyl-2-phenylthiazole (57 mg, 0.26 mmol) and the reaction stirred for 18 hrs. The MeOH was removed in vacuo and the residue stirred with 1:1 ether/EtOAc. Impurities dissolved into the ether/EtOAc which were discarded and the remaining material taken up into 90:10 CH$_2$Cl$_2$/MeOH and then loaded onto a short SiOH plug. The title compound was eluted by increasing MeOH content in 10% steps to 60%. The compound was then taken up into 90:10 CH$_2$Cl$_2$/MeOH and filtered through a plug of celite which gave after drying the title compound as a yellow powder (6 mg, 12%). $^1$H NMR (400 MHz, CD$_3$OD) δ 7.85-7.82 (m, 2H), 7.47-7.41 (m, 3H), 4.73-4.71 (m, 1H), 3.82-3.57 (m, 2H), 3.26 (s, 9H), 2.79-2.75 (m, 2H), 2.37 (s, 3H); MS ESI 377.1 [M+H]+, calcd for [C$_{18}$H$_{24}$N$_4$O$_3$S+H]+ 377.47.

Example S10

(R)-3-(3-(4-(heptyloxy)phenyl)ureido)-4-(trimethylammonio)butanoate

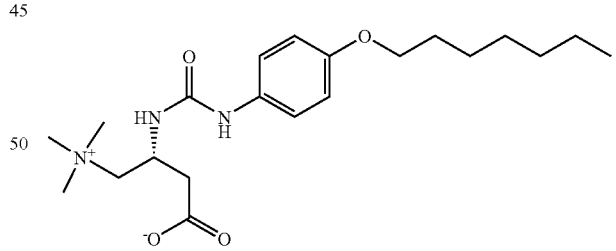

To a solution of (R)-aminocarnitine (16 mg, 0.10 mmol) and diisopropylethylamine (52 uL, 0.30 mmol) in MeOH (2 mL) was added 1-(heptyloxy)-4-isocyanatobenzene (46 uL, 0.20 mmol) and the reaction stirred for 18 h. The MeOH was removed in vacuo and the residue stirred with 1:1 ether/EtOAc. Impurities dissolved into the ether/EtOAc which were discarded and the remaining material taken up into 90:10 CH$_2$Cl$_2$/MeOH and then loaded onto a short SiOH plug. The title compound was eluted by increasing MeOH content in 10% steps to 60%. The compound was then taken up into 90:10 CH$_2$Cl$_2$/MeOH and filtered through a plug of celite which gave after drying the title compound as a white powder (9 mg, 23%). ¹H NMR (400 MHz, CD₃OD) δ 7.24 (d, 2H, J=9.2 Hz), 6.84 (d, 2H, J=8.8 Hz), 4.71-4.69 (m, 1H), 3.93 (t, 2H, J=6.4 Hz), 3.77-3.53 (m, 2H), 3.25 (s, 9H), 2.74-2.70 (m, 2H), 1.77-1.72 (m, 2H), 1.49-1.34 (m, 8H), 0.92 (t, 3H, J=6.8 Hz); MS ESI 394.3 [M+H]⁺, calcd for [C₂₁H₃₅N₃O₄+H]⁺ 394.52.

Example S11

(R)-3-(3-(4-(thiophen-2-yl)phenyl)ureido)-4-(trimethylammonio)butanoate

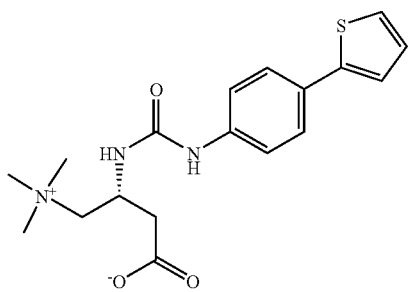

To a solution of (R)-aminocarnitine (17 mg, 0.11 mmol) and diisopropylethylamine (55 uL, 0.32 mmol) in MeOH (2 mL) was added 2-(4-isocyanatophenyl)thiophene (43 mg, 0.22 mmol) and the reaction stirred for 18 h. The MeOH was removed in vacuo and the residue stirred with 1:1 ether/EtOAc. Impurities dissolved into the ether/EtOAc which were discarded and the remaining material taken up into 90:10 CH₂Cl₂/MeOH and then loaded onto a short SiOH plug. The title compound was eluted by increasing MeOH content in 10% steps to 60%. The compound was then taken up into 90:10 CH₂Cl₂/MeOH and filtered through a plug of celite which gave after drying the title compound as a white powder (5 mg, 13%). ¹H NMR (400 MHz, CD₃OD) δ 7.53 (d, 2H, J=8.0 Hz), 7.42 (d, 2H, J=8.0 Hz), 7.29 (s, 2H), 7.05 (s, 1H), 4.65-4.63 (m, 1H), 3.77-3.53 (m, 2H), 3.23 (s, 9H), 2.58-2.48 (m, 2H); MS ESI 362.1 [M+H]⁺, calcd for [C₁₈H₂₃N₃O₃S+H]⁺ 362.46.

Example S12

(R)-3-(3-(4-(Benzyloxy)phenyl)ureido)-4-(trimethylammonio)butanoate acetate

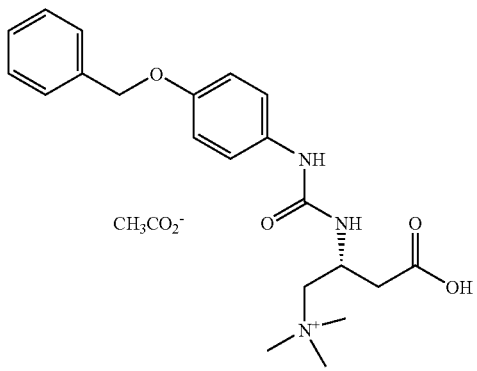 [SMILES: C[N+](C)(C)C[C@@H](CC(=O)O)NC(=O)Nc1ccc(OCc2ccccc2)cc1 ; "CH3CO2-"]

A solution of aminocarnitine (35 mg) in anhydrous MeOH (2 mL) was treated with DIPEA (2.5 equiv) and 1-(benzyloxy)-4-isocyanatobenzene (2 equiv) at rt. The reaction was sealed and stirred at rt overnight. The reaction mixture were concentrated under reduced pressure and purified on silica gel using MeOH/DCM (0->80%) and/or 55% DCM:22% MeOH:23%AcOH. The purified material was then taken into 10% MeOH/DCM, filtered through a plug of Celite, concentrated under reduced pressure and optionally triturated with Et₂O and/or hexanes to provide the title compound as a white solid (1.8 mg). ¹H NMR (400 MHz, CD₃OD): δ=7.42 (d, J=8.0 Hz, 2H), 7.36 (t, J=7.6, 2H), 7.30 (d, J=7.60 Hz, 1H), 7.28-7.20 (m, 2H), 6.92 (d, J=8.80 Hz, 2H), 5.04 (s, 2H), 5.59 (br s, 1H), 3.80-3.45 (m, 2H), 3.21 (s, 9H), 2.60-2.45 (br, 2H), 1.96 (s, 3H); MS ESI [M+H]⁺, calcd for [C₂₁H₂₆N₃O₄+H]⁺ 386.5 found m/z 386.2 (100).

Example S13

(R)-2-(3-(4-Butyl-2-methylphenyl)ureido)-3-carboxy-N,N,N-trimethylpropan-1-aminium

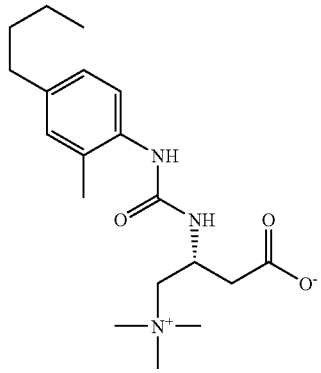 [SMILES: CCCCc1ccc(NC(=O)N[C@H](CC(=O)[O-])C[N+](C)(C)C)c(C)c1]

According to the method described in example S11, aminocarnitine (35 mg) was reacted with 4-butyl-1-isocyanato-2-methylbenzene to yield the title compound as a white solid (10.4 mg). ¹H NMR (400 MHz, CD₃OD): δ=7.27 (d, J=8.0 Hz, 1H), 7.01 (s, 1H), 6.97 (dd, J=8.0 Hz, 1.6 Hz, 1H), 4.60 (br s, 1H), 3.75-3.45 (m, 2H), 3.22 (s, 9H), 2.49 (t, J=7.60, 2H), 2.48 (t, J=5.20 Hz, 2H), 1.65-1.50 (m, 2H), 1.45-1.20 (m, 4H), 0.93 (t, J=7.20 Hz, 3H); MS ESI [M+H]⁺, calcd for [C₁₉H₃₁N₃O₃+H]⁺ 350.5 found m/z 350.2 (100).

Example S14

(R)-3-Carboxy-N,N,N-trimethyl-2-(3-(2,3,4-trifluorophenyl)ureido)-propan-1-aminium acetate

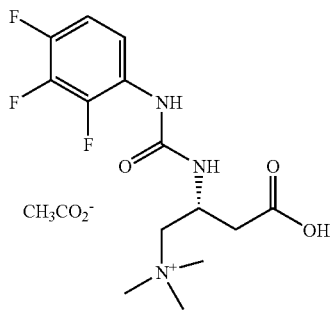 [SMILES: "CH3CO2-" ; C[N+](C)(C)C[C@@H](CC(=O)O)NC(=O)Nc1ccc(F)c(F)c1F]

According to the method described in example S11, aminocarnitine (41 mg) was reacted with 1,2,3-trifluoro-4-isocyanatobenzene to yield the title compound as a white solid (2.3 mg). $^1$H NMR (400 MHz, CD$_3$OD): δ=7.70-7.60 (m, 1H), 7.10-7.00 (m, 1H), 4.61 (br s, 1H), 3.80-45 (m, 2H), 3.22 (s, 9H), 2.40-2.60 (m, 2H), 1.97 (s, 3H); MS ESI [M+H]$^+$, calcd for [C$_{14}$H$_{18}$F$_3$N$_3$O$_3$+H]$^+$ 334.3 found m/z 334.1 (100)

Example S15

(R)-3-Carboxy-N,N,N-trimethyl-2-(3-(4-pentylphenyl)ureido)propan-1-aminium

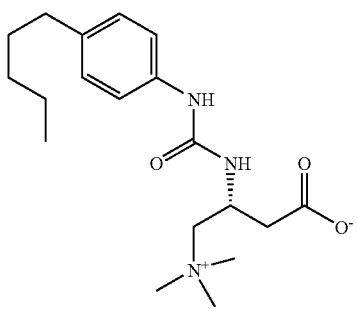 [SMILES: CCCCCc1ccc(NC(=O)N[C@H](CC(=O)[O-])C[N+](C)(C)C)cc1]

According to the method described in example S11, aminocarnitine (43 mg) was reacted with 1-isocyanato-4-pentylbenzene to yield the title compound as a white solid (12 mg). $^1$H NMR (400 MHz, CD$_3$OD): δ=7.26 (d, J=7.60 Hz, 2H), 7.05 (d, J=7.20 Hz, 2H), 4.62 (br s, 1H), 3.90-3.45 (br m, 2H), 3.21 (s, 9H), 2.52 (t, 7.20 Hz, 2H), 1.65-1.52 (m, 2H), 1.40-1.25 (m, 4H), 0.90 (t, J=6.8 Hz, 3H); MS ESI [M+H]$^+$, calcd for [C$_{19}$H$_{31}$N$_3$O$_3$+H]$^+$ 350.5 found m/z 350.2 (100)

Example S16

(R)-2-(3-(4-Benzoylphenyl)ureido)-3-carboxy-N,N,N-trimethylpropan-1-aminium acetate

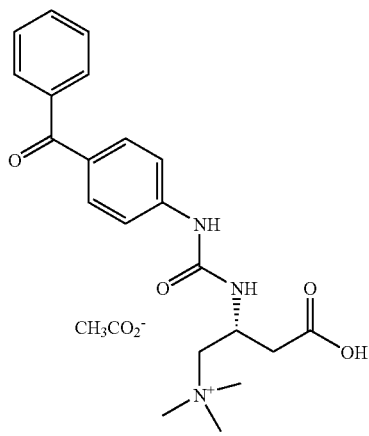 [SMILES: C[N+](C)(C)C[C@@H](CC(=O)O)NC(=O)Nc1ccc(C(=O)c2ccccc2)cc1 ; "CH3CO2-"]

According to the method described in example S11, aminocarnitine (40 mg) was reacted with (4-isocyanatophenyl)(phenyl)methanone to yield the title compound as a white solid (13.4 mg). $^1$H NMR (400 MHz, CD$_3$OD): δ=7.76-7.68 (m, 4H), 7.66-7.55 (m, 3H), 7.55-7.48 (m, 2H), 4.66 (brs, 1H), 3.78 (dd, J=9.20 Hz, 13.60 Hz, 1H), 3.60-3.50 (m, 1H), 3.24 (s, 9H), 2.65-2.50 (m, 2H), 1.98 (s, 3H); MS ESI [M+H]$^+$, calcd for [C$_{21}$H$_{26}$N$_3$O$_4$+H]$^+$ 384.4 found m/z 384.2 (100)

Example S17

(R)-2-(3-Biphenyl-4-ylureido)-3-carboxy-N,N,N-trimethylpropan-1-aminium acetate

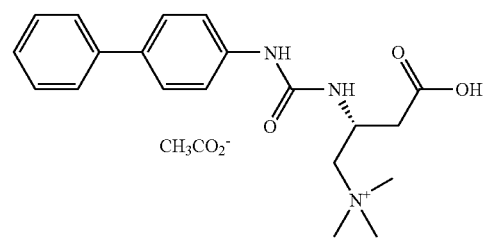

According to the method described in example S11, aminocarnitine (40 mg) was reacted with 4-isocyanatobiphenyl to yield the title compound as a white solid (25.7 mg). $^1$H NMR (400 MHz, CD$_3$OD): δ=7.58-7.45 (m, 6H), 7.39 (t, J=7.60 Hz, 2H), 7.28 (t, J=7.20 Hz, 1H), 4.66 (br s, 1H), 3.74 (dd, J=9.20 Hz, 13.20 Hz, 1H), 3.54 (d, 13.6 Hz, 1H), 3.23 (s, 9H), 2.65-2.55 (m, 2H), 1.98 (s, 3H). MS ESI [M+H]$^+$, calcd for [C$_{20}$H$_{25}$N$_3$O$_3$+H]$^+$: 356.4 found m/z 356.2 (100).

Example S18

(R)-3-(4-(trifluoromethyl)phenylsulfonamido)-4-(trimethylammonio)-butanoate

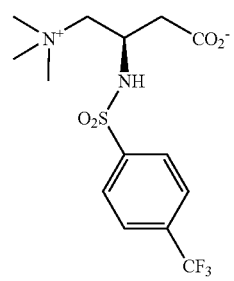

a) R-aminocarnitine benzyl ester mesylate (20 mg, 0.06 mmol) is dissolved into DMF (1 mL). The solution is treated with triethylamine (33 μL, 0.24 mmol) followed by 4-trifluoromethylsulfonyl chloride (0.09 mmol). The mixture is stirred overnight at room temperature. DMF is removed under vacuum. The mixture is loaded onto a silica gel column and eluted with 4:1 MeOH/CH$_2$Cl$_2$ to obtain (R)-4-(benzyloxy)-N,N,N-trimethyl-4-oxo-2-(4-(trifluoromethyl)phenylsulfonamido)butan-1-aminium methanesulfonate.

b) The above ester is treated with MeOH (5 mL) and 10% Pd/C. The mixture is stirred under hydrogen gas for 16 h, filtered through celite and concentrated. The residue is dissolved in water and transferred onto Amberlite IRA-402 (OH— form) and eluted with deionized water to afford the title compound.

Example S19

(R)-3-carboxy-N,N,N-trimethyl-2-(6-phenoxypyridine-3-sulfonamido)propan-1-aminium 2,2,2-trifluoroacetate

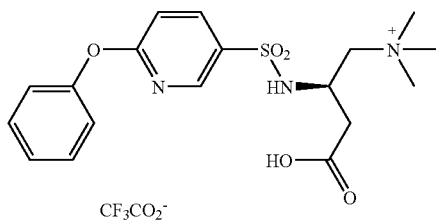

a) (R)-benzyl 4-(dimethylamino)-3-(6-phenoxypyridine-3-sulfonamido)butanoate To a solution of (R)-benzyl 3-amino-4-(dimethylamino)butanoate (32 mg, 0.086 mmol), triethylamine (50 µL, 0.36 mmol) and DMAP (1 mg, 0.008 mmol) in anhydrous $CH_2Cl_2$ (1 mL) was added 6-phenoxypyridine-3-sulfonyl chloride is reacted with R-aminocarnitine benzyl ester (67 mg, 0.25 mmol). The solution was stirred overnight at room temperature. The solvents were removed in vacuo and the residue was purified by preparatory HPLC. The residue was dissolved into $CH_2Cl_2$ (50 mL) and washed with 0.1 N NaOH (5 mL), dried over $MgSO_4$ and concentrated to give the title compound as a white solid (18 mg, 37%). MS ESI 470.2 [M+H]+, calcd for $[C_{24}H_{27}N_3O_5S+H]^+$ 470.17.

b) (R)-4-(benzyloxy)-N,N,N-trimethyl-4-oxo-2-(6-phenoxypyridine-3-sulfonamido)butan-1-aminium iodide To a solution of (R)-benzyl 4-(dimethylamino)-3-(6-phenoxypyridine-3-sulfonamido)butanoate in $CH_2Cl_2$ (2 mL) was added methyl iodide (100 pit). The reaction was stirred overnight and concentrated to dryness to give the title compound in quantitative yield. $^1H$ NMR (400 MHz, $CDCl_3$) δ ppm 8.63 (s, 1H), 8.26 (d, J=8.8 Hz, 1H), 7.43 (t, J=7.7 Hz, 2H), 7.39-7.29 (m, 5H), 7.13 (d, J=8.1 Hz, 2H), 6.99 (d, 1H, J=8.8 Hz, 1H) 5.14-5.03 (m, 2H), 4.49-4.41 (m, 1H), 4.36-4.30 (m, 1H), 3.74-3.71 (m, 1H), 3.42 (s, 9H), 2.91-2.84 (m, 1H), 2.46-2.42 (m, 1H).

c) (R)-3-carboxy-N,N,N-trimethyl-2-(6-phenoxypyridine-3-sulfonamido)propan-1-aminium 2,2,2-trifluoroacetate To a solution of (R)-4-(benzyloxy)-N,N,N-trimethyl-4-oxo-2-(6-phenoxypyridine-3-sulfonamido)butan-1-aminium iodide in MeOH (1 mL) was added 1 N NaOH (1 mL). The reaction was stirred for 1 h and acidified to pH 1. The mixture was purified by preparatory HPLC to give the title compound as a white solid (8 mg, 42%). $^1H$ NMR (400 MHz, $D_2O$) δ 8.44 (d, 1H, J=2.6 Hz), 8.14 (dd, 1H, J=8.8, 2.6 Hz), 7.41 (t, 2H, J=7.7 Hz) 7.26 (t, 1H, J=7.4 Hz), 7.10 (dd, 1H, J=8.7, 2.2 Hz) 4.29-4.26 (m, 1H), 3.62-3.56 (m, 1H), 3.42-3.38 (m, 1H), 3.16 (s, 9H), 2.42-2.36 (m, 1H), 2.23-2.18 (m, 1H); MS ESI 394.14 [M+H]+, calcd for $[C_{18}H_{23}N_3O_5S+H]^+$ 394.2

Example S20

(R)-3-(4'-fluorobiphenyl-4-ylsulfonamido)-4-(trimethylammonio)butanoate

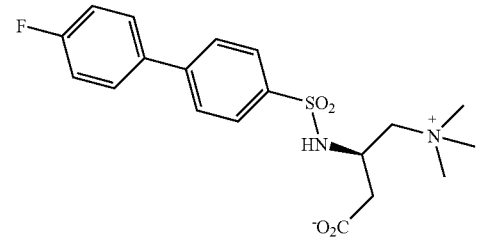

According to the method described in example S18a, 4'-fluorobiphenyl-4-sulfonyl chloride is reacted with R-aminocarnitine benzyl ester mesylate followed by hydrogenation of the benzyl ester as described in S18b to give the title compound.

Example S21

(R)-3-(5-(pyridin-2-yl)thiophene-2-sulfonamido)-4-(trimethylammonio)-butanoate 2,2,2-trifluoroacetate

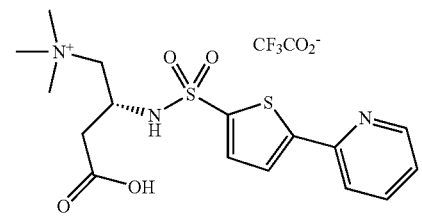

a) (R)-benzyl 4-(dimethylamino)-3-(5-(pyridin-2-yl)thiophene-2-sulfonamido)butanoate According to the method described in example S20a, (R)-benzyl 3-amino-4-(dimethylamino)butanoate (27 mg, 0.086 mmol) was reacted with 5-(pyridin-2-yl)thiophene-2-sulfonyl chloride to yield the title compound as a white solid (16 mg, 40%). MS ESI 460.2 [M+H]+, calcd for $[C_{22}H_{25}N_3O_4S_2+H]^+$ 460.13 b) (R)-4-(benzyloxy)-N,N,N-trimethyl-4-oxo-2-(5-(pyridin-2-yl)thiophene-2-sulfonamido)butan-1-aminium iodide According to the method described in example S20b, (R)-benzyl 4-(dimethylamino)-3-(4-(octyloxycarbonylamino) phenylsulfonamido)butanoate was reacted with methyl iodide to give the title compound as a white solid in quantitative yield.

c) (R)-3-carboxy-N,N,N-trimethyl-2-(5-(pyridin-2-yl)thiophene-2-sulfonamido)propan-1-aminium 2,2,2-trifluoroacetate According to the method described in example S20, (R)-4-(benzyloxy)-N,N,N-trimethyl-4-oxo-2-(5-(pyridin-2-yl)thiophene-2-sulfonamido)butan-1-aminium iodide was hydrolysed with 1 N NaOH and purified by HPLC to give the title compound as a white solid (4 mg, 23%). $^1$H NMR (400 MHz, D$_2$O) δ 8.50-8.47 (m, 1H), 8.13-8.08 (m, 1H), 7.96 (d, J=8.0 Hz, 1H), 7.71-7.68 (m, 2H), 7.59-7.55 (m, 1H), 4.32-4.28 (m, 1H), 3.62-3.56 (m, 1H), 3.42-3.39 (m, 1H), 3.15 (s, 9H), 2.46-2.39 (m, 1H), 2.23-2.18 (m, 1H); MS ESI 384.1 [M+H]$^+$, calcd for [C$_{16}$H$_{22}$N$_3$O$_4$S$_2$+H]$^+$ 384.10

Example S22

(R)-3-carboxy-2-(5-(isoxazol-5-yl)thiophene-2-sulfonamido)-N,N,N-trimethylpropan-1-aminium 2,2,2-trifluoroacetate

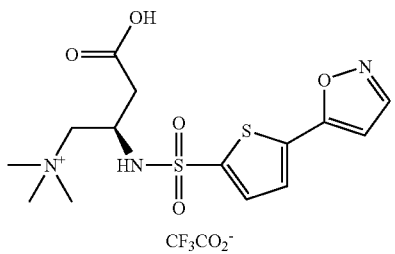

a) (R)-benzyl 4-(dimethylamino)-3-(5-(isoxazol-3-yl)thiophene-2-sulfonamido)butanoate According to the method described in example S20a, (R)-benzyl 3-amino-4-(dimethylamino)butanoate (27 mg, 0.086 mmol) was reacted with 5-(isoxazol-3-yl)thiophene-2-sulfonyl chloride to yield the title compound as a white solid (38 mg, 84%). MS ESI 450.2 [M+H]$^+$, calcd for [C$_{20}$H$_{23}$N$_3$O$_5$S$_2$+H]$^+$ 450.11 b) (R)-4-(benzyloxy)-N,N,N-trimethyl-4-oxo-2-(5-(pyridin-2-yl)thiophene-2-sulfonamido)butan-1-aminium iodide According to the method described in example S20b, (R)-benzyl 4-(dimethylamino)-3-(5-(isoxazol-3-yl)thiophene-2-sulfonamido)butanoate was reacted with methyl iodide to give the title compound as a white solid in quantitative yield.

c) (R)-3-carboxy-N,N,N-trimethyl-2-(5-(pyridin-2-yl)thiophene-2-sulfonamido)propan-1-aminium 2,2,2-trifluoroacetate According to the method described in example S20, (R)-4-(benzyloxy)-N,N,N-trimethyl-4-oxo-2-(5-(pyridin-2-yl)thiophene-2-sulfonamido)butan-1-aminium iodide was hydrolysed with 1 N NaOH and purified by HPLC to give the title compound as a white solid (6 mg, 16%). NMR (400 MHz, D$_2$O) δ 7.80 (d, J=4.1 Hz, 1H), 7.68 (d, J=4.1 Hz, 1H), 4.32-4.28 (m, 1H), 3.62-3.56 (m, 1H), 3.43-3.39 (m, 1H), 3.15 (s, 9H), 2.43-2.36 (m, 1H), 2.20-2.15 (m, 1H); MS ESI 374.1 [M+H]$^+$, calcd for [C$_{14}$H$_{19}$N$_3$O$_5$S$_2$+H]$^+$ 374.08

Example S23

(R)-3-(4-pentylphenylsulfonamido)-4-(trimethylammonio)butanoate 2,2,2-trifluoroacetate

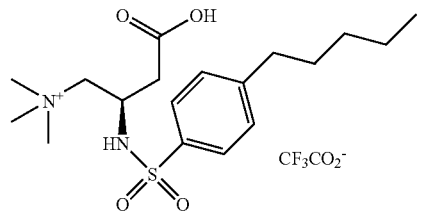

a) (R)-benzyl 4-(dimethylamino)-3-(4-pentylphenylsulfonamido)butanoate

According to the method described in example S20a, (R)-benzyl 3-amino-4-(dimethylamino)butanoate (27 mg, 0.086 mmol) was reacted with 4-pentylbenzene-1-sulfonyl chloride to yield the title compound as a white solid (9 mg, 25%). MS ESI 447.3 [M+H]$^+$, calcd for [C$_{24}$H$_{34}$N$_2$O$_4$S+H]$^+$ 447.22 b) (R)-4-(benzyloxy)-N,N,N-trimethyl-4-oxo-2-(4-pentylphenylsulfonamido)butan-1-aminium iodide According to the method described in example S20b, (R)-benzyl 4-(dimethylamino)-3-(4-pentylphenylsulfonamido)butanoate was reacted with methyl iodide to give the title compound as a white solid in quantitative yield.

c) (R)-3-carboxy-N,N,N-trimethyl-2-(5-(pyridin-2-yl)thiophene-2-sulfonamido)propan-1-aminium 2,2,2-trifluoroacetate According to the method described in example S20, (R)-4-(benzyloxy)-N,N,N-trimethyl-4-oxo-2-(4-pentylphenylsulfonamido)butan-1-aminium iodide was hydrolysed with 1 N NaOH and purified by HPLC to give the title compound as a white solid (6 mg, 16%). $^1$H NMR (400 MHz, D$_2$O) δ 7.70 (d, J=8.3 Hz, 2H), 7.39 (d, J=8.3 Hz, 1H), 4.16-4.10 (m, 1H), 3.54-3.48 (m, 1H), 3.32-3.29 (m, 1H), 3.13 (s, 9H), 2.61 (t, J=7.5 Hz, 2H), 2.26-2.19 (m, 1H), 1.93-1.87 (m, 1H), 1.56-1.48 (m, 2H), 1.19-1.12 (m, 4H), 0.72 (t, J=7.1 Hz, 3H); MS ESI 371.2 [M+H]$^+$, calcd for [C$_{18}$H$_{30}$N$_2$O$_4$S+H]$^+$ 371.20.

Example S24

(R)-3-(benzofuran-2-sulfonamido)-4-(trimethylammonio)butanoate

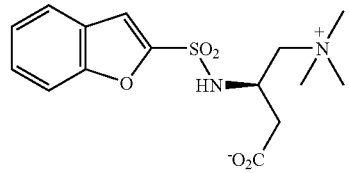

According to the method described in example S18a, benzofuran-2-sulfonyl chloride is reacted with R-aminocarnitine benzyl ester mesylate followed by hydrogenation of the benzyl ester as described in 18b to give the title compound.

Example S25

(R)-3-(3-(benzyloxy)phenylsulfonamido)-4-(trimethylammonio)butanoate

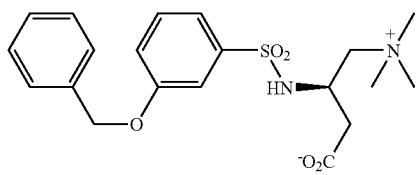

According to the method described in example S18a, 3-(benzyloxy)benzene-1-sulfonyl chloride is reacted with R-aminocarnitine benzyl ester followed by hydrogenation of the benzyl ester mesylate as described in 18b to give the title compound.

Example S26

(R)-3-(3-phenoxyphenylsulfonamido)-4-(trimethylammonio)butanoate

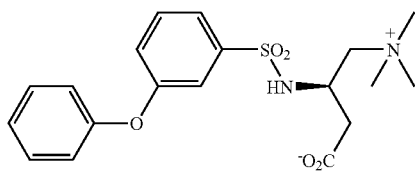

According to the method described in example S18a, 3-phenoxybenzene-1-sulfonyl chloride is reacted with R-aminocarnitine benzyl ester mesylate followed by hydrogenation of the benzyl ester as described in 18b to give the title compound.

Example S27

(R)-3-(N-(4-heptylphenyl)sulfamoylamino)-4-(trimethylammonio)-butanoate

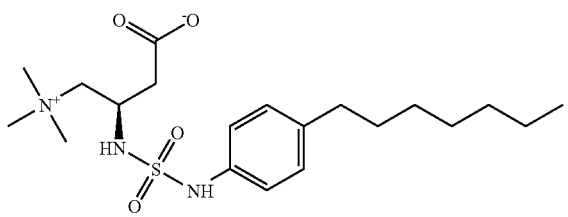

a) (R)-4-methoxy-N,N,N-trimethyl-4-oxo-2-(2-oxooxazolidine-3-sulfonamido)butan-1-aminium chloride To a solution of (R)-aminocarnitine methyl ester (500 mg, 2 mmol) and triethylamine (1.12 mL, 8 mmol) in dichloromethane (150 mL) was added the solution of 2-chloroethyl chlorosulfonylcarbamate in dichloromethane (0.77 M, 2.6 mL, 2 mmol). The resulting mixture was stirred overnight at rt. After removal of solvent, crude product was obtained as a white solid which was used without further purification. MS ESI 324.0 [M+H]$^+$, calcd for [$C_{11}H_{21}N_3O_6S$+H]$^+$ 324.12.

b) (R)-3-(N-(4-heptylphenyl)sulfamoylamino)-4-(trimethylammonio)-butanoate

A portion of this material (250 mg) was treated with 4-n-heptylanline (64 mg, 0.34 mmol) and triethylamine (0.4 mL, 2.86 mmol) in CH$_3$CN (10 mL) and refluxed for 2 h then cooled to rt. Solvents were removed and the residue was dissolved in MeOH (15 mL) and treated with 3.5 mL of 1 M NaOH (3.5 mmol). The resulting mixture was stirred at rt and monitored by LC-MS. When disappearance of the ester was complete, the MeOH was removed and brine (10 mL) and H$_2$O (10 mL) were added. The mixture was extracted with n-BuOH (30 mL×2) and the combined extracts were dried (Na$_2$SO$_4$). After evaporation of nBuOH, the residue was dissolved in MeOH and purified by flash chromatography (eluent: MeOH) to give the title compound (31 mg, 26%) as white solid. $^1$H NMR (400 MHz, CD$_3$OD+1 drop CDCl$_3$) δ 7.15-7.00 (m, 4H), 4.20-4.08 (m, 1H), 3.40-3.26 (m, 2H, overlapping with MeOH), 3.18 (s, 9H), 2.58-2.47 (m, 2H), 2.42 (d, 1H, J=16.0 Hz), 2.27 (dd, 1H, J=14.8 Hz, 7.6 Hz), 1.62-1.50 (m, 2H), 1.40-1.25 (m, 8H), 0.89 (t, 3H, J=0.68 Hz); MS ESI 414.3 [M+H]$^+$, calcd for [$C_{20}H_{35}N_3O_4S$+H]$^+$ 414.24.

Example S28

(R)-3-(N-methyl-N-(4-phenylbutyl)sulfamoylamino)-4-(trimethylammonio)-butanoate

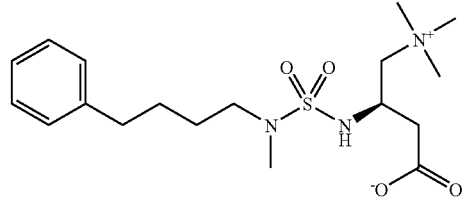

According to the method described in example S27, (R)-4-methoxy-N,N,N-trimethyl-4-oxo-2-(2-oxooxazolidine-3-sulfonamido)butan-1-aminium chloride is reacted with N-methyl-4-phenylbutan-1-amine followed by saponification to yield the title compound.

Example S29

(R)-3-(N-methyl-N-(4-phenoxyphenyl)sulfamoylamino)-4-(trimethyl-ammonio)butanoate

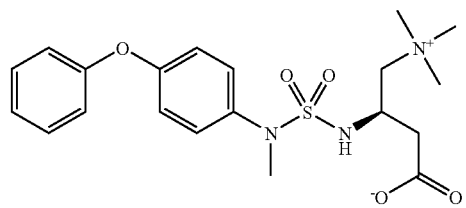

According to the method described in example S27, (R)-4-methoxy-N,N,N-trimethyl-4-oxo-2-(2-oxooxazolidine-3-sulfonamido)butan-1-aminium chloride is reacted with N-methyl-4-phenoxyaniline followed by saponification to yield the title compound.

Example S30

(R)-3-(N-(4-octylphenyl)sulfamoylamino)-4-(trimethylammonio)butanoate

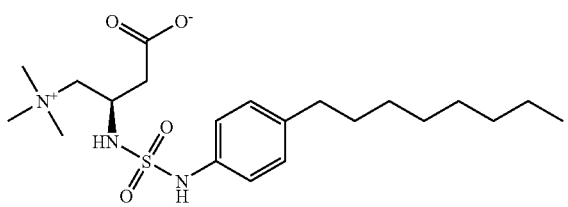 [SMILES: CCCCCCCCc1ccc(NS(=O)(=O)N[C@H](CC(=O)[O-])C[N+](C)(C)C)cc1]

A solution of 2-chloroethyl N-(4-tetradecylphenyl)sulfamoylcarbamate (600 mg, 1.54 mmol) and triethylamine (0.5 mL, 3.59 mmol) in acetonitrile (20 mL) was refluxed 25 min before cooling. A suspension of (R)-aminocarnitine methyl ester (200 mg, 0.81 mmol) and triethylamine (0.3 mL, 2.16 mmol) in acetonitrile (10 mL) was added and the resulting mixture was refluxed for additional 90 min. After removal of solvent, the residue was redissolved in methanol (10 mL) and 1 M NaOH (4 mL) was added. The reaction mixture was stirred for 2 h at rt. After removal of solvent, the residue was purified by flash chromatography ($CH_2Cl_2$/MeOH 10:1 to MeOH) to give the tile compound (86 mg, 25%) as white solid. $^1$H NMR (400 MHz, $CD_3OD$) δ 7.15 (d, 2H, J=8.8 Hz), 7.11 (d, 2H, J=8.4 Hz), 4.23-4.13 (m, 1H), 3.45-3.30 (m, 2H), 3.19 (s, 9H), 2.54 (t, 2H, J=7.6 Hz), 2.43 (dd, 1H, J=16.0 Hz, 3.0 Hz), 1.62-1.54 (m, 2H), 1.38-1.25 (m, 10H), 0.91 (t, 3H, J=6.6 Hz); MS ESI 428.3 [M+H]$^+$, calcd for [$C_{21}H_{37}N_3O_4S$+ H]$^+$ 428.26

Example S31

(R)-3-carboxy-N,N,N-trimethyl-2-(N-(3-phenoxyphenyl)sulfamoyl-amino)propan-1-aminium 2,2,2-trifluoroacetate

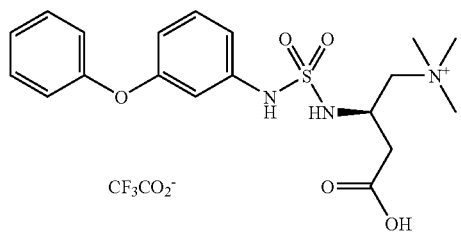

a) (R)-2-(1H-imidazole-1-sulfonamido)-4-methoxy-N,N,N-trimethyl-4-oxobutan-1-aminium chloride A solution of (R)-2-amino-4-methoxy-N,N,N-trimethyl-4-oxobutan-1-aminium chloride (35 mg) in anhydrous MeCN (5 mL) is treated with triethyl amine (2.5 equiv.) and 3-(Imidazole-1-sulfonyl)-1-methyl-3H-imidazol-1-ium triflate (1.5 equiv.). The reaction mixture is stirred at ambient temperature for 16 h then concentrated under reduced pressure and the resulting residue is purified on silica gel using MeOH/DCM (0->80%).

b) (R)-1-(N-(4-methoxy-4-oxo-1-(trimethylammonio)butan-2-yl)sulfamoyl)-3-methyl-1H-imidazol-3-ium chloride trifluoromethanesulfonate To a solution of (R)-2-(1H-imidazole-1-sulfonamido)-4-methoxy-N,N,N-trimethyl-4-oxobutan-1-aminium chloride in DCM (5 mL), cooled at 0° C., is added methyl triflate (1.05 equiv). After being stirring for 2 h at 0° C., the reaction mixture is concentrated under reduced pressure to give the title compound.

c) (R)-1-(N-(4-methoxy-4-oxo-1-(trimethylammonio)butan-2-yl)sulfamoyl)-3-methyl-1H-imidazol-3-ium chloride trifluoromethanesulfonate A solution of (R)-1-(N-(4-methoxy-4-oxo-1-(trimethylammonio)butan-2-yl)sulfamoyl)-3-methyl-1H-imidazol-3-ium chloride trifluoromethanesulfonate and 3-phenoxyaniline (1 equiv.) in MeCN (5 mL) is stirred at 80° C. for 18 h. The reaction mixture is concentrated under reduced pressure and purified by silica gel chromatography to yield the title compound.

d) (R)-3-carboxy-N,N,N-trimethyl-2-(N-(3-phenoxyphenyl)sulfamoyl-amino)propan-1-aminium 2,2,2-trifluoroacetate The product of the above reaction, in MeOH (5 mL), is treated with 1 N NaOH (1 mL). The reaction is stirred for 1 h and acidified to pH 1. The mixture is purified by preparatory HPLC to give the title compound as a white solid Example S32

(R)-3-(N-dodecyl-N-phenylsulfamoylamino)-4-(trimethylammonio)-butanoate

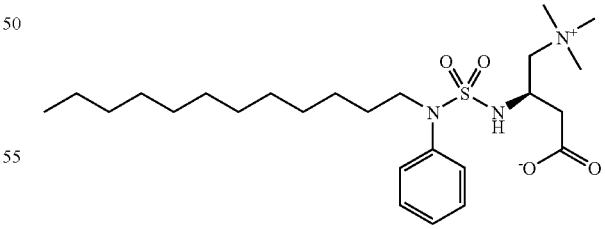

According to the method described in S27, the title compound (5.4 mg, 4%) was obtained from crude (R)-4-methoxy-N,N,N-trimethyl-4-oxo-2-(2-oxooxazolidine-3-sulfonamido)butan-1-aminium chloride (247 mg, 0.284 mmol) and N-dodecylaniline (88 mg, 0.34 mmol). $^1$H NMR (400 MHz, $CD_3OD$) δ 7.45-7.37 (m, 4H), 7.35-7.28 (m, 1H), 4.21-4.14 (m, 1H), 3.76-3.56 (m, 2H), 3.45-3.35 (m, 2H), 3.12 (s, 9H), 2.57 (dd, 1H, J=16.4 Hz, 3.2 Hz), 2.45 (dd, 1H, J=16.4 Hz, 9.2

Hz), 1.45 (quint, 2H, J=6.8 Hz), 1.38-1.20 (m, 18H), 0.91 (t, 3H, J=6.4 Hz); MS ESI 484.4 [M+H]$^+$, calcd for [C$_{25}$H$_{45}$N$_3$O$_4$S+H]$^+$ 484.32.

Example S33

(R)-4-(dimethylammonio)-3-(3-methyl-3-(4-phenoxyphenyl)-ureido)butanoate and Example S34. (R)-3-(3-methyl-3-(4-phenoxyphenyl)ureido)-4-(trimethylammonio)butanoate

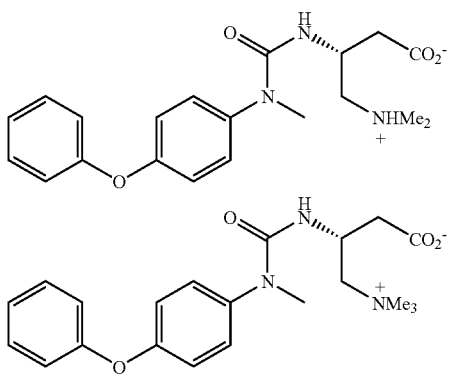

a) (R)-benzyl 4-(Dimethylamino)-3-(3-methyl-3-(4-phenoxyphenyl)-ureido)butanoate To a stirred solution of N-methyl-4-phenoxyaniline (110 mg, 0.55 mmol) in anh THF (10 mL) under Ar was added triphosgene (60 mg, 0.20 mmol) in one portion at 0° C. followed by DIPEA (0.1 mL, 0.58 mmol). The reaction was stirred at the temperature for 10 min and then at rt for 2 h. At this time, the reaction was cooled and treated with (R)-2-amino-4-(benzyloxy)-N,N-dimethyl-4-oxobutan-1-aminium 2,2,2-trifluoroacetate (193 mg, 0.55 mmol) in anh THF (6 mL) at 0° C. followed by DIPEA (0.3 mL, 1.7 mmol). The reaction was allowed to slowly warm to rt overnight. The mixture was then concentrated under reduced pressure and purified by preparative TLC (SiO$_2$, 20% MeOH/DCM) to afford the title compound as a light yellow oil (129 mg, 51%). $^1$H NMR (400 MHz, CD$_3$OD) δ ppm 7.22-7.42 (m, 8 H), 7.08-7.19 (m, 3 H), 7.00-7.06 (m, 2 H), 6.90-6.95 (m, 2 H), 5.05-5.20 (m, 2 H), 4.50-4.62 (m, 1 H), 3.19 (s, 3 H), 2.99-3.17 (m, 2 H), 2.86 (s, 6 H), 2.50-2.71 (m, 2 H). MS ESI [M+H]$^+$, calcd for [C$_{27}$H$_{31}$N$_3$O$_4$+H]$^+$: 462.56 found m/z 462.3 (100).

b) (R)-4-(dimethylammonio)-3-(3-methyl-3-(4-phenoxyphenyl)ureido)butanoate and (R)-3-(3-methyl-3-(4-phenoxyphenyl)ureido)-4-(trimethylammonio) butanoate (R)-benzyl 4-(dimethylamino)-3-(3-methyl-3-(4-phenoxyphenyl)ureido)butanoate (129 mg, 0.28 mmol) in DCM (6 mL) was treated with MeI (0.20 mL, 2.1 mmol) and stirred at rt overnight. The reaction was evaporated to dryness, taken into EtOH (10 mL) and stirred with Pd (10% on Carbon, 50% H$_2$O, 44 mg, 0.02 mmol) under an atmosphere of H$_2$ (1 atm) for 1 d. The reaction flask was purged with N$_2$. H$_2$O (2.5 mL) and LiOH (73 mg, 3.1 mmol) were added and the mixture was stirred at rt overnight. The reaction was concentrated under reduced pressure then dissolved in H$_2$O (0.05% TFA)-MeCN-MeOH and purified by preparative HPLC followed by preparative TLC (silica gel, 70% MeOH/DCM). Two separate substances recovered from silica gel were filtered through Celite using MeOH as the eluent then concentrated under reduced pressure and filtered again through a plug of Celite using 5% MeOH in DCM.

The higher eluting fraction consisted of (R)-4-(dimethylammonio)-3-(3-methyl-3-(4-phenoxyphenyl)ureido)butanoate) which was isolated as a clear glass solid (15.2 mg, 15%), $^1$H NMR (400 MHz, CD$_3$OD) δ ppm 7.38 (t, J=7.83 Hz, 2 H), 7.28 (d, J=8.59 Hz, 2 H), 7.14 (t, J=7.33 Hz, 1 H), 7.03 (t, J=8.21 Hz, 4 H), 4.30 (br. s, 1 H), 3.23 (s, 3 H), 2.89-3.14 (m, 2 H), 2.78 (s, 6 H), 2.30-2.53 (m, 2 H). MS ESI [M+H]$^+$, calcd for [C$_{20}$H$_{25}$N$_3$O$_4$+H]$^+$: 372.44 found m/z 372.2 (100)

The lower eluting fraction consisted of (R)-3-(3-methyl-3-(4-phenoxyphenyl)ureido)-4-(trimethylammonio)butanoate also isolated as clear glassy solid (4.6 mg, 4.2%). $^1$H NMR (400 MHz, CD$_3$OD) δ ppm=7.39 (t, J=7.58 Hz, 2 H), 7.22-7.30 (m, 2 H), 7.15 (t, J=7.33 Hz, 1 H), 7.00-7.08 (m, 4 H), 4.57 (br. s, 1 H), 3.50-3.61 (m, 1 H), 3.37-3.47 (m, 1 H), 3.23 (s, 3 H), 3.18 (s, 9 H), 2.40 (m, 2 H). MS ESI [M+H]$^+$, calcd for [C$_{21}$H$_{27}$N$_3$O$_4$+H]$^+$: 386.46 found m/z 386.2 (100).

Example S35

(R)-3-(3-(3-(4-Fluorophenyl)-3-oxopropyl)-3-(4-phenoxyphenyl)ureido)-4-(trimethylammonio)butanoate

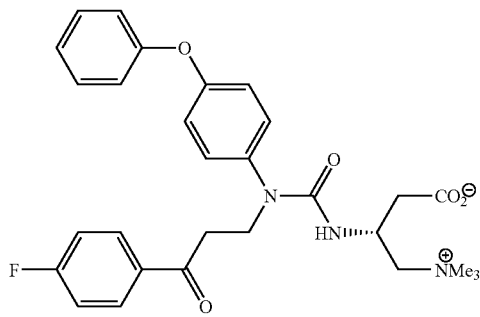

According to the methods described in example S34, 1-(4-fluorophenyl)-3-(4-phenoxyphenylamino)-propan-1-one is reacted with of triphosgene and (R)-benzyl 3-amino-4-(dimethylamino)butanoate to yield the title compound.

Example S36

(R)-3-(3-methyl-3-(4-octylphenyl)ureido)-4-(trimethylammonio)butanoate

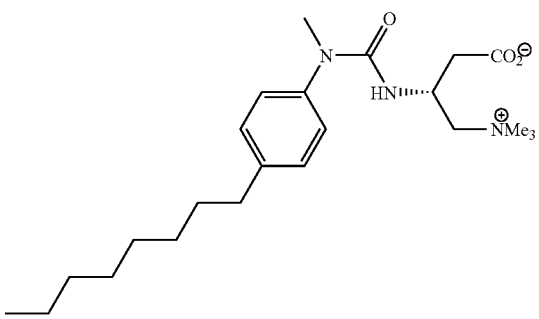

According to the method described in example S34, N-methyl-4-octylaniline is reacted with of triphosgene and (R)-benzyl 3-amino-4-(dimethylamino)butanoate to yield the title compound.

Example S37

(R)-3-(3-(Biphenyl-4-yl)-3-(2-methoxyethyl)ureido)-4-(trimethylammonio)-butanoate

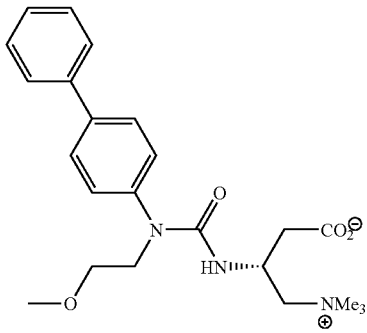

According to the method described in example S34, N-(2-methoxyethyl)biphenyl-4-amine is reacted with of triphosgene and (R)-benzyl 3-amino-4-(dimethylamino)butanoate to yield the title compound.

Example S38

(R)-3-(3-(3-Phenoxyphenyl)ureido)-4-(trimethylammonio)butanoate

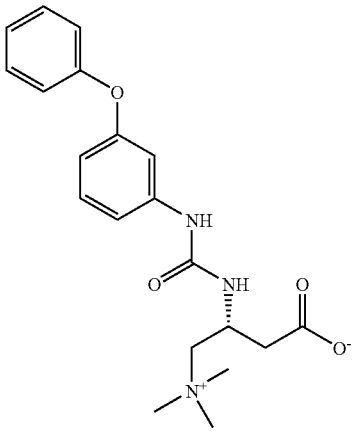 [SMILES: C[N+](C)(C)C[C@@H](CC(=O)[O-])NC(=O)Nc1cccc(Oc2ccccc2)c1]

According to the method described in example S11, aminocamitine (1.28 HBr salt, 68 mg, 0.31 mmol) was reacted with 1-isocyanato-3-phenoxybenzene to yield the title compound as a white solid (69 mg, 58%). $^1$H NMR (400 MHz, CD$_3$OD) 7.34 (t, J=7.96 Hz, 2 H), 7.17-7.23 (m, 2 H), 7.04-7.12 (m, 2 H), 6.95-7.00 (m, 1 H), 6.59 (dd, J=7.83, 2.02 Hz, 1 H), 4.57 (br. s, 1 H), 3.72 (dd, J=13.64, 9.09 Hz, 1 H), 3.46-3.56 (m, 1 H), 3.20 (s, 9 H), 2.42-2.56 (m, 2 H). MS ESI [M]$^+$, calcd for [C$_{20}$H$_{24}$N$_3$O$_4$+H]$^+$: 371.43 found m/z 371.7 (100).

Example S39

(R)-3-(3-(3-(phenylsulfonamido)phenyl)ureido)-4-(trimethylammonio)-butanoate

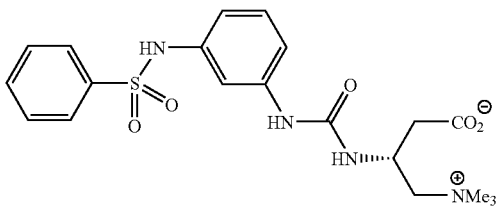

According to the method described in example S34, N-(4-(phenylamino)phenyl)-benzene-sulfonamide is reacted with of triphosgene and (R)-benzyl 3-amino-4-(dimethylamino)-butanoate to yield the title compound.

Example S40

(R)-3-(3-methyl-3-tetradecylureido)-4-(trimethylammonio)-butanoate

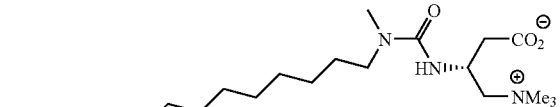

a) A solution of (R)-benzyl 3-amino-4-(dimethylamino)butanoate in anhydrous DCM (2 mL) is treated with triethylamine (2.5 equiv) and dropwise with triphosgene (0.33 equiv) at 0° C. The reaction mixture is stirred at ambient temperature for 4 h then treated with triethylamine (1.5 equiv) and N-methyltetradecan-1-amine (1.05 equiv). The reaction mixture is partitioned between saturated bicarbonate and methylene chloride. The organic layer is dried and concentrated under reduced pressure. The resulting residue is purified by silica gel chromatography to obtain (R)-benzyl 4-(dimethylamino)-3-(3-methyl-3-tetradecylureido)butanoate.

b) The product of the previous step is treated with and methyl iodide to yield (R)-4-(benzyloxy)-N,N,N-trimethyl-2-(3-methyl-3-tetradecylureido)-4-oxobutan-1-aminium iodide c) The product of the previous step is treated with methanol and 10% palladium on carbon under an atmosphere of hydrogen to obtain the title compound

Example S41

(R)-3-(3-Dodecyl-3-phenylureido)-4-(trimethylammonio)butanoate

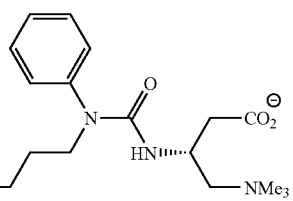

According to the method described in example S40a, (R)-benzyl 3-amino-4-(dimethylamino)butanoate is reacted with of triphosgene and N-dodecylaniline to yield (R)-benzyl 4-(dimethylamino)-3-(3-dodecyl-3-phenylureido)butanoate. According to the methods described in example S40b,c the preceding benzyl ester is converted to the title compound.

Example S42

(R)-3-(5-phenethylfuran-2-carboxamido)-4-(trimethylammonio)-butanoate

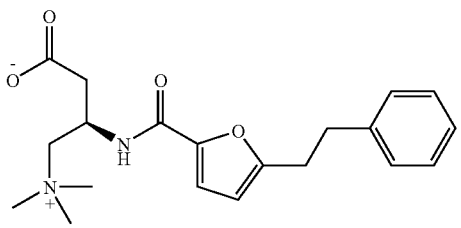

According to the method described in example S1, R-aminocarnitine (20 mg, 0.12 mmol) was reacted with 2,5-dioxopyrrolidin-1-yl 5-phenethylfuran-2-carboxylate, prepared as described in preparation 1, (44 mg, 0.14 mmol) to give the title compound (32 mg, 74%) as a white solid. NMR (300 MHz, CD$_3$OD) δ 7.29-7.25 (m, 2H), 7.25-7.15 (m, 3H), 7.07-7.04 (m, 1H), 6.23-6.18 (m, 1H), 4.85-4.77 (m, 1H), 3.77-3.60 (m, 2H), 3.21 (s, 9H), 3.00 (s, 4H), 2.63-2.48 (m, 2H); MS ESI 359.2 [M+H]$^+$, calcd for [C$_{20}$H$_{26}$N$_2$O$_4$+H]$^+$ 359.2

Example S43

(R)-3-(5-(phenylethynyl)thiophene-2-carboxamido)-4-(trimethylammonio)-butanoate

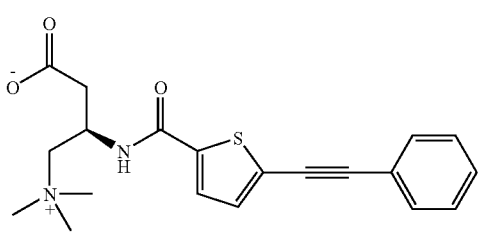

According to the method described in example S1, R-aminocarnitine (20 mg, 0.12 mmol) was reacted with 2,5-dioxopyrrolidin-1-yl 5-(phenylethynyl)thiophene-2-carboxylate (54 mg, 0.16 mmol), prepared as described in preparation 1, to give the title compound as a beige solid (31 mg, 70%). $^1$H NMR (400 MHz, CD$_3$OD) δ 7.65 (d, 1H, J=3.9 Hz), 7.54-7.51 (m, 2H), 7.41-7.39 (m, 3H), 7.31 (d, 1H, J=4.0 Hz), 4.90-4.80 (m, 1H), 3.68-3.58 (m, 2H), 3.23 (s, 9H), 2.61-2.50 (m, 2H); MS ESI 371.1 [M+H]$^+$, calcd for [C$_{20}$H$_{22}$N$_2$O$_3$S+H]$^+$ 371.1

Example S44

(R)-3-(2,2'-bithiophene-5-carboxamido)-4-(trimethylammonio)butanoate

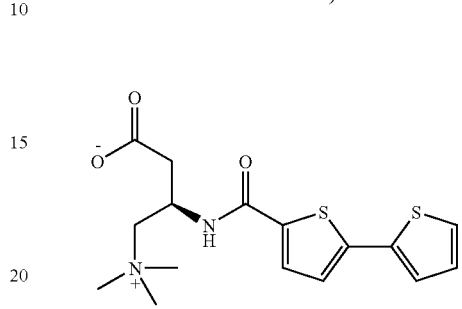

According to the method described in example S2, R-aminocarnitine was reacted with 2,5-dioxopyrrolidin-1-yl 2,2'-bithiophene-5-carboxylate, prepared as described in preparation 4, to give the title compound as a white powder (7 mg, 21%). $^1$H NMR (400 MHz, D$_2$O) δ 7.48 (d, 1H, J=4 Hz), 7.35 (dd, 1H, J=5 Hz, 0.8 Hz), 7.28 (dd, 1H, J=3.6 Hz, 0.8 Hz), 7.14 (d, 1H, J=4 Hz), 7.00 (dd, 1H, J=5 Hz, 3.6 Hz), 4.83 (m, 1H), 3.65-3.60 (m, 1H), 3.47 (d, 1H, J=14 Hz), 3.09 (s, 9H), 2.54 (d, 2H, J=7.2 Hz); MS ESI 353.1 [M+H]$^+$, calcd for [C$_{16}$H$_{20}$N$_2$O$_3$S$_2$+H]$^+$ 353.10.

Example S45

(R)-3-(5-phenethylthiophene-2-carboxamido)-4-(trimethylammonio)-butanoate

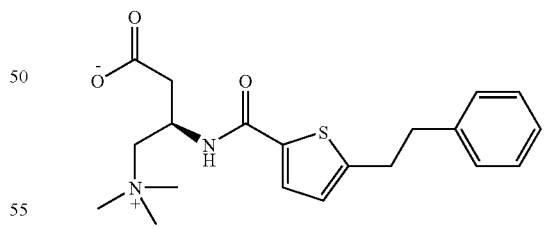

(R)-3-(5-(phenylethynyl)thiophene-2-carboxamido)-4-(trimethylammonio)-butanoate (15 mg, 0.04 mmol) was dissolved into MeOH (3 mL). The solution was purged with nitrogen and 10% palladium on carbon (5 mg) was added. The vessel was purged with hydrogen and stirred for 1 h. The mixture was filtered through celite and solvents removed in vacuo to give the title compound (13 mg, 88%) as a white solid. $^1$H NMR (400 MHz, CD$_3$OD) δ 7.51 (d, 1H, J=3.9 Hz), 7.27-7.23 (m, 2H), 7.19-7.14 (m, 3H), 6.81 (d, 1H, J=3.8 Hz), 4.85-4.77 (m, 1H), 3.72-3.58 (m, 2H), 3.22 (s, 9H), 3.16 (t, 2H, J=7.8 Hz), 2.98 (t, 2H, J=7.4 Hz), 2.59-2.48 (m, 2H); MS ESI 375.2 [M+H]⁺, calcd for [$C_{20}H_{26}N_2O_3S$+H]⁺ 375.2

Example S46

(R)-3-(3-phenethylbenzamido)-4-(trimethylammonio)butanoate

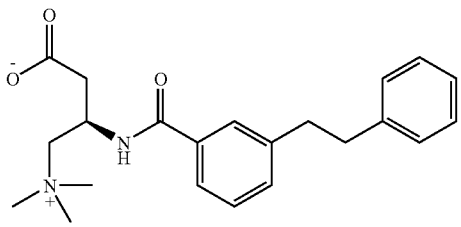

According to the method described in example S64, (R)-3-(3-(phenylethynyl)-benzamido)-4-(trimethylammonio)butanoate was treated with 10% Pd/C under hydrogen and the product purified to give the title compound as a white powder (7.2 mg, 89%). ¹H NMR (400 MHz, D₂O) δ 7.41 (d, 1H, J=8 Hz), 7.34 (s, 1H), 7.07 (t, 1H, J=8 Hz), 7.02-6.90 (m, 4H), 6.86 (d, 2H, J=8 Hz), 4.76 (m, 1H), 3.60-3.54 (m, 1H), 3.41 (d, 1H, J=13.2 Hz), 3.00 (s, 9H), 2.61 (br, 4H), 2.41-2.28 (m, 2H); MS ESI 369.2 [M+H]⁺, calcd for [$C_{22}H_{28}N_2O_3$+H]⁺ 369.22.

Example S47

(R)-3-(5-(benzyloxymethyl)furan-2-carboxamido)-4-(trimethylammonio)-butanoate

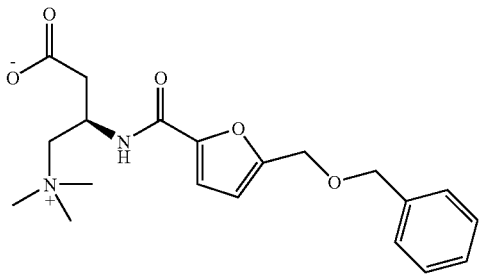

According to the method described in example S1, R-aminocarnitine is reacted with 2,5-dioxopyrrolidin-1-yl 5-(benzyloxymethyl)furan-2-carboxylic acid, prepared as described in preparation 1, to give the title compound.

Example S48

(R)-3-(3-(phenylethynyl)benzamido)-4-(trimethylammonio)butanoate

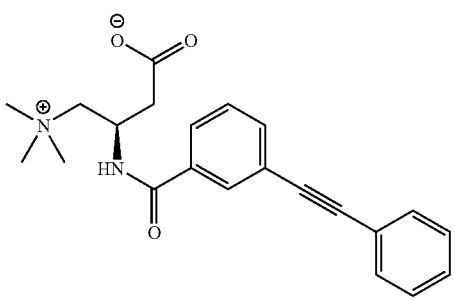 [SMILES: C[N+](C)(C)C[C@@H](CC(=O)[O-])NC(=O)c1cccc(C#Cc2ccccc2)c1]

According to the method described in example S2, R-aminocarnitine was reacted with 2,5-dioxopyrrolidin-1-yl-3-(phenylethynyl)benzoate, prepared as described in preparation 4, to give the title compound as a white powder (15 mg, 43%). ¹H NMR (400 MHz, D₂O) δ 7.64 (s, 1H), 7.45 (d, 1H, J=7.2 Hz), 7.10 (m, 3H), 6.99 (t, 1H, J=7.6 Hz), 6.90 (br, 3H), 4.70 (m, 1H), 3.61-3.55 (m, 1H), 3.39 (d, 1H, J=12.8 Hz), 2.98 (s, 9H), 2.41-2.28 (m, 2H); MS ESI 365.2 [M+H]⁺, calcd for [$C_{22}H_{24}N_2O_3$+H]⁺ 365.19.

Example S49

(R)-3-carboxy-N,N,N-trimethyl-2-(4-methyloxazole-5-carboxamido)-propan-1-aminium trifluoroacetate

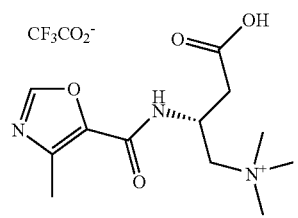 [SMILES: "CF3CO2-" ; Cc1ncoc1C(=O)N[C@H](CC(=O)O)C[N+](C)(C)C]

According to the method described in example S2, R-aminocarnitine is reacted with 2,5-dioxopyrrolidin-1-yl 4-methyloxazole-5-carboxylate, prepared as described in preparation 4, and purified by HPLC to give the title compound (1.4 mg, 6%).

¹H NMR (400 MHz, D₂O) δ 8.05 (s, 1H), 4.90-4.80 (m, 1H), 3.67-3.50 (m, 2H), 3.09 (s, 9H), 2.73-2.66 (m, 2H), 2.31 (s, 3H); MS ESI 270.1 [M+H]⁺, calcd for [$C_{12}H_{20}N_3O_4$H]⁺ 270.14

Example S50

(R)-3-(6-phenoxynicotinamido)-4-(trimethylammonio)butanoate

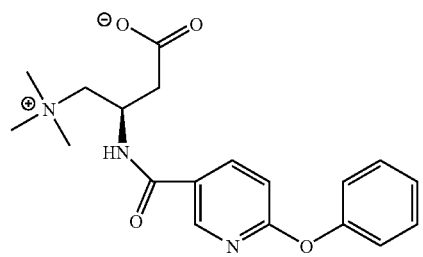 [SMILES: C[N+](C)(C)C[C@@H](CC(=O)[O-])NC(=O)c1ccc(Oc2ccccc2)nc1]

According to the method described in example S2, R-aminocarnitine was reacted with 2,5-dioxopyrrolidin-1-yl 6-phenoxynicotinate, prepared as described in preparation 4, to give the title compound as a white powder (13 mg, 39%). ¹H NMR (400 MHz, D₂O) δ 8.34 (s, 1H), 8.07 (m, 1H), 7.39 (t, 2H, J=7.6 Hz), 7.24 (m, 1H), 7.09 (d, 2H, J=7.6 Hz), 6.98 (m, 1H), 4.84 (m, 1H), 3.64-3.46 (m, 2H), 3.10 (s, 9H), 2.46 (d, 2H, J=6.4 Hz); MS ESI 358.2 [M+H]⁺, calcd for [$C_{19}H_{23}N_3O_4$H]⁺ 358.17.

Example S51

(R)-3-(4-methyl-2-(pyrazin-2-yl)thiazole-5-carboxamido)-4-(trimethyl-ammonio)butanoate

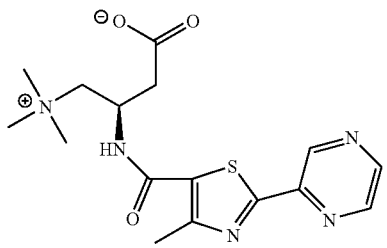 [SMILES: Cc1nc(-c2cnccn2)sc1C(=O)N[C@H](CC(=O)[O-])C[N+](C)(C)C]

According to the method described in example S2, R-aminocarnitine was reacted with 2,5-dioxopyrrolidin-1-yl 4-methyl-2-(pyrazin-2-yl)thiazole-5-carboxylate, prepared as described in preparation 4, to give the title compound as a white powder (3 mg, 8%). $^1$H NMR (400 MHz, D$_2$O) δ 9.13 (d, 1H, J=1.2 Hz), 8.00 (d, 1H, J=2.8 Hz), 8.57 (m, 1H), 4.85-4.80 (m, 1H), 3.66-3.61 (m, 1H), 3.48 (d, 1H, J=12.8 Hz), 3.13 (s, 9H), 2.55 (s, 3H), 2.50 (d, 2H, J=6.8 Hz); MS ESI 364.1 [M+H]$^+$, calcd for [C$_{16}$H$_{21}$N$_5$O$_3$S+H]$^+$ 364.14.

Example S52

(R)-3-(6-(2,2,2-trifluoroethoxy)nicotinamido)-4-(trimethylammonio)butanoate

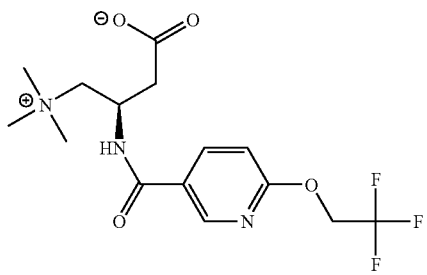 [SMILES: C[N+](C)(C)C[C@@H](CC(=O)[O-])NC(=O)c1ccc(OCC(F)(F)F)nc1]

According to the method described in example S2, R-aminocarnitine was reacted with 2,5-dioxopyrrolidin-1-yl 6-(2,2,2-trifluoroethoxy)nicotinate, prepared as described in preparation 4, to give the title compound as a white powder (3 mg, 8%). $^1$H NMR (400 MHz, D$_2$O) δ 8.43 (d, 1H, J=2.4 Hz), 8.0 (dd, 1H, J=2.4, 8.8 Hz), 6.93 (d, 1H, J=8.8 Hz), 4.86 (m, 1H), 4.78 (q, 2H, J=8.4 Hz), 3.65-3.60 (m, 1H), 3.48 (dd, 1H, J=1.2, 14 Hz), 3.10 (s, 9H), 2.49 (d, 2H, J=7.2 Hz); MS ESI 364.1 [M+H]$^+$, calcd for [C$_{15}$H$_{20}$F$_3$N$_3$O$_4$+H]$^+$ 364.15.

Example S53

(R)-3-(4-acetamidobenzamido)-4-(trimethylammonio)butanoate

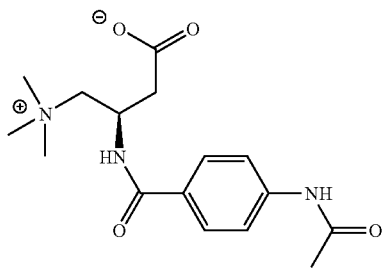 [SMILES: CC(=O)Nc1ccc(C(=O)N[C@H](CC(=O)[O-])C[N+](C)(C)C)cc1]

According to the method described in example S2, R-aminocarnitine was reacted with 2,5-dioxopyrrolidin-1-yl 4-acetamidobenzoate, prepared as described in preparation 4, to give the title compound as a white powder (5 mg, 16%). $^1$H NMR (400 MHz, D$_2$O) δ 7.64 (d, 2H, J=8.8 Hz), 7.44 (d, 2H, J=8.8 Hz), 4.87-4.81 (m, 1H), 3.64-3.58 (m, 1H), 3.47 (d, 1H, J=13.6 Hz), 3.10 (s, 9H), 2.46 (d, 2H, J=6.8 Hz), 2.05 (s, 3H); MS ESI 322.1 [M+H]$^+$, calcd for [C$_{16}$H$_{23}$N$_3$O$_4$+H]$^+$ 322.18.

Example S54

(R)-3-(3-methyl-1-propyl-1H-pyrazole-4-carboxamido)-4-(trimethyl-ammonio)butanoate

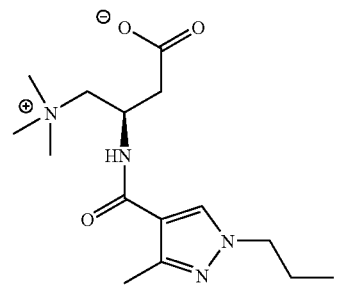 [SMILES: CCCn1cc(C(=O)N[C@H](CC(=O)[O-])C[N+](C)(C)C)c(C)n1]

According to the method described in example S2, R-aminocarnitine was reacted with 2,5-dioxopyrrolidin-1-yl 3-methyl-1-propyl-1H-pyrazole-4-carboxylate, prepared as described in preparation 4, to give the title compound as a white powder (16 mg, 24%). $^1$H NMR (400 MHz, D$_2$O) δ 7.90 (s, 1H), 4.77 (m, 1H), 3.93 (t, 2H, J=6.8 Hz), 3.61-3.56 (m, 1H), 3.44 (d, 1H, J=13.6 Hz), 3.09 (s, 9H), 2.44 (d, 2H, J=5.6 Hz), 2.26 (s, 3H), 1.71-1.64 (m, 2H), 0.70 (t, 3H, J=7.6 Hz); MS ESI 311.1 [M+H]$^+$, calcd for [C$_{15}$H$_{26}$N$_4$O$_3$+H]$^+$ 311.21.

Example S55

(R)-3-(5-((2-methoxy-4-propylphenoxy)methyl)furan-2-carboxamido)-4-(trimethylammonio)butanoate

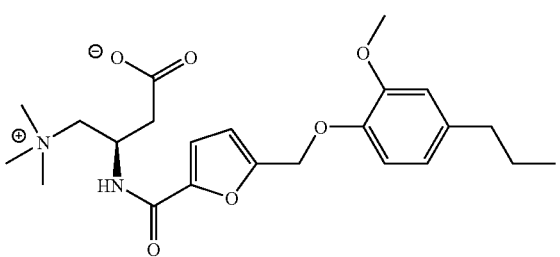 [SMILES: CCCc1ccc(OCc2ccc(C(=O)N[C@H](CC(=O)[O-])C[N+](C)(C)C)o2)c(OC)c1]

According to the method described in example S2, R-aminocarnitine was reacted with 2,5-dioxopyrrolidin-1-yl 5-((2-methoxy-4-propylphenoxy)methyl)furan-2-carboxylate, prepared as described in preparation 4, to give the title compound as a white powder (17 mg, 32%). $^1$H NMR (400 MHz, D$_2$O) δ 6.88 (d, 1H, J=3.6 Hz), 6.60 (d, 1H, J=8 Hz), 6.46 (s, 1H), 6.32 (d, 1H, J=8 Hz), 6.21 (d, 1H, J=3.6 Hz), 4.73 (br, 3H), 3.60-3.41 (m, 5H), 3.03 (m, 9H), 2.47-2.33 (m, 2H), 2.14 (t, 2H, J=7.2 Hz), 1.29-1.20 (m, 2H), 0.60 (t, 3H, J=7.2 Hz); MS ESI 433.3 [M+H]$^+$, calcd for [C$_{23}$H$_{32}$N$_2$O$_6$+H]$^+$ 433.23.

Example S56

(R)-3-(5-(benzylthiomethyl)furan-2-carboxamido)-4-(trimethylammonio)-butanoate

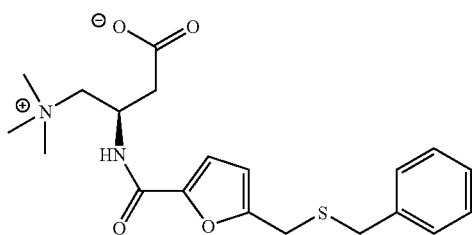 [SMILES: C[N+](C)(C)C[C@@H](CC(=O)[O-])NC(=O)c1ccc(CSCc2ccccc2)o1]

According to the method described in example S2, R-aminocarnitine was reacted with 2,5-dioxopyrrolidin-1-yl 5-(benzylthiomethyl)furan-2-carboxylate, prepared as described in preparation 4, to give the title compound as a white powder (50 mg, 89%). $^1$H NMR (400 MHz, D$_2$O) δ 7.20-7.13 (m, 5H), 6.94 (d, 1H, J=3.2 Hz), 6.28 (d, 1H, J=3.2 Hz), 4.77 (m, 1H), 3.70-3.44 (m, 6H), 3.07 (s, 9H), 2.50 (d, 2H, J=6.4 Hz); MS ESI 391.2 [M+H]$^+$, calcd for [C$_{20}$H$_{26}$N$_2$O$_4$S+H]$^+$ 391.17.

Example S57

(R)-3-(3-(1H-pyrazol-3-yl)benzamido)-4-(trimethylammonio)butanoate trifluoroacetate

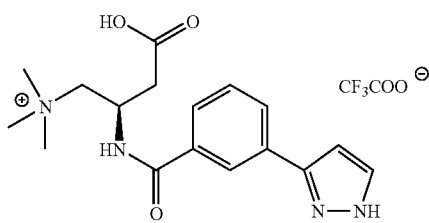 [SMILES: C[N+](C)(C)C[C@@H](CC(=O)O)NC(=O)c1cccc(-c2cc[nH]n2)c1 ; "CF3COO"]

According to the method described in example S2, R-aminocarnitine was reacted with 2,5-dioxopyrrolidin-1-yl 3-(1H-pyrazol-3-yl)benzoate, prepared as described in preparation 4. The crude product was purified by preparatory HPLC to give the title compound as a white powder (1 mg, 3%). $^1$H NMR (400 MHz, D$_2$O) δ 8.02 (s, 1H), 7.90 (d, 1H, J=8 Hz), 7.76 (d, 1H, J=2.4 Hz), 7.65 (d, 1H, J=8 Hz), 7.51 (t, 1H, J=8 Hz), 6.76 (d, 1H, J=2.4 Hz), 4.99-4.93 (m, 1H), 3.73-3.67 (m, 1H), 3.56 (d, 1H, J=12 Hz), 3.14 (s, 9H), 2.82-2.70 (m, 2H); MS ESI 331.1 [M+H]$^+$, calcd for [C$_{17}$H$_{22}$N$_4$O$_3$+H]$^+$ 331.18.

Example S58

(R)-3-(5-((naphthalen-1-yloxy)methyl)furan-2-carboxamido)-4-(trimethyl-ammonio)butanoate

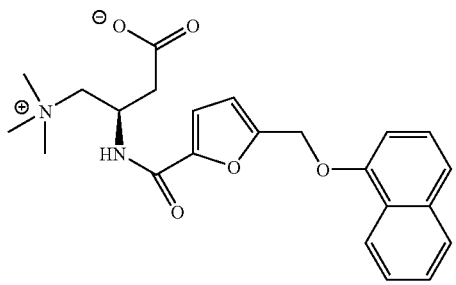 [SMILES: C[N+](C)(C)C[C@@H](CC(=O)[O-])NC(=O)c1ccc(COc2cccc3ccccc23)o1]

According to the method described in example S2, R-aminocarnitine was reacted with 2,5-dioxopyrrolidin-1-yl 5-((naphthalen-1-yloxy)methyl)furan-2-carboxylate, prepared as described in preparation 4, to give the title compound as a white powder (37 mg, 67%). $^1$H NMR (400 MHz, D$_2$O) δ 7.58 (m, 1H), 6.90 (m, 1H), 6.72 (d, 1H, J=2.8 Hz), 6.64 (br, 4H), 6.15 (m, 1H), 5.73 (d, 1H, J=2.8 Hz), 4.65 (m, 1H), 4.37 (s, 2H), 3.42-3.39 (m, 2H), 2.84 (s, 9H), 2.35-2.20 (m, 2H); MS ESI 411.2 [M+H]$^+$, calcd for [C$_{23}$H$_{26}$N$_2$O$_5$+H]$^+$ 411.19.

Example S59

(R)-3-(5-(morpholinomethyl)furan-2-carboxamido)-4-(trimethylammonio)-butanoate

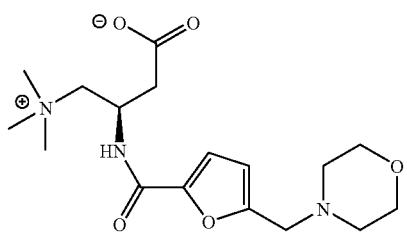 [SMILES: C[N+](C)(C)C[C@@H](CC(=O)[O-])NC(=O)c1ccc(CN2CCOCC2)o1]

According to the method described in example S2, R-aminocarnitine was reacted with 2,5-dioxopyrrolidin-1-yl 5-(morpholinomethyl)furan-2-carboxylate, prepared as described in preparation 4, to give the title compound as a white powder (23 mg, 58%). $^1$H NMR (400 MHz, D$_2$O) δ 7.05 (d, 1H, J=3.6 Hz), 6.43 (d, 1H, J=3.6 Hz), 4.83-4.77 (m, 1H), 3.63-3.58 (m, 5H), 3.54 (s, 2H), 3.46 (d, 1H, J=14 Hz), 3.09 (s, 9H), 2.45 (br, 6H); MS ESI 354.2 [M+H]$^+$, calcd for [C$_{17}$H$_{27}$N$_3$O$_5$+H]$^+$ 354.20.

Example S60

(R)-3-(5-((4-tert-butylphenoxy)methyl)furan-2-carboxamido)-4-(trimethyl-ammonio)butanoate

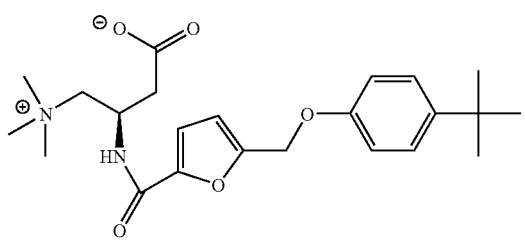 [SMILES: CC(C)(C)c1ccc(OCc2ccc(C(=O)N[C@H](CC(=O)[O-])C[N+](C)(C)C)o2)cc1]

According to the method described in example S2, R-aminocarnitine was reacted with 2,5-dioxopyrrolidin-1-yl 5-((4-tert-butylphenoxy)methyl)furan-2-carboxylate, prepared as described in preparation 4, to give the title compound as a white powder (7 mg, 12%). $^1$H NMR (400 MHz, D$_2$O) δ 6.92 (m, 3H), 6.62 (d, 2H, J=8 Hz), 6.18 (s, 1H), 4.71 (m, 3H), 3.60 (m, 1H), 3.42 (d, 1H, J=13.2 Hz), 3.02 (s, 9H), 2.44-2.31 (m, 2H), 0.88 (s, 9H); MS ESI 417.3 [M+H]$^+$, calcd for [C$_{23}$H$_{32}$N$_2$O$_5$+H]$^+$ 417.24.

Example S61

(R)-3-(5-(benzylsulfonylmethyl)furan-2-carboxamido)-4-(trimethyl-ammonio)butanoate 2,2,2-trifluoroacetate

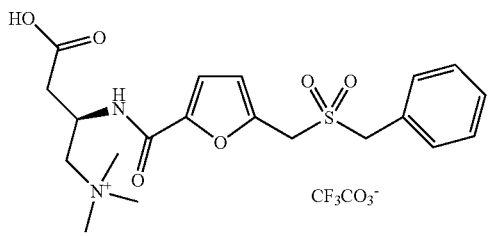

(R)-3-(5-(benzylthiomethyl)furan-2-carboxamido)-4-(trimethyl-ammonio)butanoate (20 mg, 0.05 mmol) was added into 1:1:1 DCM/H$_2$O/$^t$BuOH (1.5 mL). The mixture was treated with oxone (65 mg, 0.1 mmol) and stirred overnight at room temperature. Solvents were removed under vacuum. The residue was purified by preparatory HPLC to give the title compound as a white powder (7 mg, 24%). $^1$H NMR (400 MHz, D$_2$O) δ 7.30 (m, 5H), 7.10 (s, 1H), 6.59 (s, 1H), 4.84 (m, 1H), 4.62 (s, 2H), 4.48 (s, 2H), 3.67-3.61 (m, 1H), 3.49 (d, 1H, J=14 Hz), 3.10 (s, 9H), 2.76-2.63 (m, 2H); MS ESI 423.2 [M+H]$^+$, calcd for [C$_{20}$H$_{26}$N$_2$O$_6$S+H]$^+$ 423.16.

Example S62

(R)-3-(4-(phenylethynyl)benzamido)-4-(trimethylammonio)butanoate 2,2,2-trifluoroacetate

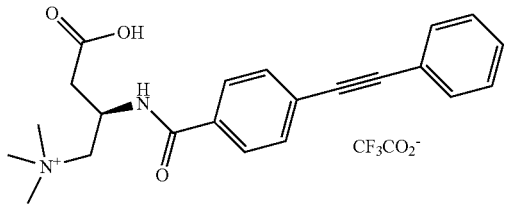

According to the method described in example S2, R-aminocarnitine was reacted with 2,5-dioxopyrrolidin-1-yl 4-(phenylethynyl)benzoate, prepared as described in preparation 4. The crude product was purified by preparatory HPLC to give the title compound as a white powder (30 mg, 38%). $^1$H NMR (400 MHz, D$_2$O) δ 7.60 (d, 2H, J=7.2 Hz), 7.40 (d, 2H, J=7.2 Hz), 7.34 (m, 2H), 7.17 (m, 3H), 4.88 (m, 1H), 3.71-3.50 (m, 2H), 3.09 (s, 9H), 2.74-2.59 (m, 2H); MS ESI 365.2 [M+H]$^+$, calcd for [C$_{22}$H$_{24}$N$_2$O$_3$+H]$^+$ 365.19.

Example S63

(R)-3-(4-(decyloxy)benzamido)-4-(trimethylammonio)butanoate 2,2,2-trifluoroacetate

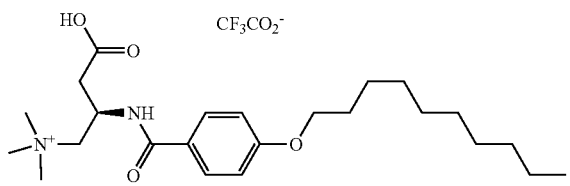 [SMILES: CCCCCCCCCCOc1ccc(C(=O)N[C@H](CC(=O)O)C[N+](C)(C)C)cc1 ; "CF3CO2-"]

According to the method described in example S2, R-aminocarnitine was reacted with 2,5-dioxopyrrolidin-1-yl 4-(decyloxy)benzoate, prepared as described in preparation 4, to give crude product. Purification by HPLC gave the title compound as a white powder (571 mg, 76%). $^1$H NMR (400 MHz, D$_2$O) δ 7.58 (d, 2H, J=8 Hz), 6.55 (d, 2H, J=8 Hz), 4.76 (m, 1H), 3.67-3.40 (m, 4H), 2.99 (s, 9H), 2.48-2.39 (m, 2H), 1.41 (br, 2H), 1.10 (br, 14H), 0.74 (t, 3H, J=6.4 Hz); MS ESI 421.3 [M+H]$^+$, calcd for [C$_{24}$H$_{40}$N$_2$O$_4$+H]$^+$ 421.31.

Example S64

(R)-3-(4-phenethylbenzamido)-4-(trimethylammonio)butanoate

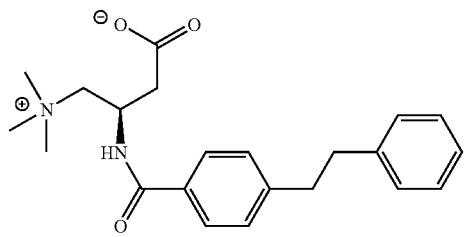 [SMILES: C[N+](C)(C)C[C@@H](CC(=O)[O-])NC(=O)c1ccc(CCc2ccccc2)cc1]

(R)-3-(4-(phenylethynyl)benzamido)-4-(trimethylammonio)butanoate (10 mg, 0.027 mmol) was dissolved into MeOH (1 mL). The solution was treated with 10% Pd/C (0.5 mg). The mixture was stirred under hydrogen at room temperature overnight, and filtered through celite. MeOH was removed under vacuum. The residue was loaded onto a silica gel column and eluted with 4:1 MeOH/DCM to give the title compound as a white powder (2 mg, 22%). $^1$H NMR (400 MHz, D$_2$O) δ 7.54 (d, 2H, J=8 Hz), 7.22-7.18 (m, 4H), 7.13-7.10 (m, 3H), 4.87-4.81 (m, 1H), 3.65-3.59 (m, 1H), 3.70 (d, 1H, J=13.2 Hz), 3.10 (s, 9H), 2.92-2.85 (m, 4H), 2.46 (d, 2H, J=6.8 Hz); MS ESI 369.2 [M+H]$^+$, calcd for [C$_{22}$H$_{28}$N$_2$O$_3$+H]$^+$ 369.22.

Example S65

(R)-3-(3-methyl-5-(phenoxymethyl)furan-2-carboxamido)-4-(trimethyl-ammonio)butanoate

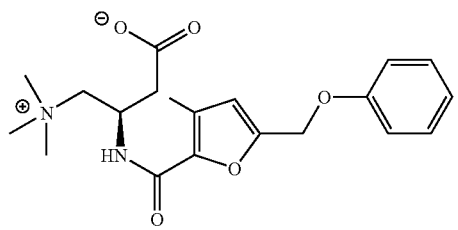 [SMILES: Cc1cc(COc2ccccc2)oc1C(=O)N[C@H](CC(=O)[O-])C[N+](C)(C)C]

According to the method described in example S2, R-aminocarnitine was reacted with 2,5-dioxopyrrolidin-1-yl 3-methyl-5-(phenoxymethyl)furan-2-carboxylate, prepared as described in preparation 4, to give the title compound as a white powder (24 mg, 68%). $^1$H NMR (400 MHz, D$_2$O) δ 7.29-7.25 (m, 2H), 6.99-6.94 (m, 3H), 6.37 (s, 1H), 5.0 (s, 2H), 4.78 (m, 1H), 3.63-3.57 (m, 1H), 3.45 (d, 1H, J=14 Hz), 3.07 (s, 9H), 2.44 (d, 2H, J=6.4 Hz), 2.18 (s, 3H); MS ESI 375.2 [M+H]$^+$, calcd for [C$_{20}$H$_{26}$N$_2$O$_5$+H]$^+$ 375.19.

Example S66

(R)-3-(4-decylbenzamido)-4-(trimethylammonio)butanoate

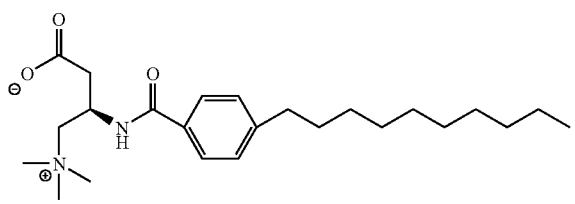 [SMILES: CCCCCCCCCCc1ccc(C(=O)N[C@H](CC(=O)[O-])C[N+](C)(C)C)cc1]

According to the method described in example S2, R-aminocarnitine was reacted with 2,5-dioxopyrrolidin-1-yl 4-decylbenzoate, prepared as described in preparation 4, to give the title compound as a white powder (29 mg, 76%). $^1$H NMR (400 MHz, D$_2$O) δ 7.64 (d, 2H, J=7.6 Hz), 6.86 (d, 2H, J=7.6 Hz), 4.75 (m, 1H), 3.8-3.77 (m, 1H), 3.37 (d, 1H, J=12.8 Hz), 2.97 (s, 9H), 2.33-2.17 (m, 4H), 1.23 (m, 2H), 1.10 (br, 14H), 0.73 (t, 3H, J=6 Hz); MS ESI 405.2 [M+H]$^+$, calcd for [C$_{24}$H$_{40}$N$_2$O$_3$+H]$^+$ 405.30.

Example S67

(R)-3-(3-(decyloxy)benzamido)-4-(trimethylammonio)butanoate

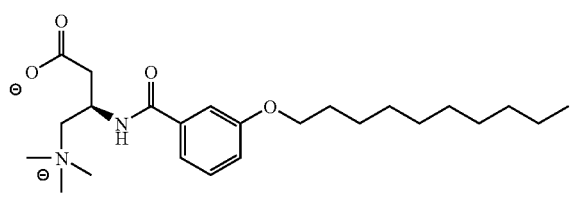

According to the method described in example S2, R-aminocarnitine was reacted with 2,5-dioxopyrrolidin-1-yl 3-(decyloxy)benzoate, prepared as described in preparation 4, to give the title compound as a white powder (24 mg, 60%). $^1$H NMR (400 MHz, D$_2$O) δ 7.16 (m, 2H), 6.95 (m, 1H), 6.50 (m, 1H), 3.64-3.57 (m, 3H), 4.69 (m, 1H), 3.37 (d, 1H, J=12 Hz), 2.97 (s, 9H), 2.35-2.18 (m, 2H), 1.42 (br, 2H), 1.12 (br, 14H), 0.77 (t, 3H, J=6.4 Hz); MS ESI 421.3 [M+H]$^+$, calcd for [C$_{24}$H$_{40}$N$_2$O$_4$+H]$^+$ 421.31.

Example S68

(R)-3-(5-((4-ethoxyphenoxy)methyl)furan-2-carboxamido)-4-(trimethyl-ammonio)butanoate

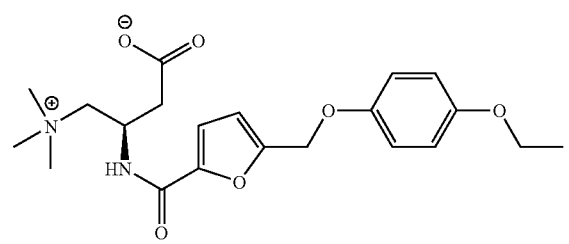 [SMILES: CCOc1ccc(OCc2ccc(C(=O)N[C@H](CC(=O)[O-])C[N+](C)(C)C)o2)cc1]

According to the method described in example S2, R-aminocarnitine was reacted with 2,5-dioxopyrrolidin-1-yl 5-((4-ethoxyphenoxy)methyl)furan-2-carboxylate, prepared as described in preparation 4, to give the title compound as a white powder (13 mg, 28%). $^1$H NMR (400 MHz, D$_2$O) δ 7.06 (d, 1H, J=3.6 Hz), 6.91 (d, 2H, J=9.2 Hz), 6.85 (d, 2H, 9.2 Hz), 6.55 (d, 1H, J=3.6 Hz), 5.02 (s, 2H), 4.83-4.76 (m, 1H), 3.96 (q, 2H, J=6.8 Hz), 3.61 (m, 1H), 3.46 (d, 1H, J=13.6 Hz), 3.10 (m, 9H), 2.45 (d, 2H, J=6.8 Hz), 1.24 (t, 3H, J=6.8 Hz); MS ESI 405.2 [M+H]$^+$, calcd for [C$_{21}$H$_{28}$N$_2$O$_6$+H]$^+$ 405.20.

Example S69

(R)-3-(2,2-difluoro-2-phenylacetamido)-4-(trimethylammonio)butanoate

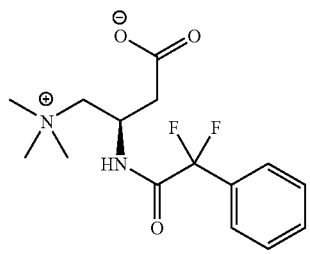 [SMILES: C[N+](C)(C)C[C@@H](CC(=O)[O-])NC(=O)C(F)(F)c1ccccc1]

According to the method described in example S2, R-aminocarnitine was reacted with 2,5-dioxopyrrolidin-1-yl 2,2-difluoro-2-phenylacetate, prepared as described in preparation 4, to give the title compound as a white powder (8 mg, 27%). $^1$H NMR (400 MHz, D$_2$O) δ 7.53-7.42 (m, 5H), 4.65 (m, 1H), 3.56-3.50 (m, 1H), 3.42 (d, 1H, J=13.6 Hz), 2.4 (s, 9H), 2.46-2.36 (m, 2H); MS ESI 315.1 [M+H]$^+$, calcd for [C$_{15}$H$_{20}$F$_2$N$_2$O$_3$+H]$^+$ 315.15.

Example S70

(R)-3-(5-(m-tolyloxymethyl)furan-2-carboxamido)-4-(trimethylammonio)-butanoate

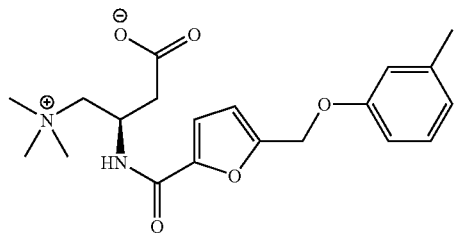

According to the method described in example S2, R-aminocarnitine was reacted with 2,5-dioxopyrrolidin-1-yl 5-(m-tolyloxymethyl)furan-2-carboxylate, prepared as described in preparation 4, to give the title compound as a white powder (16 mg, 45%). $^1$H NMR (400 MHz, D$_2$O) δ 7.15 (t, 1H, J=8 Hz), 7.06 (d, 1H, J=3 Hz), 6.83-6.76 (m, 3H), 6.57 (d, 1H, J=3 Hz), 5.05 (s, 2H), 4.81-4.76 (m, 1H), 3.63-3.57 (m, 1H), 3.46 (d, 1H, J=13.6 Hz), 3.08 (s, 9H), 2.45 (d, 2H, J=6.8 Hz), 2.20 (s, 3H); MS ESI 375.2 [M+H]$^+$, calcd for [C$_{20}$H$_{26}$N$_2$O$_5$+H]$^+$ 375.19.

Example S71

(R)-3-(5-((4-chlorophenylthio)methyl)furan-2-carboxamido)-4-(trimethyl-ammonio)butanoate

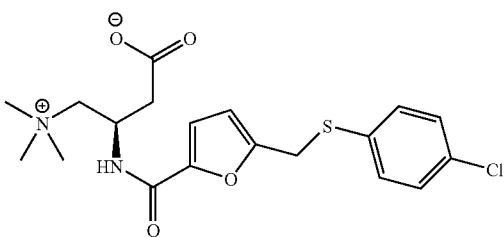 [SMILES: C[N+](C)(C)C[C@@H](CC(=O)[O-])NC(=O)c1ccc(CSc2ccc(Cl)cc2)o1]

According to the method described in example S2, R-aminocarnitine was reacted with 2,5-dioxopyrrolidin-1-yl 5-((4-chlorophenylthio)methyl)furan-2-carboxylate, prepared as described in preparation 4, to give the title compound as a white powder (19 mg, 50%). $^1$H NMR (400 MHz, D$_2$O) δ 6.93 (br, 4H), 6.81 (d, 1H, J=3.2 Hz), 5.92 (d, 1H, J=3.2 Hz), 4.73 (m, 1H), 3.90 (s, 2H), 3.65-3.59 (m, 1H), 3.45 (d, 1H, J=13.2 Hz), 3.05 (s, 9H), 2.48-2.35 (m, 2H); MS ESI 411.2 [M+H]$^+$, calcd for [C$_{19}$H$_{23}$ClN$_2$O$_4$S+H]$^+$ 411.11.

Example S72

(R)-3-carboxy-N,N,N-trimethyl-2-(5-(1-methyl-3-(trifluoromethyl)-1H-pyrazol-5-yl)thiophene-2-sulfonamido)propan-1-aminium 2,2,2-trifluoroacetate

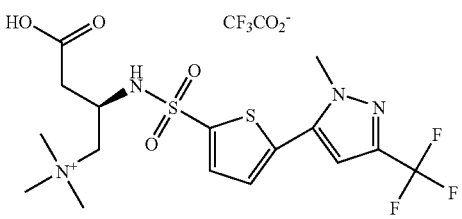 [SMILES: Cn1nc(C(F)(F)F)cc1-c1ccc(S(=O)(=O)N[C@H](CC(=O)O)C[N+](C)(C)C)s1 ; "CF3CO2-"]

a) (R)-benzyl 4-(dimethylamino)-3-(5-(1-methyl-3-(trifluoromethyl)-1H-pyrazol-5-yl)thiophene-2-sulfonamido)butanoate To a solution of (R)-benzyl 3-amino-4-(dimethylamino) butanoate (27 mg, 0.086 mmol), triethylamine (50 μL, 0.36 mmol) and DMAP (1 mg, 0.008 mmol) in anhydrous CH$_2$Cl$_2$ (1 mL) was added 5-(1-methyl-3-(trifluoromethyl)-1H-pyrazol-5-yl)thiophene-2-sulfonyl chloride (82 mg, 0.25 mmol). The solution was stirred overnight at room temperature. The solvents were removed in vacuo and the residue was purified by preparatory HPLC. The residue was dissolved into CH$_2$Cl$_2$ (50 mL) and washed with 0.1 N NaOH (5 mL), dried over MgSO$_4$ and concentrated to give the title compound as a white solid (26 mg, 57%). MS ESI 531.2 [M+H]$^+$, calcd for [C$_{22}$H$_{25}$F$_3$N$_4$O$_4$S$_2$+H]$^+$ 531.13.

b) (R)-4-(benzyloxy)-N,N,N-trimethyl-2-(5-(1-methyl-3-(trifluoromethyl)-1H-pyrazol-5-yl)thiophene-2-sulfonamido)-4-oxobutan-1-aminium iodide To a solution of (R)-benzyl 4-(dimethylamino)-3-(5-(1-methyl-3-(trifluoromethyl)-1H-pyrazol-5-yl)thiophene-2-sulfonamido)butanoate in CH$_2$Cl$_2$ (2 mL) was added methyl iodide (100 μL). The reaction was stirred overnight and concentrated to dryness to give the title compound in quantitative yield.

c) (R)-3-carboxy-N,N,N-trimethyl-2-(5-(1-methyl-3-(trifluoromethyl)-1H-pyrazol-5-yl)thiophene-2-sulfonamido)propan-1-aminium 2,2,2-trifluoroacetate To a solution of (R)-4-(benzyloxy)-N,N,N-trimethyl-2-(5-(1-methyl-3-(trifluoromethyl)-1H-pyrazol-5-yl)thiophene-2-sulfonamido)-4-oxobutan-1-aminium iodide in MeOH (1 mL) was added 1 N NaOH (1 mL). The reaction was stirred for 1 h and acidified to pH 1. The mixture was purified by preparatory HPLC to give the title compound as a white solid (12 mg, 44%). $^1$H NMR (400 MHz, CD$_3$OD) δ 7.67 (d, 1H, J=3.8 Hz), 7.31 (d, 1H, J=3.9 Hz), 6.83 (s, 1H), 4.29-4.26 (m, 1H), 3.87 (s, 3H), 3.62-3.56 (m, 1H), 3.42-3.39 (m, 1H), 3.16 (s, 9H), 2.47-2.41 (m, 1H), 2.19-2.15 (m, 1H); MS ESI 455.2 [M+H]$^+$, calcd for [C$_{16}$H$_{21}$F$_3$N$_4$O$_4$S$_2$+H]$^+$ 455.10

Example S73

(R)-3-carboxy-N,N,N-trimethyl-2-(4-(octyloxycarbonylamino)phenyl-sulfonamido)propan-1-aminium 2,2,2-trifluoroacetate

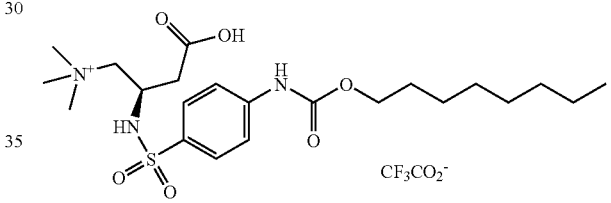

a) (R)-benzyl 4-(dimethylamino)-3-(4-(octyloxycarbonylamino)phenylsulfonamido) butanoate According to the method described in example S72a, (R)-benzyl 3-amino-4-(dimethylamino)butanoate (27 mg, 0.086 mmol) was reacted with octyl 4-(chlorosulfonyl)phenylcarbamate to yield the title compound as a white solid (15 mg, 33%). MS ESI 548.4 [M+H]$^+$, calcd for [C$_{28}$H$_{41}$N$_3$O$_6$S+H]$^+$ 548.27 b) (R)-4-(benzyloxy)-N,N,N-trimethyl-2-(4-(octyloxycarbonylamino)phenyl-sulfonamido)-4-oxobutan-1-aminium iodide According to the method described in example S72b, (R)-benzyl 4-(dimethylamino)-3-(4-(octyloxycarbonylamino)phenylsulfonamido)butanoate was reacted with methyl iodide to give the title compound as a white solid in quantitative yield. MS ESI 563.3 [M]$^+$, calcd for [C$_{29}$H$_{44}$N$_3$O$_6$S$^+$] 562.74 c) (R)-3-carboxy-N,N,N-trimethyl-2-(4-(octyloxycarbonylamino)phenylsulfonamido)-propan-1-aminium 2,2,2-trifluoroacetate According to the method described in example S72, (R)-4-(benzyloxy)-N,N,N-trimethyl-2-(4-(octyloxycarbonylamino)phenylsulfonamido)-4-oxobutan-1-aminium iodide was hydrolysed with 1 N NaOH and purified by HPLC to give the title compound as a white solid (5 mg, 31%). ¹H NMR (400 MHz, CD$_3$OD) δ 7.82 (d, 2H, J=7.6 Hz), 7.69 (d, 2H, J=7.6 Hz), 4.21-4.15 (m, 3H), 3.53-3.39 (m, 2H), 3.29 (s, 9H), 2.20-2.14 (m, 1H), 1.95-1.91 (m, 1H), 1.43-1.32 (m, 12H), 0.92-0.90 (m, 3H); MS ESI 472.3 [M+H]$^+$, calcd for [C$_{22}$H$_{38}$N$_3$O$_6$S+H]$^+$ 472.25

Example S74

(R)-3-carboxy-2-(4-ethoxy-3-(morpholine-4-carboxamido)phenyl-sulfonamido)-N,N,N-trimethyl-propan-1-aminium 2,2,2-trifluoroacetate

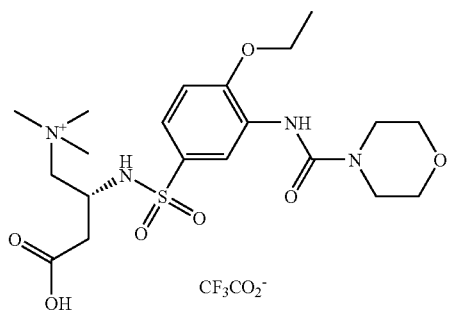

a) (R)-benzyl 4-(dimethylamino)-3-(4-ethoxy-3-(morpholine-4-carboxamido)phenyl-sulfonamido) butanoate According to the method described in example S72a, (R)-benzyl 3-amino-4-(dimethylamino)butanoate (30 mg, 0.086 mmol) was reacted with 4-ethoxy-3-(morpholine-4-carboxamido)benzene-1-sulfonyl chloride to yield the title compound as a white solid (32 mg, 68%). MS ESI 549.3 [M+H]$^+$, calcd for [C$_{26}$H$_{36}$N$_4$O$_7$S+H]$^+$ 549.23 b) (R)-4-(benzyloxy)-2-(4-ethoxy-3-(morpholine-4-carboxamido)phenylsulfonamido)-N,N,N-trimethyl-4-oxobutan-1-aminium iodide According to the method described in example S72b, (R)-benzyl 4-(dimethylamino)-3-(4-ethoxy-3-(morpholine-4-carboxamido)phenylsulfonamido)butanoate was reacted with methyl iodide to give the title compound as a white solid in quantitative yield. MS ESI 563.3 [M+H]$^+$, calcd for [C$_{27}$H$_{38}$N$_4$O$_7$S+H]$^+$ 563.25 c) (R)-3-carboxy-2-(4-ethoxy-3-(morpholine-4-carboxamido) phenylsulfonamido)-N,N,N-trimethylpropan-1-aminium 2,2,2-trifluoroacetate According to the method described in example S72, (R)-4-(benzyloxy)-2-(4-ethoxy-3-(morpholine-4-carboxamido) phenylsulfonamido)-N,N,N-trimethyl-4-oxobutan-1-aminium iodide was hydrolysed with 1 N NaOH and purified by HPLC to give the title compound as a white solid (9 mg, 25%). ¹H NMR (400 MHz, CD$_3$OD) δ 8.36 (s, 1H), 7.59 (m, 1H), 7.17 (m, 1H), 4.25-4.21 (m, 3H), 3.74 (s, 4H), 3.57-3.42 (m, 6H), 3.31-3.28 (m, 9H), 2.37-2.30 (m, 1H), 2.11-2.09 (m, 1H), 1.48 (t, 3H, J=6.8 Hz); MS ESI 473.3 [M+H]$^+$, calcd for [C$_{20}$H$_{32}$N$_4$O$_7$S+H]$^+$ 473.21

Example S75

(R)-3-carboxy-2-(4-decylphenylsulfonamido)-N,N,N-trimethylpropan-1-aminium 2,2,2-trifluoroacetate

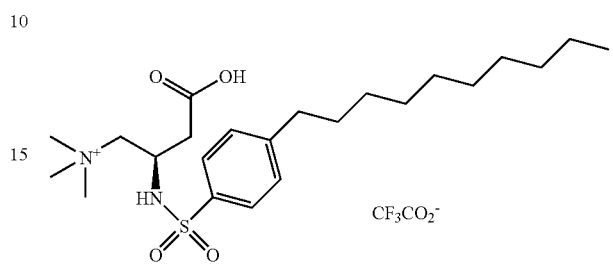

a). (R)-benzyl 3-(4-decylphenylsulfonamido)-4-(dimethylamino)butanoate

According to the method described in example S72a, (R)-benzyl 3-amino-4-(dimethylamino)butanoate (27 mg, 0.086 mmol) was reacted with 4-decylbenzene-1-sulfonyl chloride to yield the title compound as a white solid (50 mg, 94%). MS ESI 517.4 [M+H]$^+$, calcd for [C$_{29}$H$_{44}$N$_2$O$_4$S+H]$^+$ 517.3 b) (R)-4-(benzyloxy)-2-(4-decylphenylsulfonamido)-N,N,N-trimethyl-4-oxobutan-1-aminium iodide According to the method described in example S75b, (R)-benzyl 3-(4-decylphenylsulfonamido)-4-(dimethylamino) butanoate was reacted with methyl iodide to give the title compound as a white solid (quantitative). MS ESI 531.4 [M+H]$^+$, calcd for [C$_{30}$H$_{46}$N$_2$O$_4$S+H]$^+$ 531.3 c) (R)-3-carboxy-2-(4-decylphenylsulfonamido)-N,N,N-trimethylpropan-1-aminium 2,2,2-trifluoroacetate According to the method described in example S72, (R)-4-(benzyloxy)-2-(4-decylphenylsulfonamido)-N,N,N-trimethyl-4-oxobutan-1-aminium iodide was hydrolysed with 1 N NaOH and purified by HPLC to give the title compound as a white solid (2 mg, 5%). ¹H NMR (400 MHz, CD$_3$OD) δ 7.84 (d, 2H, J=7.8 Hz), 7.43 (d, 2H, J=7.8 Hz), 4.25-4.21 (m, 1H), 3.51-3.40 (m, 2H), 3.31 (s, 9H), 2.37-2.30 (m, 1H), 1.85-1.55 (m, 5H), 1.35-1.05 (m, 12H), 0.90-0.86 (m, 6H); MS ESI 441.3 [M+H]$^+$, calcd for [C$_{23}$H$_{40}$N$_2$O$_4$S+H]$^+$ 441.28.

Example S76

(R)-3-carboxy-N,N,N-trimethyl-2-(5-(m-tolylethynyl)thiophene-2-sulfonamido)propan-1-aminium 2,2,2-trifluoroacetate

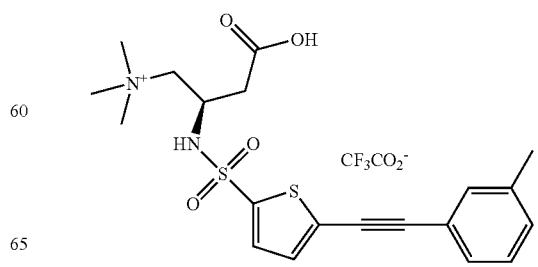

a) (R)-benzyl 4-(dimethylamino)-3-(5-(m-tolylethynyl)thiophene-2-sulfonamido)-butanoate A solution of (R)-benzyl 3-(5-bromothiophene-2-sulfonamido)-4-(dimethylamino)butanoate (25 mg, 0.05 mmol) and 3-ethynyltoluene (6 mg, 0.055 mmol) in ethyl acetate (0.5 mL) and H$_2$O (50 μL) was purged with argon. Triethylamine (15 μL, 0.1 mmol), copper iodide (0.5 mg, 0.05 eq) and Bis(triphenylphosphine)palladium(II) dichloride (0.9 mg, 0.025 eq) were added and the solution was heated to 60° C. for 2 h. The mixture was cooled and purified by silica gel chromatography (CH$_2$Cl$_2$ to 2% MeOH in CH$_2$Cl$_2$) to give the title compound as a green oil (25 mg, 92%). MS ESI 497.3 [M+H]$^+$, calcd for [C$_{26}$H$_{28}$N$_2$O$_4$S+H]$^+$ 497.15.

b) (R)-4-(benzyloxy)-N,N,N-trimethyl-4-oxo-2-(5-(m-tolylethynyl)thiophene-2-sulfonamido)butan-1-aminium iodide To a solution of (R)-benzyl 4-(dimethylamino)-3-(5-(m-tolylethynyl)thiophene-2-sulfonamido)butanoate (25 mg, 0.05 mmol) and methyl iodide (100 μL, 40 eq) in CH$_2$Cl$_2$ (1 mL) was stirred overnight at room temperature. The solution was concentrated to give the title compound in quantitative yield. MS ESI 511.3 [M]$^+$, calcd for [C$_{27}$H$_{31}$N$_2$O$_4$S$_2$]$^+$ 511.17.

c) (R)-3-carboxy-N,N,N-trimethyl-2-(5-(m-tolylethynyl)thiophene-2-sulfonamido)-propan-1-aminium 2,2,2-trifluoroacetate To a solution of (R)-4-(benzyloxy)-N,N,N-trimethyl-4-oxo-2-(5-(m-tolylethynyl)thiophene-2-sulfonamido)butan-1-aminium iodide (30 mg, 0.045 mmol) was dissolved into MeOH (1 mL). Sodium hydroxide (1 mL, 1N) was added and the mixture was stirred for 1 h. The mixture was acidified to pH 2 and purified by HPLC to give the title compound as a white solid (16 mg, 62%). $^1$H NMR (400 MHz, CD$_3$OD) δ 7.65 (d, 1H, J=4.1 Hz), 7.38-7.25 (m, 5H), 4.36-4.32 (m, 1H), 3.63-3.49 (m, 2H), 3.31 (s, 9H), 2.50-2.44 (m, 1H), 2.36 (s, 3H), 2.20-2.15 (m, 1H); MS ESI 421.2 [M+H]$^+$, calcd for [C$_{20}$H$_{24}$N$_2$O$_4$S$_2$+H]$^+$ 421.13.

Example S77

(R)-3-carboxy-N,N,N-trimethyl-2-(5-(3-methylphenethyl)thiophene-2-sulfonamido)propan-1-aminium 2,2,2-trifluoroacetate

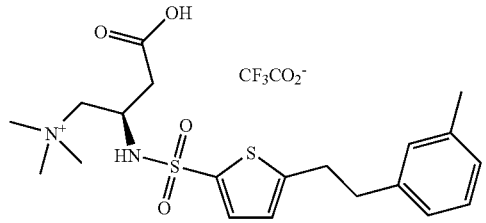

A solution of (R)-3-carboxy-N,N,N-trimethyl-2-(5-(m-tolylethynyl)thiophene-2-sulfonamido)propan-1-aminium 2,2,2-trifluoroacetate (7 mg, 0.013 mmol) in MeOH (3 mL) was purged with nitrogen and Pd/C (10 mg) was added and the flask was purged with hydrogen and stirred for 1 h. The mixture was filtered through celite and concentrated. The residue was dissolved into H$_2$O and lyophilized to give the title compound as a white solid (7 mg, 100%). $^1$H NMR (400 MHz, D$_2$O) δ 7.42 (d, 1H, J=3.8 Hz), 7.08 (t, 1H, J=7.4 Hz), 6.97-6.94 (m, 2H), 6.88 (d, 1H, J=7.1 Hz), 6.74 (d, 1H, J=3.9 Hz) 4.14-4.11 (m, 1H), 3.52-3.49 (m, 1H), 3.46-3.44 (m, 1H), 3.15-3.07 (m, 2H), 3.10 (s, 9H), 2.84 (m, 2H) 2.32-2.25 (m, 1H) 2.15 (s, 3H), 2.01-1.96 (m, 1H); MS ESI 425.2 [M+H]$^+$, calcd for [C$_{20}$H$_{29}$N$_2$O$_4$S$_2$+H]$^+$ 425.16.

Example S78

(R)-3-carboxy-N,N,N-trimethyl-2-(5-(phenylethynyl)thiophene-2-sulfonamido)propan-1-aminium 2,2,2-trifluoroacetate

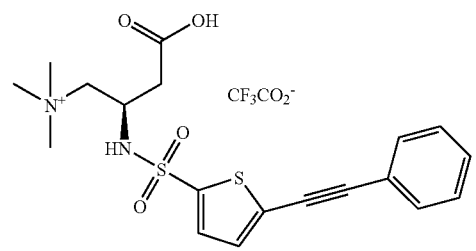

a) (R)-benzyl 4-(dimethylamino)-3-(5-(phenylethynyl)thiophene-2-sulfonamido)-butanoate According to the method described in example S76a, (R)-benzyl 3-(5-bromothiophene-2-sulfonamido)-4-(dimethylamino)butanoate was reacted with ethynylbenzene to give the title compound as a brown oil (55 mg, 87%). MS ESI 483.3 [M+H]$^+$, calcd for [C$_{25}$H$_{26}$N$_2$O$_4$S$_2$+H]$^+$ 483.13.

b) (R)-4-(benzyloxy)-N,N,N-trimethyl-4-oxo-2-(5-(phenylethynyl)thiophene-2-sulfonamido)butan-1-aminium iodide According to the method described in example S76b, (R)-benzyl 4-(dimethylamino)-3-(5-(phenylethynyl)thiophene-2-sulfonamido)butanoate was reacted with methyl iodide to give the title compound as a yellow solid (quantitative). ESI 497.3 [M]$^+$, calcd for [C$_{26}$H$_{29}$N$_2$O$_4$S$_2$]$^+$ 497.16.

c) (R)-3-carboxy-N,N,N-trimethyl-2-(5-(phenylethynyl)thiophene-2-sulfonamido)propan-1-aminium 2,2,2-trifluoroacetate According to the method described in example S76, (R)-4-(benzyloxy)-N,N,N-trimethyl-4-oxo-2-(5-(phenylethynyl)thiophene-2-sulfonamido)butan-1-aminium iodide was hydrolyzed with sodium hydroxide and purified by HPLC give the title compound as a white solid (35 mg, 60%). $^1$H NMR (400 MHz, CD$_3$OD) δ 7.65 (d, 1H, J=4.0 Hz), 7.56-7.54 (m, 2H), 7.43-7.40 (m, 3H), 7.35 (d, 1H, J=4.0 Hz), 4.37-4.32 (m, 1H), 3.64-3.49 (m, 2H), 3.32 (s, 91-1), 2.51-

2.44 (m, 1H), 2.20-2.15 (m, 1H); MS ESI 411.2 [M+H]+, calcd for [C19H23N2O4S2+H]+ 407.11.

Example S79

(R)-3-carboxy-N,N,N-trimethyl-2-(5-phenethylthiophene-2-sulfonamido)-propan-1-aminium 2,2,2-trifluoroacetate

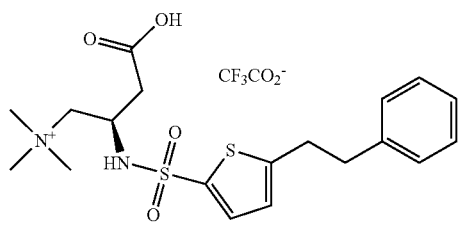

According to the method described in example S77, (R)-3-carboxy-N,N,N-trimethyl-2-(5-(phenylethynyl)thiophene-2-sulfonamido)propan-1-aminium 2,2,2-trifluoroacetate was reduced to give the title compound as a white solid (22 mg, 88%). ¹H NMR (400 MHz, CD3OD) δ 7.50 (d, 1H, J=3.6 Hz), 7.29-7.26 (m, 2H), 7.20-7.18 (m, 3H), 6.86 (d, 1H, J=3.4 Hz), 4.26-4.22 (m, 1H), 3.55-3.43 (m, 2H), 3.31 (s, 9H), 3.26 (t, 2H, J=7.6 Hz), 2.99 (t, 2H, J=7.6 Hz), 2.38-2.32 (m, 1H), 2.05-2.00 (m, 1H); MS ESI 411.2 [M+H]+, calcd for [C19H26N2O4S2+H]+ 411.14.

Example S80

(R)-3-carboxy-N,N,N-trimethyl-2-(5-(p-tolylethynyl)thiophene-2-sulfonamido)propan-1-aminium 2,2,2-trifluoroacetate

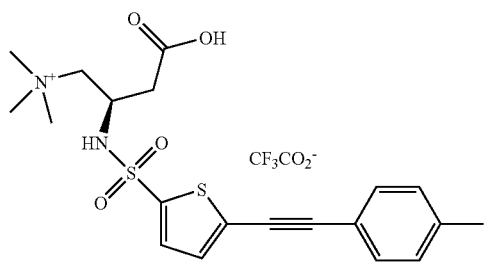

a) (R)-benzyl 4-(dimethylamino)-3-(5-(p-tolylethynyl)thiophene-2-sulfonamido)-butanoate According to the method described in example S76a, (R)-benzyl 3-(5-bromothiophene-2-sulfonamido)-4-(dimethylamino)butanoate was reacted with p-ethynyltoluene to give the title compound as a black oil (55 mg, 89%). MS ESI 497.3 [M+H]+, calcd for [C26H28N2O4S2+H]+ 497.15.

b) (R)-4-(benzyloxy)-N,N,N-trimethyl-4-oxo-2-(5-(p-tolylethynyl)thiophene-2-sulfonamido)butan-1-aminium iodide According to the method described in example S76b, (R)-benzyl 4-(dimethylamino)-3-(5-(p-tolylethynyl)thiophene-2-sulfonamido)butanoate was reacted with methyl iodide to give the title compound as a yellow solid (quantitative). MS ESI 511.2 [M+H]+, calcd for [C27H30N2O4S2+H]+ 511.17.

c) (R)-3-carboxy-N,N,N-trimethyl-2-(5-(p-tolylethynyl)thiophene-2-sulfonamido)propan-1-aminium 2,2,2-trifluoroacetate According to the method described in example S76, (R)-4-(benzyloxy)-N,N,N-trimethyl-4-oxo-2-(5-(p-tolylethynyl)thiophene-2-sulfonamido)butan-1-aminium iodide was hydrolyzed with sodium hydroxide and purified by HPLC give the title compound as a white solid (30 mg, 50%). ¹H NMR (400 MHz, CD3OD) δ 7.64 (d, 1H, J=3.3 Hz), 7.43 (d, 2H, J=8.1 Hz), 7.32 (d, 1H, J=3.3 Hz), 7.24 (d, 2H, J=8.2 Hz), 4.36-4.31 (m, 1H), 3.63-3.49 (m, 2H), 3.31 (s, 9H), 2.50-2.43 (m, 1H), 2.38 (s, 3H), 2.20-2.14 (m, 1H); MS ESI 421.2 [M+H]+, calcd for [C20H25N2O4S2+H]+ 421.13.

Example S81

(R)-3-carboxy-N,N,N-trimethyl-2-(5-(4-methylphenethyl)thiophene-2-sulfonamido)propan-1-aminium 2,2,2-trifluoroacetate

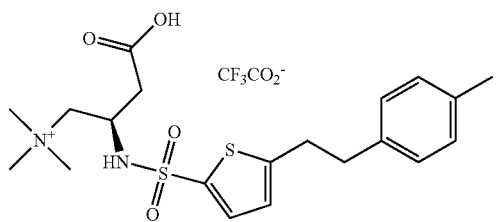

According to the method described in example S77, (R)-3-carboxy-N,N,N-trimethyl-2-(5-(p-tolylethynyl)thiophene-2-sulfonamido)propan-1-aminium 2,2,2-trifluoroacetate was reduced to give the title compound as a white solid (15 mg, 98%). ¹H NMR (400 MHz, D2O) δ 7.36-7.34 (m, 1H), 6.91-6.89 (m, 4H), 6.61 (m, 1H), 4.13-4.09 (m, 1H), 3.53-3.47 (m, 1H), 3.31-3.23 (m, 1H), 3.09 (s, 9H), 2.94-2.92 (m, 2H), 2.74-2.71 (m, 2H) 2.33-2.26 (m, 1H), 2.06 (s, 3H), 2.00-1.97 (m, 1H); MS ESI 425.2 [M+H]+, calcd for [C21H28N2O4S2+H]+ 425.16.

Example S82

(R)-3-carboxy-N,N,N-trimethyl-2-(5-((4-pentylphenyl)-ethynyl)thiophene-2-sulfonamido)propan-1-aminium 2,2,2-trifluoroacetate

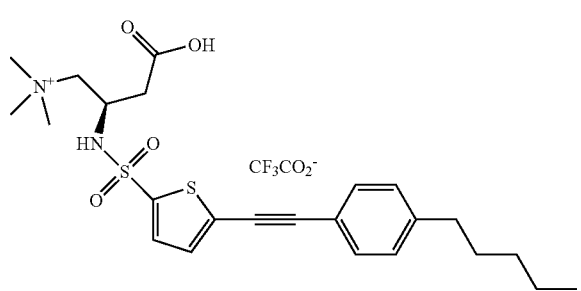 [SMILES: CCCCCc1ccc(C#Cc2ccc(S(=O)(=O)N[C@H](CC(=O)O)C[N+](C)(C)C)s2)cc1 ; "CF3CO2-"]

a) (R)-benzyl 4-(dimethylamino)-3-(5-((4-pentylphenyl)ethynyl)thiophene-2-sulfonamido)butanoate According to the method described in example S76a, (R)-benzyl 3-(5-bromothiophene-2-sulfonamido)-4-(dimethylamino)butanoate was reacted with 1-ethynyl-4-pentylbenzene to give the title compound as a black oil (68 mg, 91%). MS ESI 553.3 $[M+H]^+$, calcd for $[C_{30}H_{36}N_2O_4S_2+H]^+$ 553.21.

b) (R)-4-(benzyloxy)-N,N,N-trimethyl-4-oxo-2-(5-((4-pentylphenypethynyl)thiophene-2-sulfonamido)butan-1-aminium iodide According to the method described in example S76b, (R)-benzyl 4-(dimethylamino)-3-(5-((4-pentylphenyl)ethynyl)thiophene-2-sulfonamido)-butanoate was reacted with methyl iodide to give the title compound as a brown solid (quantitative). MS ESI 567.4 $[M]^+$, calcd for $[C_{31}H_{39}N_2O_4S_2]^+$ 567.24.

c) (R)-3-carboxy-N,N,N-trimethyl-2-(5-((4-pentylphenyl)ethynyl)thiophene-2-sulfonamido)propan-1-aminium 2,2,2-trifluoroacetate According to the method described in example S76, (R)-4-(benzyloxy)-N,N,N-trimethyl-4-oxo-2-(5-((4-pentylphenyl)ethynyl)thiophene-2-sulfonamido)butan-1-aminium iodide was hydrolyzed with sodium hydroxide and purified by HPLC give the title compound as a white solid (32 mg, 52%). $^1$H NMR (400 MHz, CD$_3$OD) δ 7.64 (dd, 1H, J=4.0, 1.0 Hz), 7.45 (d, 2H, J=7.8 Hz), 7.32 (dd, 1H, J=4.1, 1.0 Hz), 7.24 (d, 2H, J=7.8 Hz), 4.36-4.31 (m, 1H), 3.63-3.49 (m, 2H), 3.31 (s, 9H), 2.65 (t, 2H, J=7.6 Hz), 2.50-2.43 (m, 1H), 2.20-2.14 (m, 1H), 1.67-1.64 (m, 2H), 1.40-1.36 (m, 4H), 0.92 (t, 3H, J=6.6 Hz); MS ESI 477.3 $[M+H]^+$, calcd for $[C_{20}H_{24}N_2O_4S_2+H]^+$ 477.19.

Example S83

(R)-3-carboxy-N,N,N-trimethyl-2-(5-(4-pentylphenethyl)thiophene-2-sulfonamido)propan-1-aminium 2,2,2-trifluoroacetate

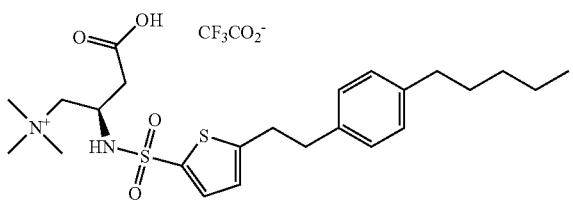

According to the method described in example S77, (R)-3-carboxy-N,N,N-trimethyl-2-(5-((4-pentylphenyl)ethynyl)thiophene-2-sulfonamido)propan-1-aminium trifluoroacetate was reduced to give the title compound as a white solid (16 mg, 96%). $^1$H NMR (400 MHz, D$_2$O) δ 7.28-7.27 (m, 1H), 6.66 (s, 4H), 6.39-6.68 (m, 1H), 4.10-4.07 (m, 1H), 3.53-3.47 (m, 1H), 3.31-3.23 (m, 1H), 3.09 (s, 9H), 2.60-2.56 (m, 2H), 2.47-2.43 (m, 2H) 2.33-2.27 (m, 1H), 2.18-2.14 (m, 2H), 2.02-1.97 (m, 1H), 1.28-1.20 (m, 2H), 1.07-1.00 (m, 4H), 0.64 (t, 3H, J=7.1 Hz); MS ESI 481.3 $[M+H]^+$, calcd for $[C_{24}H_{36}N_2O_4S_2+H]^+$ 481.22.

Example S84

(R)-3-(3-(3-(1H-pyrrol-1-yl)phenyl)ureido)-4-(trimethylammonio)butanoate

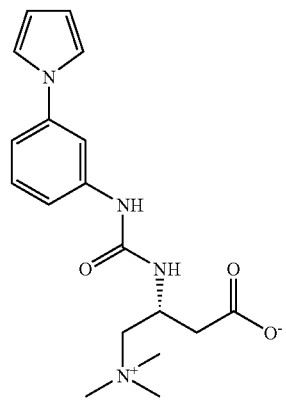 [SMILES: C[N+](C)(C)C[C@@H](CC(=O)[O-])NC(=O)Nc1cccc(-n2cccc2)c1]

According to the method described in example S11, aminocarnitine (1.28 HBr salt, 68 mg, 0.31 mmol) was reacted with 1-(3-isocyanatophenyl)-1H-pyrrole (116 mg, 0.63 mmol) to yield the title compound as a white solid (68 mg, 62%). $^1$H NMR (400 MHz, CD$_3$OD) δ ppm=7.69 (t, J=1.89 Hz, 1 H), 7.29 (t, J=7.96 Hz, 1 H), 7.11-7.18 (m, 3 H), 6.25 (t, J=2.15 Hz, 1 H), 4.62 (br. s, 1 H), 3.76 (dd, J=13.64, 9.09 Hz, 1 H), 3.51-3.58 (m, 1 H), 3.23 (s, 9 H), 2.46-2.61 (m, 2 H). MS ESI $[M+H]^+$, calcd for $[C_{18}H_{23}N_4O_3+H]^+$: 344.41 found m/z 344.7 (100).

Example S85

(R)-3-(3-(2-chloro-5-(trifluoromethyl)phenyl)ureido)-4-(trimethyl-ammonio)butanoate

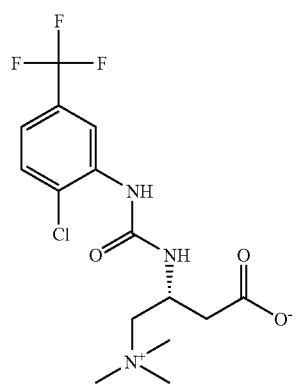 [SMILES: C[N+](C)(C)C[C@@H](CC(=O)[O-])NC(=O)Nc1cc(C(F)(F)F)ccc1Cl]

According to the method described in example S11, aminocarnitine (1.28 HBr salt, 74 mg, 0.33 mmol) was reacted with 1-chloro-2-isocyanato-4-(trifluoromethypbenzene (140 mg, 0.63 mmol) to yield the title compound as a white solid (112 mg, 90%). $^1$H NMR (400 MHz, CD$_3$OD) δ ppm=8.53 (d, J=1.77 Hz, 1 H), 7.56 (d, J=8.59 Hz, 1 H), 7.28 (dd, J=8.46, 1.64 Hz, 1 H), 4.65 (br. s, 1 H), 3.72 (dd, J=13.77, 8.97 Hz, 1 H), 3.54-3.60 (m, 1 H), 3.24 (s, 9 H), 2.51-2.54 (m, 2 H). MS ESI [M+H]$^+$, calcd for [C$_{15}$H$_{19}$ClF$_3$N$_3$O$_3$+H]$^+$: 382.79 found m/z 382.1 (100).

Example S86

(R)-3-(3-(3-benzylphenyl)ureido)-4-(trimethylammonio)butanoate

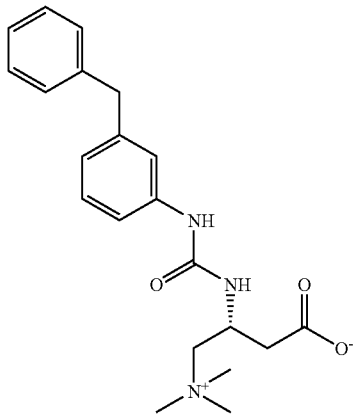 [SMILES: C[N+](C)(C)C[C@@H](CC(=O)[O-])NC(=O)Nc1cccc(Cc2ccccc2)c1]

According to the method described in example S11, aminocarnitine (1.28 HBr salt, 68 mg, 0.31 mmol) was reacted with 1-benzyl-3-isocyanatobenzene (132 mg, 0.63 mmol) to yield the title compound as a white solid (107 mg, 92%). NMR (400 MHz, CD$_3$OD) δ=ppm 7.11-7.29 (m, 8H), 6.83 (d, J=7.33 Hz, 1H), 4.58 (br. s, 1 H), 3.89 (s, 2 H), 3.71 (dd, J=13.64, 9.35 Hz, 1 H), 3.50 (d, J=13.39 Hz, 1 H), 3.17 (s, 9 H), 2.40-2.58 (m, 2 H). MS ESI [M+H]$^+$, calcd for [C$_{21}$H$_{27}$N$_3$O$_3$+H]$^+$ 370.46 found m/z 370.2 (100).

Example S87

(R)-3-(3-(4-Octylphenyl)-3-phenylureido)-4-(trimethylammonio)butanoate

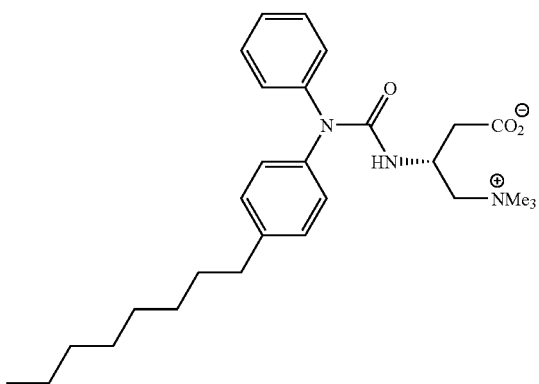

According to the methods described in example S34, 4-octyl-N-phenylaniline is reacted with of triphosgene and (R)-benzyl 3-amino-4-(dimethylamino)butanoate to yield the title compound.

Example S88

(R)-3-(N-dodecyl-N-methylsulfamoylamino)-4-(trimethylammonio)-butanoate

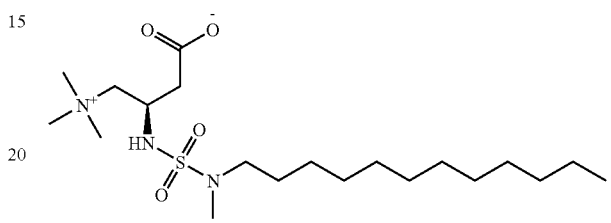

According to the method described in example S27, the title compound (42 mg, 35%) was obtained from crude (R)-4-methoxy-N,N,N-trimethyl-4-oxo-2-(2-oxooxazolidine-3-sulfonamido)butan-1-aminium chloride (250 mg, 0.288 mmol) and N-Methyldodecan-1-amine (67 mg, 0.34 mmol). $^1$H NMR (400 MHz, CD$_3$OD) δ 4.07-3.95 (m, 1H), 3.50-3.37 (m, 2H), 3.37-3.05 (m, 2H overlapping with 9H at δ 3.25), 3.28 (s, 3H), 2.50-2.35 (m, 2H), 1.65-1.50 (m, 2H), 1.35-1.10 (m, 18H), 0.87 (t, 3H, J=6.8 Hz); MS ESI 422.3 [M+H]$^+$, calcd for [C$_{20}$H$_{43}$N$_3$O$_4$S+H]$^+$ 422.30.

Example S89

(R)-3-(N-(4-dodecylphenyl)sulfamoylamino)-4-(trimethylammonio)-butanoate

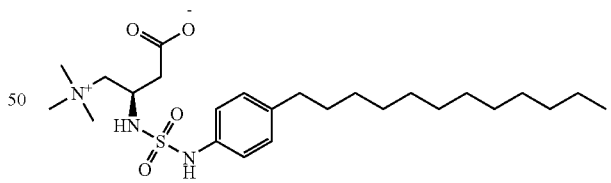

According to the method described in example S30, (R)-3-(N-(4-dodecylphenyl)sulfamoylamino)-4-(trimethylammonio)butanoate (49 mg, 18%) was obtained from (R)-aminocarnitine methyl ester (140 mg, 0.567 mmol) and 2-chloroethyl N-(4-dodecylphenyl)sulfamoylcarbamate (350 mg, 0.74 mmol). $^1$H NMR (400 MHz, CD$_3$OD+1 drop CDCl$_3$) δ 7.12 (d, 21-1, J=8.0 Hz), 7.08 (d, 2H, J=8.4 Hz), 4.20-4.10 (m, 1H), 3.40-3.32 (m, 3H), 3.17 (s, 9H), 2.52 (t, 2H, J=7.6 Hz), 2.40 (dd, 11-1, J=16.0 Hz, 2.4 Hz), 224 (dd, 1H, J=15.6 Hz, 9.2 Hz), 1.60-1.50 (m, 2H), 1.35-1.20 (m, 18H), 0.87 (t, 3H, J=6.4 Hz); MS ESI 484.4 [M+H]$^+$, calcd for [C$_{25}$H$_{45}$N$_3$O$_4$S+H]$^+$ 484.32

Example S90

(R)-3-(N-(4-tetradecylphenyl)sulfamoylamino)-4-(trimethylammonio)-butanoate

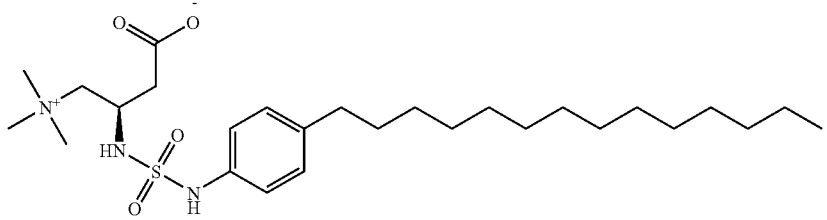 [SMILES: CCCCCCCCCCCCCCc1ccc(NS(=O)(=O)N[C@H](CC(=O)O)C[N+](C)(C)C)cc1]

According to the method described in example S30, ((R)-3-(N-(4-tetradecylphenyl)sulfamoylamino)-4-(trimethylammonio)butanoate (80 mg, 28%) was obtained from (R)-aminocarnitine methyl ester (140 mg, 0.567 mmol) and 2-chloroethyl N-(4-tetradecylphenyl)sulfamoylcarbamate (300 mg, 0.675 mmol). $^1$H NMR (400 MHz, CD$_3$OD+1 drop CDCl$_3$) δ 7.12 (d, 21-1, J=7.6 Hz), 7.08 (d, 2H, J=8.8 Hz), 4.15-4.08 (m, 1H), 3.35-3.30 (m, 3H, overlapping with MeOH), 3.18 (s, 9H), 2.52 (t, 211, J=7.6 Hz), 2.38 (d, 1H, J=16.0 Hz), 2.22 (dd, 1H, J=15.6 Hz, 9.2 Hz), 1.60-1.50 (m, 2H), 1.35-1.20 (m, 22H), 0.87 (t, 3H, J=6.2 Hz); MS ESI 512.4 [M+H]$^+$, calcd for [C$_{27}$H$_{49}$N$_3$O$_4$S+H]$^+$ 512.35.

Example S91

(R)-3-(N-(4-pentylphenyl)sulfamoylamino)-4-(trimethylammonio)butanoate

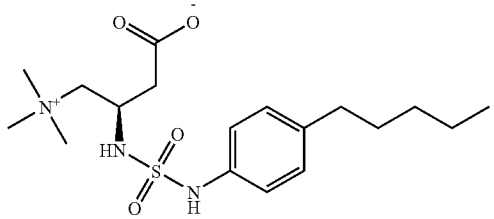 [SMILES: CCCCCc1ccc(NS(=O)(=O)N[C@H](CC(=O)O)C[N+](C)(C)C)cc1]

According to the method described in example S30, the title compound (74 mg, 63%) was obtained from (R)-aminocarnitine methyl ester (130 mg, 0.526 mmol) and 2-chloroethyl N-(4-pentylphenyl)sulfamoylcarbamate (349 mg, 1.0 mmol) followed by saponification using 1 M NaOH (4 mL) in MeOH (15 mL). $^1$H NMR (400 MHz, CD$_3$OD+1 drop CDCl$_3$) δ 7.15-7.05 (m, 4H), 4.20-4.10 (m, 1H), 3.40-3.34 (m, 2H), 3.19 (s, 9H), 2.54 (t, 2H, J=7.6 Hz), 2.42 (dd, 1H, J=16.8 Hz, 3.2 Hz), 2.27 (dd, 1H, J=16.0 Hz, 9.2 Hz), 1.65-1.50 (m, 2H), 1.40-1.25 (m, 4H), 0.91 (t, 3H, J=6.8 Hz); MS ESI 386.2 [M+H]$^+$, calcd for [C$_{18}$H$_{31}$N$_3$O$_4$S+H]$^+$ 386.21.

Example S92

(R)-3-(N-(4-decylphenyl)sulfamoylamino)-4-(trimethylammonio)butanoate

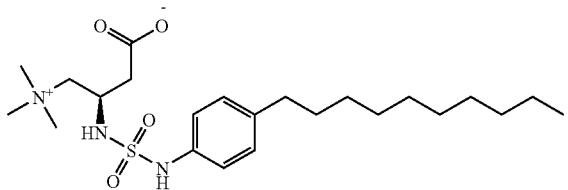 [SMILES: CCCCCCCCCCc1ccc(NS(=O)(=O)N[C@H](CC(=O)O)C[N+](C)(C)C)cc1]

According to the method described in example S30, the title compound (88 mg, 39%) was obtained from (R)-aminocarnitine methyl ester (124 mg, 0.5 mmol) and 2-chloroethyl N-(4-decyl)sulfamoylcarbamate (415 mg, 1.0 mmol) followed by saponification using 1 M NaOH (4 mL) in MeOH (15 mL). $^1$H NMR (400 MHz, CD$_3$OD+1 drop CDCl$_3$) δ 7.20-7.00 (m, 4H), 4.20-4.05 (m, 1H), 3.43-3.35 (m, 2H, overlapping with MeOH), 3.19 (s, 9H), 2.60-2.30 (m, 3H), 2.30-2.15 (m, 1H), 1.62-1.45 (m, 2H), 1.35-1.15 (m, 14H), 0.89 (pseudo s, 3H); MS ESI 456.4 [M+H]$^+$, calcd for [C$_{23}$H$_{41}$N$_3$O$_4$S+H]$^+$ 456.29.

Example S93

(R)-3-(N-methyl-N-(4-octylphenyl)sulfamoylamino)-4-(trimethylammonio)-butanoate

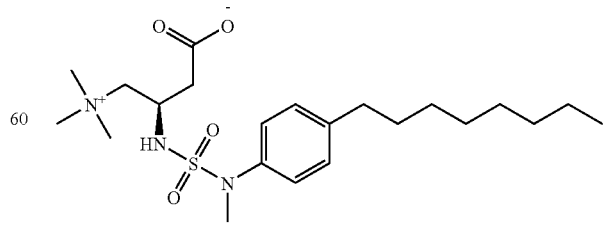

To a solution of (R)-aminocarnitine methyl ester (124 mg, 0.5 mmol) and triethylamine (0.28 mL, 2 mmol) in dichloromethane (35 mL) at 0° C. was added the solution of 2-chloroethyl chlorosulfonylcarbamate in dichloromethane (0.77 M, 0.65 mL, 0.5 mmol). After addition, the resulting mixture was stirred overnight at rt. After removal of solvent, a white solid was obtained as a mixture of desired product and $Et_3N$—HCl. The mixture was redissolved in $CH_3CN$ (30 mL) and triethylamine (0.21 mL, 1.5 mmol) and N-methyl n-octylaninline (121 mg, 0.55 mmol) were added. The resulting mixture was refluxed for 4 h. After cooling to rt, solvents were removed and the residue was redissolved in MeOH (25 mL). 1 M NaOH (5 mL) was added and reaction mixture was stirred for 2 days at rt. $H_2O$ (30 mL) and 20 mL of brine were added and the mixture was extracted with n-BuOH (60 mL×2). BuOH extracts were combined, dried ($Na_2SO_4$) and evaporated to give a white solid which was purified by flash chromatography ($CH_2Cl_2$/MeOH 10:1 to MeOH) to give the tile compound (44 mg, 20%) as white solid. $^1$H NMR (400 MHz, $CD_3OD$+1 drop $CDCl_3$) δ 7.32 (d, 2H, J=8.0 Hz), 7.18 (d, 2H, J=8.0 Hz), 4.20-4.10 (m, 1H), 3.48-3.38 (m, 2H), 3.23 (s, 3H), 3.17 (s, 9H), 2.63-2.52 (m, 3H), 2.44 (dd, 1H, J=16.0 Hz, 6.8 Hz), 1.65-1.53 (m, 2H), 1.37-1.20 (m, 10H), 0.88 (t, 3H, J=6.8 Hz); MS ESI 442.3 $[M+H]^+$, calcd for $[C_{20}H_{39}N_3O_4S+H]^+$ 442.27.

Example S94

(R)-3-(3-(5-(3-(hexyloxy)phenoxy)pentyl)-3-methylureido)-4-(trimethyl-ammonio)butanoate

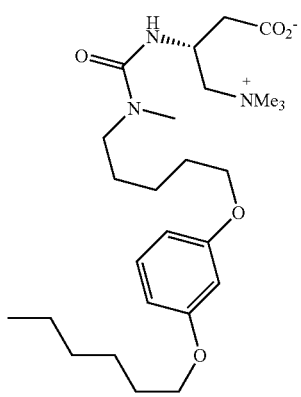

a) 1-(5,5-dimethoxypentyloxy)-3-(hexyloxy)benzene

A mixture of NaOH (100 mg, 2.5 mmol), n-$Bu_4NI$ (37 mg, 0.1 mmol), 3-(hexyloxy)phenyl benzoate (ref. Prasad K. et al. Org. Proc. Res. Dev., 2003, 7 (5), 743-749) (200 mg, 0.67 mmol) in $H_2O$ (3 mL) was evacuated and refilled with Ar three times. The reaction mix was heated with stirring to 90° C. under Ar and treated with 5-bromo-1,1-dimethoxypentane (0.24 g, 1.2 mmol), added dropwise over 30 min at 95° C. Stirring was continued at 95° C. overnight. Later, the reaction mixture was cooled to rt and extracted with $Et_2O$ (2×). The organic extracts were washed (2 M aq NaOH, brine), concentrated under reduced pressure and purified by flash chromatography on silica gel using 0-7% EtOAc/hexanes as the eluent to afford the title compound as a colorless oil (127 mg, 59%). $^1$H NMR (400 MHz, $CDCl_3$) δ ppm 7.15 (t, J=8.08 Hz, 1 H), 6.43-6.52 (m, 3 H), 4.89 (t, J=4.67 Hz, 1 H), 3.82-4.03 (m, 10 H), 1.20-1.92 (m, 14 H), 0.91 (t, J=6.82 Hz, 3 H).

b) 5-(3-(Hexyloxy)phenoxy)pentanal

A solution of 1-(5,5-dimethoxypentyloxy)-3-(hexyloxy) benzene (127 mg, 0.39 mmol) and 2 M aq HCl (0.47 mL, 0.94 mmol) in THF (4.5 mL), $H_2O$ (0.28 mL) was stirred at rt overnight. Later, the reaction was heated at 50° C. for 5 h. After cooling to rt the reaction mixture was diluted with $H_2O$, extracted with $Et_2O$ (3×), washed (aq $NaHCO_3$, brine), dried ($Na_2SO_4$) and concentrated under reduced pressure to yield 5-(3-(hexyloxy)phenoxy)pentanal as a colorless oil (117 mg). The material was used in the following step without further purification. $^1$H NMR (400 MHz, $CDCl_3$) δ ppm 9.80 (s, 1 H), 7.16 (t, J=8.08 Hz, 1 H), 6.43-6.53 (m, 3 H), 3.89-4.01 (m, 4 H), 2.50-2.57 (m, 2 H), 1.14-1.92 (m, 12 H), 0.92 (t, J=6.69 Hz, 3 H). MS ESI $[M+H]^+$, calcd for $[C_{17}H_{26}O_3+H]^+$: 279.2 found m/z 279.2 (95) and 301.1 ($[M+Na]^+$, 100).

c) 5-(3-(hexyloxy)phenoxy)-N-methylpentan-1-amine 5-(3-(hexyloxy)phenoxy)pentanal (72 mg, 0.26 mmol) in 1,2-$C_{12}C_2H_4$ (5 mL) was treated with a THF solution of $MeNH_2$ (2.0 M, 0.4 mL, 0.8 mmol). The reaction was stirred in a sealed vial for several min at rt before $NaBH(OAc)_3$ (76 mg, 0.36 mmol) was added in one portion. Again the vial was sealed and stirred at rt for 3 d. The reaction was diluted with $H_2O$ and extracted into DCM. The organic extracts were concentrated and the resulting material was purified by preparative TLC on silica gel (5% MeOH:DCM) to afford the title compound as clear oil (17 mg, 23%). $^1$H NMR (400 MHz, $CDCl_3$) δ ppm 7.15 (t, J=8.21 Hz, 1 H), 6.44-6.51 (m, 3 H), 3.90-3.98 (m, 4 H), 2.64 (t, J=7.07 Hz, 2 H), 2.46 (s, 3 H), 2.28 (br. s, 1 H), 1.72-1.85 (m, 4 H), 1.40-1.67 (m, 6 H), 1.29-1.40 (m, 4 H), 0.91 (t, J=6.57 Hz, 3 H). MS ESI $[M+H]^+$, calcd for $[C_{18}H_{31}NO_2+H]^+$: 294.45 found m/z 294.2 (100).

d) (R)-3-(3-(5-(3-(hexyloxy)phenoxy)pentyl)-3-methylureido)-4-(trimethyl-ammonio)butanoate According to the method described in example S34, 5-(3-(hexyloxy)phenoxy)-N-methylpentan-1-amine is reacted with of triphosgene and (R)-benzyl 3-amino-4-(dimethylamino)butanoate to yield the title compound.

Example S95

(R)-2-(5-bromothiophene-2-carboxamido)-3-carboxy-N,N,N-trimethyl-propan-1-aminium trifluoroacetate

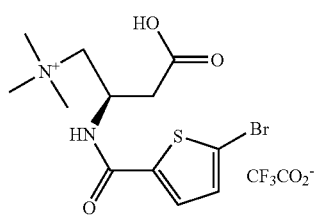

According to the method described in example S2, R-aminocarnitine was reacted with 2,5-dioxopyrrolidin-1-yl 5-bromothiophene-2-carboxylate, prepared as described in preparation 4. Purification by HPLC gave the title compound as a yellow solid. $^1$H NMR (400 MHz, $CD_3OD$) δ 7.52 (d, 1H, J=3.8 Hz), 7.19 (d, 1H, J=4.0 Hz), 4.90 (bs, 1H), 3.70-3.65

(m, 2H), 3.23 (s, 9H), 2.80-2.72 (m, 2H); MS ESI 349.02 [M+H]$^+$, calcd for [C$_{12}$H$_{17}$BrN$_2$O$_3$S+H]$^+$ 349.0, 351.0.

Example S96

(R)-3-carboxy-N,N,N-trimethyl-2-(5-((4-pentylphenyl)ethynyl)-thiophene-2-carboxamido)propan-1-aminium 2,2,2-trifluoroacetate

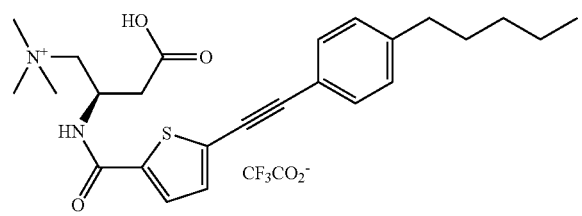

A solution of (R)-2-(5-bromothiophene-2-carboxamido)-3-carboxy-N,N,N-trimethyl-propan-1-aminium (20 mg, 0.06 mmol) and 1-ethynyl-4-pentylbenzene (11 mg, 0.063 mmol) in DMF (0.5 mL) and H$_2$O (50 µL) was purged with argon. Triethylamine (17 µL, 0.12 mmol), copper iodide (0.6 mg, 0.05 eq) and bis(triphenylphosphine) palladium(II) dichloride (1 mg, 0.025 eq) were added and the solution was heated to 60° C. for 2 h. The mixture was cooled and purified by HPLC (11 mg, 42%). $^1$H NMR (400 MHz, D$_2$O) δ 7.32 (bs, 1H), 6.96 (d, 2H, J=Hz), 6.83 (bs, 1H), 6.59 (d, 2H), 4.75-4.73 (m, 1H), 3.63-3.42 (m, 2H), 2.99 (s, 9H), 2.61-2.45 (m, 2H), 2.09-2.02 (m, 2H), 1.15-1.10 (m, 2H), 0.95-0.84 (m, 4H), 0.55-0.50 (m, 3H); MS ESI 441.3 [M+H]$^+$, calcd for [C$_{25}$H$_{32}$N$_2$O$_3$S+H]$^+$ 441.22.

Example S97

(R)-3-carboxy-N,N,N-trimethyl-2-(5-(thiophen-3-ylethynyl)thiophene-2-carboxamido)propan-1-aminium 2,2,2-trifluoroacetate

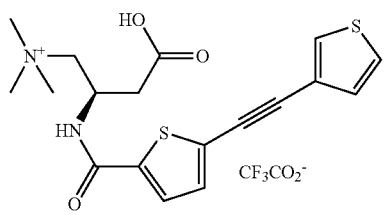

According to the method described in example S96, (R)-benzyl 3-(5-bromothiophene-2-sulfonamido)-4-(dimethylamino)butanoate was reacted with 3-ethynylthiophene and purified by HPLC to the title compound as a yellow solid (12 mg, 271%). $^1$H NMR (400 MHz, CD$_3$OD) δ 7.73 (d, 1H, J=2.1 Hz), 7.66 (d, 1H, J=3.9 Hz), 7.50-7.48 (m, 1H), 7.27 (d, 1H, J=3.9 Hz) 7.21 (d, 1H, J=4.9 Hz) 4.90-4.85 (m, 1H), 3.77-3.62 (m, 2H), 3.27 (s, 9H), 2.84-2.72 (m, 2H); MS ESI 377.1 [M+H]$^+$, calcd for [C$_{18}$H$_{20}$N$_2$O$_3$S$_2$+H]$^+$ 377.10.

Example S98

(R)-3-carboxy-N,N,N-trimethyl-2-(5-(2-(thiophen-3-yl)ethyl)thiophene-2-carboxamido)propan-1-aminium 2,2,2-trifluoroacetate

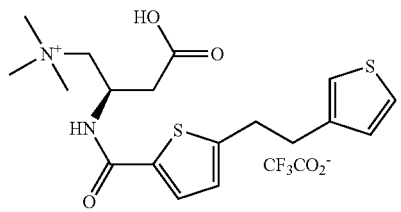

According to the method described in example S77, (R)-3-carboxy-N,N,N-trimethyl-2-(5-(thiophen-3-ylethynyl)thiophene-2-carboxamido)propan-1-aminium 2,2,2-trifluoroacetate was reduced to give the title compound as a white solid (1 mg, 12%). $^1$H NMR (400 MHz, CD$_3$OD) δ 7.52 (d, 1H, J=3.8 Hz), 7.32-7.30 (m, 1H), 7.04 (s, 1H), 6.98 (d, 1H, J=4.9 Hz), 6.85 (d, 1H, J=3.7 Hz) 4.90-4.85 (m, 1H), 3.72-3.60 (m, 2H), 3.20 (s, 9H), 3.19 (t, 2H, J=7.9 Hz), 3.02 (t, 2H, J=7.5 Hz), 2.84-2.74 (m, 2H); MS ESI 381.1 [M+H]$^+$, calcd for [C$_{18}$H$_{25}$N$_2$O$_3$S$_2$+H]$^+$ 381.13.

Example S99

(R)-3-carboxy-2-(3-(2-iodophenyl)ureido)-N,N,N-trimethylpropan-1-aminium

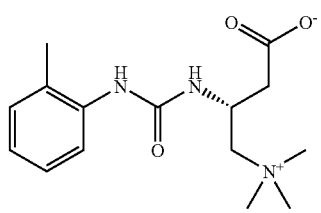 [SMILES: Cc1ccccc1NC(=O)N[C@H](CC(=O)[O-])C[N+](C)(C)C]

According to the method described in example S11, aminocarnitine was reacted with 1-iodo-2-isocyanatobenzene to yield the title compound. MS ESI [M+H]$^+$, calcd for [C$_{14}$H$_{20}$IN$_3$O$_3$+H]$^+$ 406.06; found m/z 406.0 (100).

Example S100

(R)-3-carboxy-N,N,N-trimethyl-2-(3-(2-phenoxyphenyl)ureido)propan-1-aminium

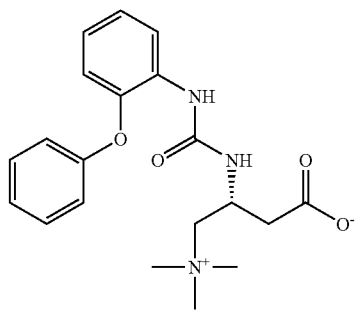 [SMILES: C[N+](C)(C)C[C@@H](CC(=O)[O-])NC(=O)Nc1ccccc1Oc1ccccc1]

According to the method described in example S11, aminocarnitine was reacted with 1-isocyanato-2-phenoxybenzene to yield the title compound. MS ESI 372.2 [M+H]$^+$, calcd. for [C$_{20}$H$_{25}$N$_3$O$_4$+H]$^+$372.43; found m/z 372.2 (100).

Example S101

(R)-2-(3-biphenyl-2-ylureido)-3-carboxy-N,N,N-trimethylpropan-1-aminium

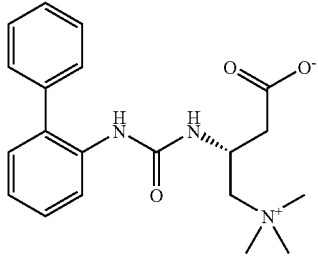 [SMILES: C[N+](C)(C)C[C@@H](CC(=O)[O-])NC(=O)Nc1ccccc1-c1ccccc1]

According to the method described in example S11, aminocarnitine was reacted with 1-isocyanato-2-phenylbenzene to yield the title compound.

Example S102

(R)-3-carboxy-N,N,N-trimethyl-2-(5-(4-pentylphenethyl)thiophene-2-carboxamido)propan-1-aminium 2,2,2-trifluoroacetate

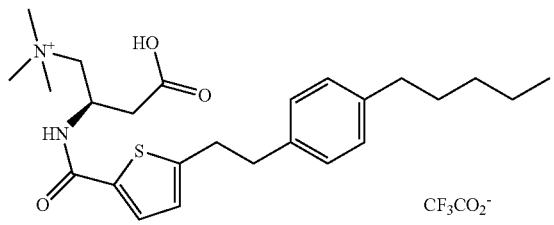 [SMILES: CCCCCc1ccc(CCc2ccc(C(=O)N[C@H](CC(=O)O)C[N+](C)(C)C)s2)cc1 ; "CF3CO2-"]

According to the method described in example S77, (R)-3-carboxy-N,N,N-trimethyl-2-(5-((4-pentylphenyl)ethynyl)-thiophene-2-carboxamido)propan-1-aminium 2,2,2-trifluoroacetate was reduced to give the title compound as a white solid (5 mg, 20%). $^1$H NMR (400 MHz, D$_2$O) δ 7.38 (s, 1H), 7.15-7.08 (m, 1H), 7.00-6.97 (m, 1H), 6.63 (s, 4H), 6.29 (s, 1H), 4.58-4.48 (m, 1H), 3.63-3.60 (m, 1H), 3.43-3.39 (m, 1H), 2.95 (s, 9H), 2.57-2.50 (m, 1H), 2.49-2.38 (m, 5H), 2.15-2.09 (m, 2H), 1.25-1.16 (m, 2H), 1.02-0.96 (m, 4H), 0.63-0.60 (m, 3H); MS ESI 445.3 [M+H]$^+$, calcd for [C$_{25}$H$_{36}$N$_2$O$_3$S+H]$^+$ 445.25.

Example S103

(R)-3-(N-(4-(octyloxy)phenyl)sulfamoylamino)-4-(trimethylammonio) butanoate

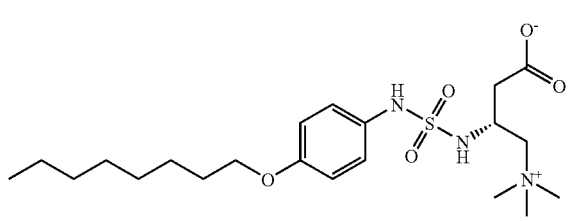 [SMILES: CCCCCCCCOc1ccc(NS(=O)(=O)N[C@H](CC(=O)[O-])C[N+](C)(C)C)cc1]

According to the method described in example S30, the title compound (16.5 mg, 12%) was obtained as white solid from (R)-aminocarnitine methyl ester dichloride (75 mg, 0.3 mmol), and 2-chloroethyl N-(4-(octyloxy)phenyl)sulfamoyl-carbamate (146 mg, 0.36 mmol). NMR (400 MHz, CD$_3$OD) δ 7.14 (d, 2H, J=8.8 Hz), 6.84 (d, 2H, J=8.8 Hz), 4.18-4.10 (m, 1H), 3.92 (t, 2H, J=6.2 Hz), 3.37 (d, 2H, J=5.2 Hz), 3.32 (s, 9H), 2.45 (d, 1H, J=16.4 Hz), 2.31 (dd, 1H, J=16.4 Hz, J=8.2 Hz), 1.75 (quint, 2H, J=6.4 Hz), 1.50-1.25 (m, 10H), 0.92 (t, 3H, J=6.4 Hz); MS ESI 444.3 [M+H]$^+$, calcd for [C$_{21}$H$_{37}$N$_3$O$_5$S+H]$^+$ 444.3.

Example S104

(R)-3-(N-(4-(non-1-ynyl)phenyl)sulfamoylamino)-4-(trimethylammonio) butanoate

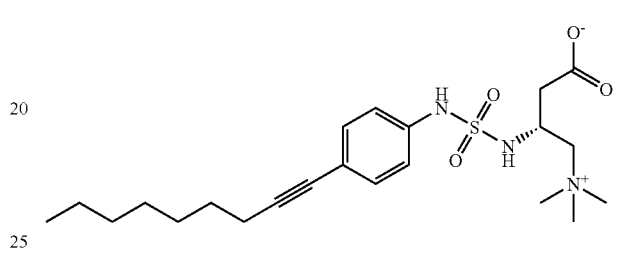

a) 4-(non-1-ynyl)aniline

To a mixture of 4-iodoaniline (2.19 g, 10 mmol), CuI (38 mg, 0.2 mmol, 2 mol %) and Pd(PPh$_3$)$_2$Cl$_2$ (70 mg, 0.1 mmol, 1 mol %) under argon was added THF (60 mL), followed by non-1-yne (1.49 g, 12 mmol, 1.2 equiv.). After stirring for 1 min at rt, 0.5 M NH$_4$OH (40 mL) was added dropwise. After addition, the resulting mixture was stirred 0/N at rt. It was extracted with ether (60 mL+30 mL) and combined extracts were dried (Na$_2$SO$_4$) and purified by flash chromatography (eluent: EtOAc/Hex=1:6) to give 4-(non-1-ynyl) aniline as a light yellow oil (1.85 g, 86%). $^1$H NMR (400 MHz, CDCl$_3$) δ 7.22 (d, 2H, J=8.4 Hz), 6.60 (d, 2H, J=8.4 Hz), 3.65 (s, br, 2H, NH$_2$), 2.38 (t, 2H, J=7.0 Hz), 1.59 (quint, 2H, J=7.2 Hz), 1.44 (quint, 2H, J=6.8 Hz), 1.38-1.25 (m, 6H), 0.90 (t, 3H, J=6.4 Hz).

b) (R)-3-(N-(4-(non-1-ynyl)phenyl)sulfamoylamino)-4-(trimethylammonio) butanoate According to the method described in example S93, the title compound (43 mg, 15%) was obtained as white solid from (R)-3-(2-oxooxazolidine-3-sulfonamido)-4-(trimethylammonio)-butanoate (0.5 mmol), and 4-(non-1-ynyl)aniline (118 mg, 0.55 mmol). $^1$H NMR (400 MHz, CD$_3$OD) δ 7.28 (d, 21-1, J=8.4 Hz), 7.12 (d, 2H, J=8.4 Hz), 4.20-4.10 (m, 1H), 3.40-3.35 (m, 2H), 3.21 (s, 9H), 2.40-2.20 (m, 4H), 1.58 (quint, 2H, J=7.2 Hz), 1.47 (quint, 2H, J=6.4 Hz), 1.40-1.25 (m, 6H), 0.92 (t, 3H, J=6.8 Hz); MS ESI 438.3 [M+H]$^+$, calcd for [C$_{22}$H$_{35}$N$_3$O$_4$S+H]$^+$ 438.2.

Example S105

(R)-3-(N-(4-nonylphenyl)sulfamoylamino)-4-(trimethylammonio)-butanoate

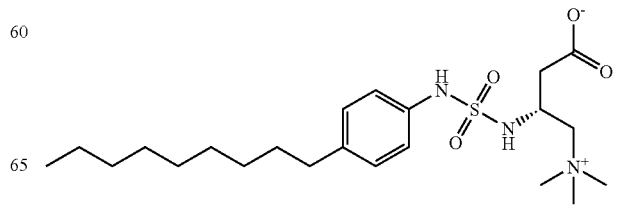

To a solution of (R)-3-(N-(4-(non-1-ynyl)phenyl)sulfamoylamino)-4-(trimethylammonio) butanoate (29 mg, 0.066 mmol) in MeOH (40 mL) was added 10% wt. Pd/C (10 mg). The resulting mixture was stirred under hydrogen balloon O/N. Pd/C was filtered off by filter paper and rinsed with MeOH. The filtrate was concentrated, redissolved in MeOH (10 mL) and filtered by a plastic filter to the title compound as a white solid (28.8 mg, 99%). $^1$H NMR (400 MHz, CD$_3$OD) δ 7.13 (s, 4H), 4.21-4.13 (m, 1H), 3.40-3.35 (m, 2H), 3.20 (s, 9H), 2.55 (t, 2H, J=7.6 Hz), 2.40 (dd, 1H, J=16.4 Hz, J=2.8 Hz), 2.25 (dd, 1H, J=8.0 Hz, J=9.6 Hz), 1.52-1.50 (m, 2H), 1.36-1.20 (m, 12H), 0.91 (t, 3H, J=6.8 Hz); MS ESI 442.3 [M+H]% calcd for [C$_{22}$H$_{39}$N$_3$O$_4$S+H]$^+$ 442.3.

Example S106

(R)-3-(N-(4-(oct-1-ynyl)phenyl)sulfamoylamino)-4-(trimethylammonio) butanoate

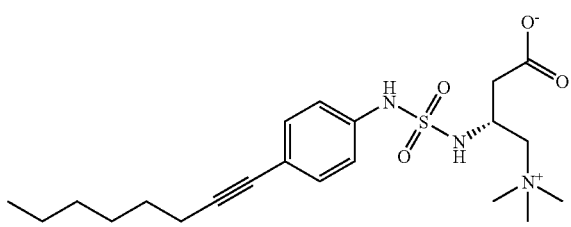 [SMILES: CCCCCCC#Cc1ccc(NS(=O)(=O)N[C@H](CC(=O)[O-])C[N+](C)(C)C)cc1]

a) 4-(oct-1-ynyl)aniline

Using the method for the preparation of 4-(non-1-ynyl) aniline (example S104), 4-(oct-1-ynyl)aniline was obtained as a light yellow oil (363 mg, 90%) from 4-iodoaniline (438 mg 2 mmol) and oct-1-yne (264 mg, 2.4 mmol). $^1$H NMR (400 MHz, CDCl$_3$) δ 7.22 (d, 2H, J=8.4 Hz), 6.60 (d, 2H, J=8.0 Hz), 3.57 (s, br, 2H, NH$_2$), 2.39 (t, 2H, J=7.0 Hz), 1.59 (quint, 2H, J=7.2 Hz), 1.45 (quint, 21-1, J=6.0 Hz), 1.38-1.23 (m, 4H), 0.92 (t, 3H, J=6.0 Hz).

b) (R)-3-(N-(4-(oct-1-ynyl)phenyl)sulfamoylamino)-4-(trimethylammonio) butanoate According to the method described in example S93, the title compound (19 mg, 15%) was obtained as white solid from crude (R)-3-(2-oxooxazolidine-3-sulfonamido)-4-(trimethylammonio)-butanoate (0.3 mmol) and 4-(oct-1-ynyl) aniline (66 mg, 0.33). $^1$H NMR (400 MHz, CD$_3$OD) δ 7.24 (d, 2H, J=8.4 Hz), 7.09 (d, 2H, J=8.4 Hz), 4.15-4.08 (m, 1H), 3.40-3.33 (m, 2H), 3.20 (s, 9H), 2.42-2.25 (m, 4H), 1.58 (quint, 2H, J=6.9 Hz), 1.47 (quint, 2H, J=6.4 Hz), 1.40-1.28 (m, 4H), 0.94 (t, 3H, J=6.6 Hz); MS ESI 424.3 [M+H]$^+$, calcd for [C$_{21}$H$_{33}$N$_3$O$_4$S+H]$^+$ 424.2.

Example S107

(R)-3-(N-(4-((4-pentylphenyl)ethynyl)phenyl)sulfamoylamino)-4-(trimethylammonio)butanoate

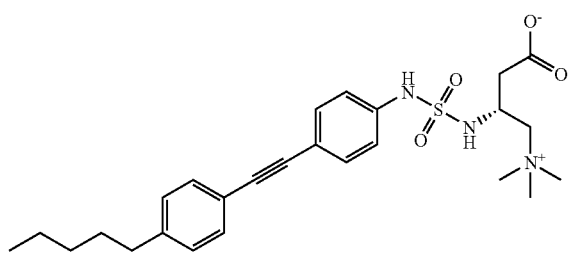 [SMILES: CCCCCc1ccc(C#Cc2ccc(NS(=O)(=O)N[C@H](CC(=O)[O-])C[N+](C)(C)C)cc2)cc1]

a) 4-((4-pentylphenyl)ethynyl)aniline

Using the method for the preparation of 4-(non-1-ynyl) aniline (example S104),), 4-((4-pentylphenyl)ethynyl)aniline was obtained as a slightly brown oil (220 mg, 84%) from 4-iodoaniline (219 mg 1 mmol) and 1-ethynyl-4-pentylbenzene (189 mg, 1.1 mmol). $^1$H NMR (400 MHz, CDCl$_3$) δ 7.47 (d, 211, J=7.6 Hz), 7.38 (d, 2H, J=8.0 Hz), 7.19 (d, 2H, J=7.6 Hz), 6.63 (d, 2H, J=7.6 Hz), 3.81 (s, 2H, NH$_2$), 2.64 (t, 2H, J=7.6 Hz), 1.66 (quint, 2H, J=6.8 Hz), 1.45-1.35 (m, 4H), 0.96 (t, 3 h, J=6.0 Hz).

b) According to the method described in example S93, the title compound (30 mg, 12%) was obtained from (R)-3-(2-oxooxazolidine-3-sulfonamido)-4-(trimethylammonio)-butanoate (0.5 mmol) and 4-((4-pentylphenyl)ethynyl)aniline (145 mg, 0.55 mmol). $^1$H NMR (400 MHz, CD$_3$OD) δ 7.45-7.30 (m, 4H), 7.20-7.05 (m, 4H), 4.22-4.10 (m, 1H), 3.40 (s, 2H), 3.23 (s, 9H), 2.62 (t, 2H, J=7.2 Hz), 2.52-2.25 (m, 2H), 1.68-1.55 (m, 2H), 1.40-1.25 (m, 4H), 0.92 (t, 311, J=6.4 Hz); MS ESI 486.3 [M+H]$^+$, calcd for [C$_{26}$H$_{35}$N$_3$O$_4$S+H]$^+$ 486.2.

Example S108

(R)-3-(N-(4-(4-pentylphenethyl)phenyl)sulfamoylamino)-4-(trimethyl-ammonio)butanoate

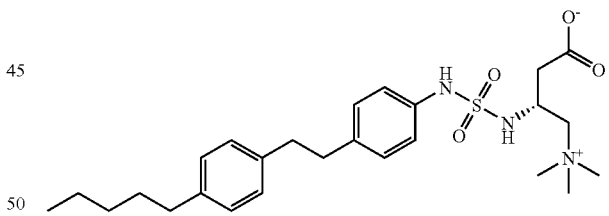

According to the method described in example S105, the title compound (16.0 mg, 97%) was obtained from (R)-3-(N-(4-(4-pentylphenethyl)phenyl)sulfamoylamino)-4-(trimethyl-ammonio)butanoate (16.5 mg, 0.034 mmol). $^1$H NMR (400 MHz, CD$_3$OD) δ 7.15-6.95 (m, 8H), 4.20-4.08 (m, 1H), 3.40-3.33 (m, 2H), 3.18 (s, 9H), 2.83 (s, 4H), 2.56 (t, 2H, J=7.6 Hz), 2.40 (dd, 1H, J=16.4 Hz, J=2.8 Hz), 2.25 (dd, 1H, J=16.0 Hz, J=9.2 Hz), 1.63-1.50 (m, 2H), 1.40-1.25 (m, 4H), 0.91 (t, 3H, J=6.6 Hz); MS ESI 490.3 [M+H]$^+$, calcd for [C$_{26}$H$_{39}$N$_3$O$_4$S+H]$^+$ 490.3.

Example S109

(R)-3-(N-(5-(3-(hexyloxy)phenoxy)pentyl)-N-methylsulfamoylamino)-4-(trimethylammonio)butanoate

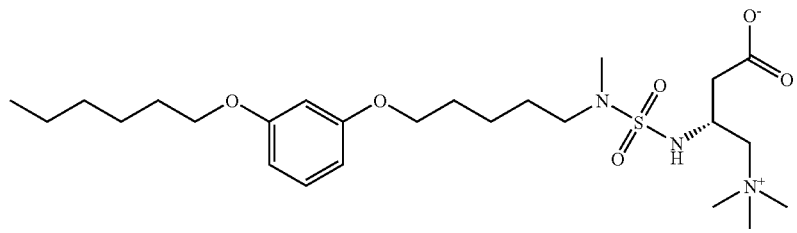 [SMILES: CCCCCCOc1cccc(OCCCCCN(C)S(=O)(=O)N[C@H](CC(=O)[O-])C[N+](C)(C)C)c1]

According to the method described in example S93, the title compound (11 mg, 20%) was obtained from (R)-3-(2-oxooxazolidine-3-sulfonamido)-4-(trimethylammonio)-butanoate (0.108 mmol) and 5-(3-(hexyloxy)phenoxy)-N-methylpentan-1-amine (30 mg, 0.108 mmol). $^1$H NMR (400 MHz, CD$_3$OD) δ 7.13 (t, 1H, J=8.0 Hz), 6.52-6.43 (m, 3H), 4.15-4.08 (m, 1H), 4.00-3.90 (m, 4H), 3.50-3.38 (m, 2H), 3.27 (s, 9H), 3.21 (t, 2H, J=7.2 Hz), 2.81 (s, 3H), 2.57-2.40 (m, 2H), 1.85-1.65 (m, 6H), 1.57-1.43 (m, 4H), 1.40-1.30 (m, 4H), 0.94 (t, 3H, J=6.0 Hz); MS ESI 516.4 [M+H]$^+$, calcd for [C$_{25}$H$_{45}$N$_3$O$_6$S+H]$^+$ 516.3.

Example S110

(R)-3-(N-(3-(oct-1-ynyl)phenyl)sulfamoylamino)-4-(trimethylammonio) butanoate

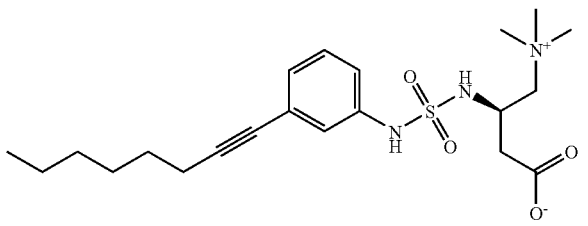 [SMILES: CCCCCCC#Cc1cccc(NS(=O)(=O)N[C@H](CC(=O)[O-])C[N+](C)(C)C)c1]

a) 3-(oct-1-ynyl)aniline

Using the method for the preparation of 4-(non-1-ynyl)aniline (example S104), 3-(oct-1-ynyl)aniline was obtained as a light yellow oil (1.75 g, 87%) from 3-iodoaniline (2.19 g, 10 mmol) and oct-1-yne (2.5 mL). $^1$H NMR (400 MHz, CDCl$_3$) 7.08 (t, 1H, J=7.6 Hz), 6.82 (d, 1H, J=6.0 Hz), 6.74 (s, 1H), 6.62 (d, 1H, J=6.0 Hz), 3.69 (s, br, 2H, NH$_2$), 2.39 (t, 2H, J=6.8 Hz), 1.65-1.25 (m, 8H), 0.91 (t, 3H, J=6.8 Hz).

b) (R)-3-(N-(3-(oct-1-ynyl)phenyl)sulfamoylamino)-4-(trimethylammonio) butanoate According to the method described in example S93, the title compound (52 mg, 25%) was obtained from (R)-3-(2-oxooxazolidine-3-sulfonamido)-4-(trimethylammonio)-butanoate (0.5 mmol) and 3-(oct-1-ynyl)aniline (131 mg, 0.65 mmol). $^1$H NMR (400 MHz, CD$_3$OD) δ 7.25-7.18 (m, 2H), 7.12 (d, 1H, J=7.6 Hz), 7.01 (d, 1H, J=7.6 Hz), 4.21-4.04 (m, 1H), 3.40-3.35 (m, 2H), 3.21 (s, 9H), 2.42-2.35 (m, 3H), 2.25 (dd, 1H, J=16.4 Hz, J=8.8 Hz), 1.59 (quint, 2H, J=7.6 Hz), 1.48 (quint, 2H, J=7.6 Hz), 1.40-1.28 (m, 4H), 0.94 (t, 3H, J=6.6 Hz); MS ESI 424.3 [M+H]$^+$, calcd for [C$_{21}$H$_{33}$N$_3$O$_4$S+H]$^+$ 424.2.

Example S111

(R)-3-(N-(3-octylphenyl)sulfamoylamino)-4-(trimethylammonio)-butanoate

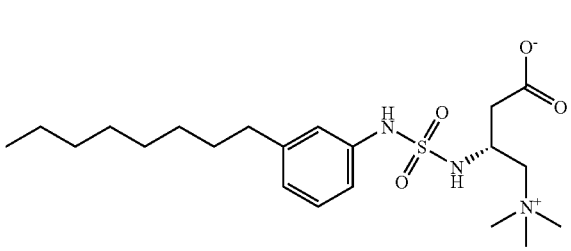 [SMILES: CCCCCCCCc1cccc(NS(=O)(=O)N[C@H](CC(=O)[O-])C[N+](C)(C)C)c1]

According to the method described in example S105, the title compound (24 mg, 96%) was obtained from (R)-3-(N-(3-(oct-1-ynyl)phenyl)sulfamoylamino)-4-(trimethyl-ammonio) butanoateate (25 mg, 0.059 mmol). $^1$H NMR (400 MHz, CD$_3$OD) δ 7.20 (t, 1H, J=8.2 Hz), 7.07-7.02 (d, 1H, J=6.4 Hz at 7.05 and s, 1H at 7.04, overlapping with each other), 6.89 (d, 1H, J=7.6 Hz), 4.22-4.15 (m, 1H), 3.39 (d, 2H, J=5.6 Hz), 3.21 (s, 9H), 2.58 (t, 2H, J=7.6 Hz), 2.38 (dd, 1H, J=16.0 Hz, J=3.2 Hz), 2.21 (dd, 1H, J=16.4 Hz, J=9.2 Hz), 1.61 (quint, 2H, J=7.2 Hz), 1.40-1.35 (m, 10H), 0.91 (t, 3H, j=6.6 Hz); MS ESI 428.3 [M+H]+, calcd for [C21H37N3O4S+H]+ 428.3.

Example S112

(R)-3-(N—(N-methyl-N-(3-(oct-1-ynyl)phenyl)sulfamoyl)amino)-4-(trimethyl-ammonio)butanoate

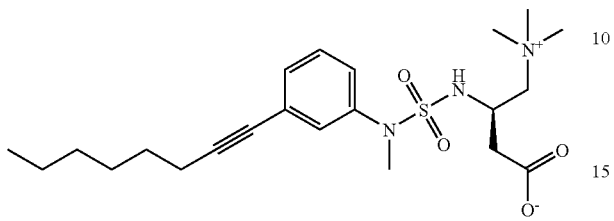

1) N-methyl-3-(oct-1-ynyl)aniline

To a solution of 3-(oct-1-ynyl)aniline (1.34 g, 6.67 mmol) in MeOH (35 mL) was added NaOMe (25% wt. in MeOH, 7.7 mL), followed by paraformaldehyde (1.0 g, 33.3 mmol). The resulting mixture was refluxed 2 h under argon. After cooling to 0° C., NaBH4 (1.27 g, 33.4 mmol) was added and the mixture was refluxed for 90 min. The reaction mixture was then cooled to rt, quenched with ice and extracted with dichloromethane (50 mL+30 mL). The combined extracts were washed with H2O and brine and dried (Na2SO4). Flash chromatography (eluent: EtOAc/Hex=1:10 to 1:6) gave N-methyl-3-(oct-1-ynyl)aniline as a light yellow oil (920 mg, 64%). 1H NMR (400 MHz, CDCl3) δ 7.10 (t, 1H, J=7.8 Hz), 6.77 (d, 1H, J=7.2 Hz), 6.66 (s, 1H), 6.55 (d, 1H, J=8.4 Hz), 3.80 (s, br, 1H, NH), 2.84 (s, 3H), 2.40 (t, 3H, J=7.0 Hz), 1.61 (quint, 2H, J=7.4 Hz), 1.46 (quint, 2H, J=6.8 Hz), 1.38-1.25 (m, 4H), 0.92 (t, 3H, J=6.6 Hz).

b) (R)-3-(N—(N-methyl-N-(3-(oct-1-ynyl)phenyl)sulfamoyl)amino)-4-(trimethyl-ammonio)butanoate According to the method described in example S93, the title compound (18 mg, 8%) was obtained from crude (R)-3-(2-oxooxazolidine-3-sulfonamido)-4-(trimethylammonio)-butanoate (0.5 mmol) and N-methyl-3-(oct-1-ynyl)aniline (118 mg, 0.55 mmol). 1H NMR (400 MHz, CD3OD) δ 7.45 (s, 1H), 7.38 (d, 1H, J=8.0 Hz), 7.30 (t, 1H, J=7.8 Hz), 7.22 (d, 1H, J=7.6 Hz), 4.23-4.16 (m, 1H), 3.50-3.35 (m, 2H), 3.26 (s, 3H), 3.20 (s, 9H), 2.60 (dd, 1H, J=16.4 Hz, J=3.2 Hz), 2.43-2.35 (m, 3H), 1.60 (quint, 2H, J=7.3 Hz), 1.48 (quint, 2H, J=7.4 Hz), 1.40-1.30 (m, 4H), 0.94 (t, 3H, J=6.8 Hz); MS ESI 438.3 [M+H]+, calcd for [C22H35N3O4S+H]+ 438.2.

Example S113

(R)-3-carboxy-N,N,N-trimethyl-2-(N-methyl-N-(3-octylphenyl)sulfamoylamino)propan-1-aminium 2,2,2-trifluoroacetate

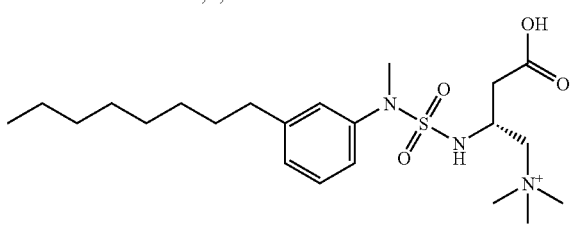

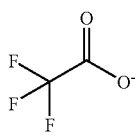

According to the method described in example S105, the title compound (3.0 mg, 24%) was obtained as TFA salt from (R)-3-(N-methyl-N-(3-(oct-1-ynyl)phenyl)sulfamoyl-amino)-4-(trimethyl-ammonio)butanoate (10 mg, 0.023 mmol) after purification by prep-HPLC. 1H NMR (400 MHz, CD3OD) δ 7.34-7.23 (m, 3H), 7.14 (d, 1H, J=7.6 Hz), 4.23-4.17 (m, 1H), 3.56-3.44 (m, 2H), 3.32 (m, 2H), 3.27 (s, 3H), 3.17 (s, 9H), 2.66-2.58 (m, 4H), 1.67-1.58 (m, 2H), 1.38-1.27 (m, 10H), 0.91 (t, 3H, J=7.2 Hz); MS ESI 442.3 [M+H]+, calcd for [C22H39N3O4S+H]+ 442.3.

Example S114

(R)-3-(5-bromofuran-2-carboxamido)-4-(trimethylammonio)butanoate

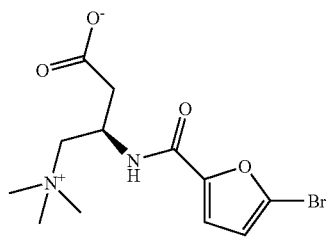 [SMILES: C[N+](C)(C)C[C@@H](CC(=O)[O-])NC(=O)c1ccc(Br)o1]

According to the method described in example 2, R-aminocarnitine was reacted with 2,5-dioxopyrrolidin-1-yl 5-bromofuran-2-carboxylate, prepared as described in preparation 4, to give the title compound as a white powder (943 mg, 55%). 1H NMR (400 MHz, D2O) δ 7.07 (d, 1H, J=3.6 Hz), 6.53 (d, 1H, J=3.6 Hz), 4.80 (m, 1H), 3.63-3.45 (m, 2H), 3.10 (s, 9H), 2.46 (m, 2H); MS ESI [M+H]+, calcd for [C12H17BrN2O4+H]+333.04; found m/z 333.0.

Example S115

(R)-3-carboxy-N,N,N-trimethyl-2-(5-((4-pentylphenyl)ethynyl)furan-2-carboxamido)propan-1-aminium 2,2,2-trifluoroacetate

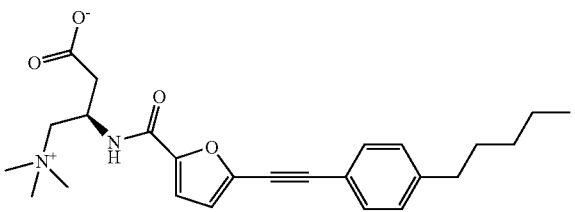 [SMILES: CCCCCc1ccc(C#Cc2ccc(C(=O)N[C@H](CC(=O)[O-])C[N+](C)(C)C)o2)cc1]

To a solution of (R)-3-(5-bromofuran-2-carboxamido)-4-(trimethylammonio)butanoate (40 mg, 0.12 mmol) in DMF (1 mL) and water (0.1 mL). was added triethylamine (0.033 mL, 0.24 mmol), copper iodide (1.1 mg, 0.006 mmol) and bis(triphenylphosphine) palladium (II) dichloride (2.1 mg, 0.003 mmol). The mixture was purged with nitrogen, then 1-ethynyl-4-pentylbenzene (0.026 mL, 0.13 mmol) was added. After stirring at 60° C. for 1.5 hours, the mixture was cooled and filtered through celite. The filter cake was washed with methanol, and the filtrate was concentrated. The residue was purified by reverse phase. HPLC to give the title compound as a white powder (8.8 mg, 13%). 1H NMR (400 MHz, D2O) δ 7.11 (br, 3H), 6.76 (br, 2H), 6.41 (br, 1H), 4.81 (br, 1H), 3.71-3.49 (m, 2H), 3.07 (s, 9H), 2.63-2.56 (m, 2H), 2.20 (br, 2H), 1.21 (br, 2H), 0.96 (br, 4H), 0.58 (br, 3H); MS ESI [M+H]+, calcd for [C25H32N2O4+H]+ 425.24; found m/z 425.3.

Example S116

(R)-3-carboxy-N,N,N-trimethyl-2-(5-(thiophen-3-ylethynyl)furan-2-carboxamido)propan-1-aminium 2,2,2-trifluoroacetate

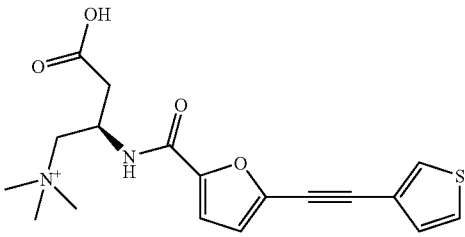 [SMILES: C[N+](C)(C)C[C@@H](CC(=O)O)NC(=O)c1ccc(C#Cc2ccsc2)o1]

According to the method described in Example S115, (R)-3-(5-bromofuran-2-carboxamido)-4-(trimethylammonio)butanoate was reacted with 3-ethynylthiophene to give the title compound as a white powder (2.5 mg, 4%). $^1$H NMR (400 MHz, D$_2$O) δ 7.66 (br, 1H), 7.36 (br, 1H), 7.13 (m, 1H), 7.10 (d, 1H, J=3.6 Hz), 6.70 (d, 1H, J=3.6 Hz), 4.90-4.85 (m, 1H), 3.70-3.51 (m, 2H), 3.09 (s, 9H), 2.78-2.66 (m, 2H); MS ESI [M+H]$^+$, calcd for [C$_{18}$H$_{20}$N$_2$O$_4$S+H]$^+$ 361.12; found m/z 361.1.

Example S117

(R)-3-carboxy-2-(54(2-methoxypyrimidin-5-yl)ethynyl)furan-2-carboxamido)-N,N,N-trimethylpropan-1-aminium 2,2,2-trifluoroacetate

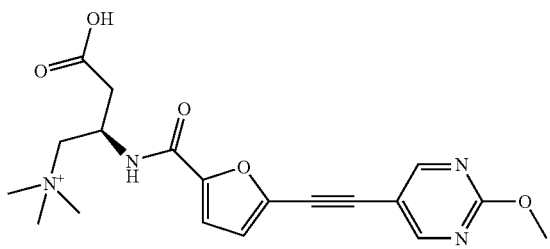

a) 2-methoxy-5-((trimethylsilyl)ethynyl)pyrimidine

To a solution of 5-bromo-2-methoxypyrimidine (500 mg, 2.7 mmol) in ethyl acetate (2 mL) and water (0.2 mL) was added trimethylsilylethane (0.41 mL, 3 mmol), triethylamine (0.75 mL, 5.4 mmol), copper iodide (25 mg, 0.13 mmol) and bis(triphenylphosphine)palladium(II) dichloride (47 mg, 0.067 mmol). The solution was heated to 60° C. for 16 h. Ethyl acetate (100 mL) was added and the solution was washed with water (3×10 mL), dried over MgSO$_4$ and treated with decolorizing charcoal. Ethyl acetate was removed in vacuo to give the title compound as a clear oil (547 mg, 97%). $^1$H NMR (400 MHz, CDCl$_3$) δ 8.56 (s, 2H), 4.01 (s, 3H), 0.24 (s, 9H).

b) 5-ethynyl-2-methoxypyrimidine

To a solution of 2-methoxy-5-((trimethylsilyl)ethynyl)pyrimidine (520 mg, 2.5 mmol) in DMF (10 mL) and water (1 mL) was added potassium fluoride (290 mg, 5 mmol) and the mixture was stirred at 0° C. for 1 h. Diethyl ether (100 mL) was added and the solution was washed with water (2×10 mL) and brine (10 mL), dried over MgSO$_4$ and concentrated. The title compound was isolated by silica gel:chromatography (9:1 CH$_2$Cl$_2$/hexane) as a clear oil (120 mg, 36%). $^1$H NMR (400 MHz, CDCl$_3$) δ 8.62 (s, 2H), 4.05 (s, 3H), 3.28 (s, 1H).

c) (R)-3-carboxy-2-(54(2-methoxypyrimidin-5-yl)ethynyl)furan-2-carboxamido)-N,N,N-trimethylpropan-1-aminium 2,2,2-trifluoroacetate According to the method described in example 5115, (R)-3-(5-bromofuran-2-carboxamido)-4-(trimethylammonio)butanoate was reacted with 5-ethynyl-2-methoxypyrimidine to give the title compound as a white powder (6.5 mg, 11%). $^1$H NMR (400 MHz, D$_2$O) δ 8.63 (s, 2H), 7.13 (d, 1H, J=3.6 Hz), 6.80 (d, 1H, J=3.6 Hz), 4.92-4.87 (m, 1H), 3.92 (s, 3H), 3.73-3.53 (m, 2H), 3.11 (s, 9H), 2.80-2.68 (m, 2H). MS ESI [M+H]$^+$, calcd for [C$_{19}$H$_{22}$N$_4$O$_5$+H]$^+$ 387.17; found m/z 387.1.

Example S118

(R)-3-carboxy-2-(5-((5-hexylthiophen-2-yl)ethynyl)furan-2-carboxamido)-N,N,N-trimethylpropan-1-aminium 2,2,2-trifluoroacetate

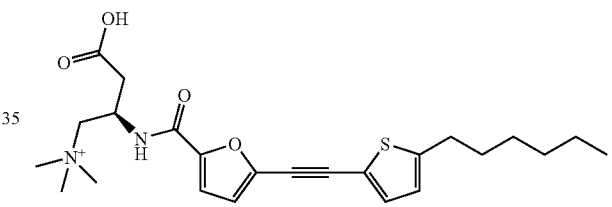

a) ((5-hexylthiophen-2-yl)ethynyl)trimethylsilane

According to the method described in S117a, 2-bromo-5-hexylthiophene (1 g, 4 mmol) was reacted with trimethylsilylethane (0.43 g, 4.4 mmol) to give the title compound as a yellow oil (1.07 g, 100%). $^1$H NMR (400 MHz, CDCl$_3$) δ 7.05 (d, 1H, J=3.6 Hz), 6.61 (d, 1H, J=3.6 Hz), 2.77 (t, 2H, J=7.2 Hz) 1.65-1.56 (m, 2H), 1.36-1.30 (m, 6H), 0.89 (t, 3H, J=6.4 Hz), 0.24 (s, 9H).

b) 2-ethynyl-5-hexylthiophene

According to the method of S117b, ((5-hexylthiophen-2-yl)ethynyl)trimethylsilane (1 g, 3.7 mmol) was reacted with potassium fluoride (429 mg, 7.4 mmol) to give the title compound as a yellow oil following silica gel purification (hexane) (500 mg, 70%). $^1$H NMR (400 MHz, CDCl$_3$) δ 7.10 (d, 1H, J=3.6 Hz), 6.64 (d, 1H, J=3.6 Hz), 2.78 (t, 2H, J=7.2 Hz) 1.68-1.55 (m, 2H), 1.36-1.28 (m, 6H), 0.89 (t, 3H, J=6.4 Hz).

c) (R)-3-carboxy-2-(54(5-hexylthiophen-2-yl)ethynyl)furan-2-carboxamido)-N,N,N-trimethylpropan-1-aminium 2,2,2-trifluoroacetate According to the method described in example 5115, (R)-3-(5-bromofuran-2-carboxamido)-4-(trimethylammonio)butanoate was reacted with 2-ethynyl-5-hexylthiophene to give the title compound as a white powder (5.2 mg, 8%). $^1$H NMR (400 MHz, D$_2$O) δ 6.99 (br, 1H), 6.92 (br, 1H), 6.39 (br, 1H), 6.33 (br, 1H), 4.78 (br, 1H), 3.70-3.46 (m, 2H), 3.04 (s, 9H), 2.66-2.54 (m, 2H), 2.44 (br, 2H), 1.33 (br, 2H), 1.02 (br, 6H), 0.64 (br, 3H); MS ESI [M+H]$^+$, calcd for [C$_{24}$H$_{32}$N$_2$O$_4$S+H]$^+$ 445.22; found m/z 445.3.

Example S119

(R)-3-(5-(2-(5-hexylthiophen-2-yl)ethyl)furan-2-carboxamido)-4-(trimethylammonio)butanoate

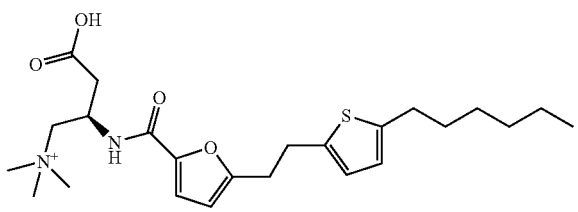 [SMILES: CCCCCCc1ccc(CCc2ccc(C(=O)N[C@H](CC(=O)O)C[N+](C)(C)C)o2)s1]

According to the method described in example S64, (R)-3-(5-((5-hexylthiophen-2-yl)ethynyl)furan-2-carboxamido)-4-(trimethylammonio)butanoate was treated with 10% Pd/C under hydrogen and the product purified to give the title compound as a white powder (14.6 mg, 72%), $^1$H NMR (400 MHz, D$_2$O) δ 6.85 (br, 1H), 6.32 (br, 1H), 6.21 (br, 1H), 5.65 (br, 1H), 3.64 (m, 1H), 3.41-3.38 (m, 2H), 3.01 (s, 9H), 2.72 (br, 2H), 2.61 (br, 2H), 2.38-2.23 (m, 4H); 1.34 (br, 2H), 1.07 (br, 6H), 0.68 (br, 3H); MS ESI [M+H]$^+$, calcd for [C$_{24}$H$_{36}$N$_2$O$_4$S+H]$^+$ 449.25; found m/z 449.3.

Example S120

(R)-3-carboxy-N,N,N-trimethyl-2-(2-oxooctanamido)propan-1-aminium 2,2,2-trifluoroacetate

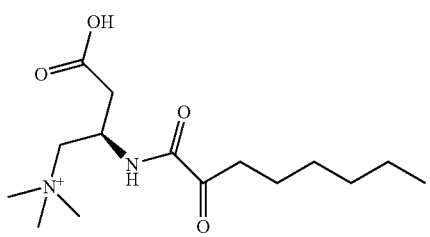 [SMILES: CCCCCCC(=O)C(=O)N[C@H](CC(=O)O)C[N+](C)(C)C]

According to the method described in example 2, R-aminocarnitine was treated with (isobutyl carbonic) 2-oxooctanoic anhydride at room temperature for 2 days and resulting mixture was purified by prep. HPLC to give the title compound as a white powder (7.8 mg, 4%). MS ESI [M+H]$^+$, calcd for [C$_{15}$H$_{28}$N$_2$O$_4$+H]$^+$301.21; found m/z 301.1.

Example S121. (3R)-3-(5-(4-pentylphenethyl)tetrahydrofuran-2-carboxamido)-4-(trimethylammonio)butanoate

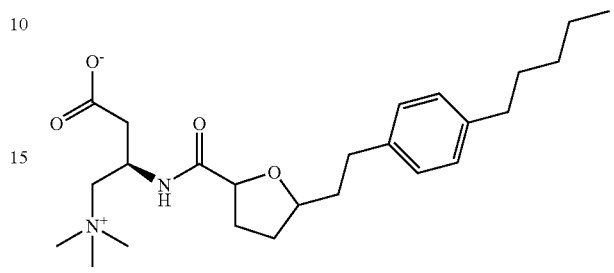

According to the method described in example S64, (R)-3-(5-((4-pentylphenyl)ethynyl)furan-2-carboxamido)-4-(trimethylammonio)butanoate was treated with 10% Pd/C under hydrogen overnight and the product purified to give the title compound as a white powder (16.5 mg, 48%). $^1$H NMR (400 MHz, D$_2$O) δ 6.86 (d, 2H, J=8.2 Hz), 6.75 (d, 2H, J=7.6 Hz), 4.60-4.53 (m, 1H), 4.08-4.01 (m, 1H), 3.61-3.36 (m, 3H), 3.02 (s, 9H), 2.45-2.32 (m, 6H), 1.87-1.50 (m, 5H), 1.35-1.27 (m, 2H), 1.25-1.05 (m, 5H), 0.60-0.55 (m, 3H); MS ESI [M+H]$^+$, calcd for [C$_{25}$H$_{40}$N$_2$O$_4$+H]$^+$ 433.31; found m/z 433.3.

Example S122

(R)-3-(5-((3-(hexyloxy)phenyl)ethynyl)furan-2-carboxamido)-4-(trimethylammonio)butanoate

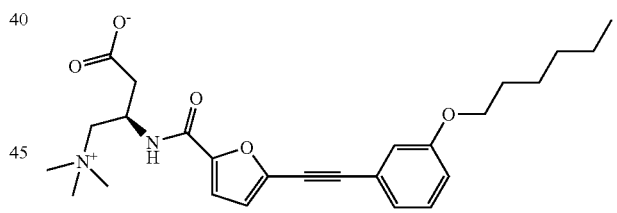

a) ((3-(hexyloxy)phenyl)ethynyl)trimethylsilane

According to the method described in Example S117a, 1-bromo-3-(heptyloxy)benzene (1 g, 4 mmol) was reacted with trimethylsilylethane (0.43 g, 4.4 mmol) to give the title compound as a yellow oil (575 mg, 55%). $^1$H NMR (400 MHz, CDCl$_3$) δ 7.19 (t, 1H, J=7.6 Hz), 7.05 (d, 1H, J=7.2 Hz), 6.99 (s, 1H), 6.87 (d, 1H, J=7.0 Hz), 3.94 (t, 2H, J=6.8 Hz), 1.79-1.75 (m, 2H), 1.47-1.30 (m, 6H), 0.91 (t, 3H, J=6.8 Hz), 0.26 (s, 9H).

b) 1-ethynyl-3-(hexyloxy)benzene

According to the method of Example S117b, ((3-(heptyloxy)phenyl)ethynyl)trimethyl silane (575 mg, 2.1 mmol) was reacted with potassium fluoride (429 mg, 7.4 mmol) to give the title compound as a clear oil following silica gel purification (hexane) (390 mg, 93%). $^1$H NMR (400 MHz, CDCl$_3$) $^1$H NMR (400 MHz, CDCl$_3$) δ 7.22 (t, 1H, J=7.6 Hz), 7.08 (d, 1H, J=7.2 Hz), 7.02 (s, 1H), 6.90 (d, 1H, J=7.0 Hz), 3.95 (t, 2H, J=6.4 Hz), 3.06 (s, 1H) 1.80-1.75 (m, 2H), 1.48-1.30 (m, 6H), 0.92 (t, 3H, J=6.8 Hz).

c) (R)-3-(5-((3-(hexyloxy)phenyl)ethynyl)furan-2-carboxamido)-4-(trimethylammonio)-butanoate According to the method described in example S115, (R)-3-(5-bromofuran-2-carboxamido)-4-(trimethylammonio) butanoate was reacted with 1-ethynyl-3-(hexyloxy)benzene. The crude product was purified by silica gel chromatography (CH$_2$Cl$_2$/MeOH 3:2) to give the title compound as a white powder (11.1 mg, 20%). $^1$H NMR (400 MHz, D$_2$O) δ 6.94-6.89 (m, 2H), 6.81-6.79 (m, 1H), 6.57 (s, 1H), 6.46-6.44 (m, 1H), 6.30 (s, 1H), 4.80-4.76 (m, 1H), 3.67-3.45 (m, 4H), 3.01 (s, 9H), 2.44-2.35 (m, 2H), 1.38-1.32 (m, 2H), 1.10-0.95 (m, 6H), 0.61 (t, 3H, J=6.4 Hz); MS ESI [M+H]$^+$, calcd for [C$_{26}$H$_{34}$N$_2$O$_5$+H]$^+$ 455.25; found m/z 455.3.

Example S123. (R)-3-carboxy-N,N,N-trimethyl-2-(5-(4-pentylphenethyl)furan-2-carboxamido)propan-1-aminium 2,2,2-trifluoroacetate

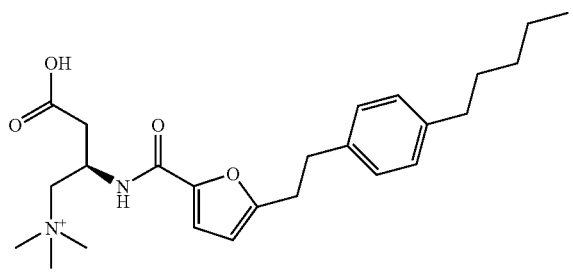 [SMILES: CCCCCc1ccc(CCc2ccc(C(=O)N[C@H](CC(=O)O)C[N+](C)(C)C)o2)cc1]

According to the method described in example S64, (R)-3-(5-((4-pentylphenyl)ethynyl)furan-2-carboxamido)-4-(trimethylammonio)butanoate was treated with 10% Pd/C under hydrogen and the product purified by prep. HPLC to give the title compound as a white powder (4.9 mg, 39%). $^1$H NMR (400 MHz, D$_2$O) δ 6.83 (d, 1H, J=2.8 Hz), 6.70-6.65 (m, 4H), 5.61 (d, 1H, J=2.8 Hz), 4.80-4.76 (m, 1H), 3.69-3.63 (m, 1H), 3.45-3.42 (m, 1H), 3.00 (s, 9H), 2.65-2.49 (m, 6H), 2.18-2.12 (m, 2H), 1.27-1.13 (m, 2H), 1.05-0.95 (m, 4H), 0.60 (t, 3H, J=7.0 Hz); MS ESI [M+H]$^+$, calcd for [C$_{25}$H$_{36}$N$_2$O$_4$+H]$^+$ 429.27; found m/z 429.3.

Example S124
(R)-3-carboxy-N,N,N-trimethyl-2-(5-(2-(thiophen-3-yl)ethyl)furan-2-carboxamido)propan-1-aminium 2,2,2-trifluoroacetate

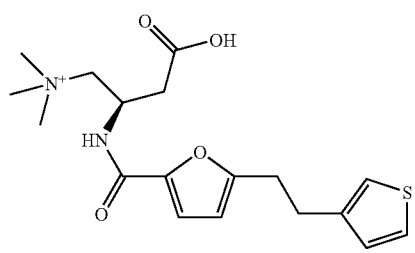 [SMILES: C[N+](C)(C)C[C@@H](CC(=O)O)NC(=O)c1ccc(CCc2ccsc2)o1]

According to the method described in example S64, (R)-3-(5-(thiophen-3-ylethynyl)furan-2-carboxamido)-4-(trimethylammonio)butanoate was treated with 10% Pd/C under hydrogen and the product purified by prep. HPLC to give the title compound as a white powder (1.4 mg, 6%). $^1$H NMR (400 MHz, D$_2$O) δ 7.25-7.23 (m, 1H), 6.98 (d, 1H, J=3.2 Hz), 6.94 (s, 1H), 6.85 (d, 1H, J=4.8 Hz), 6.14 (d, 1H, J=3.2 Hz), 4.89-4.86 (m, 1H), 3.66-3.49 (m, 2H), 3.08 (s, 9H), 2.92 (s, 4H), 2.75-2.63 (m, 2H); MS ESI [M+H]$^+$, calcd for [C$_{18}$H$_{24}$N$_2$O$_4$S+H]$^+$ 365.15; found m/z 365.2.

Example S125

(R)-3-carboxy-2-(5-(3-(hexyloxy)phenethyl)furan-2-carboxamido)-N,N,N-trimethylpropan-1-aminium 2,2,2-trifluoroacetate

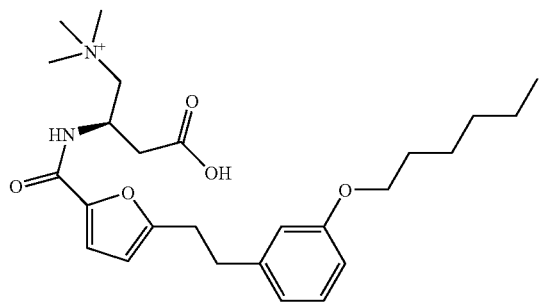 [SMILES: CCCCCCOc1cccc(CCc2ccc(C(=O)N[C@H](CC(=O)O)C[N+](C)(C)C)o2)c1]

According to the method described in example S64, (R)-3-(5-((3-(hexyloxy)phenyl)ethynyl)furan-2-carboxamido)-4-(trimethylammonio)butanoate was treated with 10% Pd/C under hydrogen and the product purified by prep. HPLC to give the title compound as a white powder (7.3 mg, 14.5%). $^1$H NMR (400 MHz, D$_2$O) δ 6.81-6.75 (m, 2H), 6.40 (d, 1H, J=7.2 Hz), 6.35 (s, 1H), 6.30 (d, 1H, J=7.6 Hz), 5.60 (s, 1H), 4.80-4.76 (m, 1H), 3.69-3.63 (m, 1H), 3.48-3.42 (m, 3H), 3.01 (s, 9H), 2.65-2.49 (m, 6H), 1.42-1.32 (m, 2H), 1.18-0.95 (m, 6H), 0.65 (t, 3H, J=6.4 Hz); MS ESI [M+H]$^+$, calcd for [C$_{26}$H$_{38}$N$_2$O$_5$+H]$^+$ 459.29; found m/z 459.4.

Example 2

Expression and Preparation of CPT1 Proteins

Nucleotide sequences encoding human CPT1 enzymes were individually cloned into the yeast expression vector pESC-trp at the Cla1 (5' terminus) and Pac1 (3' terminus) restriction sites by PCR amplification of the open reading frame using oligonucleotide primers designed to encode the wild-type CPT1 protein sequence. Standard molecular biology techniques were used to transform and express the CPT1 proteins in the yeast *Saccharomyces cerevisiae*. The yeast cells were lysed by enzymatic degradation of the cell wall by Zymolase, and the mitochondria were isolated by standard biochemical techniques. The integrity of the isolated mitochondria was monitored by determining the activity of succinate dehydrogenase in the mitochondrial preparations. The mitochondrial extracts were stored at −80° C. in buffer containing 10 mM HEPES pH 7.4 and 250 mM sucrose.

Human CPT1 (A, B, C) genes were additionally cloned into the pCDNA3.1 vector individually for expression in cultured mammalian cells. Cells expressing the exogenous CPT1A were identified and grown under standard conditions. Mammalian cells were harvested, and mitochondrial extracts prepared using standard biochemical methods. The mitochondrial extracts were stored at −80° C. in buffer containing 10 mM HEPES pH 7.4 and 250 mM sucrose.

Example 3

Human CPT1A LC/MS Assay

Assays were performed in 96-well plate format. Each 100 µL reaction contained 40 mM KCl, 50 mM TrisHCl pH 7.5, and 250 mM mannitol (Assay Buffer), and 1.6 µg protein of an extract, 20 µM palmitoyl-CoA, 50 µM L-carnitine, and 10 ug/mL BSA. Reactions were incubated at room temperature and stopped after 10 minutes by extraction with 200 µL of water saturated n-butanol containing myristoyl carnitine (500 nM) as an internal standard. The samples were thoroughly mixed, and the phases separated by centrifugation. Samples were prepared for analysis with a 10 fold dilution of the n-butanol phase containing the reaction product palmitoyl carnitine into a 50:50 (acetonitrile:water) solvent for analysis. 5 of prepared sample was separated on a Phenomenex Jupiter 5µ C4 reverse-phase column using an Agilent 1100 HPLC with a gradient from 50% acetonitrile (0.5% acetic acid) to 100% acetonitrile and quantified by detection with a Bruker Esquire 3000plus mass spectrometer. The abundance of the palmitoyl carnitine product was determined relative to the internal standard and the actual quantity of palmitoyl carnitine can be determined from a standard curve prepared using the n-butanol solution containing the internal standard.

Compounds were evaluated in two formats, a screening format, and a dose response format. The screening format was performed by adding 25 µL compound in 20% DMSO and Assay Buffer to 25 µL of extract containing 100 µM carnitine and Assay Buffer, followed by a 10 minute incubation at room temperature. 50 µL of 40 µM palmitoyl-CoA in Assay Buffer was added to the reaction mixture, mixed and incubated for 10 minutes at room temperature. A negative control for activity was also performed where the carnitine was omitted from the reaction. A positive control for activity was also performed by omitting compound from the solution containing 20% DMSO and Assay Buffer. The reaction mixture was extracted and analyzed as described above. The inhibition by compound was determined by comparing the control relative activity to the relative activity observed in wells containing the compound. Relative activity was determined by subtracting the relative intensity (area palmitoyl carnitine/area myristoyl carnitine) observed in the negative control from the relative intensity observed in the experimental well, and dividing by the relative activity observed in the positive control.

$$\% \text{ Inhibition} = 1 - \left( \frac{\left(\frac{\text{Experimental Target}}{\text{ISTD ratio}}\right) - \left(\frac{\text{Negative Control Target}}{\text{ISTD ratio}}\right)}{\left(\frac{\text{Positive Control Target}}{\text{ISTD ratio}}\right) - \left(\frac{\text{Negative Control Target}}{\text{ISTD ratio}}\right)} \right) \times 100$$

Compound characterization by dose response format was performed using the above described assay conditions and a 16 point compound titration in 2 fold compound dilution steps. The DMSO concentration was kept constant at 20% (v/v) for all compound concentrations. The inhibitory activity of a compound was determined using an iterative 4 parameter logistic non linear curve fitting method, and the concentration of compound that inhibits the enzyme reaction by 50% is defined as the $IC_{50}$.

$y = (A + (B/(1+((x/C)^D))))$ where

A=background activity
B=dynamic range
C=x value at inflection point
D=stoichiometry parameter Using the dose response assay the $IC_{50}$ for L-aminocarnitine was determined to be 7.0±2.5 µM (n=17). Similarly, using the dose response assay, the compounds of this invention were determined to have $IC_{50}$ values of less than or equal to about 5 millimolar and greater than 10 nanomolar.

The results of human CPT1A LC/MS assayes are summarized in Table 1 below. In Table 1, $IC_{50}$ values are indicated as "A," "B," "C," "D," "E" and "F" for those of less than or equal to 1 µM; those of greater than 1 µM, and less than or equal to 10 µM; those of greater than 10 µM, and less than or equal to 100 µM; those of greater than 100 µM, and less than or equal to 1,000 µM; those of greater than 1,000 µM, and less than or equal to 2,500 µM those of greater than 2,500 µM, respectively. As shown in Table 1, numerous compounds of the invention were shown to be CPT1A inhibitors.

TABLE 1

$IC_{50}$ Values of CPT1A Inhibitors of the Invention

| Compounds | $IC_{50}$ |
|---|---|
| Example S1. (R)-3-(4-propoxybenzamido)-4-(trimethylammonio)butanoate | D |
| Example S6. (R)-3-(3-(2-chloro-4-(trifluoromethyl)phenyl)ureido)-4-(trimethylammonio)-butanoate | D |
| Example S7. (R)-3-(3-(4-octylphenyl)ureido)-4-(trimethylammonio)butanoate | B |
| Example S8. (R)-3-(3-(4-phenoxyphenyl)ureido)-4-(trimethylammonio)butanoate | C |
| Example S9. (R)-3-(3-(4-methyl-2-phenylthiazol-5-yl)ureido)-4-(trimethylammonio)-butanoate | E |
| Example S10. (R)-3-(3-(4-(heptyloxy)phenyl)ureido)-4-(trimethylammonio)butanoate | C |
| Example S11. (R)-3-(3-(4-(thiophen-2-yl)phenyl)ureido)-4-(trimethylammonio)butanoate | D |
| Example S17. (R)-2-(3-Biphenyl-4-ylureido)-3-carboxy-N,N,N-trimethylpropan-1-aminium acetate | D |
| Example S16. (R)-2-(3-(4-Benzoylphenyl)ureido)-3-carboxy-N,N,N-trimethylpropan-1-aminium acetate | C |
| Example S15. (R)-3-Carboxy-N,N,N-trimethyl-2-(3-(4-pentylphenyl)ureido)propan-1-aminium | C |
| Example S2. (R)-3-(4-(thiophene-2-sulfonamido)benzamido)-4-(trimethylammonio)-butanoate | D |
| Example S3. (R)-3-(5-(phenylethynyl)furan-2-carboxamido)-4-(trimethylammonio)-butanoate | C |
| Example S4. (R)-3-(5-(hex-1-ynyl)furan-2-carboxamido)-4-(trimethylammonio)butanoate | C |
| Example S5. (R)-3-(4-(3-methylfuran-2-carboxamido)benzamido)-4-(trimethylammonio)-butanoate | D |
| Example S14. (R)-3-Carboxy-N,N,N-trimethyl-2-(3-(2,3,4-trifluorophenyl)ureido)-propan-1-aminium acetate | E |
| Example S13. (R)-2-(3-(4-Butyl-2-methylphenyl)ureido)-3-carboxy-N,N,N-trimethylpropan-1-aminium | E |
| Example S100. (R)-3-carboxy-N,N,N-trimethyl-2-(3-(2-phenoxyphenyl)ureido)propan-1-aminium | F |
| Example S12. (R)-3-(3-(4-(Benzyloxy)phenyl)ureido)-4-(trimethylammonio)butanoate acetate | D |
| Example S44. (R)-3-(2,2'-bithiophene-5-carboxamido)-4-(trimethylammonio)butanoate | D |
| Example S42. (R)-3-(5-phenethylfuran-2-carboxamido)-4-(trimethylammonio)-butanoate | A |
| Example S43. (R)-3-(5-(phenylethynyl)thiophene-2-carboxamido)-4-(trimethylammonio)-butanoate | A |
| Example S45. (R)-3-(5-phenethylthiophene-2-carboxamido)-4-(trimethylammonio)-butanoate | A |
| Example S101. (R)-2-(3-biphenyl-2-ylureido)-3-carboxy-N,N,N-trimethylpropan-1-aminium | E |
| Example S50. (R)-3-(6-phenoxynicotinamido)-4-(trimethylammonio)butanoate | D |
| Example S51. (R)-3-(4-methyl-2-(pyrazin-2-yl)thiazole-5-carboxamido)-4-(trimethyl-ammonio)butanoate | F |

TABLE 1-continued

IC$_{50}$ Values of CPT1A Inhibitors of the Invention

| Compounds | IC$_{50}$ |
|---|---|
| Example S49. (R)-3-carboxy-N,N,N-trimethyl-2-(4-methyloxazole-5-carboxamido)-propan-1-aminium | D |
| Example S52. (R)-3-(6-(2,2,2-trifluoroethoxy)nicotinamido)-4-(trimethylammonio)butanoate | E |
| Example S38. (R)-3-(3-(3-Phenoxyphenyl)ureido)-4-(trimethylammonio)butanoate | D |
| Example S84. (R)-3-(3-(3-(1H-pyrrol-1-yl)phenyl)ureido)-4-(trimethylammonio)butanoate | D |
| Example S53. (R)-3-(4-acetamidobenzamido)-4-(trimethylammonio)butanoate | F |
| Example S85. (R)-3-(3-(2-chloro-5-(trifluoromethyl)phenyl)ureido)-4-(trimethyl-ammonio)butanoate | E |
| Example S54. (R)-3-(3-methyl-1-propyl-1H-pyrazole-4-carboxamido)-4-(trimethyl-ammonio)butanoate | E |
| Example S23. (R)-3-(4-pentylphenylsulfonamido)-4-(trimethylammonio)butanoate 2,2,2-trifluoroacetate | B |
| Example S86. (R)-3-(3-(3-benzylphenyl)ureido)-4-(trimethylammonio)butanoate | D |
| Example S55. (R)-3-(5-((2-methoxy-4-propylphenoxy)methyl)furan-2-carboxamido)-4-(trimethylammonio)butanoate | C |
| Example S21: (R)-3-(5-(pyridin-2-yl)thiophene-2-sulfonamido)-4-(trimethylammonio)-butanoate 2,2,2-trifluoroacetate | E |
| Example S56. (R)-3-(5-(benzylthiomethyl)furan-2-carboxamido)-4-(trimethylammonio)-butanoate | B |
| Examples S33 (R)-4-(dimethylammonio)-3-(3-methyl-3-(4-phenoxyphenyl)-ureido)butanoate | F |
| Example S22: (R)-3-carboxy-2-(5-(isoxazol-5-yl)thiophene-2-sulfonamido)-N,N,N-trimethylpropan-1-aminium 2,2,2-trifluoroacetate | E |
| Examples S34. (R)-3-(3-methyl-3-(4-phenoxyphenyl)ureido)-4-(trimethyl-ammonio)butanoate | D |
| Example S72. (R)-3-carboxy-N,N,N-trimethyl-2-(5-(1-methyl-3-(trifluoromethyl)-1H-pyrazol-5-yl)thiophene-2-sulfonamido)propan-1-aminium 2,2,2-trifluoroacetate | D |
| Example S19. (R)-3-carboxy-N,N,N-trimethyl-2-(6-phenoxypyridine-3-sulfonamido)propan-1-aminium 2,2,2-trifluoroacetate | D |
| Example S57. (R)-3-(3-(1H-pyrazol-3-yl)benzamido)-4-(trimethylammonio)butanoate trifluoroacetate | F |
| Example S58. (R)-3-(5-((naphthalen-1-yloxy)methyl)furan-2-carboxamido)-4-(trimethyl-ammonio)butanoate | B |
| Example S59. (R)-3-(5-(morpholinomethyl)furan-2-carboxamido)-4-(trimethylammonio)-butanoate | E |
| Example S60. (R)-3-(5-((4-tert-butylphenoxy)methyl)furan-2-carboxamido)-4-(trimethylammonio)-butanoate | D |
| Example S73. (R)-3-carboxy-N,N,N-trimethyl-2-(4-(octyloxycarbonylamino)phenyl-sulfonamido)propan-1-aminium 2,2,2-trifluoroacetate | C |
| Example S74. (R)-3-carboxy-2-(4-ethoxy-3-(morpholine-4-carboxamido)phenyl-sulfonamido)-N,N,N-trimethylpropan-1-aminium 2,2,2-trifluoroacetate | F |
| Example S61. (R)-3-(5-(benzylsulfonylmethyl)furan-2-carboxamido)-4-(trimethyl-ammonio)butanoate 2,2,2-trifluoroacetate | D |
| Example S62. (R)-3-(4-(phenylethynyl)benzamido)-4-(trimethylammonio)butanoate 2,2,2-trifluoroacetate | C |
| Example S63. (R)-3-(4-(decyloxy)benzamido)-4-(trimethylammonio)butanoate 2,2,2-trifluoroacetate | A |
| Example S30 (R)-3-(N-(4-octylphenyl)sulfamoylamino)-4-(trimethylammonio)butanoate | A |
| Example S64. (R)-3-(4-phenethylbenzamido)-4-(trimethylammonio)butanoate | C |
| Example S65. (R)-3-(3-methyl-5-(phenoxymethyl)furan-2-carboxamido)-4-(trimethyl-ammonio)butanoate | D |
| Example S66. (R)-3-(4-decylbenzamido)-4-(trimethylammonio)butanoate | A |
| Example S75. (R)-3-carboxy-2-(4-decylphenylsulfonamido)-N,N,N-trimethylpropan-1-aminium 2,2,2-trifluoroacetate | B |
| Example S76. (R)-3-carboxy-N,N,N-trimethyl-2-(5-(m-tolylethynyl)thiophene-2-sulfonamido)propan-1-aminium 2,2,2-trifluoroacetate | D |
| Example S67. (R)-3-(3-(decyloxy)benzamido)-4-(trimethylammonio)butanoate | C |
| Example S78. (R)-3-carboxy-N,N,N-trimethyl-2-(5-(phenylethynyl)thiophene-2-sulfonamido)propan-1-aminium 2,2,2-trifluoroacetate | D |
| Example S77. (R)-3-carboxy-N,N,N-trimethyl-2-(5-(3-methylphenethyl)thiophene-2-sulfonamido)propan-1-aminium 2,2,2-trifluoroacetate | C |
| Example S82. (R)-3-carboxy-N,N,N-trimethyl-2-(5-((4-pentylphenyl)ethynyl)thiophene-2-sulfonamido)propan-1-aminium 2,2,2-trifluoroacetate | B |
| Example S80. (R)-3-carboxy-N,N,N-trimethyl-2-(5-(p-tolylethynyl)thiophene-2-sulfonamido)propan-1-aminium 2,2,2-trifluoroacetate | C |
| Example S79. (R)-3-carboxy-N,N,N-trimethyl-2-(5-phenethylthiophene-2-sulfonamido)-propan-1-aminium 2,2,2-trifluoroacetate | C |
| Example S90. (R)-3-(N-(4-tetradecylphenyl)sulfamoylamino)-4-(trimethylammonio)-butanoate | A |
| Example S89. (R)-3-(N-(4-dodecylphenyl)sulfamoylamino)-4-(trimethylammonio)-butanoate | A |
| Example S83. (R)-3-carboxy-N,N,N-trimethyl-2-(5-(4-pentylphenethyl)thiophene-2-sulfonamido)propan-1-aminium 2,2,2-trifluoroacetate | B |
| Example S81. (R)-3-carboxy-N,N,N-trimethyl-2-(5-(4-methylphenethyl)thiophene-2-sulfonamido)propan-1-aminium 2,2,2-trifluoroacetate | B |
| Example S68. (R)-3-(5-((4-ethoxyphenoxy)methyl)furan-2-carboxamido)-4-(trimethyl-ammonio)butanoate | A |
| Example S69. (R)-3-(2,2-difluoro-2-phenylacetamido)-4-(trimethylammonio)butanoate | D |
| Example S70. (R)-3-(5-(m-tolyloxymethyl)furan-2-carboxamido)-4-(trimethylammonio)-butanoate | B |
| Example S99. (R)-3-carboxy-2-(3-(2-iodophenyl)ureido)-N,N,N-trimethylpropan-1-aminium | F |
| Example S27. (R)-3-(N-dodecyl-N-methylsulfamoylamino)-4-(trimethylammonio)-butanoate | A |
| Example S32 (R)-3-(N-dodecyl-N-phenylsulfamoylamino)-4-(trimethylammonio)-butanoate | C |
| Example S46. (R)-3-(3-phenethylbenzamido)-4-(trimethylamnionio)butanoate | D |
| Example S48. (R)-3-(3-(phenylethynyl)benzamido)-4-(trimethylammonio)butanoate | D |
| Example S71. (R)-3-(5-((4-chlorophenylthio)methyl)furan-2-carboxamido)-4-(trimethyl-ammonio)butanoate | A |
| Example S88. (R)-3-(N-(4-heptylphenyl)sulfamoylamino)-4-(trimethylammonio)butanoate | A |
| Example S91. (R)-3-(N-(4-pentylphenyl)sulfamoylamino)-4-(trimethylammonio)butanoate | A |
| Example S92. (R)-3-(N-(4-decylphenyl)sulfamoylamino)-4-(trimethylammonio)butanoate | A |
| Example S93 (R)-3-(N-methyl-N-(4-octylphenyl)sulfamoylamino)-4-(trimethylammonio)-butanoate | C |
| Example S95. (R)-2-(5-bromothiophene-2-carboxamido)-3-carboxy-N,N,N-trimethyl-propan-1-aminium | C |
| Example S96. (R)-3-carboxy-N,N,N-trimethyl-2-(5-((4-pentylphenyl)ethynyl)-thiophene-2-carboxamido)propan-1-aminium 2,2,2-trifluoroacetate | A |
| Example S97. (R)-3-carboxy-N,N,N-trimethyl-2-(5-(thiophen-3-ylethynyl)thiophene-2-carboxamido)propan-1-aminium 2,2,2-trifluoroacetate | A |
| Example S98. (R)-3-carboxy-N,N,N-trimethyl-2-(5-(2-(thiophen-3-yl)ethyl)thiophene-2-carboxamido)propan-1-aminium 2,2,2-trifluoroacetate | A |
| Example S102. (R)-3-carboxy-N,N,N-trimethyl-2-(5-(4-pentylphenethyl)thiophene-2-carboxamido)propan-1-aminium 2,2,2-trifluoroacetate | A |
| Example S103. (R)-3-(N-(4-(octyloxy)phenyl)sulfamoylamino)-4-(trimethylammonio) butanoate | A |
| Example S104 (R)-3-(N-(4-(non-1-ynyl)phenyl)sulfamoylamino)-4-(trimethylammonio)-butanoate | B |
| Example S105. (R)-3-(N-(4-nonylphenyl)sulfamoylamino)-4-(trimethylammonio)-butanoate | A |
| Example S106. (R)-3-(N-(4-(oct-1-ynyl)phenyl)sulfamoylamino)-4-(trimethylammonio) butanoate | B |
| Example S107. (R)-3-(N-(4-((4-pentylphenyl)ethynyl)phenyl)sulfamoylamino)-4-(trimethylammonio)butanoate | B |

TABLE 1-continued

IC$_{50}$ Values of CPT1A Inhibitors of the Invention

| Compounds | IC$_{50}$ |
|---|---|
| Example S108. (R)-3-(N-(4-(4-pentylphenethyl)phenyl) sulfamoylamino)-4-(trimethyl-ammonio)butanoate | A |
| Example S109. (R)-3-(N-(5-(3-(hexyloxy)phenoxy)pentyl)-N-methylsulfamoylamino)-4-(trimethylammonio)butanoate | A |
| Example S110. (R)-3-(N-(3-(oct-1-ynyl)phenyl)sulfamoylamino)-4-(trimethylammonio) butanoate | C |
| Example S111. (R)-3-(N-(3-octylphenyl)sulfamoylamino)-4-(trimethylammonio)-butanoate | A |
| Example S112. (R)-3-(N-(N-methyl-N-(3-(oct-1-ynyl)phenyl)sulfamoyl)amino)-4-(trimethyl-ammonio)butanoate | C |
| Example S113. (R)-3-carboxy-N,N,N-trimethyl-2-(N-methyl-N-(3-octylphenyl)sulfamoylamino)propan-1-aminium 2,2,2-trifluoroacetate | B |
| Example S114. (R)-3-(5-bromofuran-2-carboxamido)-4-(trimethylammonio)butanoate | D |
| Example S115. (R)-3-carboxy-N,N,N-trimethyl-2-(5-((4-pentylphenyl)ethynyl)furan-2-carboxamido)propan-1-aminium 2,2,2-trifluoroacetate | A |
| Example S116. (R)-3-carboxy-N,N,N-trimethyl-2-(5-(thiophen-3-ylethynyl)furan-2-carboxamido)propan-1-aminium 2,2,2-trifluoroacetate | C |
| Example S117. (R)-3-carboxy-2-(5-((2-methoxypyrimidin-5-yl)ethynyl)furan-2-carboxamido)-N,N,N-trimethylpropan-1-aminium 2,2,2-trifluoroacetate | D |
| Example S118. (R)-3-carboxy-2-(5-((5-hexylthiophen-2-yl)ethynyl)furan-2-carboxamido)-N,N,N-trimethylpropan-1-aminium 2,2,2-trifluoroacetate | B |
| Example S119. (R)-3-(5-(2-(5-hexylthiophen-2-yl)ethyl)furan-2-carboxamido)-4-(trimethylammonio)butanoate | A |
| Example S120. (R)-3-carboxy-N,N,N-trimethyl-2-(2-oxooctanamido)propan-1-aminium 2,2,2-trifluoroacetate | B |
| Example S121. (3R)-3-(5-(4-pentylphenethyl)tetrahydrofuran-2-carboxamido)-4-(trimethylammonio)butanoate | B |
| Example S122. (R)-3-(5-((3-(hexyloxy)phenyl)ethynyl)furan-2-carboxamido)-4-(trimethylammonio)butanoate | B |
| Example S123. (R)-3-carboxy-N,N,N-trimethyl-2-(5-(4-pentylphenethyl)furan-2-carboxamido)propan-1-aminium 2,2,2-trifluoroacetate | A |
| Example S124. (R)-3-carboxy-N,N,N-trimethyl-2-(5-(2-(thiophen-3-yl)ethyl)furan-2-carboxamido)propan-1-aminium 2,2,2-trifluoroacetate | A |
| Example S125. (R)-3-carboxy-2-(5-(3-(hexyloxy)phenethyl)furan-2-carboxamido)-N,N,N-trimethylpropan-1-aminium 2,2,2-trifluoroacetate | A |

Example 4

Cells and Cell Cultures

Human cancer cells (MCF-7, H358, H460, HCT116 p53$^{+/+}$, HCT116 p53$^{-/-}$, A172, PC-3, DU-145 and SW626) were maintained in DMEM medium containing 10% Fetal Bovine Serum (FBS) (Invitrogen, Burlington, ON, Canada) and normal cells HMEC, 184A1, NHBE and PrEC were cultured in MEGM, MEGM plus transferring and cholera toxin, BEGM and PrEGM supplemented with various growth factors (Cambrex, Charles city, IA, USA), respectively.

Example 5

Inhibition of Growth of Various Cancer Cell Lines with Compound of Example S7 of the Invention Compounds were dissolved in DMSO and further diluted in cell culture medium for the experiments performed. Cells were seeded into 96-well plates with 1,500-5,000 cells/well according to cell growth rate. After 24 h, DMEM medium containing 10% FBS were changed to DMEM containing 3% FBS for cancer cells and additional 3% FBS were added into the culture medium for normal cells. The compound was added into the cell culture at the indicated concentrations, and the final concentration of DMSO was adjusted to a final concentration of 0.1%. Cells were subjected to either normoxic condition (20% $O_2$) for 6 days or hypoxic condition (0.2% $O_2$) for 2 days and then transferred to normoxic condition for 4 days. Cell viability was assessed by Sulforhodamine B (SRB) assay at Day 6.

Sulforhodamine B (SRB) (Sigma, Oakville, ON, Canada) is a water-soluble dye that binds to the basic amino acids of the cellular proteins. Thus, colorimetric measurement of the bound dye provides an estimate of the total protein mass that is related to the cell number. The cells were fixed in situ by gently aspirating off the culture media and adding 50 ul of cold 10% trichloroacetic Acid (TCA) per well and incubated at 4° C. for 30-60 min. The plates were washed five times with water and allowed to air dry for 5 min. 50 ul of 0.4% (w/v) SRB dissolved in 1% (v/v) acetic acid were added into each well, plates were then incubated at RT for 30 min for staining, washed four times with 1% acetic acid to remove any unbound dye and then allowed to air dry for 5 min. Stain was solubilized with 100 ul of 10 mM Tris pH 10.5 per well. Absorbance was read at 570 nm on a spectrophotometer. GI$_{50}$ (compound concentration required for 50% of growth inhibition) was calculated using GraphPad Prism 4.0 software (GraphPad Software, Inc., San Diego, Calif., USA).

The results are shown in Table 2 for the compound of Example S7. The values were mean±SD from 2 independent experiments with triplicated data per experiment.

TABLE 2

GI$_{50}$ Data of Compound of Example S7 of the Invention

| Cell Lines | Normoxi | GI$_{50}$ Compound of Example S7 (μM) Hypoxia |
|---|---|---|
| MCF-7 | 5.3 ± 1.3 | 2.5 ± 0.6 |
| H460 | 8.8 ± 1.2 | 2.6 ± 0.6 |
| HCT116 | 9.3 ± 0.7 | 5.7 ± 0.6 |
| A172 | 3.8 ± 0.5 | 1.9 ± 0.8 |

Example 6

Inhibition of Growth of Various Cancer Cell Lines with CPT Inhibitors of the Invention Cell viability of various cell lines treated with 3-carboxy-N,N,N-trimethyl-2-pentadecanamidopropan-1-aminium ("nPAC") and compound of Examples S7, S63, S66, S90, S89, S67, S75 and S10 was also assessed in a manner as described above in Example 5. GI$_{50}$ data of these compounds are shown in Table 3.

TABLE 3

GI$_{50}$ Data of CPT Inhibitors of the Invention

| Cell Lines | | GI$_{50}$(μM) | | | | | | | |
|---|---|---|---|---|---|---|---|---|---|
| | (3% FBS) | nPAC | Ex. S7 | Ex. S63 | Ex. S66 | Ex. S90 | Ex. S89 | Ex. S67 | Ex. S75 | Ex. S10 |
| Breast | MCF-7 | 6.6 | 4.5 | 0.4 | 0.1 | 4.0 | 4.2 | 0.7 | 11 | 44 |
| | MDA-231 | 10 | 27 | 8.5 | 9.4 | | | | | >50 |
| | Hs578T | 19 | 33 | 3.7 | 8.2 | 8.2 | 7.3 | 17 | 13 | >50 |
| Lung | H358 | 0.7 | 0.5 | 0.4 | 0.4 | 1.1 | 1.4 | 0.7 | 2.8 | 3.4 |
| | A54 | 20 | 25 | 14 | 28 | 21 | 21 | 88 | 31 | >50 |
| Colon | COLO-205 | 0.4 | 0.9 | 0.3 | 0.4 | 2.4 | 1.4 | 2.7 | 3.6 | 4.6 |
| | HCT-15 | 1.5 | 1.3 | 0.5 | 1.1 | 3.3 | 2.2 | 14 | 5.6 | 28 |
| | SW480 | 0.4 | 0.8 | 0.4 | 0.3 | 1.3 | 1.5 | 0.7 | 1.9 | 9.3 |
| | SW620 | 0.5 | 1.5 | 0.5 | 0.6 | 2.4 | 1.9 | 5.5 | 4.1 | 19 |
| Brain | A172 | 3.2 | 3 | 0.9 | 1.8 | 6.6 | 4.1 | 3.6 | 18 | 40 |
| Prostate | PC-3 | 2.5 | 0.7 | 0.3 | 0.3 | 1.3 | 1.6 | 1.5 | 1.5 | 5.3 |
| Ovarian | SW626 | 1.2 | 0.8 | 1.2 | 1.5 | 3.1 | 2.3 | 2.7 | 4.1 | 15 |
| | Caov-3 | 1.3 | 1.3 | | | 1.6 | 1.5 | 0.8 | | 13 |

While this invention has been particularly shown and described with references to example embodiments thereof, it will be understood by those skilled in the art that various changes in form and details may be made therein without departing from the scope of the invention encompassed by the appended claims.

What is claimed is:

1. A compound represented by the following structural formula or a pharmaceutically acceptable salt thereof:

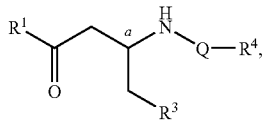

Wherein $R^1$ is —OH or —$OC_{1-6}$ alkyl;

$R^3$ is —$N(R^7R^8)$ or —$N^{\pm}(R^7R^8R^9)X^-$;

each of $R^7$, $R^8$, $R^9$ independently is —H or $C_{1-6}$ alkyl;

$X^-$ is a pharmaceutically acceptable counter ion; and a) Q is —C(=O)—, —C(=S)—, —C(O)NH— or —C(S)NH—; and $R^4$ is a substituted aryl group, or a substituted or unsubstituted heteroaryl group, provided that when $R^4$ is a substituted phenyl group, then $R^3$ is —$N^{\pm}(R^7R^8R^9)X^-$; or b) Q is —C(=NH)—, —S(O)—, —S(O)$_2$—, —S(O)—NH—, or —S(O)$_2$—NH—; and $R^4$ is a substituted or unsubstituted aryl group, or substituted or unsubstituted heteroaryl group, provided that when Q is —S(O)$_2$—, then $R^4$ is not a tolyl group; or c) Q is —C(=O)—N(R$^5$)—, —C(=S)—N(R$^5$)—, —C(=NH)—N(R$^5$)—, —S(O)—N(R$^5$)— or —S(O)$_2$—N(R$^5$)—; and $R^4$ and $R^5$ are each independently a substituted or unsubstituted aliphatic group, a substituted or unsubstituted aryl group, or a substituted or unsubstituted heteroaryl group, or $R^4$ and $R^5$ taken together with the nitrogen atom of $N(R^4R^5)$ form a substituted or unsubstituted non-aromatic heterocyclic ring.

2. The compound of claim 1, wherein when Q is —C(=O)—, —C(O)NH—, or —C(=O)—N(R$^5$)—, then each of $R^4$ and $R^5$ is not a substituted or unsubstituted, six-membered N-containing heteroaryl group.

3. The compound of claim 1, wherein when Q is —S(O)$_2$—, then $R^4$ is not a substituted or unsubstituted naphthyl or a substituted or unsubstituted indanyl group.

4. The compound of claim 1, wherein when Q is —C(=O)— or —C(O)NH—, then $R^4$ is not a phenyl group substituted with —OCH$_2$-(optionally substituted quinolyl), and not a phenyl group substituted with one or more substituents selected from the group consisting of benzoyloxy, formyloxy, acetyloxy, trifluoroacetyloxy, glycosyloxy and silyloxy.

5. The compound of claim 1, wherein $R^4$ is an aryl or a heteroaryl group optionally substituted with one or more substituents selected from the group consisting of halogen, $Ak^1$, $Ar^1$, —NO$_2$, —CN, —NCS, —C(O)OR$^{10}$, —C(O)R$^{10}$, —C(S)R$^{10}$, —OC(O)R$^{10}$, —C(O)N(R$^{11}$)$_2$, —C(S)N(R$^{11}$)$_2$, —S(O)R$^{12}$, —S(O)$_2$R$^{12}$, —SO$_3$R$^{12}$, —SO$_2$N(R$^{11}$)$_2$, —SO$_2$N(R$^{11}$)—NR$^{11}$, —OR$^{10}$, —SR$^{10}$, —N(R$^{11}$)$_2$, —NR$^{11}$C(O)R$^{10}$, —NR$^{11}$S(O)R$^{12}$, —NR$^{11}$C(O)OR$^{12}$, —N(R$^{11}$)C(O)N(R$^{11}$)$_2$, —NR$^{11}$SO$_2$N(R$^{11}$)$_2$, —NR$^{11}$SO$_2$R$^{12}$, —O—[CH$_2$]$_p$—O—, —S—[CH$_2$]$_p$—S— and —[CH$_2$]$_q$—, wherein:

$Ak^1$ is a $C_{1-20}$ aliphatic group optionally substituted with one or more substituents selected from the group consisting of halogen, —NO$_2$, —CN, —Ar$^2$, —OR$^{20}$, —O-Ak$^2$-Ar$^2$, —SR$^{20}$, —S-Ak$^2$-Ar$^2$, —N(R$^{21}$)$_2$, —NR$^{21}$C(O)R$^{20}$, —NR$^{21}$C(O)-Ak$^2$-Ar$^2$, —N(R$^{21}$)C(O)N(R$^{21}$)$_2$, —C(O)R$^{20}$, —C(O)-Ak$^2$-Ar$^2$, —C(S)R$^{20}$, —C(S)-Ak$^2$-Ar$^2$, —CO$_2$R$^{20}$, —CO$_2$-Ak$^2$-Ar$^2$, —OC(O)—R$^{20}$—OC(O)-Ak$^2$-Ar$^2$, —C(O)N(R$^{21}$)$_2$, —C(S)N(R$^{21}$)$_2$, —S(O)$_2$R$^{22}$, —S(O)$_2$-Ak$^2$-Ar$^2$, —SO$_2$N(R$^{21}$)$_2$, —SO$_2$N(R$^{21}$)—NR$^{21}$, —S(O)R$^{22}$, —S(O)-Ak$^2$-Ar$^2$, —SO$_3$R$^{22}$, —SO$_3$-Ak$^2$-Ar$^2$, —NR$^{21}$SO$_2$N(R$^{21}$)$_2$, —NR$^{21}$SO$_2$R$^{22}$ and —NR$^{21}$SO$_2$-Ak$^2$-Ar$^2$;

each $R^{10}$ independently is:

i) hydrogen;

ii) a $C_{1-20}$ aliphatic group optionally substituted with one or more substituents selected from the group consisting of halogen, —NO$_2$, —CN, —Ar$^0$, —OR$^{25}$, —O-Ak$^0$-Ar$^0$, —SR$^{25}$, —S-Ak$^0$-Ar$^0$, —N(R$^{26}$)$_2$, —NR$^{26}$C(O)R$^{25}$, —NR$^{26}$C(O)-Ak$^0$-Ar$^0$, —N(R$^{26}$)C(O)N(R$^{26}$)$_2$, —C(O)R$^{25}$, —C(O)-Ak$^0$-Ar$^0$, —C(S)R$^{25}$, —C(S)-Ak$^0$-Ar$^0$, —CO$_2$R$^{25}$, —CO$_2$-Ak$^0$-Ar$^0$, —OC(O)—R$^{25}$, —OC(O)-Ak$^0$-Ar$^0$, —C(O)N(R$^{26}$)$_2$, —C(S)N(R$^{26}$)$_2$, —S(O)$_2$R$^{27}$, —S(O)$_2$-Ak$^0$-Ar$^0$, —SO$_2$N(R$^{26}$)$_2$, —NR$^{26}$SO$_2$N(R$^{26}$)$_2$, —NR$^{26}$SO$_2$R$^{27}$ and —NR$^{26}$SO$_2$-Ak$^0$-Ar$^0$; or iii) a $C_{6-14}$ aryl or a 5-14 membered heteroaryl group each optionally and independently substituted with one or more substituents selected from the group consisting of halogen, nitro, cyano, hydroxy, $C_{1-20}$ alkyl, $C_{2-20}$ alkenyl, $C_{2-20}$ alkynyl, amino, $C_{1-20}$ alkylamino, $C_{1-20}$ dialkylamino, $C_{1-20}$ alkoxy, $(C_{1-10}$ alkoxy$)C_{1-20}$ alkyl, $C_{1-20}$ haloalkoxy, $(C_{1-10}$ haloalkoxy$)C_{1-20}$ alkyl and $C_{1-20}$ haloalkyl;

each $R^{11}$ independently is $R^{10}$, —$CO_2R^{10}$, —$SO_2R^{10}$ or —$C(O)R^{10}$, or —$N(R^{11})_2$ taken together is an optionally substituted, 5-14 membered non-aromatic heterocyclic group;

each $R^{12}$ independently is:
  i) a $C_{1-20}$ aliphatic group optionally and independently substituted with one or more substituents selected from the group consisting of halogen, —$NO_2$, —CN, —$Ar^0$, —$OR^{25}$, —O-$Ak^0$-$Ar^0$, —$SR^{25}$, —S-$Ak^0$-$Ar^0$, —$N(R^{26})_2$, —$NR^{26}C(O)R^{25}$, —$NR^{26}C(O)$-$Ak^0$-$Ar^0$, —$N(R^{26})C(O)N(R^{26})_2$, —$C(O)R^{25}$, —$C(O)$-$Ak^0$-$Ar^0$, —$C(S)R^{25}$, —$C(S)$-$Ak^0$-$Ar^0$, —$CO_2R^{25}$, —$CO_2$-$Ak^0$-$Ar^0$, —$OC(O)$-$R^{25}$, —$OC(O)$-$Ak^0$-$Ar^0$, —$C(O)N(R^{26})_2$—, —$C(S)N(R^{26})_2$, —$S(O)_2R^{27}$, —$S(O)_2$-$Ak^0$-$Ar^0$, —$SO_2N(R^{26})_2$, —$NR^{26}SO_2N(R^{26})_2$, —$NR^{26}SO_2R^{27}$ and —$NR^{26}SO_2$-$Ak^0$-$Ar^0$; or
  iii) a $C_{6-14}$ aryl or a 5-14 membered heteroaryl group each optionally and independently substituted with one or more substituents selected from the group consisting of halogen, nitro, cyano, hydroxy, $C_{1-20}$ alkyl, $C_{2-20}$ alkenyl, $C_{2-20}$ alkynyl, amino, $C_{1-20}$ alkylamino, $C_{1-20}$ dialkylamino, $C_{1-20}$ alkoxy, $(C_{1-10}$ alkoxy$)C_{1-20}$ alkyl, $C_{1-20}$ haloalkoxy, $(C_{1-10}$ haloalkoxy$)C_{1-20}$ alkyl and $C_{1-20}$ haloalkyl;

each of $Ak^0$ and $Ak^2$ is a $C_{1-20}$ alkylene, $C_{2-20}$ alkenylene or $C_{2-20}$ alkynylene group;

each of $R^{20}$ and $R^{25}$ independently is:
  i) hydrogen;
  ii) a $C_{6-14}$ aryl or a 5-14 membered heteroaryl group each optionally and independently substituted with one or more substituents selected from the group consisting of halogen, nitro, cyano, hydroxy, $C_{1-15}$ alkyl, $C_{2-15}$ alkenyl, $C_{2-15}$ alkynyl, amino, $C_{1-15}$ alkylamino, $C_{1-15}$ dialkylamino, $C_{1-15}$ alkoxy, $(C_{1-10}$ alkoxy$)C_{1-15}$ alkyl, $C_{1-15}$ haloalkoxy, $C_{1-15}$ haloalkyl and $(C_{1-10}$ haloalkoxy$)C_{1-15}$ alkyl; or
  iii) a $C_{1-15}$ alkyl group optionally substituted with one or more substituents selected from the group consisting of halogen, hydroxyl, amino, $C_{1-15}$ alkylamino, $C_{1-15}$ dialkylamino, $C_{1-15}$ alkoxy, nitro, cyano, $C_{1-15}$ alkoxycarbonyl, $C_{1-15}$ alkylcarbonyl and $C_{1-15}$ haloalkoxy;

each $R^{21}$ independently is $R^{20}$, —$CO_2R^{20}$, —$SO_2R^{20}$ or —$C(O)R^{20}$, or —$N(R^{21})_2$ taken together is an optionally substituted, 5-14 membered non-aromatic heterocyclic group;

each $R^{26}$ independently is $R^{25}$, —$CO_2R^{25}$, —$SO_2R^{25}$ or —$C(O)R^{25}$, or —$N(R^{26})_2$ taken together is an optionally substituted, 5-14 membered non-aromatic heterocyclic group;

each of $R^{22}$ and $R^{27}$ independently is
  i) a $C_{6-14}$ aryl or a 5-14 membered heteroaryl group each optionally and independently substituted with one or more substituents selected from the group consisting of halogen, nitro, cyano, hydroxy, $C_{1-15}$ alkyl, $C_{2-15}$ alkenyl, $C_{2-15}$ alkynyl, amino, $C_{1-15}$ alkylamino, $C_{1-15}$ dialkylamino, $C_{1-15}$ alkoxy, $(C_{1-10}$ alkoxy$)C_{1-15}$ alkyl, $C_{1-15}$ haloalkoxy, $C_{1-15}$ haloalkyl and $(C_{1-10}$ haloalkoxy$)C_{1-15}$ alkyl; or
  ii) a $C_{1-15}$ alkyl group optionally substituted with one or more substituents selected from the group consisting of halogen, hydroxyl, amino, $C_{1-15}$ alkylamino, $C_{1-15}$ dialkylamino, $C_{1-15}$ alkoxy, nitro, cyano, $C_{1-15}$ alkoxycarbonyl, $C_{1-15}$ alkylcarbonyl, $(C_{1-10}$ haloalkoxy$)C_{1-15}$ alkyl and $C_{1-15}$ haloalkoxy; and each of $Ar^0$, $Ar^1$ and $Ar^2$ is a $C_{6-14}$ aryl or a 5-14 membered heteroaryl group optionally and independently substituted with one or more substituents selected from the group consisting of halogen, nitro, cyano, hydroxy, $C_{1-20}$ alkyl, $C_{2-20}$ alkenyl, $C_{2-20}$ alkynyl, amino, $C_{1-20}$ alkylamino, $C_{1-20}$ dialkylamino, $C_{1-20}$ alkoxy, $(C_{1-10}$ alkoxy$)C_{1-20}$ alkyl, $C_{1-20}$ haloalkoxy, $(C_{1-10}$ haloalkoxy$)C_{1-20}$ alkyl and $C_{1-20}$ haloalkyl;

each of the non-aromatic heterocyclic groups represented by —$N(R^{21})_2$ and —$N(R^{26})_2$ is optionally and independently substituted with one or more substituents selected from the group consisting of halogen, $C_{1-10}$ alkyl, $C_{2-10}$ alkenyl, $C_{2-10}$ alkynyl, amino, $C_{1-10}$ alkylamino, $C_{1-10}$ dialkylamino, $C_{1-10}$ alkoxy, nitro, cyano, hydroxy, $C_{1-10}$ alkoxycarbonyl, $C_{1-10}$ alkylcarbonyl, $C_{1-10}$ haloalkoxy, $(C_{1-10}$haloakoxy$)C_{1-10}$ alkyl, $C_{1-10}$ haloalkyl, $C_{6-14}$ aryl and 5-14 membered heteroaryl;

each p independently is 1, 2, 3 or 4; and each q independently is 3, 4, 5 or 6.

6. The compound of claim 5, wherein Q is —C(=O)—, —C(=S)—, —C(O)NH—, —C(S)NH—, —C(=NH)—, —S(O)—, —S(O)$_2$—or —S(O)$_2$—NH—.

7. The compound of claim 6, wherein $R^4$ is an optionally substituted monocyclic aryl or optionally substituted monocyclic heteroaryl group.

8. The compound of claim 1, wherein each of $R^7$, $R^8$ and $R^9$ independently is $C_{1-6}$ alkyl.

9. The compound of claim 1, wherein $R^3$ is —$N^+(R^7R^8R^9)$ $X^-$.

10. The compound of claim 9, wherein the compound is represented by a structural formula selected from the group consisting of:

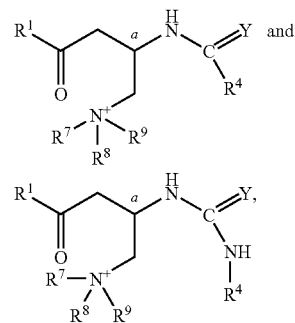

or a pharmaceutically acceptable salt thereof, wherein each Y independently is O, S or NH.

11. The compound of claim 10, wherein each Y independently is O or S.

12. The compound of claim 11, wherein $R^4$ is not a substituted or unsubstituted, six-membered N-containing heteroaryl group.

13. The compound of claim 12, wherein $R^4$ is a monocyclic aryl or heteroaryl group optionally substituted with one or more substituents selected from the group consisting of $Ak^1$, —NO₂, —CN, —OR¹⁰, —SR¹⁰, —C(O)OR¹⁰, —C(O)R¹⁰, —C(S)R¹⁰, —OC(O)R¹⁰, —C(O)N(R¹¹)₂, —C(S)N(R¹¹)₂, —N(R¹¹)₂, —NR¹¹C(O)R¹⁰, —NR¹¹C(O)R¹², —N(R¹¹)C(O)N(R¹¹)₂ and —NR¹¹SO²R¹².

14. The compound of claim 13, wherein Ak¹ is optionally substituted with one or more substituents selected from the group consisting of —Ar², —OR²⁰, —O-Ak²-Ar², —SR²⁰, —S-Ak²-Ar², —N(R²¹)₂, —NR²¹C(O)R²⁰, —NR²¹C(O)-Ak²-Ar², —C(O)R²⁰, —C(O)-Ak²-Ar², —C(S)R²⁰, —C(S)-Ak²-Ar², —CO₂R²⁰, —CO₂-Ak²-Ar², —OC(O)—R²⁰—OC(O)-Ak²-Ar², —C(O)N(R²¹)₂—, —S(O)₂—R²², —S(O)₂-Ak²-Ar², —SO₂N(R²¹)₂, —SO₂N(R²¹)—NR²¹, —S(O)R²², —S(O)-Ak²-Ar², —NR²¹SO₂R²² and —NR²¹SO₂-Ak²-Ar².

15. The compound of claim 14, wherein each of R¹⁰ and R¹² independently is:
  i) a C₁₋₁₀ aliphatic group optionally substituted with one or more substituents selected from the group consisting of halogen, —NO₂ —CN, —Ar⁰, —OR²⁵, —O-Ak⁰-Ar⁰, —SR²⁵, —S-Ak⁰-Ar⁰, —N(R²⁶)₂, —NR²⁶C(O)R²⁵, —NR²⁶C(O)-Ak⁰-Ar⁰, —C(O)R²⁵, —C(O)-Ak⁰-Ar⁰, —CO₂R²⁵, —CO₂-Ak⁰-Ar⁰ and —C(O)N(R²⁶)₂—; or
  ii) a C₆₋₁₄ aryl or a 5-14 membered heteroaryl group each optionally and independently substituted with one or more substituents selected from the group consisting of halogen, nitro, cyano, hydroxy, C₁₋₁₀ alkyl, C₂₋₁₀ alkenyl, C₂₋₁₀ alkynyl, amino, C₁₋₁₀ alkylamino, C₁₋₁₀ dialkylamino, C₁₋₁₀ alkoxy, (C₁₋₆ alkoxy)C₁₋₁₀ alkyl, C₁₋₁₀ haloalkoxy, (C₁₋₆ haloalkoxy)C₁₋₁₀ alkyl and C₁₋₁₀ haloalkyl.

16. The compound of claim 15, wherein:
  each Ak⁰ and Ak² independently is a C1-C10 alkylene group;
  each of R²⁰ and R²⁵ independently is:
    i) hydrogen,
    ii) a C₆₋₁₄ aryl or a 5-14 membered heteroaryl group optionally and independently substituted with one or more substituents selected from the group consisting of halogen, nitro, cyano, hydroxy, C₁₋₁₀ alkyl, C₂₋₁₀ alkenyl, C₂₋₁₀ alkynyl, amino, C₁₋₁₀ alkylamino, C₁₋₁₀ dialkylamino, C₁₋₁₀ alkoxy, (C₁₋₆ alkoxy)C₁₋₁₀ alkyl, C₁₋₁₀ haloalkoxy, C₁₋₁₀ haloalkyl and (C₁₋₆ haloalkoxy)C₁₋₁₀ alkyl; or
    iii) a C₁₋₁₀ alkyl group optionally and independently substituted with one or more substituents selected from the group consisting of halogen, hydroxyl, amino, C₁₋₁₀ alkylamino, C₁₋₁₀ dialkylamino, C₁₋₁₀ alkoxy, nitro, cyano, C₁₋₁₀ alkoxycarbonyl, C₁₋₁₀ alkylcarbonyl and C₁₋₁₀ haloalkoxy; and
  each R²¹ independently is R²⁰, —CO₂R²⁰, —SO₂R²⁰ or —C(O)R²⁰, or —N(R²¹)₂ taken together is an optionally substituted, 5-14 membered non-aromatic heterocyclic group;
  each R²⁶ independently is R²⁵, —CO₂R²⁵, —SO₂R²⁵ or —C(O)R²⁵, or —N(R²⁶)₂ taken together is an optionally substituted, 5-14 membered non-aromatic heterocyclic group;
  each of the non-aromatic heterocyclic groups represented by —N(R²¹)₂ and —N(R²⁶)₂ is optionally and independently substituted with one or more substituents selected from the group consisting of halogen, C₁₋₆ alkyl, C₂₋₆ alkenyl, C₂₋₆ alkynyl, amino, C₁₋₆ alkylamino, C₁₋₆ dialkylamino, C₁₋₆ alkoxy, nitro, cyano, hydroxy, C₁₋₆ alkoxycarbonyl, C₁₋₆ alkylcarbonyl, C₁₋₆ haloalkoxy, (C₁₋₆ haloalkoxy)C₁₋₆ alkyl, C₁₋₆ haloalkyl, C₆₋₁₄ aryl and 5-14 membered heteroaryl; and
  each R²² independently is:
    i) a C₆₋₁₄ aryl or a 5-14 membered heteroaryl group optionally and independently substituted with one or more substituents selected from the group consisting of halogen, nitro, cyano, hydroxy, C₁₋₁₀ alkyl, C₂₋₁₀ alkenyl, C₂₋₁₀ alkynyl, amino, C₁₋₁₀ alkylamino, C₁₋₁₀ dialkylamino, C₁₋₁₀ alkoxy, (C₁₋₆ alkoxy)C₁₋₁₀ alkyl, C₁₋₁₀ haloalkoxy, C₁₋₁₀ haloalkyl and (C₁₋₆ haloalkoxy)C₁₋₁₀ alkyl; or
    ii) a C₁₋₁₀ alkyl group optionally substituted with one or more substituents selected from the group consisting of halogen, hydroxyl, amino, C₁₋₁₀ alkylamino, C₁₋₁₀ dialkylamino, C₁₋₁₀ alkoxy, nitro, cyano, C₁₋₁₀ alkoxycarbonyl, C₁₋₁₀ alkylcarbonyl and C₁₋₁₀ haloalkoxy.

17. The compound of claim 16, wherein R⁴ is selected from the group consisting of:

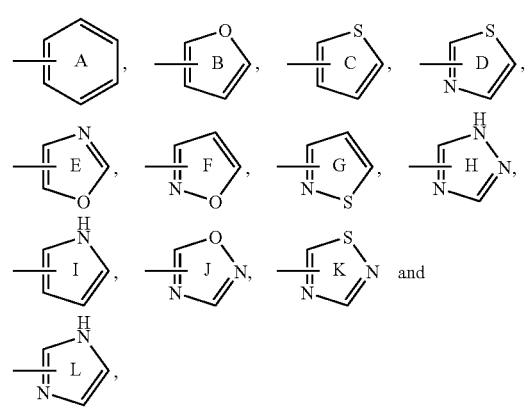

wherein ring A is substituted and each of rings B-L is optionally substituted.

18. The compound of claim 17, wherein ring A is substituted with one or more substituents selected from the group consisting of halogen, Ak¹, —OR¹⁰ and —SR¹⁰ and each of rings B-L is optionally substituted with one or more substituents selected from the group consisting of halogen, Ak¹, —OR¹⁰ and —SR¹⁰.

19. The compound of claim 18, wherein Ak¹ is a C1-C15 aliphatic group optionally substituted with one or more substituents selected from the group consisting of halogen, —Ar², —OR²⁰, —O-Ak²-Ar², —SR²⁰, —S-Ak²-Ar², —N(R²¹)₂ and —S(O)₂-Ak²-Ar².

20. The compound of claim 1, wherein:
  a) Q is C(=S)—, —C(O)NH— or —C(S)NH—; and
    R⁴ is a substituted aryl group, or a substituted or unsubstituted heteroaryl group, provided that when R⁴ is a substituted phenyl group, then R³ is —N⁺(R⁷R⁸R⁹) X⁻; or
  b) Q is —C(=NH)—, —S(O)—, —S(O)₂—, —S(O)—NH—, or —S(O)₂—NH—; and
    R⁴ is a substituted or unsubstituted aryl group, or substituted or unsubstituted heteroaryl group, provided that when Q is —S(O)₂—, then R⁴ is not a tolyl group; or
  c) Q is —C(=O)—N(R⁵)—, —C(=S)—N(R⁵)—, —C(=NH)—N(R⁵)—, —S(O)—N(R⁵)—or —S(O)₂—N(R⁵)—; and R⁴ and R⁵ are each independently a substituted or unsubstituted aliphatic group, a substituted or unsubstituted aryl group, or a substituted or unsubstituted heteroaryl group, or R⁴ and R⁵ taken together with the nitrogen atom of N(R⁴R⁵) form a substituted or unsubstituted non-aromatic heterocyclic ring.

* * * * *

UNITED STATES PATENT AND TRADEMARK OFFICE
CERTIFICATE OF CORRECTION

| | | |
|---|---|---|
| PATENT NO. | : 8,410,150 B2 | Page 1 of 1 |
| APPLICATION NO. | : 12/530429 | |
| DATED | : April 2, 2013 | |
| INVENTOR(S) | : Heinz W. Pauls | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 605 days.

Signed and Sealed this
Fifth Day of November, 2013

Teresa Stanek Rea
*Deputy Director of the United States Patent and Trademark Office*